US012790619B2

(12) United States Patent
Harling et al.

(10) Patent No.: US 12,790,619 B2
(45) Date of Patent: *Nov. 10, 2026

(54) METHODS AND HYBRIDS FOR TARGETED NUCLEIC ACID EDITING IN PLANTS USING CRISPR/CAS SYSTEMS

(71) Applicant: KWS SAAT SE & Co. KGaA, Einbeck (DE)

(72) Inventors: Hinrich Harling, Bovenden (DE); Susana Martin-Ortigosa, Einbeck (DE); Markus Niessen, Hannover (DE); Corinna Streitner, Melle (DE); Nadine Schumann, Einbeck (DE); Erik Jongedijk, Lokeren (DE)

(73) Assignee: KWS SAAT SE & Co. KGaA, Einbeck (DE)

( * ) Notice: Subject to any disclaimer, the term of this patent is extended or adjusted under 35 U.S.C. 154(b) by 744 days.

This patent is subject to a terminal disclaimer.

(21) Appl. No.: 17/934,089

(22) Filed: Sep. 21, 2022

(65) Prior Publication Data

US 2023/0242926 A1 Aug. 3, 2023

Related U.S. Application Data

(62) Division of application No. 15/575,167, filed as application No. PCT/EP2016/061237 on May 19, 2016, now Pat. No. 11,492,630.

(30) Foreign Application Priority Data

May 19, 2015 (DE) ......................... 102015006335.9
Nov. 5, 2015 (DE) ......................... 102015014252.6

(51) Int. Cl.

| | |
|---|---|
| ***C12N 15/82*** | (2006.01) |
| ***A01H 5/04*** | (2018.01) |
| ***A01H 5/12*** | (2018.01) |
| ***C12N 9/22*** | (2006.01) |
| ***C12N 15/113*** | (2010.01) |

(52) U.S. Cl.

CPC ........... *C12N 15/8213* (2013.01); *A01H 5/04* (2013.01); *A01H 5/12* (2013.01); *C12N 9/222* (2025.05); *C12N 15/113* (2013.01); *C12N 15/8201* (2013.01); *C12N 15/8203* (2013.01); *C12N 15/8205* (2013.01); *C12N 15/8207* (2013.01)

(58) Field of Classification Search

None

See application file for complete search history.

(56) References Cited

U.S. PATENT DOCUMENTS 5,500,360 A * 3/1996 Ahlquist ................ C12N 15/85 435/235.1
5,736,369 A 4/1998 Bowen et al.
5,910,631 A 6/1999 Topfer et al.
6,187,994 B1 2/2001 Baszczynski et al.
6,410,329 B1 6/2002 Hansen et al.
6,583,335 B1 6/2003 Peffley et al.
6,603,061 B1 8/2003 Armstrong et al.
6,846,970 B1 1/2005 Christou et al.
7,799,566 B2 9/2010 Lowe et al.
8,399,218 B2 3/2013 Gupta et al.
8,697,359 B1 4/2014 Zhang
9,719,108 B2 8/2017 Samuel et al.
2003/0135891 A1 7/2003 Gould et al.
2005/0039228 A1 2/2005 Ding et al.
2011/0189775 A1 8/2011 Ainley et al.
2012/0090053 A1 4/2012 Yoshikawa et al.
2013/0145488 A1 6/2013 Wang et al.
2013/0263324 A1 10/2013 Lassner et al.
2014/0068797 A1 3/2014 Doudna et al.
2014/0096284 A1 4/2014 Martin-Ortigosa et al.
2014/0170753 A1 6/2014 Zhang
2014/0242702 A1 8/2014 Chen et al.
2015/0059010 A1 2/2015 Cigan
2015/0067922 A1 3/2015 Yang
(Continued)

FOREIGN PATENT DOCUMENTS

CN 1541270 A 10/2004
CN 102558309 A 7/2012
(Continued)

OTHER PUBLICATIONS

Barcelo, P. and Lazzeri, P. A. (1995) Transformation of cereals by microprojectile bombardment of immature inflorescence and scutellum tissues, pp. 113-123 (Meth Molecular biology—plant gene transfer and expression protocols (vol. 49). Jones, H. (ed.) Humana Press Inc., Totowa, NJ.*
Springer et al. (1979) Protoplasma 101:269-81.*
Murashige et al., "A Revised Medium for Rapid Growth and Bio Assays with Tobacco Tissue Cultures", Physiologia Plantarum, 1962, vol. 15, p. 473-497.
(Continued)

*Primary Examiner* — Russell T Boggs

(74) *Attorney, Agent, or Firm* — Troutman Pepper Locke LLP

(57) ABSTRACT

The present invention relates to methods and hybrids for the targeted modification of a nucleic acid-target region in a plant target structure. The invention specifically relates to methods and hybrids for directly obtaining a plant or plant material which comprises an editing of a nucleic acid introduced in a targeted manner into a meristematic cell. The hybrids can be introduced in a transient and/or stable manner. The invention also relates to novel plant-optimized introduction strategies. The invention further relates to a method for carrying out an in vitro screening assay in order to first check the suitable gRNA candidates in vitro with respect to their efficiency.

11 Claims, 27 Drawing Sheets

Specification includes a Sequence Listing.

(56) References Cited

U.S. PATENT DOCUMENTS

| | | | |
|---|---|---|---|
| 2016/0145631 | A1 | 5/2016 | Voytas et al. |
| 2017/0260536 | A1 | 9/2017 | Vainstein et al. |

FOREIGN PATENT DOCUMENTS

| | | | | |
|---|---|---|---|---|
| CN | 102812034 | A | | 12/2012 |
| CN | 103343120 | A | | 10/2013 |
| CN | 103382468 | A | | 11/2013 |
| CN | 103555711 | A | | 2/2014 |
| CN | 103667338 | A | | 3/2014 |
| CN | 103898099 | A | | 7/2014 |
| CN | 103952405 | A | | 7/2014 |
| CN | 104212778 | A | | 12/2014 |
| CN | 104293828 | A | | 1/2015 |
| DE | 10 2015 004 187 | A1 | | 10/2016 |
| EP | 2 274 973 | A1 | | 1/2011 |
| JP | 2002-526080 | A | | 8/2002 |
| JP | 2010-539930 | | | 12/2010 |
| JP | 2012-523234 | Å | | 10/2012 |
| KR | 1020150006469 | | | 1/2015 |
| WO | 00/66746 | A1 | | 11/2000 |
| WO | 2004/009761 | | | 1/2004 |
| WO | 2009/042164 | A1 | | 4/2009 |
| WO | 2011/072246 | | | 6/2011 |
| WO | 2013/096567 | | | 6/2013 |
| WO | 2013/142578 | A1 | | 9/2013 |
| WO | 2013/166315 | A1 | | 11/2013 |
| WO | 2013/169802 | A1 | | 11/2013 |
| WO | 2013/176772 | A1 | | 11/2013 |
| WO | 2014/018423 | | | 1/2014 |
| WO | 2014/039872 | A1 | | 3/2014 |
| WO | 2014/065596 | A1 | | 5/2014 |
| WO | 2014/104878 | A1 | | 7/2014 |
| WO | 2014/144155 | A1 | | 9/2014 |
| WO | 2014/161821 | A1 | | 10/2014 |
| WO | 2014/194190 | A1 | | 12/2014 |
| WO | 2014/199358 | A1 | | 12/2014 |
| WO | 2015/026885 | A1 | | 2/2015 |
| WO | WO 2015/026886 | A1 | * | 2/2015 |
| WO | 2015/066637 | A1 | | 5/2015 |
| WO | 2015/077290 | | | 5/2015 |
| WO | 2016/021973 | A1 | | 2/2016 |
| WO | 2017/092201 | A1 | | 6/2017 |

OTHER PUBLICATIONS

Dong et al., "Natural variation of TaGASR7-A1 affects grain length in common wheat under multiple cultivation conditions", Mol Breeding, 2014, vol. 34, pp. 937-947.

Mali et al., "RNA-Guided Human Genome Engineering via Cas9", Science, 2013, vol. 339, No. 6121, pp. 823-826.

Hwang et al., "Efficient In Vivo Genome Editing Using RNA-Guided Nucleases", Nature Biotechnology, 2013, vol. 31, No. 3, pp. 227-229.

Bin Shen et al., "Generation of gene-modified mice via Cas9/RNA-mediated gene targeting", Cell Research, 2013, vol. 23, p. 720-723.

Bassett et al., "CRISPR/Cas9 mediated genome engineering in *Drosophila*", Methods, 2014, vol. 69, No. 2, pp. 128-136.

Yang et al., "Particle-Mediated Gene Delivery In Vivo and In Vitro", Current Protocols in Human Genetics, 1997, 12.6.1-12.6.14, John Wiley & Sons Inc., 14 pages.

Niu et al., "Applications of TALENs and CRISPR/Cas9 in human cells and their potentials for gene therapy", Mol. Biotechnol., 2014, vol. 56, No. 8, pp. 681-688.

Yasue et al., "Highly efficient targeted mutagenesis in one-cell mouse embryos mediated by the TALEN and CRISPR/Cas systems", Scientific Reports, 2014, vol. 4, Article 5705, 10 pages.

Belhaj et al., "Editing plant genomes with CRISPR/Cas9", Current Opinion in Biotechnology, 2015, vol. 32, pp. 76-84.

Beckert et al., "Synthesis of RNA by in vitro transcription", Methods Mol. Biol., 2011, vol. 703, pp. 29-41.

Zahir et al., "The Efficient Virus-Mediated Genome Editing in Plants Using the CRISPR/Cas9 System", Molecular Plant, vol. 8, No. 8, 2015, pp. 1288-1291.

Anonymous: "A Streamlined Method for the Production, Screening, and Application of sgRNAs for CRISPR/Cas9 Gene Editing" Bio Techniques, vol. 57, No. 3, Sep. 2014, p. 157.

Barrangou et al., "CRISPR provides acquired resistance against viruses in prokaryotes", Science, 2007, vol. 315, 1709-1712.

Zetsche et al., "Cpf1 Is a single RNA-guided endonuclease of a Class 2 CRISPR-Cas system", Cell, vol. 163, No. 3, 2015, pp. 759-771.

Clough et al., "Floral Dip: a simplified method for Agrobacterium-mediated transformation of *Arabidopsis thaliana*", The Plant Journal, vol. 16, No. 6, 1998, pp. 735-743.

Deltcheva et al., "CRISPR RNA maturation by trans-encoded small RNA and host factor RNase III", Nature, 2011, vol. 471, No. 7340, pp. 602-607.

Gelvin, "Viral-mediated plant transformation gets a boost", Nature Biotechnology, vol. 23, No. 6, 2005, pp. 684-685.

Guilinger et al., "Fusion of catalytically inactive Cas9 to Fokl nuclease improves the specificity of genome modification", Nat Biotechnol., 2014, vol. 32, No. 6, pp. 577-582.

Helenius et al., "Gene delivery into intact plants using the Hellos Gene Gun", Plant Molecular Biology Reporter, 2000, vol. 18, No. 3, pp. 287a-287l.

Xing et al., "Å CRISPR/Cas9 toolkit for multiplex genome editing in plants", BMC Plant Biology, 2014, vol. 14, Article No. 327, pp. 1-12.

International Search Report and Written Opinion issued in International Application No. PCT/EP2016/061237, dated Feb. 20, 2017.

Jansen et al., "Identification of genes that are associated with DNA repeats in pokaryotes", Molecular Microbiology, 2002, vol. 43, No. 6, pp. 1565-1575.

Jinek et al. "A programmable dual-RNA-guided DNA Endonuclease in Adaptive Bacterial Immunity", Science, 2012, vol. 337, pp. 816-821.

Kim et al., "Highly efficient RNA-guided genome editing in human cells via delivery of purified Cas9 ribonucleoproteins", Genome Research, 2014, vol. 24, No. 6, pp. 1012-1019.

Krens et al., "Transformation and regeneration in sugar beet (*Beta vulgaris* L.) induced by 'shooter' mutants of Agrobacterium tumefaciens", Euphytica, 1988, vol. 39, No. 3, pp. 185-194.

Leduc et al., "Gene transfer to inflorescence and flower meristems using ballistic micro-targeting", Sexual Plant Reproduction, 1994, vol. 7, No. 2, pp. 135-143.

Bortesi et al., "The CRISPR/Cas9 system for plant genome editing and beyond", Biotechnology Advances, vol. 33, No. 1, Dec. 20, 2014, pp. 41-52.

Mahn et al., "Transient gene expression in shoot apical meristems of sugarbeet seedlings after particle bombardment", Journal of Experimental Botany, 1995, vol. 46, No. 291, pp. 1625-1628.

Makarova et al., "An updated evolutionary classification of CRISPR-Cas systems", Nature Rev. Microbiol., 2015, vol. 13, No. 11, pp. 722-736.

Makarova et al., "Annotation and Classification of CRISPR-Cas Systems", Methods Mol. Biol., 2015, vol. 1311, pp. 47-75.

Makarova et al., "Unification of Cas protein famllies and a simple scenario for the origin and evolution of CRISPR-Cas systems", Biology Direct, vol. 6, No. 38, 2011, 27 pages.

Mali et al., "CAS9 transcriptional activators for target specificity screening and paired nickases for cooperative genome engineering", Nat Biotechnol., 2013, vol. 31, No. 9, pp. 833-838.

Martin-Ortigosa et al., "Proteolistics: a biolistic method for intracellular delivery of proteins", Transgenic Research, 2014, vol. 23, pp. 743-756.

Baltes et al., "DNA Replicons for Plant Genome Engineering" The Plant Cell, American Society of Plant Biologist, vol. 26, No. 1, Jan. 17, 2014, pp. 151-163.

Quinn et al., "A Streamlined Method for the Production, Screening, Application of sgRNAs for CRISPR/Cas Gene Editing", Molecular Therapy, vol. 22, Supplement 1, 2014, 2 pages.

(56) References Cited

OTHER PUBLICATIONS

Ramakrishna et al., "Gene disruption by cell-penetrating peptide-mediated delivery of Cas9 protein and guide RNA", Genome Research, 2014, vol. 24, No. 6, pp. 1020-1027.
Sapranauskas et al., "The *Streptococcus thermophilus* CRISPR/Cas system provides immunity in *Escherichia coli*", Nucleic Acids Research, 2011, vol. 39, No. 21, pp. 9275-9282.
Maruyama et al., "Inhibition of non-homologous end joining increases the efficiency of CRISPR/Cas9-mediated precise [TM: inserted] genome editing", Nat Biotechnol, vol. 33, No. 5, May 2015, pp. 538-542.
Jacobs et al., "Targeted genome modifications in soybean with CRISPR/Cas9", BMC Biotechnology, vol. 15, No. 16, 2015, pp. 1-10.
Van der Oost et al., "Unravelling the structural and mechanistic basis of CRISPR-Cas systems", Nat Rev Microbiol., 2014, vol. 12, No. 7, pp. 479-492.
Jiang et al., "Demonstration of CRISPR/Cas9/sgRNA-mediated targeted gene modification in *Arabidopsis,* tobacco, sorghum and rice", Nucleic Acids Research, 2013, vol. 41, No. 20, pp. e188, 12 pages total.
Wiedenheft et al., "Structures of the RNA-guided surveillance complex from a bacterial immune system", Nature, 2011, vol. 477, No. 7365, pp. 486-489.
Yoo et al., "*Arabidopsis* mesophyll protoplasts: a versatile cell system for transient gene expression analysis", Nature Protocols, 2007, vol. 2, No. 7, pp. 1565-1572.
Hyun et al. "Site-directed mutagenesis in Arabidopsis thaliana using dividing tissue-targeted RGEN of the CRISPR/Cas System to generate heritable null alleles". Planta, vol. 241, No. 1, Oct. 1, 2014, pp. 271-284.
Zhang et al., "The CRISPR/Cas9 System Produces Specific and Homozygous Targeted Gene Editing in Rice in One Generation," Plant Biotechnology Journal, 2014, vol. 12, No. 6, pp. 797-807.
International Search Report and Written Opinion issued by the International Searching Authority in International Application No. PCT/EP2016/061338, dated Aug. 5, 2016.
Abhishek et al., "Tissue Culture Independent Agrobacterium tumefaciens Mediated In Planta Transformation Method for Tropical Maize (*Zea mays.* L)", Proceedings of the National Academy of Sciences, India, Section B, Biological Sciences, 2016, vol. 86, No. 2, pp. 375-384.
Bent et al., "Arabidopsis in Planta Transformation. Uses, mechanisms, and Prospects for Transformation of Other Species", Plant Physiology, 2000, vol. 124, No. 4, p. 1540-1547.
Chowrira et al., "Transgenic Grain Legumes Obtained by In Planta Electroporation-Mediated Gene Transfer", Molecular Biotechnology, vol. 5, No. 2, 1996, pp. 85-96.
Razzaq et al., "Development of in planta transformation protocol for wheat", African Journal of Biotechnology, vol. 10, No. 5, 2011, pp. 740-750.
Collins et al., "The Effect of Cotyledon Excision on Reproductive Development in Pea (*Pisum sativum* L.)", Annals of Botany, vol. 38, No. 1, 1974, pp. 181-188.
Springer et al., "A Histological Examination of Tissue Culture Initiation From Immature Embryos of Maize",Protoplasma, 1979, vol. 101, pp. 269-281.
Ma et al., "Plant multiplex genome editing vector pYLCRISPR/Cas9P35s-B, complete sequence", GenBank KR 029113, 2015.
European Search Report Issued in EP 15202060 dated Aug. 5, 2016.
Hu et al., "Agrobacterium-mediated vacuum infiltration and floral dip transformation of rapid-cycling Brassica rapa", BMC Plant Biology, 2019, vol. 19, Article No. 246, 9 pages.
Ghedira et al., "The Efficiency of Arabidopsis thaliana Floral Dip Transformation is Determined Not Only by the Agrobacterium Strain Used but Also by the Physiology and the Ecotype of the Dipped Plant", MPMI, vol. 26, No. 7, 2013, pp. 823-832.
Takacs et al., "Ontogeny of the Maize Shoot Apical Meristem", The Plant Cell, vol. 24, Aug. 2012, pp. 3219-3234.
Al-Abed et al. "Split-seed: a new tool for maize researchers", Planta, 2006, vol. 223, pp. 1355-1360.
Liang et al., "Efficient DNA-free genome editing of bread wheat using CRISPR/Cas9 ribonucleoprotein complexes", Nature Communications, 2017, vol. 8, Article 14261, 15 pages.
Svitashev et al., "Genome editing in maize directed by CRISPR-Cas9 ribonucleoprotein complexes", Nature Communications, 2016, vol. 7, Article 13274, 7 pages.
Russell, "Registration of B70 and B73 parental lines of maize", Crop Sci., 1972, vol. 12, p. 721.
Koornneef et al., "Linkage map of *Arabidopsis thaliana*", The Journal of Heredity, 1983, vol. 74, pp. 265-272.
Li et al., "Multiplex and homologous recombination-mediated plant genome editing via guide RNA/Cas9", Nature Biotechnology, 2013, vol. 31, No. 8, pp. 688-691.
Written Opinion issued in PCT/CN2016/072352 malled on Apr. 27, 2016 and English Translation thereof.
Luo et al., "A Simple Method for the Transformation of Rice Via the Pollen-Tube Pathway", Plant Molecular Biology Reporter, 1988, vol. 6, No. 3, pp. 165-174.
Yang et al., "Transgenic soybean with low phytate content constructed by Agrobacterium transformation and pollen-tube pathway", Euphytica, 2011, vol. 177, pp. 375-382.
Naito et al., "CRISPRdirect: software for designing CRISPR/Cas guide RNA with reduced off-target sites", Bioinfomatics, 2015, vol. 31, No. 7, pp. 1120-1123.
Basic knowledge of the database DIAM biotechnology, (a) Bioindustry Association, "Select temperature," URL :<http://togodb.biosciencedbc.jp/togodb/show/diam_bioterm_list/96>.
Ishida et al., "Agrobacterium-mediated transformation of malze", Nature Protocols, 2007, vol. 2, No. 7, pp. 1614-1621.
International Search Report and Written Opinion by the International Searching Authority in International Application No. PCT/CN2016/095307 dated Nov. 23, 2016.
Weinthal et al., "Nonhomologous End Joining-Mediated Gene Replacement in Plant Cells", Plant Physiology, 2013, vol. 162, pp. 390-400.
Chen et al., "TALENs: Customizable Molecular DNA Scissors for Genome Engineering of Plants", Journal of Genetics and Genomics, 2013, vol. 40, No. 6, pp. 271-279.
Gilles et al., "Efficient CRISPR-mediated gene targeting and transgene replacement in the beetle Tribolium castaneum", Development, vol. 142, No. 16, 2015, pp. 2832-2839.
Li et al., "Gene replacements and insertions in rice by intron targeting using CRISPR-Cas9", Nature Plants, vol. 2, No. 10, 2016, Article No. 16139, 6 pages.
Zu et al., "TALEN-mediated precise genome modification by homologous recombination in zebrafish", Nature Methods, 2013, vol. 10, No. 4, pp. 329-331.
Kanchiswamy et al., "Non-GMO genetically edited crop plants", Trends in Biotechnology, 2015, vol. 33, No. 9, pp. 489-491.
Xu et al., "Cloning of genomic DAN of rice 5-enolpyruvishikimate 3-phsphate synthase gene and chromosomal localization of the gene", Science in China, 2002, vol. 45, No. 3, pp. 251-259.
Elhiti et al., 2011, "The use of zygotic embryos as explants for in vitro propagation: an overview", Plant Embryo Culture, Thrope et al. Eds., Mth Mol. Biol, Humana Press 229-55.
Doshi et al., "Anthocyanin expression in marker free transgenic wheat and triticale embryos", In Vitro Cell Dev. Biol. - Plant, 2007, vol. 43, pp. 429-435.
De Vetten et al., "A transformation method for obtaining marker-free plants of a cross-pollinating and vegetatively propagated crop", Nature Biotechnology, 2003, vol. 21, No. 4, pp. 439-442.
Pastori et al., "Age-dependent transformation frequency in elite wheat varieties", Journal of Experimental Botany, 2001 vol. 52, No. 357, pp. 857-863.
Hamada et al., "Biolistic-delivery-bsed transient CRISPR/Cas9 expression enables in planta genome editing in wheat", Scientific Reports, 2018, vol. 8, Article 14422, 7 pages.
Carroll, "Genome Engineering with Targetable Nucleases", Annu. Rev. Biochem., 2014, vol. 83, pp. 409-439.
Vasil et al., "Transformation of wheat via particle bombardment", Methods in Molecular Biology, 2006, vol. 318, pp. 273-283.

(56) References Cited

OTHER PUBLICATIONS

Zhang et al., "Efficient and transgene-free genome editing in wheat through transient expression CRISPR/Cas9 DNA or RNA", Nature Communications, 2016, vol. 7, Article 12617, 8 pages.
Nathalia Maira Cabral de Medeiros et al., "Recent Advances in Plant DNA Repair", Intech, 2015, pp. 3-42 (available at http://dx.doi.org/10.5772/59998).
Yoshiyama, "SOG1: a master regulator of the DNA damage response in plants", Genes & Genetic Systems, 2015, vol. 90, pp. 209-216.
Feng et al., "Efficient genome editing in plants using a CRISPR/Cas System", Cell Research, 2013, vol. 23, No. 10, pp. 1229-1232.
Woo et al., "DNA-free genome editing in plants with preassembled CRISPR-Cas9 ribonucleoproteins," Nature Biotechnology, vol. 33, No. 11, 2015, pp. 1162-1165.
Curtin et al., "Targeted Mutagenesis of Duplicated Genes in Soybean with Zinc-Finger Nucleases", Plant Physiology, 2011, vol. 156, No. 2, pp. 466-473.
Fang et al., "New Method of Genome Editing Derived from CRISPR/Cas9", Progress in Biochemistry and Biophysics, 2013, vol. 40, No. 8, pp. 691-702 and English Abstract Thereof.
International Search Report and Written Opinion issued in PCT/CN2016/076244, dated Jun. 15, 2016 and English Translation thereof, 22 pages.
Liang et al., "Targeted Mutagenesis in *Zea mays* Using TALENs and the CRISPR/Cas System", Journal of Genetics and Genomics, 2013, vol. 41, No. 2, pp. 63-68.
Xiao et al., "Progress in Zinc Finger Nuclease Engineering for Targeted Genome Modification", Hereditas, 2011, vol. 33, No. 7, pp. 665-683 and English Abstract Thereof.
Zhang et al., "TALENs: A New Genome Site-Specific Modification Technology", Chinese Bulletin of Life Sciences, 2013, vol. 25, No. 12, pp. 126-132 and English Abstract Thereof.
Armstrong et al., "Development and availability of germplasm with high Type II culture formation response", Maize Genet. Coop. News Lett., 1991, vol. 65, https://mnl.maizegdb.org/mn1/65/146armstrong.html. 3 pages.
Wang et al., "Simultaneous editing of three homoeoalleles in hexaploid bread wheat confers heritable resistance to powdery mildew", Nature Biotechnology, 2014, vol. 32, No. 9, pp. 947-952.
Weeks et al., "Rapid production of multiple independent lines of fertile transgenic wheat (Triticum aestivum)", Plant Physiol., 1993, vol. 102, pp. 1077-1084.
Chang et al., "Genome editing with RNA-guided Cas9 nuclease in Zebrafish embryos", Cell Research, 2013, vol. 23, No. 4, pp. 465-472.
Shan et al., "Rapid and Efficient Gene Modification in Rice and Brachypodium Using TALENs", Molecular Plant, 2013, vol. 6, No. 4, pp. 1365-1368.
Song et al., "Application of a transformation method via the pollen-tube pathway in agriculture molecular breeeding", Life Science Journal, 2007, vol. 4, No. 1, pp. 77-79.
Gasiunas et al., "Cas9-crRNA ribonucleoprotein complex mediates specific DNA cleavage for adaptive immunity in bacteria", Proc. Natl Acad Sci USA, 2012, vol. 109, No. 39, pp. E2579-E2586.
Wang et al., "One-step generation of mice carrying mutations in multiple genes by CRISPR/Cas-mediated genome engineering", Cell, 2013, vol. 153, No. 4, pp. 910-918.
Klein et al.,"Transformation of microbes, plants and animals by particle bombardment", Biotechnology, 1992, vol. 10, No. 3, pp. 286-291.
Barcelo et al., "Transgenic cereal (tritodeum) plants obtained at high efficiency by microprojectile bombardment of inflorescence tissue", The Plant Journal, 1994, vol. 5, No. 4, pp. 583-592.
Wang et al., "Cotton transformation via pollen tube pathway", Methods in Molecular Biology, 2013, vol. 958, pp. 71-77.
Dudas et al., "DNA double-strand break repair by homologous recombination", Mutation Research, 2004, vol. 566, No. 2, pp. 131-167.
Kim et al., "A guide to genome engineering with programmable nucleases", Nt. Rev. Genet, 2014, vol. 15, No. 5, pp. 321-334.
Vainstein et al., "Permanent genome modifications in plant cells by transient viral vectors", Trends In Biotechnology, 2011, vol. 29, No. 8, pp. 363-369.
Martin-Ortigosa et al., "Mesoporous silica nanoparticle-mediated intracellular cre protein delivery for maize genome editing via loxP site excision", Plant Physiology, 2014, vol. 164, No. 2, pp. 537-647.
Lee et al., "RNA-guided genome editing in Drosophila with the purified Cas9 protein", G3, 2014, vol. 4, No. 7, pp. 1291-1295.
Bassett et al., "Highly efficient targeted mutagenesis of Drosophila with the CRISPR/Cas9 system", Cell Reports, 2013, vol. 4, No. 1, pp. 220-228.
Fernando et al., "Transient gene expression in pine pollen tubes following particle bombardment", Plant Cell Reports, 2000, vol. 19, pp. 224-228.
Jiang et al., "Efficient CRISPR/Cas9-mediated gene editing in *Arabidopsis thaliana* and Inheritance of modified genes in the T2 and T3 generations", PloS one, 2014, vol. 9, Issue 6, pp. 1-10.
Shan et al., "Targeted genome modification of crop plants using a CRISPR-Cas System", Nature Biotechnology, vol. 31, No. 8. Aug. 1, 2013, pp. 686-688.
Shan et al., "Supplementary Material for Targeted genome modification of crop plants using a CRISPR-Cas system", Nature Biotechnology, vol. 31, No. 8, Aug. 1, 2013, 19 pages.
Zhang et al., "Transcription Activator-Like Effector Nucleases Enable Efficient Plant Genome Engineering", Plant Physiology, 2013, vol. 161, No. 1, pp. 20-27.
Kumar et al., "The CRISPR-Cas system for plant genome editing: advances and opportunities", Journal of Experimental Botany, 2015, vol. 66, No. 1, pp. 47-57.
Voytas et al., "Precision Genome Engineering and Agriculture: Opportunities and Regulatory Challenges", PLOS Biology, Jun. 2014, vol. 12, No. 6, e1001877, pp. 1-6.
Puchta et al., "Synthetic nucleases for genome engineering in plants prospects for a bright future", The Plant Journal, vol. 78, No. 5, 2014, pp. 727-741.
Marton et al., "Nontransgenic Genome Modification in Plant Cells", Plant Physiology, 2010, vol. 154, No. 3, pp. 1079-1087.
International Search Report and Written Opinion issued PCT/CN2016/071352, dated Apr. 25, 2016, 9 pages.
Ling et al., "Draft genome of the wheat A-genome progenitor Triticum urartu", Nature, 2013, vol. 496, pp. 87-90.
Shan et al., "Genome editing in rice and wheat using the CRISPR/Cas system", Nature Protocols, 2014, vol. 9, No. 10, pp. 2395-2410.
Mao et al., "Overexpression of a NAC-domain protein promotes shoot branching in rice", New Phytologist, 2007, vol. 176, pp. 288-298.
Xu et al., "A PIN1 Family Gene, OsPIN1, involved in Auxin-dependent Adventitious Root Emergence and Tillering in Rice", Plant Cell Physiol., 2005, vol. 46, No. 10, pp. 1674-1681.
Feng et al., "Molecular analysis of lipoxygenase (LOX) genes in common wheat and phylogenetic investigation of LOX proteins from model and crop plants", Journal of Cereal Science, 2010, vol. 52, pp. 387-394.
Lawrenson et al., "Induction of targeted, heritable mutations in barley and Brassica oleracea using RNA-guided Cas9 nuclease", Genome Biology, 2015, vol. 16, 258, 13 pages.
Zhang et al., "Biolistic Genetic Transformation of a Wide Range of Chinese Elite Wheat (*Triticum aestivum* L.) Varieties", Journal of Genetics and Genomics, 2015, vol. 42, pp. 39-42.
Larsen et al., "ALS3 encodes a phloem-localized ABC transporter-like protein that is required for aluminum tolerance in *Arabidopsis*", The Plant Journal, 2005, vol. 41, No. 3, pp. 353-363.
Laursen et al., "Production of fertile transgenic maize by electroporation of suspension culture cells", Plant Molecular Biology, 1994, vol. 24, No. 1, pp. 51-61.
Aragao et al., "Particle bombardment-mediated transient expression of a Brazil nut methionine-rich albumin in bean (*Phaseolus vulgaris* L.)", Plant Molecular Biology, 1992, vol. 20, No. 2, pp. 357-359.
Brooks et al., "Efficient Gene Editing in Tomato in the First Generation Using the Clustered Regularly Interspaced Short Palindromic Repeats/CRISPR-Associated9 System", Plant Physiology, 2014, vol. 166, pp. 1292-1297.

(56) References Cited

OTHER PUBLICATIONS

International Search Report Issued In PCT/CN2016/072352 mailed on Apr. 27, 2016 and English Translation thereof 10 pages.

* cited by examiner

Figure 3
Figure 3 (B)
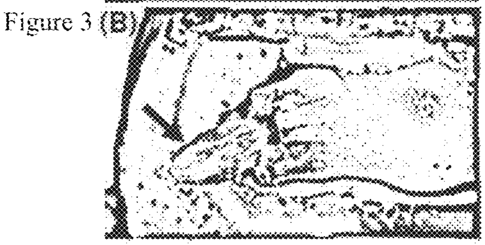
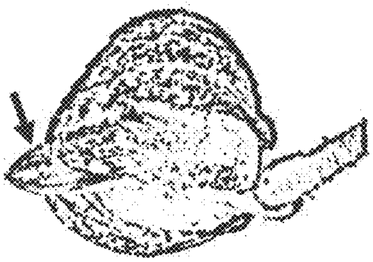
Figure 3A
Figure 3D
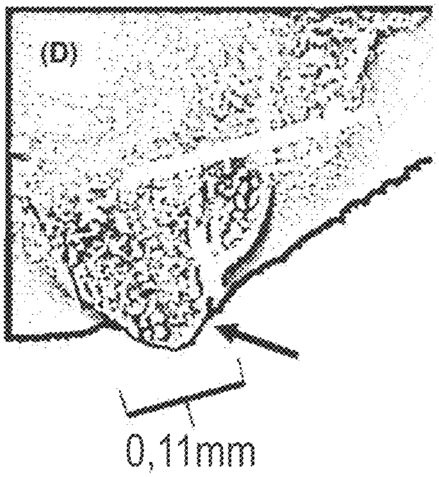

Column:

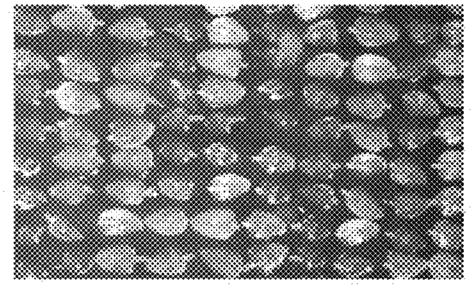
Figure 25A
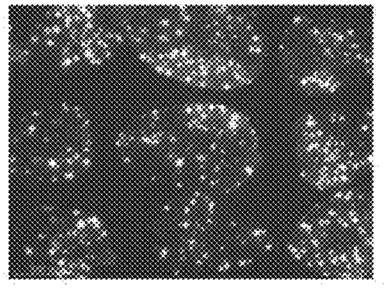
Figure 25B
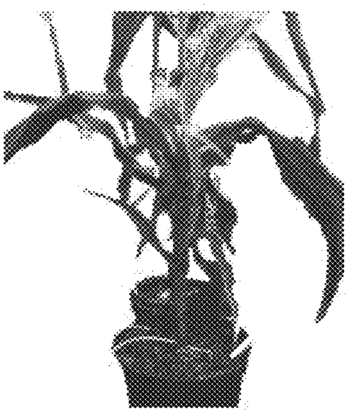
Figure 25C
Figure 26
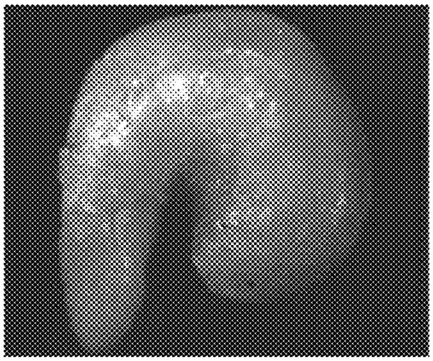

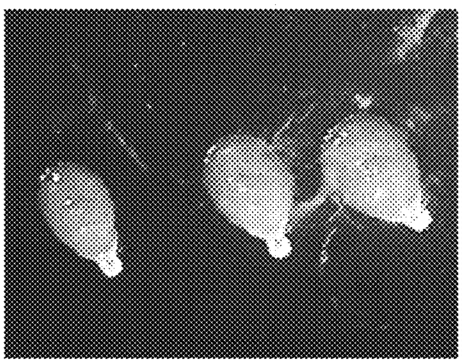
Figure 27A
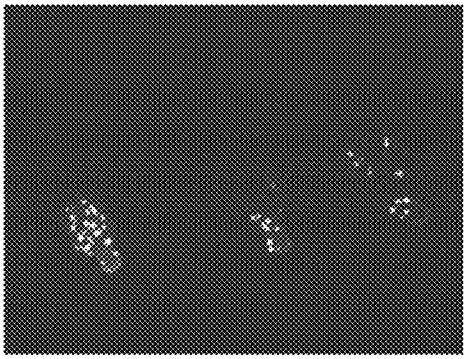
Figure 27B
Figure 28
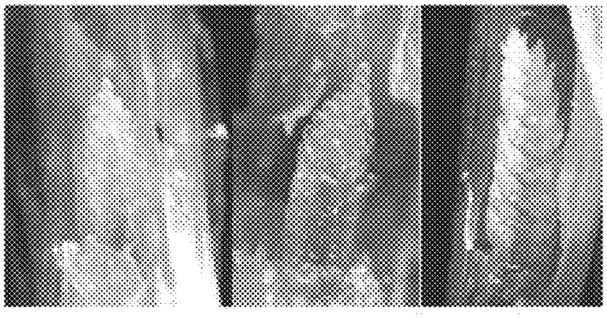

SEQUENCE LISTING

```
Sequence total quantity: 62
SEQ ID NO: 1            moltype = DNA  length = 259
FEATURE                 Location/Qualifiers
source                  1..259
                        mol_type = other DNA
                        organism = synthetic construct
                        note = VP16 activator comprising sequence
SEQUENCE: 1
ctaagctttc gacggccccc ccgaccgacg tcagcctggg ggacgagctc cacttagacg  60
gcgaggacgt ggcgatggcg catgccgacg cgctagacga tttcgatctg gacatgttgg  120
gggacgggga ttccccgggg ccgggattta ccccccacga ctccgccccc tacggcgctc  180
tggatacggc cgacttcgag tttgagcaga tgtttaccga tgcccttgga attgacgagt  240
acggtgggta gagatcttc                                               259

SEQ ID NO: 2            moltype = AA  length = 11
FEATURE                 Location/Qualifiers
source                  1..11
                        mol_type = protein
                        organism = synthetic construct
                        note = VP16 activator
SEQUENCE: 2
DALDDFDLDM L                                                       11

SEQ ID NO: 3            moltype = AA  length = 50
FEATURE                 Location/Qualifiers
source                  1..50
                        mol_type = protein
                        organism = synthetic construct
                        note = VP64 activator with glycine serine spacers
SEQUENCE: 3
DALDDFDLDM LGSDALDDFD LDMLGSDALD DFDLDMLGSD ALDDFDLDML             50

SEQ ID NO: 4            moltype = DNA  length = 615
FEATURE                 Location/Qualifiers
source                  1..615
                        mol_type = genomic DNA
                        organism = Arabidopsis thaliana
misc_feature            1..615
                        note = EAR 1 repressor
SEQUENCE: 4
```

```
atggagagat caaacagcat agagttgagg aacagcttct atggccgtgc aagaacttca  60
ccatggagct atggagatta tgataattgc caacaggatc atgattatct tctagggttt  120
tcatggccac caagatccta cacttgcagc ttctgcaaaa gggaattcag atcggctcaa  180
gcacttggtg gccacatgaa tgttcacaga agagacagag caagactcag attacaacag  240
tctccatcat catcttcaac accttctcct ccttacccta accctaatta ctcttactca  300
accatggcaa actctcctcc tcctcatcat tctcctctaa ccctatttcc aaccctttct  360
cctccatcct caccaagata tagggcaggt ttgatccgtt ccttgagccc caagtcaaaa  420
catacaccag aaaacgcttg taagactaag aaatcatctc ttttagtgga ggctggagag  480
gctacaaggt tcaccagtaa agatgcttgc aagatcctga ggaatgatga aatcatcagc  540
ttggagcttg agattggttt gattaacgaa tcagagcaag atctggatct agaactccgt  600
ttgggtttcg cttaa                                                   615

SEQ ID NO: 5            moltype = DNA  length = 972
FEATURE                 Location/Qualifiers
source                  1..972
                        mol_type = genomic DNA
                        organism = Petroselinum crispum
misc_feature            1..972
                        note = Parsley_Ubi4
SEQUENCE: 5
aaaaattacg gatatgaata taggcatatc cgtatccgaa ttatccgttt gacagctagc  60
aacgattgta caattgcttc tttaaaaaag gaagaaagaa agaaagaaaa gaatcaacat  120
cagcgttaac aaacggcccc gttacggccc aaacggtcat atagagtaac ggcgttaagc  180
gttgaaagac tcctatcgaa atacgtaacc gcaaacgtgt catagtcaga tcccctcttc  240
cttcaccgcc tcaaacacaa aaataatctt ctacagccta tatatacaac ccccccttct  300
atctctcctt tctcacaatt catcatcttt ctttctctac ccccaatttt aagaaatcct  360
ctcttctcct cttcatttc aaggtaaatc tctctctctc tctctctctc tgttattcct  420
tgttttaatt aggtatgtat tattgctagt ttgttaatct gcttatctta tgtatgcctt  480
atgtgaatat ctttatcttg ttcatctcat ccgtttagaa gctataaatt tgttgatttg  540
actgtgtatc tacacgtggt tatgtttata tctaatcaga tatgaatttc ttcatattgt  600
tgcgtttgtg tgtaccaatc cgaaatcgtt gattttttc atttaatcgt gtagctaatt  660
gtacgtatac atatggatct acgtatcaat tgttcatctg tttgtgtttg tatgtataca  720
gatctgaaaa catcacttct ctcatctgat tgtgttgtta catacataga tatagatctg  780
ttatatcatt ttttttatta attgtgtata tatatatgtg catagatctg gattacatga  840
ttgtgattat ttacatgatt ttgttattta cgtatgtata tatgtagatc tggacttttt  900
ggagttgttg acttgattgt atttgtgtgt gtatatgtgt gttctgatct tgatatgtta  960
tgtatgtgca gc                                                      972

SEQ ID NO: 6            moltype = DNA  length = 384
FEATURE                 Location/Qualifiers
source                  1..384
                        mol_type = genomic DNA
                        organism = Arabidopsis thaliana
misc_feature            1..384
                        note = Arabidopsis_U6
SEQUENCE: 6
ctttttttct tcttcttcgt tcatacagtt ttttttgtt tatcagctta catttcttg  60
aaccgtagct ttcgttttct tctttttaac tttccattcg gagtttttgt atcttgtttc  120
atagtttgtc ccaggattag aatgattagg catcgaacct tcaagaattt gattgaataa  180
aacatcttca ttcttaagat atgaagataa tcttcaaaag gcccctggga atctgaaaga  240
agagaagcag gcccatttat atgggaaaga acaatagtat ttcttatata ggcccattta  300
agttgaaaac aatcttcaaa agtcccacat cgcttagata agaaaacgaa gctgagttta  360
tatacagcta gagtcgaagt agtg                                         384

SEQ ID NO: 7            moltype = DNA  length = 1502
FEATURE                 Location/Qualifiers
source                  1..1502
                        mol_type = genomic DNA
                        organism = Zea sp.
misc_feature            1..1502
                        note = Maize_Ubi_Intron
SEQUENCE: 7
tgcagcgtga cccggtcgtg cccctctcta gagataatga gcattgcatg tctaagttat  60
aaaaaattac cacatatttt ttttgtcaca cttgtttgaa gtgcagttta tctatcttta  120
tacatatatt taaactttac tctacgaata atataatcta tagtactaca ataatatcag  180
tgttttagag aatcatataa atgaacagtt agacatggtc taaaggacaa ttgagtattt  240
tgacaacagg actctacagt tttatctttt tagtgtgcat gtgttctcct ttttttttgc  300
aaatagcttc acctatataa tacttcatcc attttattag tacatccatt tagggtttag  360
ggttaatggt ttttatagac taattttttt agtacatcta ttttattcta ttttagcctc  420
taaattaaga aaactaaaac tctattttag tttttttatt taataattta gatataaaat  480
agaataaaat aaagtgacta aaaattaaac aaataccctt taagaaatta aaaaaactaa  540
ggaaacattt ttcttgtttc gagtagataa tgccagcctg ttaaacgccg tcgatcgacg  600
agtctaacgg acaccaacca gcgaaccagc agcgtcgcgt cgggccaagc gaagcagacg  660
gcacggcatc tctgtcgctg cctctggacc cctctcgaga gttccgctcc accgttggac  720
ttgctccgct gtcggcatcc agaaattgcg tggcggagcg gcagacgtga gccggcacgg  780
caggcggcct cctcctcctc tcacggcacc ggcagctacg gggattcct ttcccaccgc  840
tccttcgctt tcccttcctc gcccgccgta ataaatagac acccccctcca caccctcttt  900
ccccaacctc gtgttgttcg gagcgcacac acacacaacc agatctcccc caaatccacc  960
cgtcggcacc tccgcttcaa ggtacgccgc tcgtcctccc cccccccccc tctctacctt  1020
```

-continued

```
ctctagatcg gcgttccggt ccatggttag ggcccggtag ttctacttct gttcatgttt  1080
gtgttagatc cgtgtttgtg ttagatccgt gctgctagcg ttcgtacacg gatgcgacct  1140
gtacgtcaga cacgttctga ttgctaactt gccagtgttt ctctttgggg aatcctggga  1200
tggctctagc cgttccgcag acgggatcga tctaggatag gtatacatgt tgatgtgggt  1260
tttactgatg catatacatg atggcatatg cagcatctat tcatatgctc taaccttgag  1320
tacctatcta ttataataaa caagtatgtt ttataattat tttgatcttg atatacttgg  1380
atgatggcat atgcagcagc tatatgtgga ttttttagc cctgccttca tacgctattt  1440
atttgcttgg tactgtttct tttgtcgatg ctcaccctgt tgtttggtgt tacttctgca  1500
gg                                                                 1502

SEQ ID NO: 8           moltype = DNA  length = 360
FEATURE                Location/Qualifiers
source                 1..360
                       mol_type = genomic DNA
                       organism = Triticum sp.
misc_feature           1..360
                       note = U6
SEQUENCE: 8
gaccaagccc gttattctga cagttctggt gctcaacaca tttatattta tcaaggagca  60
cattgttact cactgctagg agggaatcga actaggaata ttgatcagag gaactacgag  120
agagctgaag ataactgccc tctagctctc actgatctgg gcgcatagtg agatgcagcc  180
cacgtgagtt cagcaacggt ctagcgctgg gcttttaggc ccgcatgatc gggctttgtc  240
gggtggtcga cgtgttcacg attggggaga gcaacgcagc agttcctctt agtttagtcc  300
cacctcgcct gtccagcaga gttctgaccg gtttataaac tcgcttgctg catcagactt  360

SEQ ID NO: 9           moltype = DNA  length = 377
FEATURE                Location/Qualifiers
source                 1..377
                       mol_type = genomic DNA
                       organism = Oryza sp.
misc_feature           1..377
                       note = U3
SEQUENCE: 9
aaggaatctt taaacatacg aacagatcac ttaaagttct tctgaagcaa cttaaagtta  60
tcaggcatgc atggatcttg gaggaatcag atgtgcagtc agggaccata gcacaagaca  120
ggcgtcttct actggtgcta ccagcaaatg ctggaagccg ggaacactgg gtacgttgga  180
aaccacgtga tgtggagtaa gataaactgt aggagaaaag catttcgtag tgggccatga  240
agcctttcag gacatgtatt gcagtatggg ccggcccatt acgcaattgg acgacaacaa  300
agactagtat tagtaccacc tcggctatcc acatagatca aagctggttt aaaagagttg  360
tgcagatgat ccgtggc                                                 377

SEQ ID NO: 10          moltype = DNA  length = 763
FEATURE                Location/Qualifiers
source                 1..763
                       mol_type = genomic DNA
                       organism = Zea sp.
misc_feature           1..763
                       note = U3
SEQUENCE: 10
gaattccatc taagtatctt ggtaaagcat ggattaattt ggatgcccac ttcaggtcta  60
tgcagctccg gtgccttgtg attgtgagtt gtgaccgatg ctcatgctat tctgcatttc  120
tgcgatgtat gtagctagta gatcttcaaa actaacaccg catgccatca tcatccactg  180
cttgatttta gtctcaccgc tggccaaaaa tgtgatgatg ccagaaacct caactacctt  240
gaatcaacac gggcccaaca gtgtgatgac gacagaaaca aaaaaaaatg agccaatagt  300
tcagaaggag gcactatgca gaaactacat ttctgaaggt gactaaaagg tgagcgtaga  360
gtgtaattac tagtagttta gccaccatta cccaaatgct ttcgagcttg tattaagatt  420
tcctaagctg agcatcatca ctgatctgca ggccaccctc gcttcgctgc caagatcaac  480
agcaaccatg tggcggcaac atccagcatt gcacatgggc taaagattga gctttgtgcc  540
tcgtctaggg atcagctgag gttatcagtc tttccttttt ttcatccagg tgaggcatca  600
agctactact gcctcgattg gctggacccg aagcccacat gtaggatacc agaatgggcc  660
gacccaggac gcagtatgtt ggccagtccc accggttagt gccatctcgg ttgctcacat  720
gcgtagaagc cagcttaaaa atttagcttt ggtgactcac agc                    763

SEQ ID NO: 11          moltype = DNA  length = 1880
FEATURE                Location/Qualifiers
source                 1..1880
                       mol_type = genomic DNA
                       organism = Brachypodium sp.
misc_feature           1..1880
                       note = EF1
SEQUENCE: 11
cttcaccgcc attgcaaaaa ttgtcaataa atatttagag tgggtggcat cagaaaaaca  60
tctctagtgg actctcttcc tatcatagct actcgggctg tagatagaac gagggcacaa  120
gagttgggtg gcgtaggttt actcgtgacc tcaactcttt tggctgtgtc ttacgtctaa  180
gatgggtttg gcatgtgaga aacataggtc taagcaattc atgttagggc tgttgcattg  240
ttgttgcatc aaccaaatgt ccagatagca gttcatgcta catctagttg aaaaccctca  300
tcattaggcg gaacatgtgt tctttttttag catagtcaaa gtcagattgc ggcactcgct  360
catccacgga aagaatttc cctgtgcagg catctcgatc aaaagacgca aattaatttt  420
tgaatagcga tataacaata tctaattaac gtttcttgtt ttctgcgaaa tgtctttcat  480
```

```
cataaaatga gtcatctcga tgagcccaag tgacatagcc caacacccca ccccaccaat  540
aaaagtgaag aaaacatgtt gggaaaacta taccaagtaa aatacgagtt gttctaaaga  600
aaaagtaaag tacgagttag atcgcaccct gtcctggagt gtggcttgat gatccaactc  660
ctagcattgt atccctgttt ttggatgatg taactattat ttacaatgaa taaagaggtg  720
ttttactagt aaaaaaatct tgaggggagg agaaaataat ggaggtcttt tttcaaaccg  780
atggactatt atttttagtg aaagagaata atattattgg aaaaattatt ctatccactt  840
attttatatt ggcagaatac aaagaatggt ggggtccacg cggaacttgc ggcccccgaa  900
acctatcgag ggcgcggtac ccaagcaagg aacggaggaa acttgcgggg cccgaaacct  960
agtgataaaa ggcatatcat ccacacgatg aagatctgac ggaccatatc tcccaccacg  1020
gaaagccatc agacgaggat cagacggcca ggaaggaacc ctagcgcccg ccggtgccaa  1080
tataaagcgc cactctctct cgtcttaagc cccagcctct ccattcccct ctccctctcg  1140
ccgccgccgt ctccttctcc tactcccttc gaggtgtgtt gttcatccgt cccgaatcca  1200
tccatcccct cttcagatgt gttgttcatg gctctaatag ctctagatct gcttgtttgt  1260
gttgtttagc tctagatcta ctcgcgcgcg cttctctctc gatctcctgt agaacaattt  1320
tggttggttt tttgtgcata tccatggtaa ttttgtctgc aatatggagg aggctttcta  1380
agctcctacg tagcatcgat ctttagaatt ccctcggttt ctgtttattt cttcgcgagg  1440
gctctctgtt atctgtagga gtagctgtaa gcgcggttcg ttacggatta atcgtcatgc  1500
ttagttgaac ctatcggtcg aaggatttgt gtgggttgtc gtgtagaatt gacaccatct  1560
acttactgta ctgatatgcc gatctgtagg atactcttca ttacttttgt ttactgctag  1620
ttgtggtgta gatttagcat tctcaaaccc atgctgtagc gtttctaata ttgttacata  1680
gatctaccgg tgcctgttaa ttgtattcga tcgggcgttt ctacatctgt ccgcccacct  1740
agttttatat gtggtaatca aaattgcgtt gacttcgtga tgctgtctgt gtactgtttt  1800
taatcgctct tacttagatg atcaacatgg tgatggttac gatttactgt tttctaatcc  1860
ctgttacttc gatgctgcag                                              1880
```

```
SEQ ID NO: 12          moltype = DNA  length = 2690
FEATURE                Location/Qualifiers
source                 1..2690
                       mol_type = genomic DNA
                       organism = Maize streak virus
                       note = Maize Streak Virus (MSV) South African Strain
SEQUENCE: 12
atggatccac agaacgccct gtattatcag ccgcgggtac ccactgcagc tccgacatcc  60
ggaggagtgc cgtggagtcg cgtaggcgag gtagctattt tgagctttgt tgcattgatt  120
tgcttttacc tgctttacct ttgggtgctg agagacctta tcttagttct gaaggctcga  180
caaggcagat ccacggagga gctgatattt ggtggacaag ctgtggatag gagcaaccct  240
atccctaatc taccagcacc accaagtcag ggcaatcccg ggccatttgt tccaggcacg  300
ggataagcaa tcagccatgt ccacgtccaa gaggaagcgg ggagatgatg cgaattggag  360
taagcgggtg cctaagaaga agccttcttc agctgggctg aagagggctg gaagcaaggc  420
cgataggcca tccctccaaa tccagacact ccagcatgct gggaccacca tgataactgt  480
cccatccgga ggagtatgtg acctcatcaa cacctatgcc cgaggatctg acgagggcaa  540
ccgccacacc agcgagactc tgacgtacaa gatcgccgtc gactaccact tcgttgccga  600
cgcggctgcc tgccgctact ccaacaccgg aaccggtgta atgtggctgg tgtatgacac  660
cactcccggc ggacaagctc cgacccccgca aactatattt gcctaccctg acacgctaaa  720
agcgtggccg gccacatgga aagtgagccg ggagctgtgt catcgcttcg tggtgaaacg  780
gcgatggttg ttcaacatgg agaccgacgg tcggattggt tcggatatcc ctccctcgaa  840
tacaagttgg aagccttgca agcgcaacat ctacttccac aagttcacga gtgggttggg  900
agtgagaacg cagtggaaga atgtaacgga cggaggagtt ggtgccatcc agagaggagc  960
tttgtacatg gtcattgccc ccggcaatgg ccttacattt actgcccatg ggcagacccg  1020
cctgtacttt aagagtgttg gcaaccagta atgaataaaa acgcccgttt tattatatct  1080
gatgaatgct gaaagcttac attaatatgt cgtgcgatgg cacgaaaaaa cacacgcaat  1140
caatacaggg gggtagtcgg cgggcggcta agggtggtgc tcggcgggca aaacatcgaa  1200
aaatcaagat ctatatgaat tacacttcct ccgtaggagg aagcacaggg ggagaatacc  1260
acttctcccc cggcgacata atgtaaatga tgcagtttgc ctcgaaatac tccagctgcc  1320
ctggagtcat ttccttcatc caatcttcat ccgagttggc gaggattatt gtaggcttag  1380
acttcttctg caccttttc ttcttaccat acttggggtt tacaatgaaa tccctctgac  1440
agccaactaa ctgtttccaa caaggacaga atttaaacgg aatatcatct acgatgttgt  1500
agattgcgtc ttcgttgtat gaagaccaat caacattatt ttgccagtaa ttatgaaccc  1560
ctaggcttct ggcccaagta gattttccgg ttcttgttgg gccgacgatg tagaggctct  1620
gctttcttga tctttcatct gatgactgga tacagaatcc atccattgga ggtcagagat  1680
tgcatcctcg agggtataac aggtaggttg aaggagcatg taagcttcgg gactaacctg  1740
gaagatgtta ggctggagcc aatcattgat tgactcatta caaagtaaat caggtgagga  1800
gggtggatga ggattggtga actcttcctg aatctcagga aaaagcttat ttgcagagta  1860
ttcaaaatac tgcaatttg tggaccaatc aaagggaagc tctttctgga tcatggagag  1920
gtactctgct ttggaagtag cgtgtgaaat aatgtctcgc attatttcat ctttagaagg  1980
cttttttcc tttacctctg aatcagattt tcctaggaag gggacttcc taggaatgaa  2040
agtacctctc tcaaacacag ccagaggttc cttgagaatg taatccctca ctctgttaac  2100
tgacttggca ctctgaatat ttgggtgaaa cccatttata tcaaagaacc ttgagtcaga  2160
tatccttacc ggcttctctg tctgaagcaa tgcatgtaaa tgcaaacttc catctttatg  2220
tgcctctcgg gcacatagaa tatacttggg aatccaacga acgacgagct cccagatcat  2280
ctgacaggcg atttcaggat tttctggaca ctttggatag gttaggaacg tgttagcgtt  2340
cctgtgtgag aactgacggt tggatgagga ggaggccata gcagacgacg gaggctgagg  2400
ctgagggatg gcagactggg agctccaaac tctatagtat acccgtgcgc cttcgaaatc  2460
cgccgctccc ttgtcttata gtggttgtaa atgggccgga ccggtccggc ccagcaggaa  2520
aagaaggcgc gcactaatat taccgcgcct tcttttcctg cgagggcccg gtagggaccg  2580
agcgctttga tttaaagcct ggttctgctt tgtatgattt atctaaagca gcccaatcta  2640
aagaaaccgg tcccgggcac tataaattgc ctaacaagtg cgattcattc            2690
```

```
SEQ ID NO: 13          moltype = DNA  length = 6337
```

```
FEATURE                Location/Qualifiers
source                 1..6337
                       mol_type = genomic DNA
                       organism = Maize rayado fino virus
                       note = Maize rayado fino virus (MYDV)
SEQUENCE: 13
gtcctctgcc cccttcttgc gcccgatcgc cgcaagtcgc attctgcacc agctctcgct  60
cgtccagaaa cagatcaatc tttcggcctc ttttcttgca ctcttcttcg ttgcacctct  120
ctagatgtct agtttcctgc gtggtggcca tctcctcagc ggagtcgagt ccctcacacc  180
aaccactcac cgcgacacca tcactgcacc catcgttgag tcccttgcca cccccccttcg  240
ccgatccctc gaacgctacc cttggtccat cccaaaggag ttccattcgt tcctccatac  300
ctgtggcgtc gacatctccg gcttcggcca tgccgctcat ccccaccctg tccacaagac  360
catcgagacc cacctccttc tcgatgtctg gcccaattac gcccggggct tgtctgatgt  420
catgttcatc aagcccgaga agttcgccaa gctccagtcc cgacagccca atttcgccca  480
cctcatcaac taccggctcg tgcctaaaga caccacccgg tacccttcca cttccacgaa  540
tctcccggac tgcgagaccg tcttcatgca tgatgcgctc atgtactaca ccccagggca  600
gatcgctgac ctcttcttcc tttgccccca gctccagaag atctacgcct cgctggtcgt  660
ccctgcagag tcgagtttca cgcatctctc gctccatccg gaactttacc gcttccgttt  720
ccagggttct gaccttgtct acgagccgga gggcaaccct gccgccaact acacgcagcc  780
gcgttcggcc ctcgactggc tccagaccac cggcttcacc gtcggtcacg aattcttctc  840
cgtcacactt ctcgactctt tcggcccggt ccattccctc ctcatccagc gtggccgccc  900
ccctgtcttt caggccgaag acgtcgcttc cttccgcgtc ccggacgccg tcgccctccc  960
tgctcctgcc tccctccacc aggacctgcg tcaccgactg gtcccccgca aggtgtacga  1020
cgcactcttc aactacgtcc gagccgtccg caccccttcgg gtcacagacc ccgctggttt  1080
cgtccggacc caggtcggta agcctgagta cagttgggtc acctcttccg cctgggacaa  1140
tctccagcac ttcgcgctcc agactgccgc cgttcgtccc aacacctcgc atcccctctt  1200
tcagtcgccc ttcgcccgtt tgtcccattg gctccgcacc cacacttggg cgctctggtg  1260
catggcttcc ccctcggcct ctgtctccgc ttgggccgct gccagcgctc ttggccggct  1320
cctcccgctt cacaccgacc gtctcaggtt gttcggcttc gacatcgttg ggcggagatt  1380
ctggcctcgt ctcccattcc atggccccga gccaaggttc ctttgggaga cccatccagc  1440
ctgccgcccg ccagtgctct tcgccgactc ggcctttgag tgccaaatcc ttgctggttt  1500
ggcaaaccgg tgttctccct cccccttctg gtcgcgcttg ttccccacgg cctctccgcc  1560
gcactgggtc gcctattcag ccttggccct agctgcagtg ccacttgctg cgttagcgtt  1620
gcgctggttt tacggcccgg attctcccca ggctcttcat gatcagtacc acgccacctt  1680
ccatcccgac ccgtggactc ttgacctccc ccgccggctt cgccgcttcg agcgcgagcc  1740
cttcatgcgg acgggttccg caccttcgcc tcagtcgctc cctccttctg gaggctctct  1800
tcttcctgtc gagcctcctc ttgcttcgag cgagcccgag cctgcccttg agccgccatc  1860
ccccgcggcc ccggtcccga ctccttctcc agctccagtt ccagagcctc ctccttctcc  1920
cgagtcagtc gcccctccag tcgccgtcgc ctcgcccgcc gtgcaacctg ttcgggctcc  1980
gtccccctct ccagcgcttt tgggcgccga gcttcgtttc ggggatcttc ctcctgtctc  2040
tgcttgggac agtgaccccg agatttcgaa gcttggtgag tccacccaag gcaccgtttt  2100
tgctgtcacc cccggccctc gcgctcctga gccagacact gcccgcttag acgctgatcc  2160
ttcggctagc ggccccgtta tggagttccg cgagcttcag aagggcgctt acatcgagcc  2220
gactggcgct ttcctcaccc gggctcgcaa ctcggtgtcc tccagcatcc cttatcctgc  2280
gagggcggct tgtcttctcg tggccgtcag tcaagcaaca gggctcccca cccgcactct  2340
ctgggctgcc ctctgtgcta atcttccgga ttccgttctt gacgacggct cgctcgccac  2400
cttgggcctc accaccgacc acttcgccgt cctcgcccgc atcttctcct tgaggtgccg  2460
cttcgtgagt gagcatggcg atgttgagct cgggctccac gacgccacct ctcgctttac  2520
gatccgccac acccccggcc acttcgagct cgtggccgac aacttctccc ttcccgctct  2580
cgtcggcgcc tcttctgttc caggctccga cctagccgaa gcgtgcaagc gtttcgtggc  2640
tccggaccgc accgttcttc cattccggga cgtccacatc catcgcaccg acgtccgccg  2700
tgccaaaaac ctcatttcca acatgaagaa cggcttcgac ggtgtcatgg cgcaggccaa  2760
tcctctggat ccgaagagtg cccgagagcg gttcctcatg ctcgactcct gcctcgacat  2820
tgccgcgcct cgccgggtcc gtcttatcca catagcgggc ttcgctggtt gcgggaaatc  2880
ctggccgatc tcccatctgc tccgtacccc cgccttccgt gttttcaagc tcgccgttcc  2940
aaccaccgag cttcgcgacg agtggaaggc cctcatggat cctcgcgacc aggacaagtg  3000
gcgcttcggc acctgggagt cctctctcct caagactgcc cgcgtccttg tcattgatga  3060
ggtgtacaag atgcctcgcg ggtaccttga tctggccatc catgcggacg ccgccattca  3120
gttcgtgatt ttgctcggcg atccaattca aggcgagtac cattccacac atcccagctc  3180
ctccaatgcc cgcctttctc ccgagcatcg gtatctccgc ccgtatgtgg acttctactg  3240
cttctggagt cgtcgcatcc ctcggaacgt ggcccgcgcc ctcgatgtgc ccacgacctc  3300
gaccgagatg ggttttgctc gctactcgca gcagttccca ttctccggga agatcctcat  3360
ctcggcgcgc gactccgcca agagcttggc tgactgtggt tatcatgctg tcaccatagc  3420
tagcagccaa gggtccacta ttgccggccc agcttatgtc cacctcgaca atcattcgag  3480
gcgcctctca catcaacatt cgcttgtcgc catcactcga tccaagtccg gcatagtatt  3540
cactggcgac aaggctgcag cggatggcac ctcctctgct aatctccttt tctccgctgt  3600
gctcctcgac cgacgcctct cggtgcgctc tctcttcagc gcgctcctgc cttgctgtcc  3660
gtttgtcacg gagcctccaa cgtctcgagc cgttctcctt cgcggagccg gctacggcgt  3720
cgctcggccc cttcgcgctc gtgacgcccc tcctctcggc cccgatttcg tcggagatgt  3780
tattctggac tcctccgccc cgattcttgg cgacggatcg gccaacgctc cccaggtcag  3840
cactcacttt cttccagaga cgcgtcggcc tttgcacttc gacatccctt ccgcccgcca  3900
tcaagtggcc gatcatcctc tcgcgcccga tcactccgcc tgcgctatcg agcccgtgta  3960
ccctggcgag agcttcgaat ctctggcctc tcttttcctc cccccctacgg atgccgagag  4020
caaggagact tacttccgag gggagatgtc gaatcaattc cctcatctcg acaagccgtt  4080
cgagttaggt gcgcagacgt cgagcctcct cgcgccactc cacaactcca aacatgatcc  4140
cacgcttctc ccggcttcca tcggtaagag actgcgcttc cgtcactcag aggctcccta  4200
cgtcatcgct cctcgcgacg agatcttggg gtcactcctc tatgaggcct ggtgtcgagc  4260
ctatcgccgt tctcctcggg acgtcgagcc gttcgaccca gacctctacg ctgagtgcat  4320
taacctcaac gagttcgcgc agctctcctc caagacccag gcgactatca tggccaacgc  4380
```

```
caaccgcagc gacccagact ggcgctggtc cgccgttcgc attttcgcca agacgcagca  4440
taaggtcaac gagggctcgc ttttcggctc ctggaaagct tgccagaccc tcgcgcttat  4500
gcacgacgcc gtcgttttgc tccttggccc cgtcaagaag tatcaacgct tcttcgacca  4560
gcgcgatcgg ccttccactc tttacgtcca tgcgggccac accccccttcg agatggctga  4620
ctggtgccgc gcccatttga cccccgcggt caagctggcc aatgactaca ccgcctttga  4680
ccagtcacag cacggcgagg ctgttgtctt cgagcgctac aagatgaatc gtctctcaat  4740
tcctgccgag ctcgtggact tgcacgtcta tctgaagacc aatgtctcca cccagtttgg  4800
cccgttgacg tgcatgcgcc tcactggtga gcccggcacc tacgacgaca acaccgacta  4860
caacatcgcc gtgctccatc tcgagtacgc tgtcggctct actccgctca tggtctctgg  4920
tgatgactcg ctgctcgact ccgagcctcc tgtccgtgac cagtggtccg ccatcgctcc  4980
catgctcgct ctcaccttca agaaggagcg cggccgttat gccacttttt gcggctatta  5040
cgtcggcttc accggcgcgg tccgatcgcc tccggccctt tttgcgaagc ttatgattgc  5100
ggttgacgac ggatccatct ccgacaagct catcgcctat ctcacggagt tcaccgttgg  5160
tcattcttcc ggcgatgctt tctggaccat cctcccagtc gaagctgttc cttaccagag  5220
cgcctgcttt gacttcttct gccgtcgagc tccggcgcaa gccaaagtga tgttgcggct  5280
tggcgaggcc ccagagtctc ttctttccct ggcgttcgag ggtctgaagt gggcttccca  5340
ctcggtgtac gcccttatga attccagtca ccgacgccag ttgcttcata gctcccgccg  5400
ccctcgctct ctccccgagg accccgaagt gtcgcagctt cagggtgaat tgcttcatca  5460
gttccaatcg cttcacctcc cgcttcgtgg tggcctcatg ccaaatccgc tcgctgcgcc  5520
cttcaggctc cttcagcaaa gcagctccct tggtcccact tacgcagtcg cccccatcgc  5580
tcgcgctccc caggtccctc tgccctctat ggccgacaat gccacccaag tcgggcctgt  5640
tcctcctcgc gacgaccgcg ttgatcgcca gcctcctctt cctgatcctc ctcgtgtgct  5700
cgagacgacc ccgtcgcact tcctcgacct ccctttccaa tggaaggtca cggacttcac  5760
aggatacgcc gcctaccacg gaaccgacga cctgtccgcc tccgcggtac tgaccacgct  5820
ctgtgctccg taccgccacg ccgagctcct ctatgtcgag atctccgtcg ctccgtgtcc  5880
cccgtcgttc tccaagccca tcatgttcac cgtcgtctgg acaccggcca ccctgtcccc  5940
cgctgacggc aaggagaccg actactacgg gggccgtcag atcactgtgg gcgggcctgt  6000
cctgttgtcc agcaccaccg ccgtacccgc agacctggcc cgcatgaacc ccttcatcaa  6060
gtccagcgtc tcctacaatg acacgccccg ctggaccatg tctgtccccc ccgtcaccgg  6120
tggggacacc aagatcccgc tcgccactgc cttcgttcgc gggatcgtcc gcgtgtcagc  6180
cccctctggg actgccaccc cctctgcctg atccatcaag gcagcaataa tgcgagaagg  6240
aaaactcgcc cagccttgag ctggtaagct gttaaacctc cgcccatcca tgtttgcaaa  6300
atctaaggta gcaggtcggc cataagacct gtgggcc                          6337

SEQ ID NO: 14          moltype = DNA  length = 5612
FEATURE                Location/Qualifiers
source                 1..5612
                       mol_type = genomic DNA
                       organism = Maize yellow dwarf virus RMV
                       note = Maize yellow dwarf virus (MYDV)
SEQUENCE: 14
acaaaagggt tctagaggga ccctttatag cactcttctt tcaccagaag tttcatgcgc  60
tgtgagattc actttgacgg gacactcacg tttgctgaaa tccccccgtga tctcacaatc  120
cgccttttag agtttcaaac agctctaaga accatcgctt gttgtgttct caaccaacga  180
tacgatgctg aaactctggt gcgctctgct tttactattc tgcctctcat gctccgtgaa  240
ctcccattca cttgggagtt ccctagtgcg gtacacgccg cctttgcgaa gcatgcgtta  300
cgtaccgccg gcagaatacc tcctcccatg gaactcatct tccatggtga cacgccaaaa  360
cacatgtata gagatttcct ataccgcgtt gtcacgagag atattgcagc tagcctacag  420
agatctcacg agaatttcat ctgtggctat aaacgcttcc aactccggct ggaaagtgtt  480
tgcagaagag ttgagctcct tggtgacaca tttgcaccaa aacatatcga ggagctttca  540
tggtcttcgc ggactcgcgg tggacggggt gcaggcgctc gcaggaggct tcctgctcgc  600
tgtaatctac acctggagct acttgatatc gctgctcttt tgggttgtta caaccctggt  660
atgcagatat acgttccaga tgtcatcgat cgcctgtctc tacgtctgta caatgctctt  720
ggtccggctg gcttcaaaga tttttggagg gtggccggtt atgatcatct cgctgattgg  780
gactctgaca tcgaagctct ttcgggctct gtcattcaaa aagagctcaa tctcctttga  840
gatccctacc ccagggtaca agacagtaga gatacctcag aaaccaccca aagattgcgt  900
cttgctggtt caacacaacg acgctctcaa ttcccctgga ggatacgcat catgtgttcg  960
actcctcaac ggaagcaatg ctttgctcac tgcaaaacat gtttccaccc aggaaggtga  1020
tttgctcatc gcttcatcca gaactggaaa caggatcaag ttgtcattgt tcaacacaat  1080
cctaaccaca aagaattccg acgtgggtct ttatcaagga cctccaggtt gggaatcaat  1140
tcttggatgt aaagctgcag acatcgtacc agtggatggg ctctcatgtt gtgaggcctc  1200
catttatagg catgatggca actggatgcg ttccaacgca tccttggtcg gaacagaagg  1260
cacttttgtc tctgttttga gcaacaccat tgagggtttt agtggaactc cctattttaa  1320
cggaaaatcc attttgggag ttcatgtggg aggcaatgaa accagaacta acaatctgat  1380
ggcccccata cccagcatcc caggcctaac aaaacacaaa tatgtgtttg aatcgccaca  1440
actcagaggc cgcctgttta cagacgagga agttgagaaa ctcgaattcg agattgatga  1500
agctttccag aaagctcata atctcataca tttcaaatct aaaacaggaa gaaactgggc  1560
tgatgatgag gatgacatcc actttgaagc tccaaagttt cagggaaacg acgcacgcgg  1620
tcccgtccgc gaaaacaaaa cggtctctcc caccccctaca cactcgcccg tcgttacttc  1680
aggcaacgac actctcaaca aggtggtgga agcgttggtc tcgaagatcg acgtctcagt  1740
aatcgagcgg atggttgttc aaaagatctc ggaatcagct ttgaaacgcc caacgaacaa  1800
caatcggaaa cacaggcgaa agcccaaaac ttctcagcct actttgcctc cctctacaga  1860
tgggaggtac gtggcgcccg ctcgcagatc cccggcttcg aagcctgcgg atccctcccc  1920
aaatactact tcacaaaaca aaaagaagaa tcagagtggg ggaggttact tgcagaggga  1980
aacccggcgc tggcaagtaa agtcagcggc ttcgggtggc cccaattcgg acccgaggcc  2040
gaattgaaga gcctgcgcct tcaggcgcag agatggctct cacgcgcgga gtttgctaaa  2100
atcccgtcat ctgaggacag ggagcgcgtg atccggaaga ctgtggaggc atacaaaact  2160
tgccaaactc aatgccccaa gacttctcaa agcaacctgc ttgtgtggga agactttctc  2220
gaagatttca aacaagcagt gttctccctc gagcccgatg ccggtgttgg tgttcctttc  2280
```

```
gtgggatacg accggcgtac gcaccgtgga tggatcgaag atccaacact tctgccagtt  2340
cttgcccgca tgaccttcga ccgattacat aagatgtcga cggttaagtt tgagcaactt  2400
acagcagaac aattggtgca acagggcttg tgtgacccga tcagactatt tgtcaagggg  2460
gaacctcaca agcagtcaaa gctcgatgaa ggccgctacc gcctcattat gagtgtttcg  2520
ttgctggatc aactggtagc ccgggttctg tttcaaaatc agaacaagag ggaaattgca  2580
ctatggcgag ccataccctc aaaacccggt tttgggttgt ctacagacgc ccaatcgcga  2640
gaatttgtgc agaatctcgc gaaacagtgt ggggtcaaca cgactgaact tttggcaaat  2700
tggccaacct acactgttcc gactgactgc tctggtttcg actggagtgt tgcggattgg  2760
atgctccagg atgatatgga ggtccgcaac cgactcactc gcaacaacac agatctcacc  2820
aagcgcttgc gcgcttgctg gttgaaatgt atatccaatt ctgtgttgtg cttgagtgat  2880
ggcactctgc tagcccagcg catagcggga atccagaaat ctggttctta caacaccagt  2940
tcgagtaact ctcgaatccg agtgatggcc gcatatcatt gcggtgctac ctgggcgatg  3000
gctatgggtg atgatgcact cgagtcagtc gacacgaacc tagacgtgta taaaacacta  3060
ggattcaaag tcgaggtctc caaacaactg gagttttgtt ctcatatctt cgagaaggaa  3120
gaccttgctc gcccggttaa ccaaaacaag atgatctaca aactcttaca tggttacaac  3180
ccggcgaacg gctcttcgga ggtgatacag cgttatcttg acgcatgtat gagcgtactc  3240
aacgagttgc gccacgaccc cgaaaccgtt gagcttctgt accagtggct ggtcgctcca  3300
gtccagaaac aaaaagttta aaacagaagc tctcaagtca gccaggcaaa ttcgagttgc  3360
aagcactgga tgacctagtc tcgatacata aaccaccacg gattacaagt tcttagccgg  3420
gatcactctc ggcctttgca tcacattccc atttataatc cttggtgtgt acaaagtcta  3480
ccgtacggtc tccaacgata caagcaaact cgctaatgaa tttgggaggc cgtagaaatg  3540
gacgacgtgg aacacggtta cgcagacgcg tacgcattgc tcgcaccacc caaccaatgg  3600
ttgtggtcgc gcaaacccag cgtagacgcc gcatccgaag acgaggacga ccaagtggag  3660
acacttcagg aggacctcga gggcgaggag gctcgcggga gactttcgta ttttcgaagg  3720
attctatcgc gggcagtgcc tccggaaagc tcaccttcgg ggcgtctctt tctgagtgcg  3780
cagcattctc tggtggaatt ctcaaggcct accatgagta taagatcaca aaagtcatac  3840
tggagttcat ctccgaggcc ccttacaccg cagccggttc catcgcttat gagcttgatc  3900
cccacaacaa gctcagcacc ctcgcatcaa caatcaacaa attctcgatc gtcaagggtg  3960
gcaagcgtgc ctatacgtcc aaacaaatcg gaggtggagt atggcgagat tcgtccgaag  4020
accaatttgc aatactctac aagggcagtg gaaactcctc agttgccggc tcgttccgca  4080
tcacgatgga ggttcatacc caaaatccga aataggtaga cggagcttcc cctgcaccag  4140
acccaacacc gacaccaacc cccactccaa cacctactcc aactccaacg cccactcctg  4200
tgactcagga agccttctac ggctattctg gtgtcccaga atgtaagatc cagtccagaa  4260
agaactcgga attcatcgat atctattcgt tgaatttcgt taaattgttc tactggagag  4320
atgaggcgtg gagctcggag accctttcgg cgggatacat acaaaatgat tcgctccgcg  4380
caacccccta ccttttggtt ccgaccaaga agggaaaata ctctgtttat atagagtgtg  4440
agggttttca agcggttaaa gctaagggtg gtaacaacga cggcaagatg agtggttttg  4500
tcacgtatga taaagatcaa agcggttggc aagtgtactc atgggctggt tgctctctct  4560
cgcagatcaa agttaaagac actggtgtcg tggctcatcc cgacatgaag gtgaatggtt  4620
gctctttcac caaaggccaa cttattgaga gagattttat ttgttcgttc catctcgaag  4680
ctacggaaga tggatattgg gctttgcaag ccccccccagt agagaagtct gatgaccaca  4740
attttattgt gtcatacggt tcttacaccg aaaagattct tgaatggggt tcagtatcca  4800
tatcaataga tgagataaat cgaacagaag ctcgcaagat tccgaaaagg gataaggatc  4860
tatcacaaag tggacgtttg gccgacatga ccaacgtccc cacagtgggg gtggttgtag  4920
cagcgaccac gaaaccggac ctgccggtag aacagccaaa ccagttggct gtggtggagc  4980
aacccactga agagcaacaa aagaaaaggg cgactatcga ccaatggctc gatgccgttg  5040
aagctcttgc tcccccagaa cctgaagggt tggtgacaca ggtgagacta ccaacagcag  5100
ctgaacgagg tttgacctcg caaaagctac ctttgcacca acgtggaacc ttcaaagacc  5160
tcgccaaccg agacgctgat acatacagtg tcgcatctcg tggattgact gggggcttga  5220
gaggaactcc cgcaacacct caggttgaaa cgattgagga gaaccccgtc caagtggacg  5280
atgattccaa atctctcgtt tcaagctcgt caaggcttac aggcggtctt cgtcttagaa  5340
cttcatatcg catgaccact caagaggcca agcaatatga tgagatcaga cgaagctttg  5400
gtaaagcacg cgcaaaagcc tattatgacg atttgtgtaa ggcgaactgg tattagccca  5460
cacaccctgg tcagggtcac agaccactcg ccggagtata aacgagatag gatggcaacc  5520
tagccactcc ccttcctccc gatgggaaat agggtgagtt ccaagcccaa ggaatgagat  5580
ttcagtgcaa tttttccact gaaatctatg gt                               5612
```

```
SEQ ID NO: 15          moltype = DNA  length = 9515
FEATURE                Location/Qualifiers
source                 1..9515
                       mol_type = genomic DNA
                       organism = Maize dwarf mosaic virus
                       note = Maize dwarf mosaic virus (MDMV)
SEQUENCE: 15
aaaaacaaca agactcaaca caacacaacc aaacacgacc aaacacaacc aaattacacg  60
ttattggagc acattcagtt tgcaggcaac ggttcgtttg caaggtgcat cgaaaagcct  120
ctctgaacac acgatcgcaa tggcaggaac ttggacccac gttactcaca agtggcagcc  180
aaaccttgac aaccctcgtg acgtcaggag aatcatggag ctgttcgctg caaagggcca  240
ggtctatgac gagaagcgag ctctggagca caacagtaaa ttacttcgta gagctcaggt  300
ggtggatgtc gaaccaatga tcacggttca accaaagaag tgtgcacaga tatggaaaga  360
ggtggtggat cataatccaa cacaccattt cgtgtacgca cgtttctctg aggttaagaa  420
gcaacagcct accaaaccag ttgcaacctc agttaataaa ctagtgagaa agactctaga  480
aatacgagag aattttccag tgaatgttga gtttattgga aagaaacgca agaacactac  540
gagagtctca ctgaggaaag tttttaacaa aactttctta cactgtggca cgcgacatga  600
gaacaaccaa ttcaagcgag ttgacacaaa catcactcga gattggattc cagtgctatc  660
aagcgtagca aaatgttatg cgacactgtc gtctaacatg atgcacaaca tacacaaagg  720
gcacagtggt ctaacgttca ttcaaaatgg tgaacttttc atagtccgag gaagacttag  780
aggtgaacta tgcaatagct tggactgtac aaaggaagtt caggagatag aacactacgc  840
agacccacag gcagctgatt tttggaaggg atacactaat gcatatgttg agaatagaaa  900
```

```
tatttcaacg acgcatacag agcatacgcc tacaatgaac ttagaaaagt gtggcaagcg  960
tatggcgtta ttggaagttc ttttccattc aacgttcaaa atcacatgca agcattgtaa  1020
cactgatgat cttgaattat cagatgatga attcggagaa aaactttaca agaacattca  1080
gcgcatcgaa gagcaacaga gtgaatatct agccgaggac caaaaactca aacgggtgtt  1140
atcattcatc aaggctagat gcacaccaaa gtttgatcac ttacctatga attggcaagt  1200
cgcagacatc attggacatt attcagataa tcaagcaaaa caaattttag atgtcaatga  1260
agcactgatt aaagtgaaca cactcacacc ttcagatgca ttaaaggcaa gtgcagctct  1320
tctcgagtta tcgagatggt ataagaatag gaaagaatca acaaaagagg acaacttatc  1380
cactttccgc aataagatat ctccaaagag cacgattaac ttagcattaa tgtgcgacaa  1440
tcaactcgat tcaaatggta actttgtttg ggaaagagg gaatatcatg caaaaagatt  1500
cttctcaaac tactttgaag ctgtggatcc agctgattca tatgaaaaac acgtaacacg  1560
ctttaatcca aacggacaaa gaaaattatc tatcggaaaa ttggttattc ctttggactt  1620
ccaacgtatc cgtgattcat ttgctggcat acctgtaaca aaacaaccgc tttcaaatgc  1680
ttgtctgagc agaatagaca aaacctacgt ctacccttgt tgctgtgtaa ctacagagtt  1740
tggacaacct gcatactcag aaataatacc tccgacaaag gggcatttaa ccattggtaa  1800
ttctgtggat ccgaagattg tcgatctgcc aaacacagac cctccaacga tgtatatttc  1860
gaaggacgga tattgctata taaacatttt cttggcagcc atgataaatg ttaatgagga  1920
ttcagctaag gattacacaa aattcatcag agatgaactc atagagagac ttggtaaatg  1980
gcccaaactt aaaaatgtag ctactgcatg ttatgcactt tctgtaatgt tcccagagat  2040
caagaacgct gagttacctc aaatcttggt tgatcatgaa aataagacaa tgcacgttgt  2100
ggattcatat ggatcactaa gcgttggcta tcacatcttg aaagcgaata ccgtgggaca  2160
actcatcaaa atgcagtacg agtcgatgga aagcgagatg agagaatatg cagttggtgg  2220
tacaataaca cacaaatcat tttccacctt aattagccat ctaatcaaga atatgtttaa  2280
gccacgtgaa atgcggaaaa taattgaaga agaacctttc ttaattatgc tatctgttgt  2340
atctcctact gttcttatat ctctatataa taattgtcac attgagaatg caatggcgta  2400
ttggataacg aagaatcaag gagtagcagc aatgttcgca caattggaag cccttgcaaa  2460
agaaacatca aaggcagagc ttttaatcca gcagatgaca atattagaga aagcttctaa  2520
tcagctaaaa ttggccgtga tggtctaaa tcatgttgac ccagctaagc gattgctttg  2580
gtcacattta gaagtcatgt cgtcgagggc agccacaaat aaagatcttc tagaccaagg  2640
ctacgctcta tatagcgata ggttgtatgc catcatcgaa aaaacctatg tagatcagtt  2700
gaatcaagcg tggacagaat tatcattgtt tggaaaattc tccgaaacat ggcgtgtgta  2760
caaggacaag aaatactaca agccatcttt aatcctgcaa agaagcgtag atttaggcgc  2820
tgtctacaat atatcagtta cgcatcaaat atcaagttta gtgcagaaaa gtcgcagtcg  2880
agtcagctct actttaacca aactccacca aggttcatgt gataaactat atagtttgcg  2940
tactaaagct ataaatacaa tttattggtt tgttcctgat attttccgac ttattcacat  3000
tttcatagta ctaagtttat tatcaacagt agctaatact attatagtaa caatgcaaga  3060
ttacaagaaa ttacaaaaac aagttcgtga ggaagaatat gaaaaggaaa taagcgaagt  3120
acgcgctata cacgcgaagt tgcttaaaat acatgataac gaactcactt gcgaacagtt  3180
cctgcagtac attaacgaaa atcatccaag attaattgaa gcagctgttg aactatcagg  3240
agtgggtgtg atacatgagg gcaagtccaa ccttgaaatc aatctagagc aagcgatggc  3300
tattggaaca ctaatcacaa tgatatttga ccctacaaag agcgatgctg tatacaaagt  3360
attaaacaaa atgagaacaa ttttgagtac agttgaacaa gatgcacctt tcccacgcat  3420
tgatttcacg aatatctttc ggtcgcaggt aacccaccaa agtttagatt tggacgaccc  3480
tctcactatc aatactgata agaagcttac ggtggatttc gacacaaccc aagatcttcc  3540
agcagatact tttagtaatg atgtgacatt tgatcaatgg tggtcgaatc aactcgaaaa  3600
caatagaact gttccgcact acagacttgg tggtgagttc attgaattca cacgagaaaa  3660
agcagcatct gttagcatca gtatagcaca ttcgcaaatt gagaaagaat atttactcgg  3720
aggagcagtc ggttcgggaa aatcaacagg tttaccatac catttgagcc agcgaggaaa  3780
agttctttta ttagagccga cacgaccact cgcagaaaac gtctgtagac aactacaagg  3840
ggcaccgttc aatgtaagtc ctacgctaca gatgagaggt ttgagctcct ttggatcaac  3900
gcccattaca ataatgacat caggctttgc acttcatatg tacgcaaaca atccagacaa  3960
attgtcaaat tatgactttg tcattttcga tgaatgtcat attatggaag ccccagcaat  4020
ggccttttac tgtttgctaa aggagtacgc atttgatggg aaaataatta aggtctcagc  4080
cacaccacca ggaagggaat gtgaattctc tacgcaacac ccagtcgata ttcacgtttg  4140
cgagaattta actcaaaacc aattcgtgct tgaacttggg actggatcaa aagctgatgc  4200
cactaaatac ggtaacaaca ttctggttta cgtggctagc tacaacgatg ttgattcatt  4260
ggcaagagca ttaattgagc gacattattc agtgatcaaa gttgatggca gaacgatgaa  4320
gcagaacaca agtggaatcc atccaaacgg acatgatgga aagaaatgtt tcatagttgc  4380
caccaatatt atcgaaaacg gagtaacatt ggacgtcgac gtcgttgttg actttggcct  4440
taaggttacg gctgaattgg acgttgataa tagagcagta atgtatcgta aagtgagcat  4500
atcttatggt gagagaatcc aacgacttgg aagagttgga agaacaaaac cagggactgt  4560
cattagaatt ggaacaacca tgaagggact tcaagagata ccagctatga tagcaactga  4620
agcagctttc ctttgtttcg catatggcct caaggttata acacataacg tttcaactac  4680
acacctatcg aaatgcacgg ttaagcaagc gagaactatg atgccatttg agctttcacc  4740
attcattatg tctgaattag tcaaatttga tggctcaatg catcctcaaa tacatgagat  4800
tctcaagaaa tacaagctta gagaatccgt gatcatgttg cgaccaaatg caattcctca  4860
tacaaatgtt cacaactggt taacagttaa agactacaac aaaattggct gtgatcttga  4920
gctagacgat tatgtaaagg ttccatactt cataagaggc attcctgaga aagtgtattc  4980
agatatctat aagattgtac tcgaatatgg ttcgaccagt tgttatggaa gactatcaag  5040
tgcatgtgca ggaaaagtag cttacacatt acgcacggac ccctttgctt taccacgaac  5100
aatcgctatt gtgaatcagc tcatagctga ggaacacgca aaacgtgatc attataactc  5160
aatcacatca aacccatcat cttcacatgc tttttccctt acaggaattt gcaatatgtt  5220
agcctcaagg tacatgaagg accattcaag ggaaaacatt gagaaattga cacgtgttaa  5280
agaccaattg attgagttta gggggactgg aggtgagttc aaaaatccag aagatttgct  5340
tgaatttggt gggctagtta cagtcattca ccaaggctta gattccaccg cccggggtct  5400
acagctcaaa ggaaggtgga acggagactt gattcagcgc gatttgatga tatcagctgg  5460
cgttttcaca ggcggtctac tgatgctttg gttcctcttc cggaaatggt catcaacaga  5520
tgtcaaacat gaagctaaga caaaacgcag caggcaaaaa ctcaaattta ggcaagcgcg  5580
cgacagcaaa tatgcttatg acgttactgg atctaaggat gcaattgaag aaaatttgg  5640
```

```
atcagcttat gttaagaaag ataagaaaaa gggaacaaaa gttggattgg gagttaagca  5700
acataagttc tacatgctgt ataattttga tccacaagat tacaatctaa ttcgatttgt  5760
ggacccactt acaggtgcaa ctcttgatga gcaaattcac gcagatatca atatggtacg  5820
agaacatttc acagcaattc gagaagctgc cataaataat gaccaacttg agtatcaaca  5880
catttattca aatccaggaa ttaaagcata ttttatacga aatggatctc aaaatgctct  5940
caaagtcgac atgactccac acgaaccact aagggttgtt actggtaaca atatagcggg  6000
attccctgaa tacgaaggca cgctacgaca aaccggaaga gcacaagtga taccttcaga  6060
acaagtacca gcaccaaacg aggtggaagt ggagcacgaa gcaaaatcta tgttaacggg  6120
attggtggat tacacaccta tagctaatca gattggcata attgaaaatc attcagatga  6180
tgttaggctt tgcatgtatg ctataggata tggatcatac ttaatcactc ctgcacacct  6240
cttcaaagca agcaatggag agttaacatt tcgatcttcg cgaggggttt acaagatgag  6300
aaactcagtg gaagtaaagc tacaccacgt aaaggggcgc gatttggtta taattcaact  6360
ccccaaagat tttcctccat tcccacagaa actcaagttt caagcaccta atcgcgaaaa  6420
caaagtgtgc ttggttggcg tcaatttcca gcagaatcat tcttcatgtg tagtttctga  6480
gagtagcact attgcgccaa aaggaaataa tacattttgg agtcattgga tctcaacaac  6540
aggtggccaa tgtggtttac cattagttga tatgaaaacc agaagcatag ttggggtaca  6600
tagccttgca tccgtaaatg cgaacgtaaa tttcttcgta gcaatgccgg aagacttcaa  6660
cacatacctt agtgaacttg tctcgaagaa tgaatgggaa aaaggatggc aatataatcc  6720
aaatttaata tcctggagtg gactaaatct cgtatcctct gcacctaaag gcgcttttaa  6780
aacagcaaaa cttgttgagg atttatcatt tgatgttaca gaacaaggga tccaacatga  6840
aacatggcta acgaagcaca tacagcaaaa tttgcaagtt gtagccaaat gtcctggaca  6900
attggttaca aaacatgttg ttaaaggtcc gtgcccgcac tttgcactat acttatccac  6960
gcacgaggaa gctgagaagt tctttagacc gcttatgggc aaatatgata agagtagact  7020
caataaagca gctttcgtta aagatcttac aaaatatgca aaaccaactt atattggcga  7080
agtaaacact gcactatttg aaagagctgt tgagcatgtc atacaactcc tacgcaatgt  7140
tgggattcca acatgtgagt acatcacaga tgaagatgaa attttcaaat ctttaaacat  7200
gaatgctgcg gttggagcat tatacacagg aaagaagaga gaatattttt ctgaatacac  7260
acaagaggat agagcagaga taataaagca atcgtgcgaa agagtttacg aaggcaagct  7320
tggaatttgg aatgggtctc tcaaggctga aataagacct atagagaaaa cggaagcaaa  7380
taagacaagg acattcacag ccgcaccatt ggaaacattg ctagcgggta aggtgtgtgt  7440
cgatgatttc aataatcaat tttatgcaca ccacttaaat ggaccgtgga cagttggaat  7500
aactaaattc tacggtggtt ggaatagatt acttgagaag ctaccagatg gctggatcta  7560
ctgtgatgca gatggttcgc aactcgacag ttcgctcact ccttatctga taaatgcagt  7620
gctcaacatt cgattacaat ttatggagcc gtggaacatt ggtgaacaaa tgcttaaaaa  7680
tttatacacg gaaattgttt ttacaccaat tgcaacacct gatgggtcag tcatcaaaaa  7740
gtttaaaggc aacaatagtg gacagccatc aacagttgtt ggcaacacac taatggtgat  7800
catagccttt aactatacgt tgttatcgtg tggagttgac ttggagaagg ctgatgatgt  7860
gtgtcgaatg tatgcgaatg gagacgattt attacttgca gtgaacccaa cacatgttga  7920
cattctaaac gaatttggaa aacacttcgc agcgttaggg ttaaatttcg attttgaatc  7980
acgaacgaga gataaatcag aactttggtt catgtcaacg cgaggtatca agtacgaaga  8040
aatgtatatc ccaaaattgg aaaaagaacg aattgtagct attcttgaat gggatcgatc  8100
attaatccct caataccgtc ttgaagctgt ctgtgcagca atggttgagg catgggggata  8160
taaagatttg ctccatgaga tacgtaagtt ctatgcgtgg ctgctcgaaa tgcaaccttt  8220
tgctaactta gcaaaggaag gctcagcacc gtacatagcc gagacagccc tgagaaactt  8280
gtatactggt gctaaggttt cagaagatga attgaatgtc tatgcacgac aattcttcga  8340
tgatctttca gattatttgg ccgatgaagt tatagatgtc aaacatcaag ctggtgagaa  8400
tgtcgatgct gggcagaaga ctgaagcaca gaaggaagca gagaggaagg cagctgaaga  8460
gaataaagca aaggaagctg aggctaaaca aaaggaaacc aaggagaaaa cgactgagaa  8520
agctggtgat ggcgagtcca cgggaaaaga caaagacgtg gacgccggaa cttcaggctc  8580
agtatcggta cctaagctaa aagctatgtc caaaaagatg cgtttgccac aagcgaaggg  8640
aaagaatatt ctccatcttg acttcctatt gaaatacaag ccacaacaac aagacttatc  8700
gaacacccga gcaaccaggg ctgaattcga tagatggtat gaagcagtgc agaaagaata  8760
cgaacttgat gatacacaaa tgacggttgt catgagtgga ttaatggttt ggtgcattga  8820
gaatggttgc tcaccaaaca tcaatggagt ctggacaatg atggatggag acgaacagag  8880
aacatttcct ttaaaacagg ttattggaaa tgcatctcca actttcagac aaattatgca  8940
tcattttagt gatgcagctg aagcatacat tgagtataga aattcaacag aaagatatat  9000
ggcgagatat ggacttcagc gaaacttaac cgactttagc cttgcacgct atgcatttga  9060
tttttacgag atatcatctc gaactccagc acgtgcaaag gaagcccaca tgcagatgaa  9120
ggccgcagca gtccgtggtt caaacacacg gatgtttggt cttgatggga atgtcggaga  9180
aacccaagaa aatacagaac gccacacagc tggcgacgtt agtcgcaaca tccactccct  9240
tttgggagtt cagcaggggc attgatacgg ggttcaactt ttacgcagta atttagtaat  9300
atataagtaa gctattgtgg tgaggttgta cctcgttagt tttatatata tattatgcta  9360
cgtacctact atgtctgcaa gtgagtgagg ttgcacctcg acacttatag tgggcactat  9420
tactagcttc gaatcacgag acggacggtc cattgagtgg ttctaccacg aggatgcagc  9480
gagtttcgtg gtgagagaca aaaaaaaaaa aaaaa                             9515

SEQ ID NO: 16           moltype = DNA  length = 3249
FEATURE                 Location/Qualifiers
source                  1..3249
                        mol_type = genomic DNA
                        organism = Neisseria meningitidis
gene                    1..3249
                        note = NmCas9
SEQUENCE: 16
atggctgcct tcaaacctaa ttcaatcaac tacatcctcg gcctcgatat cggcatcgca  60
tccgtcggct gggcgatggt agaaattgac gaagaagaaa accccatccg cctgattgat  120
ttgggcgtgc gcgtatttga gcgtgccgaa gtaccgaaaa caggcgactc ccttgccatg  180
gcaaggcgtt tggcgcgcag tgttcgccgc ctgacccgcc gtcgcgccca ccgcctgctt  240
cggacccgcc gcctattgaa acgcgaaggc gtattacaag ccgccaattt tgacgaaaac  300
```

```
ggcttgatta aatccttacc gaatacacca tggcaacttc gcgcagccgc attagaccgc  360
aaactgacgc ctttagagtg gtcggcagtc ttgttgcatt taatcaaaca tcgcggctat  420
ttatcgcaac ggaaaaacga gggcgaaact gccgataagg agcttggcgc tttgcttaaa  480
ggcgtagccg gcaatgccca tgccttacag acaggcgatt tccgcacacc ggccgaattg  540
gctttaaata aatttgagaa agaaagcggc catatccgca atcagcgcag cgattattcg  600
catacgttca gccgcaaaga tttacaggcg gagctgattt tgctgtttga aaaacaaaaa  660
gaatttggca atccgcatgt ttcaggcggc cttaaagaag gtattgaaac cctactgatg  720
acgcaacgcc ctgccctgtc cggcgatgcc gttcaaaaaa tgttggggca ttgcaccttc  780
gaaccggcag agccgaaagc cgctaaaaac acctacacag ccgaacgttt catctggctg  840
accaagctga acaacctgcg tattttagag caaggcagcg agcggccatt gaccgatacc  900
gaacgcgcca cgcttatgga cgagccatac agaaaatcca aactgactta cgcacaagcc  960
cgtaagctgc tgggtttaga agataccgcc tttttcaaag gcttgcgcta tggtaaagac  1020
aatgccgaag cctcaacatt gatggaaatg aaggcctacc atgccatcag ccgtgcactg  1080
gaaaaagaag gattgaaaga caaaaaatcc ccattaaacc tttctcccga attacaagac  1140
gaaatcggca cggcattctc cctgttcaaa accgatgaag acattacagg ccgtctgaaa  1200
gaccgtatac agcccgaaat cttagaagcg ctgttgaaac acatcagctt cgataagttc  1260
gtccaaattt ccttgaaagc attgcgccga attgtgcctc taatggaaca aggcaaacgt  1320
tacgatgaag cctgcgccga aatctacgga gaccattacg gcaagaagaa tacggaagaa  1380
aagatttatc tgccgccgat tcccgccgac gaaatccgca accccgtcgt cttgcgcgcc  1440
ttatctcaag cacgtaaggt cattaacggc gtggtacgcc gttacggctc cccagctcgt  1500
atccatattg aaactgcaag ggaagtaggt aaatcgttta aagaccgcaa agaaattgag  1560
aaacgccaag aagaaaaccg caaagaccgg gaaaaagccg ccgccaaatt ccgagagtat  1620
ttccccaatt ttgtcggaga acccaaatcc aaagatattc tgaaactgcg cctgtacgag  1680
caacaacacg gcaaatgcct gtattcgggc aaagaaatca acttaggccg tctgaacgaa  1740
aaaggctatg tcgaaatcga ccatgccctg ccgttctcgc gcacatggga cgacagtttc  1800
aacaataaag tactggtatt gggcagcgaa aaccaaaaca aaggcaatca aaccccttac  1860
gaatacttca acggcaaaga caacagccgc gaatggcagg aatttaaagc gcgtgtcgaa  1920
accagccgtt tcccgcgcag taaaaaacaa cggattctgc tgcaaaaatt cgatgaagac  1980
ggctttaaag aacgcaatct gaacgacacg cgctacgtca accgtttcct gtgtcaattt  2040
gttgccgacc gtatgcggct gacaggtaaa ggcaagaaac gtgtctttgc atccaacgga  2100
caaattacca atctgttgcg cggcttttgg ggattgcgca aagtgcgtgc ggaaaacgac  2160
cgccatcacg ccttggacgc cgtcgtcgtt gcctgctcga ccgttgccat gcagcagaaa  2220
attacccgtt ttgtacgcta taaagagatg aacgcgtttg acggtaaaac catagacaaa  2280
gaaacaggag aagtgctgca tcaaaaaaca cacttcccac aaccttggga atttttcgca  2340
caagaagtca tgattcgcgt cttcggcaaa ccggacggca aacccgaatt cgaagaagcc  2400
gataccctag aaaaactgcg cacgttgctt gccgaaaaat tatcatctcg ccccgaagcc  2460
gtacacgaat acgttacgcc actgtttgtt tcacgcgcgc ccaatcggaa gatgagcggg  2520
caagggcata tggagaccgt caaatccgcc aaacgactgg acgaaggcgt cagcgtgttg  2580
cgcgtaccgc tgacacagtt aaaactgaaa gacttggaaa aaatggtcaa tcgggagcgc  2640
gaacctaagc tatacgaagc actgaaagca cggctggaag cacataaaga cgatcctgcc  2700
aaagcctttg ccgagccgtt ttacaaatac gataaagcag gcaaccgcac ccaacaggta  2760
aaagccgtac gcgtagagca agtacagaaa accggcgtat gggtgcgcaa ccataacggt  2820
attgccgaca acgcaaccat ggtgcgcgta gatgtgtttg agaaaggcga caagtattat  2880
ctggtaccga tttacagttg gcaggtagcg aaagggattt tgccggatag ggctgttgta  2940
caaggaaaag atgaagaaga ttggcaactt attgatgata gtttcaactt taaattctca  3000
ttacacccta atgatttagt cgaggttata acaaaaaaag ctagaatgtt tggttacttt  3060
gccagctgcc atcgaggcac aggtaatatc aatatacgca ttcatgatct tgatcataaa  3120
attggcaaaa atggaatact ggaaggtatc ggcgtcaaaa ccgccctttc attccaaaaa  3180
taccaaattg acgaactggg caaagaaatc agaccatgcc gtctgaaaaa acgcccgcct  3240
gtccgttaa                                                          3249

SEQ ID NO: 17          moltype = DNA  length = 3114
FEATURE                Location/Qualifiers
source                 1..3114
                       mol_type = genomic DNA
                       organism = Parvibaculum lavamentivorans
SEQUENCE: 17
atggagagga ttttcggctt tgacatcggc acaacaagta tcggattcag cgtgattgat  60
tacagtagca cccagtccgc aggcaacatc cagaggctgg gcgtgcgcat tttccctgag  120
gcaagggacc cagatgggac ccccctgaac cagcagcgga gacagaaacg catgatgagg  180
cgccagctgc gacggagaag gattcgccga aaggcactga atgagacact gcacgaagcc  240
ggctttctgc cagcttacgg gtctgcagat tggcccgtgg tcatggccga cgagccttat  300
gaactgcgga gaaggggact ggaggaaggc ctgagtgctt acgagttcgg acgggcaatc  360
tatcatctgg cccagcaccg gcattttaaa ggcagagaac tggaggaatc cgatacaccc  420
gaccctgatg tggacgatga gaaggaagcc gctaacgaga gagcagccac tctgaaggcc  480
ctgaaaaatg aacagaccac actgggagca tggctggccc gccgaccccc ttctgaccgc  540
aagcgaggaa tccacgccca taggaacgtg gtcgctgagg agttcgagcg cctgtgggaa  600
gtgcagtcca agtttcaccc cgctctgaaa tctgaggaaa tgcgggcaag aatcagtgat  660
acaattttcg cccagaggcc tgtgttttgg cgcaagaaca ctctgggaga gtgcagattc  720
atgcctggcg aaccactgtg tcccaagggg tcctggctgt ctcagcagcg gagaatgctg  780
gagaaactga acaatctggc tatcgcaggc gggaatgcta ggccactgga tgcagaggaa  840
cgcgacgcca ttctgagtaa gctgcagcag caggccagca tgtcctggcc aggcgtgcgg  900
tcagctctga aggcactgta caaacagaga ggcgagcccg gggctgaaaa gagcctgaaa  960
ttcaacctgg agctgggagg cgaatccaag ctgctgggaa atgccctgga ggctaaactg  1020
gcagatatgt ttggccctga ctggccagct cacccccgaa agcaggagat ccggcacgca  1080
gtgcatgaac ggctgtgggc tgcagattac ggcgagacac ccgacaagaa aagagtcatc  1140
attctgtccg agaaggatcg aaaagctcat cgggaagccg ctgcaaactc tttcgtggca  1200
gactttggaa ttactggcga gcaggcagct cagctgcagg ccctgaagct gccaaccggc  1260
tgggaacctt atagcatccc agcactgaac ctgttcctgg ccgagctgga aaagggggag  1320
```

```
aggtttggag ccctggtgaa tggacctgat tgggaaggct ggaggcgcac aaacttcccc  1380
caccgcaatc agcctactgg ggagatcctg gacaagctgc caagtcccgc ctcaaaagag  1440
gaaagggaac gcattagcca gctgcgcaac ccaaccgtgg tccgaacaca gaatgagctg  1500
agaaaggtgg tcaacaatct gatcgggctg tatggaaaac ccgatcgaat ccggattgaa  1560
gtgggccggg acgtcgggaa gtccaaaaga gaaagggagg aaatccagtc tggcattcga  1620
cggaacgaga agcagagaaa gaaagccact gaagatctga tcaaaaacgg aattgctaat  1680
cctagccggg acgatgtgga gaagtggatc ctgtggaaag agggccagga aagatgccca  1740
tacaccggcg accagattgg cttcaatgcc ctgtttagag aaggcagata tgaggtggaa  1800
cacatctggc ctcgctctcg aagttttgat aacagcccaa ggaataagac actgtgtcgc  1860
aaagacgtga acatcgagaa gggaaatagg atgcctttcg aggcatttgg ccatgacgaa  1920
gatcggtgga gcgccatcca gattagactg cagggcatgg tgtcagccaa agggggaact  1980
gggatgagcc ccggaaaggt caaacgcttc ctggctaaga ccatgcctga ggattttgca  2040
gcccggcagc tgaacgacac aagatacgct gcaaagcaga tcctggccca gctgaaaagg  2100
ctgtggccag acatgggacc tgaggctcca gtgaaggtcg aagcagtgac tggacaggtc  2160
accgcccagc tgcgcaaact gtggactctg aacaatattc tggctgacga tggggagaaa  2220
accagagcag atcacaggca ccatgccatc gacgctctga cagtggcctg cactcatcct  2280
ggaatgacca acaagctgag caggtattgg cagctgcgcg acgatccacg agcagagaag  2340
ccagctctga ctccaccctg ggataccatc cgcgccgacg ctgagaaagc cgtgtctgaa  2400
attgtggtca gtcaccgggt gagaaagaaa gtcagcggcc cactgcataa ggagactacc  2460
tacggcgata cagggactga cattaagacc aaatccggca catatagaca gttcgtgacc  2520
aggaagaaaa tcgagtcact gagcaagggg gagctggatg aaattcgcga cccccgaatc  2580
aaagaaattg tggcagctca cgtcgcagga cgaggaggcg accccaagaa ggccttccct  2640
ccatacccct gtgtgtctcc cggaggccct gagatccgga aggtcagact gaccagtaaa  2700
cagcagctga acctgatggc ccagacaggg aatggatacg ctgacctggg ctccaaccac  2760
catatcgcaa tctaccggct gcccgatggg aaggccgact tcgagattgt gtcactgttt  2820
gatgctagca gaaggctggc acagagaaat ccaatcgtgc agaggacacg agcagacgga  2880
gccagcttcg tcatgtccct ggcagccgga gaggccatca tgattcccga aggctcaaag  2940
aaagggatct ggattgtgca gggagtctgg gcaagcggac aggtggtcct ggagagggac  3000
accgatgctg accactctac aactacccgc cctatgccaa accccatcct gaaggacgat  3060
gccaagaaag tgagtatcga tcctattggc cgagtccggc catcaaatga ctaa        3114

SEQ ID NO: 18           moltype = DNA  length = 3255
FEATURE                 Location/Qualifiers
source                  1..3255
                        mol_type = genomic DNA
                        organism = Corynebacterium diphtheriae
SEQUENCE: 18
atgaagtacc atgtcggaat cgatgtcgga accttttctg tggggctggc tgctattgaa  60
gtggatgacg ctggaatgcc tattaagacc ctgagtctgg tgtcacacat tcatgactca  120
ggactggatc ctgacgagat caagagcgct gtgaccaggc tggcaagctc cggaatcgcc  180
cggagaacaa ggcgcctgta ccgacggaag agaaggcgcc tgcagcagct ggataagttc  240
atccagaggc agggctggcc agtgatcgag ctggaagatt acagcgaccc cctgtatcct  300
tggaaggtgc gcgccgaact ggccgcttct tatattgctg acgagaagga acggggggag  360
aaactgagtg tggctctgag acacatcgca aggcatcgcg gatggaggaa cccttacgcc  420
aaggtgtcta gtctgtatct gccagatggc ccctcagacg ccttcaaggc tattagggag  480
gaaatcaaac gcgctagcgg ccagcctgtg ccagagactg caaccgtcgg gcagatggtg  540
accctgtgcg aactgggcac actgaagctg cgaggagagg gaggagtgct gagtgcacgg  600
ctgcagcagt cagattacgc ccgcgagatc caggaaattt gtcgaatgca ggagatcggc  660
caggaactgt atcgcaagat cattgacgtg gtgttcgcag ccgagtcccc aaagggctct  720
gcctcaagcc gggtggggaa agatcctctg cagccaggaa agaacagagc actgaaagcc  780
agcgacgctt ttcagcgata ccggattgct gcactgatcg gcaatctgag agtcagggtg  840
gatgggggaga agaggattct gagcgtggag gagaagaacc tggtgttcga ccacctggtg  900
aatctgactc caaagaaaga gcccgaatgg gtgaccatcg ccgaaattct gggcatcgat  960
cgcgggcagc tgatcggaac agctactatg accgacgatg gagagcgagc aggagcccga  1020
cccccctacac acgatactaa cagaagtatt gtgaacagcc ggatcgcacc actggtcgac  1080
tggtggaaaa cagctagcgc actggagcag cacgccatgg tgaaggcact gtccaacgcc  1140
gaagtcgacg attttgattc tcccgaggga gcaaaagtgc aggcattctt tgccgatctg  1200
gacgatgacg tccacgccaa gctggacagc ctgcatctgc ctgtgggacg agcagcttac  1260
tccgaggaca ctctggtcag actgacccga cggatgctga gtgatggggt ggacctgtat  1320
accgcccggc tgcaggagtt cggaattgaa cctagctgga ccccacccac accaagaatc  1380
ggagagcctg tcggcaatcc agccgtcgac cgggtgctga aacagtgag cagatggctg  1440
gaatccgcaa caaagacttg ggcgccccca gagagggtca tcattgagca cgtgcgcgaa  1500
ggcttcgtca ctgagaaacg cgctcgagaa atggatgggg acatgagaag gcgcgcagcc  1560
cggaacgcca agctgtttca ggagatgcag gaaaagctga atgtgcaggg caaacccagt  1620
cgagccgatc tgtggagata ccagtcagtg cagagacaga actgccagtg tgcctattgc  1680
gggtccccaa ttacctttc taatagtgaa atggaccaca tcgtgcccag agcagggcag  1740
ggatccacca acacaaggga gaatctggtc gccgtgtgcc atcgctgtaa ccagtctaag  1800
ggcaatacac ccttcgctat ttgggcaaaa aacacttcta tcgaaggggt cagtgtgaag  1860
gaggccgtgg aacggaccag acattgggtc actgataccg gcatgagaag cactgacttc  1920
aagaagttca ccaaggctgt ggtcgagcgg tttcagagag caacaatgga tgaggaaatc  1980
gacgccagaa gcatggaatc cgtcgcctgg atggctaatg agctgaggag ccgcgtggct  2040
cagcacttcg catcccatgg aaccacagtc agggtgtacc gaggcagcct gacagcagag  2100
gctcgacggg catctgggat cagtggaaag ctgaaattct ttgatggcgt ggggaagtcc  2160
aggctggata gaaggcacca tgctattgac gctgcagtga tcgcattcac ctctgactat  2220
gtggccgaaa cactggctgt ccgctcaaac ctgaaacaga gccaggccca ccgacaggag  2280
gctcctcagt ggagagagtt caccggcaag gatgcagagc atcgagcagc ttggagagtg  2340
tggtgccaga agatggaaaa actgagcgcc ctgctgaccg aggacctgcg agatgaccgg  2400
gtggtcgtga tgtctaacgt gcgactgcgg ctgggaaatg gcagtgccca caaggaaacc  2460
attggcaaac tgtcaaaggt gaaactgtcc tctcagctgt cagtcagcga tatcgacaaa  2520
```

```
gcaagttcag aggccctgtg gtgtgctctg accagagagc ccggattcga tcctaaggaa  2580
ggcctgcccg ctaaccctga gagacacatc agggtgaatg ggacacatgt ctacgccggg  2640
gacaatattg gactgtttcc agtgtcagca ggaagcatcg cactgagggg aggatacgca  2700
gagctgggca gctccttcca ccatgctcgc gtgtataaaa ttacttccgg caagaaaccc  2760
gcatttgcca tgctgagggt gtacaccatc gatctgctgc cttatcgcaa ccaggacctg  2820
tttagcgtgg aactgaagcc acagacaatg tccatgaggc aggctgagaa gaaactgcgc  2880
gacgctctgg caactgggaa tgcagaatat ctgggatggc tggtcgtgga tgacgagctg  2940
gtcgtggata catctaagat tgccactgac caggtcaaag cagtggaggc cgaactgggg  3000
actatccgcc gatggcgggt ggatggattc ttttccccct ctaaactgag actgaggcct  3060
ctgcagatgt ccaaggaggg gatcaagaaa gagtccgctc ccgaactgtc taaaatcatt  3120
gacagaccag gatggctgcc cgccgtgaac aagctgttct ctgatggaaa tgtcaccgtc  3180
gtgcggagag actctctggg acgcgtgcga ctggagagta cagcccacct gcctgtcact  3240
tggaaggtgc agtaa                                                   3255

SEQ ID NO: 19           moltype = DNA  length = 3393
FEATURE                 Location/Qualifiers
source                  1..3393
                        mol_type = unassigned DNA
                        organism = unidentified
                        note = Streptococcus pasteurianus
SEQUENCE: 19
atgactaacg gcaagattct ggggctggac attggcatcg caagcgtggg ggtggggatt  60
attgaggcaa aaactggaaa ggtggtgcat gccaattccc ggctgttctc tgccgctaac  120
gctgagaaca atgcagaacg gagagggttt aggggatcta ggcgcctgaa tcgacggaag  180
aaacaccgcg tgaagcgagt ccgggatctg ttcgagaaat acggaatcgt caccgacttt  240
cgcaacctga atctgaaccc ttatgagctg cgagtgaagg gcctgaccga acagctgaaa  300
aacgaggaac tgttcgcagc cctgagaaca atctctaaga gaagggggat tagttacctg  360
gacgatgccg aggacgatag taccggatca acagactatg ctaagagcat cgatgagaat  420
cgccgactgc tgaaaaacaa gacaccaggc cagattcagc tggagaggct ggaaaagtac  480
ggccagctgc gcgggaattt caccgtctat gacgagaacg gggaagccca tcgcctgatc  540
aatgtgttta gtacatcaga ttacgagaaa gaagcacgga agatcctgga gacacaggcc  600
gactacaaca agaaaatcac agctgagttc attgacgatt atgtggaaat cctgacccag  660
aaacgaaagt actatcacgg ccccgggaac gaaaagagcc ggactgacta cggacggttc  720
cggaccgatg ggaccacact ggagaatatt ttcggaatcc tgattggcaa gtgcaacttt  780
taccctgatg aatatcgagc aagcaaggcc agctacaccg cacaggagta taatttcctg  840
aacgacctga acaatctgaa ggtgagcacc gaaacaggga agctgtcaac agagcagaaa  900
gaaagcctgg tggagtttgc caagaatact gctaccctgg gacccgctaa actgctgaag  960
gagatcgcaa aaattctgga ctgtaaggtg gatgagatca aggatacag agaggacgat  1020
aaaggcaagc cagatctgca taccttcgag ccctatagga aactgaagtt taatctggaa  1080
agcatcaaca ttgacgatct gtcccgcgaa gtgatcgaca agctggctga tattctgact  1140
ctgaacaccg agagagaagg aatcgaggac gcaattaaga ggaatctgcc aaaccagttc  1200
acagaggaac agatcagcga gatcatcaag gtgcggaaga gccagtccac tgctttcaat  1260
aagggctggc actcttttag tgcaaaactg atgaacgagc tgatccccga actgtacgcc  1320
acctccgacg agcagatgac aattctgact cggctggaaa aattcaaggt caataagaaa  1380
agctccaaaa acacaaagac tatcgacgag aaggaagtca ctgatgagat ctacaatcct  1440
gtggtcgcca agagcgtgag acagaccatc aaaatcatta acgctgcagt caagaaatat  1500
ggcgacttcg ataagatcgt gattgaaatg ccacgggata aaaatgctga cgatgagaag  1560
aagttcatcg acaagagaaa taaggagaac aagaaggaaa aggacgatgc cctgaaaagg  1620
gccgcttacc tgtataattc tagtgacaag ctgcccgatg aggtgttcca cggcaacaag  1680
cagctggaaa ccaaaatccg actgtggtat cagcaggggg agcggtgcct gtatagtgga  1740
aagcccatct caattcagga gctggtgcat aactctaaca atttcgaaat cgatcacatt  1800
ctgcctctgt cactgagctt tgacgatagt ctggccaata aggtgctggt ctacgcttgg  1860
acaaaccagg agaaaggcca gaaaacccct tatcaggtca tcgactccat ggatgcagcc  1920
tggtctttca gggagatgaa ggactacgtg ctgaaacaga agggactggg caagaaaaag  1980
cgcgactatc tgctgactac cgagaacatc gataagattg aagtgaagaa gaagttcatc  2040
gagaggaatc tggtggatac tcgctacgca tctcgagtgg tcctgaactc tctgcagagt  2100
gccctgagag agctggggaa agacactaag gtgtctgtgg tcaggggaca gttcaccagt  2160
cagctgcgga gaaaatggaa gatcgataag agccgcgaga cataccacca tcacgcagtg  2220
gacgccctga tcattgctgc atcaagccag ctgaaactgt gggagaagca ggacaatccc  2280
atgtttgtgg attatggcaa gaaccaggtg gtcgacaaac agactgggga gatcctgtcc  2340
gtgtctgacg atgagtacaa ggaactggtg ttccagcccc cttatcaggg ctttgtgaat  2400
accatctcct ctaaagggtt cgaggacgaa attctgttta gctaccaggt ggattccaaa  2460
tataaccgga aggtcagtga cgcaaccatc tactcaacaa gaaaagccaa gattggcaag  2520
gataagaaag aggaaaccta cgtgctggga aaaatcaagg acatctactc ccagaatggc  2580
ttcgatacct tcatcaagaa gtacaacaaa gataagactc agttcctgat gtatcagaag  2640
gactctctga catgggagaa cgtgatcgaa gtcattctga gggactaccc aacaactaag  2700
aaaagcgagg acggcaaaaa tgatgtgaag tgcaacccct ttgaggaata caggcgcgag  2760
aatgggctga tctgtaagta ttccaagaaa gggaaaggaa ctcccatcaa gagcctgaag  2820
tactatgaca agaaactggg gaactgcatc gatattaccc cagaggaatc acgcaataag  2880
gtcatcctgc agagcattaa cccttggcga gccgacgtgt acttcaatcc agagacactg  2940
aagtacgaac tgatgggcct gaaatattca gatctgagct ttgaaaaggg cactgggaac  3000
taccatatca gccaggagaa atatgacgct atcaaagaga aggaaggaat tggcaagaaa  3060
tccgagttca agtttacact gtaccgcaac gacctgatcc tgatcaagga tatcgccagt  3120
ggcgagcagg aaatctacag attcctgtca agaactatgc ccaatgtgaa ccactacgtc  3180
gagctgaagc cttacgacaa ggaaaagttc gataacgtgc aggagctggt cgaagcactg  3240
ggagaggcag ataaagtggg acgatgtatc aaaggactga ataagccaaa catcagcatc  3300
tacaaggtga gaaccgacgt cctgggaaac aaatatttcg tgaagaaaaa gggcgacaaa  3360
cccaagctgg attttaagaa caacaagaag taa                               3393
```

```
SEQ ID NO: 20          moltype = DNA  length = 3249
FEATURE                Location/Qualifiers
source                 1..3249
                       mol_type = genomic DNA
                       organism = Neisseria cinerea
SEQUENCE: 20
atggctgcct tcaaacctaa tcctatgaac tacatcctgg gcctggacat tggaatcgct  60
tctgtcgggt gggctatcgt ggaaatcgac gaggaagaga accctatcag actgattgat  120
ctgggagtca gagtgtttga aagggcagag gtgccaaaga ccggcgactc cctggccgct  180
gcacggagac tggctcggtc tgtcaggcgc ctgacacgac ggagagcaca caggctgctg  240
cgagctaggc gcctgctgaa gagagagggc gtgctgcagg ccgctgactt cgatgaaaac  300
ggcctgatca agagcctgcc caatactcct tggcagctga gagcagccgc tctggacagg  360
aagctgaccc cactggagtg gtctgccgtg ctgctgcacc tgatcaagca tcgcggctac  420
ctgagtcagc gaaaaaatga aggggagaca gcagataagg agctgggagc actgctgaaa  480
ggagtggccg acaacactca tgctctgcag accggcgatt ttaggacacc cgctgagctg  540
gcactgaata agttcgaaaa agagagtgga cacattcgaa accagcgggg cgactattca  600
catacettca accgcaagga tctgcaggcc gagctgaatc tgctgtttga aaagcagaaa  660
gagttcggga atccccacgt gtccgacggg ctgaaagaag gaatcgagac actgctgatg  720
actcagaggc ctgcactgtc tggcgatgcc gtgcagaaga tgctggggca ttgcaccttt  780
gaaccaacag agcccaaggc agccaaaaac acctacacag ccgagaggtt cgtgtggctg  840
acaaagctga acaatctgcg catcctggaa cagggcagtg agcggcccct gactgacacc  900
gaaagagcca cactgatgga tgagccttac aggaagtcta aactgactta tgcccaggct  960
cgcaagctgc tggacctgga cgatactgcc ttctttaagg gcctgaggta cgggaaagat  1020
aatgcagaag ccagcaccct gatggagatg aaggcctatc acgctatctc ccgcgccctg  1080
gaaaaagagg gcctgaagga caagaaatct cccctgaacc tgagtcctga actgcaggat  1140
gagattggga ccgcttttag cctgttcaag actgacgagg atatcaccgg acgcctgaaa  1200
gaccgagtgc agcccgaaat tctggaggca ctgctgaagc acatcagttt tgataaattc  1260
gtgcagattt cactgaaggc cctgcgacgg atcgtccctc tgatggagca gggcaatcgg  1320
tacgacgagg cctgcaccga gatctacgga gatcattatg gcaagaaaaa cacagaagag  1380
aaaatctatc tgccccctat tcctgccgac gagatccgga atccagtggt cctgagagct  1440
ctgtcacagg caagaaaagt gatcaacgga gtggtcagaa ggtacggcag ccctgctagg  1500
atccacattg aaaccgcacg cgaagtggga aagtccttta aagaccgcaa ggaaatcgag  1560
aagcgacagg aagagaatag aaaagatagg gaaaagtctg ctgcaaaatt cagggagtac  1620
tttccaaact tcgtgggcga acccaagagt aaagacatcc tgaagctgcg cctgtacgag  1680
cagcagcacg ggaagtgtct gtatagcgga aaagaaatta acctgggccg gctgaatgaa  1740
aagggctatg tggagatcga tcatgcactg ccctttcca gaacatggga cgattctttc  1800
aacaataagg tcctggctct ggggagcgag aaccagaaca agggaaatca gactccttac  1860
gaatatttca acgggaagga caatagccga gaatggcagg agtttaaagc ccgcgtggag  1920
acaagccggt tcccacgaag caagaaacag cggattctgc tgcagaagtt tgacgaagat  1980
ggattcaaag agagaaacct gaatgacacc cggtacatca acagatttct gtgccagttc  2040
gtggctgatc acatgctgct gaccggaaag ggcaaacgcc gagtctttgc aagcaacggc  2100
cagatcacaa atctgctgag gggcttctgg gggctgcgga aggtgagagc cgagaatgac  2160
cgccaccatg cactggatgc cgtggtcgtg gcttgttcca ctattgcaat gcagcagaag  2220
atcaccaggt ttgtgcgcta taaagagatg aacgccttcg acggaaagac aattgataaa  2280
gaaactggcg aggtgctgca ccagaaggca cattttcctc agccatggga gttcttcgcc  2340
caggaagtga tgatccgggt ctttgggaag cctgacggaa aaccagagtt cgaagaggcc  2400
gataccccag aaaagctgcg gacactgctg gctgaaaaac tgagctccag acccgaggca  2460
gtgcacaagt acgtcacccc cctgttcatt agcagggccc ctaatcgcaa aatgtccggg  2520
cagggacata tggagactgt gaaatcagct aagcggctgg acgaaggcat cagcgtgctg  2580
agagtcccac tgacccagct gaagctgaaa gatctggaga agatggtgaa ccgggaaaga  2640
gagcccaagc tgtatgaagc tctgaaagca agactggagg cccacaagga cgatccagct  2700
aaagcatttg ccgagccctt ctacaaatat gacaaggccg gcaatcggac acagcaggtg  2760
aaggctgtca gagtggagca ggtccagaaa actggggtct gggtgcacaa ccataatgga  2820
attgccgaca acgctacaat cgtccgggtg gatgtgttcg agaaaggcgg gaagtactat  2880
ctggtgccta tctactcctg gcaggtcgcc aagggaatcc tgccagatag agctgtcgtg  2940
cagggcaaag acgaagagga ttggactgtg atggacgatt ctttcgagtt taagttcgtc  3000
ctgtacgcaa acgacctgat caagctgaca gccaagaaaa atgaatttct ggggtatttc  3060
gtgtcactga acagggcaac tggagccatc gatattcgca cacatgacac tgatagcacc  3120
aagggaaaaa acggcatctt tcagtctgtg ggcgtcaaga ccgccctgag tttccagaaa  3180
tatcagattg acgaactggg gaaggagatc cgaccctgtc ggctgaagaa acgaccaccc  3240
gtgcggtaa                                                          3249

SEQ ID NO: 21          moltype = DNA  length = 3294
FEATURE                Location/Qualifiers
source                 1..3294
                       mol_type = genomic DNA
                       organism = Staphylococcus aureus
SEQUENCE: 21
aagcggaact acatcctggg cctggacatc ggcatcacca gcgtgggcta cggcatcatc  60
gactacgaga cacgggacgt gatcgatgcc ggcgtgcggc tgttcaaaga ggccaacgtg  120
gaaaacaacg agggcaggcg gagcaagaga ggcgccagaa ggctgaagcg gcggaggcgg  180
catagaatcc agagagtgaa gaagctgctg ttcgactaca acctgctgac cgaccacagc  240
gagctgagcg gcatcaaccc ctacgaggcc agagtgaagg gcctgagcca gaagctgagc  300
gaggaagagt tctctgccgc cctgctgcac ctggccaaga gaagaggcgt gcacaacgtg  360
aacgaggtgg aagaggacac cggcaacgag ctgtccacca aagagcagat cagccggaac  420
agcaaggccc tggaagagaa atacgtggcc gaactgcagc tggaacggct gaagaaagac  480
ggcgaagtgc ggggcagcat caacagattc aagaccagcg actacgtgaa agaagccaaa  540
cagctgctga aggtgcagaa ggcctaccac cagctggacc agagcttcat cgacacctac  600
atcgacctgc tggaaacccg gcggacctac tatgagggac ctggcgaggg cagccccttc  660
```

```
ggctggaagg acatcaaaga atggtacgag atgctgatgg gccactgcac ctacttcccc  720
gaggaactgc ggagcgtgaa gtacgcctac aacgccgacc tgtacaacgc cctgaacgac  780
ctgaacaatc tcgtgatcac cagggacgag aacgagaagc tggaatatta cgagaagttc  840
cagatcatcg agaacgtgtt caagcagaag aagaagccca ccctgaagca gatcgccaaa  900
gaaatcctcg tgaacgaaga ggatattaag ggctacagag tgaccagcac cggcaagccc  960
gagttcacca acctgaaggt gtaccacgac atcaaggaca ttaccgcccg gaaagagatt  1020
attgagaacg ccgagctgct ggatcagatt gccaagatcc tgaccatcta ccagagcagc  1080
gaggacatcc aggaagaact gaccaatctg aactccgagc tgacccagga agagatcgag  1140
cagatctcta atctgaaggg ctataccggc acccacaacc tgagcctgaa ggccatcaac  1200
ctgatcctgg acgagctgtg gcacaccaac gacaaccaga tcgctatctt caaccggctg  1260
aagctggtgc ccaagaaggt ggacctgtcc cagcagaaag agatccccac caccctggtg  1320
gacgacttca tcctgagccc cgtcgtgaag agaagcttca tccagagcat caaagtgatc  1380
aacgccatca tcaagaagta cggcctgccc aacgacatca ttatcgagct ggcccgcgag  1440
aagaactcca aggacgccca gaaaatgatc aacgagatgc agaagcggaa ccggcagacc  1500
aacgagcgga tcgaggaaat catccggacc accggcaaag agaacgccaa gtacctgatc  1560
gagaagatca agctgcacga catgcaggaa ggcaagtgcc tgtacagcct ggaagccatc  1620
cctctggaag atctgctgaa caaccccttc aactatgagg tggaccacat catccccaga  1680
agcgtgtcct tcgacaacag cttcaacaac aaggtgctcg tgaagcagga agaaaacagc  1740
aagaagggca accggacccc attccagtac ctgagcagca gcgacagcaa gatcagctac  1800
gaaaccttca agaagcacat cctgaatctg gccaagggca agggcagaat cagcaagacc  1860
aagaaagagt atctgctgga agaacgggac atcaacaggt tctccgtgca gaaagacttc  1920
atcaaccgga acctggtgga taccagatac gccaccagag gcctgatgaa cctgctgcgg  1980
agctacttca gagtgaacaa cctggacgtg aaagtgaagt ccatcaatgg cggcttcacc  2040
agctttctgc ggcggaagtg gaagtttaag aaagagcgga acaaggggta caagcaccac  2100
gccgaggacg ccctgatcat tgccaacgcc gatttcatct tcaaagagtg gaagaaactg  2160
gacaaggcca aaaaagtgat ggaaaaccag atgttcgagg aaaagcaggc cgagagcatg  2220
cccgagatcg aaaccgagca ggagtacaaa gagatcttca tcacccccca ccagatcaag  2280
cacattaagg acttcaagga ctacaagtac agccaccggg tggacaagaa gcctaataga  2340
gagctgatta acgacaccct gtactccacc cggaaggacg acaagggcaa caccctgatc  2400
gtgaacaatc tgaacggcct gtacgacaag gacaatgaca agctgaaaaa gctgatcaac  2460
aagagccccg aaaagctgct gatgtaccac cacgaccccc agacctacca gaaactgaag  2520
ctgattatgg aacagtacgg cgacgagaag aatcccctgt acaagtacta cgaggaaacc  2580
gggaactacc tgaccaagta ctccaaaaag gacaacggcc ccgtgatcaa gaagattaag  2640
tattacggca acaaactgaa cgcccatctg gacatcaccg acgactaccc caacagcaga  2700
aacaaggtcg tgaagctgtc cctgaagccc tacagattcg acgtgtacct ggacaatggc  2760
gtgtacaagt tcgtgaccgt gaagaatctg gatgtgatca aaaaagaaaa ctactacgaa  2820
gtgaatagca agtgctatga ggaagctaag aagctgaaga agatcagcaa ccaggccgag  2880
tttatcgcct ccttctacaa caacgatctg atcaagatca acggcgagct gtatagagtg  2940
atcggcgtga acaacgacct gctgaaccgg atcgaagtga acatgatcga catcacctac  3000
cgcgagtacc tggaaaacat gaacgacaag aggcccccca ggatcattaa gacaatcgcc  3060
tccaagaccc agagcattaa gaagtacagc acagacattc tgggcaacct gtatgaagtg  3120
aaatctaaga agcaccctca gatcatcaaa aagggcaaaa ggccggcggc cacgaaaaag  3180
gccggccagg caaaaaagaa aaagggatcc tacccatacg atgttccaga ttacgcttac  3240
ccatacgatg ttccagatta cgcttaccca tacgatgttc cagattacgc ttaa        3294

SEQ ID NO: 22           moltype = DNA  length = 3012
FEATURE                 Location/Qualifiers
source                  1..3012
                        mol_type = genomic DNA
                        organism = Campylobacter lari
SEQUENCE: 22
atgaggattc tggggtttga cattggcatt aacagcatcg ggtgggcttt tgtggagaac  60
gacgaactga aggactgcgg agtgcggatc ttcacaaagg ccgagaaccc aaaaaataag  120
gaaagcctgg cactgccccg gagaaatgca cgcagctcca ggcgccgact gaaacggaga  180
aaggcccggc tgatcgctat taagagaatc ctggccaaag agctgaagct gaactacaag  240
gactatgtcg cagctgatgg agagctgcca aaggcctacg aaggatccct ggcatctgtg  300
tacgagctgc ggtataaggc cctgacacag aacctggaaa ctaaagatct ggccagagtg  360
atcctgcaca ttgctaagca taggggtac atgaacaaga acgagaagaa atcaaacgac  420
gctaagaaag gaaagatcct gagcgctctg aaaaacaatg cactgaagct ggagaactac  480
cagagcgtgg gcgaatactt ctacaaggag ttctttcaga aatacaagaa aaacacaaag  540
aacttcatca agatccgcaa cactaaggat aattacaaca attgcgtgct gtctagtgac  600
ctggaaaaag agctgaagct gatcctggaa aaacagaagg agttcggcta caactactct  660
gaagatttca tcaacgagat tctgaaggtc gccttctttc agcggcccct gaaggacttc  720
agtcacctgg tgggggcctg cactttcttt gaggaagaga aaagggcctg taagaacagc  780
tactctgcct gggagtttgt ggctctgacc aagatcatta acgagatcaa gagcctggag  840
aagatcagcg gcgaaattgt gccaacccag acaatcaacg aggtcctgaa tctgatcctg  900
gacaaggggt ctatcaccta caagaaattc agaagttgta tcaatctgca tgagagtatc  960
agcttcaaga gcctgaagta tgataaagaa aacgccgaga atgctaaact gatcgacttc  1020
cgcaagctgg tggagtttaa gaaagccctg ggagtccaca gcctgtcccg gcaggaactg  1080
gatcagatct ccactcatat caccctgatt aaggacaacg tgaagctgaa aaccgtcctg  1140
gagaaataca acctgagtaa tgaacagatc aacaatctgc tggaaattga gttcaacgat  1200
tatatcaacc tgagcttcaa ggccctggga atgattctgc cactgatgcg cgagggcaaa  1260
cgatacgacg aggcctgcga gatcgccaat ctgaaaccta agaccgtgga cgagaagaaa  1320
gatttcctgc cagcattttg tgattccatt ttcgcccacg agctgtctaa ccccgtggtc  1380
aatagggcta tcagcgaata ccgcaaggtg ctgaacgcac tgctgaagaa atatggaaag  1440
gtccacaaaa ttcatctgga gctggctcgc gacgtgggcc tgtccaagaa agcacgagag  1500
aagatcgaaa aagagcagaa ggaaaaccag gccgtgaatg catgggccct gaaggaatgc  1560
gagaatattg gcctgaaggc cagcgcaaag aacatcctga aactgaagct gtggaaagaa  1620
cagaaggaga tctgtatcta ctccggaaat aagatctcta ttgagcacct gaaagatgaa  1680
```

```
aaggccctgg aggtggacca tatctacccc tattctagga gtttcgacga ttcttttatc  1740
aacaaagtgc tggtgttcac caaggaaaat caggagaaac tgaacaagac acctttcgag  1800
gcctttggca agaatattga aaaatggagc aagatccaga ccctggctca gaacctgcca  1860
tacaagaaaa agaataagat tctggacgag aacttcaaag ataagcagca ggaggacttt  1920
atctctcgaa atctgaacga caccggtat atcgctacac tgattgcaaa atacacaaag  1980
gagtatctga acttcctgct gctgagcgaa aatgagaacg ccaatctgaa gagtggcgaa  2040
aaagggtcaa agatccacgt gcagactatt agcgggatgc tgacctccgt cctgaggcac  2100
acatgggggt ttgacaaaaa ggatcgcaac aatcatctgc accatgcact ggatgccatc  2160
attgtggcct acagtacaaa ttcaatcatt aaggctttca gcgatttccg gaaaaaccag  2220
gagctgctga aggccagatt ctacgctaaa gaactgactt ccgataacta taaacatcag  2280
gtcaagttct ttgagccttt caagagtttt agagaaaaaa tcctgtcaaa gatcgacgag  2340
attttcgtgt ccaaaccacc tcgaaagcga gctaggcgcg cactgcacaa ggataccttt  2400
cattctgaga acaagatcat tgacaagtgc agctacaact ccaaggaagg cctgcagatt  2460
gccctgagct gtggaagagt gaggaaaatc ggcactaagt atgtcgagaa tgataccatc  2520
gtgagggtcg acattttcaa aaagcagaac aagttttacg ctatcccaat ctacgcaatg  2580
gattttgccc tggggatcct gcccaataag atcgtgatta ctggaaaaga taagaacaat  2640
aaccccaaac agtggcagac cattgacgaa tcatacgagt tctgctttag cctgtataag  2700
aatgacctga tcctgctgca gaaaaagaac atgcaggaac ctgagttcgc ctactataac  2760
gatttttcaa tcagcacatc aagcatttgt gtggagaaac acgacaacaa gttcgaaaat  2820
ctgactagca accagaagct gctgttttcc aatgcaaaag agggctctgt gaaggtcgaa  2880
agtctgggga tccagaacct gaaagtgttc gagaagtaca tcattacccc cctgggagat  2940
aaaattaagg ctgactttca gcctcgagaa aacatcagcc tgaaaaccag taaaaagtat  3000
ggcctgaggt aa                                                       3012
```

```
SEQ ID NO: 23           moltype = DNA  length = 16386
FEATURE                 Location/Qualifiers
source                  1..16386
                        mol_type = other DNA
                        organism = synthetic construct
                        note = Vektor1_TaU6
misc_difference         16239
                        note = misc_feature - a, c, g, or t
misc_difference         16240
                        note = misc_feature - a, c, g, or t
misc_difference         16241
                        note = misc_feature - a, c, g, or t
misc_difference         16242
                        note = misc_feature - a, c, g, or t
misc_difference         16243
                        note = misc_feature - a, c, g, or t
misc_difference         16244
                        note = misc_feature - a, c, g, or t
misc_difference         16245
                        note = misc_feature - a, c, g, or t
misc_difference         16246
                        note = misc_feature - a, c, g, or t
misc_difference         16247
                        note = misc_feature - a, c, g, or t
misc_difference         16248
                        note = misc_feature - a, c, g, or t
misc_difference         16249
                        note = misc_feature - a, c, g, or t
misc_difference         16250
                        note = misc_feature - a, c, g, or t
misc_difference         16251
                        note = misc_feature - a, c, g, or t
misc_difference         16252
                        note = misc_feature - a, c, g, or t
misc_difference         16253
                        note = misc_feature - a, c, g, or t
misc_difference         16254
                        note = misc_feature - a, c, g, or t
misc_difference         16255
                        note = misc_feature - a, c, g, or t
misc_difference         16256
                        note = misc_feature - a, c, g, or t
misc_difference         16257
                        note = misc_feature - a, c, g, or t
misc_difference         16258
                        note = misc_feature - a, c, g, or t
SEQUENCE: 23
ttgtacaaag tggttcgata attccgatcc agcctaggcc cgggcctgag gacgcgcctt  60
actagtggat cccttcaccg ccattgcaaa aattgtcaat aaatatttag agtgggtggc  120
atcagaaaaa catctctagt ggactctctt cctatcatag ctactcgggc tgtagataga  180
acgagggcac aagagttggg tggcgtaggt ttactcgtga cctcaactct tttggctgtg  240
tcttacgtct aagatgggtt tggcatgtga gaaacatagg tctaagcaat tcatgttagg  300
gctgttgcat tgttgttgca tcaaccaaat gtccagatag cagttcatgc tacatctagt  360
tgaaaaccct catcattagg cggaacatgt gttctttttt agcatagtca aagtcagatt  420
gcggcactcg ctcatccacg gaaagaattt tccctgtgca ggcatctcga tcaaaagacg  480
```

-continued

```
caaattaatt tttgaatagc gatataacaa tatctaatta acgtttcttg ttttctgcga  540
aatgtctttc atcataaaat gagtcatctc gatgagccca agtgacatag cccaacaccc  600
caccccacca ataaaagtga agaaaacatg ttgggaaaac tataccaagt aaaatacgag  660
ttgttctaaa gaaaaagtaa agtacgagtt agatcgcacc ctgtcctgga gtgtggcttg  720
atgatccaac tcctagcatt gtatccctgt ttttggatga tgtaactatt atttacaatg  780
aataaagagg tgttttacta gtaaaaaaat cttgagggga ggagaaaata atggaggtct  840
tttttcaaac cgatggacta ttatttttag tgaaagagaa taatattatt ggaaaaatta  900
ttctatccac ttattttata ttggcagaat acaaagaatg gtggggtcca cgcggaactt  960
gcggcccccg aaacctatcg agggcgcggt acccaagcaa ggaacggagg aaacttgcgg  1020
ggcccgaaac ctagtgataa aaggcatatc atccacacga tgaagatctg acggaccata  1080
tctcccacca cggaaagcca tcagacgagg atcagacggc caggaaggaa ccctagcgcc  1140
cgccggtgcc aatataaagc gccactctct ctcgtcttaa gccccagcct ctccattccc  1200
ctctccctct cgattacgag gtgtgttgtt catccgtccc gaatccatcc atcccctctt  1260
cagatgtgtt gttcatggct ctaatagctc tagatctgct tgtttgtgtt gtttagctct  1320
agatctactc gcgcgcgctt ctctctcgat ctcctgtaga acaattttgg ttggtttttt  1380
gtgcatatcc atggtaattt tgtctgcaat atggaggagg ctttctaagc tcctacgtag  1440
catcgatctt tagaattccc tcggtttctg tttatttctt cgcgagggct ctctgttatc  1500
tgtaggagta gctgtaagcg cggttcgtta cggattaatc gtcatgctta gttgaaccta  1560
tcggtcgaag gatttgtgtg ggttgtcgtg tagaattgac accatctact tactgtactg  1620
atatgccgat ctgtaggata ctcttcatta cttttgttta ctgctagttg tggtgtagat  1680
ttagcattct caaacccatg ctgtagcgtt tctaatattg ttacatagat ctaccggtgc  1740
ctgttaattg tattcgatcg ggcgtttcta catctgtccg cccacctagt tttatatgtg  1800
gtaatcaaaa ttgcgttgac ttcgtgatgc tgtctgtgta ctgtttttaa tcgctcttac  1860
ttagatgatc aacatggtga tggttacgat ttactgtttt ctaatccctg ttacttcgat  1920
gctgcagttt gattgatggg cccagaacga cgcccggccg acatccgccg tgccaccgag  1980
gcggacatgc cggcggtctg caccatcgtc aaccactaca tcgagacaag cacggtcaac  2040
ttccgtaccg agccgcagga accgcaggag tggacggacg acctcgtccg tctgcgggag  2100
cgctatccct ggctcgtcgc cgaggtggac ggcgaggtcg ccggcatcgc ctacgcgggc  2160
ccctggaagg cacgcaacgc ctacgactgg acggccgagt cgaccgtgta cgtctccccc  2220
cgccaccagc ggacgggact gggctccacg ctctacaccc acctgctgaa gtccctggag  2280
gcacagggct tcaagagcgt ggtcgctgtc atcgggctgc ccaacgaccc gagcgtgcgc  2340
atgcacgagg cgctcggata tgccccccgc ggcatgctgc gggcggccgg cttcaagcac  2400
gggaactggc atgacgtggg tttctggcag ctggacttca gcctgccggt accgccccgt  2460
ccggtcctgc ccgtcaccga gatctgaatg ccgaatttcc ccgatcgttc aaacatttgg  2520
caataaagtt tcttaagatt gaatcctgtt gccggtcttg cgatgattat catataattt  2580
ctgttgaatt acgttaagca tgtaataatt aacatgtaat gcatgacgtt atttatgaga  2640
tgggttttta tgattagagt cccgcaatta tacatttaat acgcgataga aaacaaaata  2700
tagcgcgcaa actaggataa attatcgcgc gcggtgtcat ctatgttact agatcgctcg  2760
aagatccccc gggctgcagg aattcaagct tggcactggc cgtcgtttta caacgtcgtg  2820
actgggaaaa ccctggcgtt acccaactta atcgccttgc agcacatccc cctttcgcca  2880
gctggcgtaa tagcgaagag gcccgcaccg atcgcccttc ccaacagttg cgcagcctga  2940
atggcgaatg agcttgagct tggatcagat tgtcgtttcc cgccttcagt ttaaactatc  3000
agtgtttgac aggatatatt ggcgggtaaa cctaagagaa aagagcgttt attagaataa  3060
cggatattta aaagggcgtg aaaaggttta tccgttcgtc catttgtatg tgcatgccaa  3120
ccacagggtt cccctcggga tcaaagtact ttgatccaac ccctccgctg ctatagtgca  3180
gtcggcttct gacgttcagt gcagccgtct tctgaaaacg acatgtcgca caagtcctaa  3240
gttacgcgac aggctgccgc cctgcccttt tcctggcgtt ttcttgtcgc gtgttttagt  3300
cgcataaagt agaatacttg cgactagaac cggagacatt acgccatgaa caagagcgcc  3360
gccgctggcc tgctgggcta tgcccgcgtc agcaccgacg accaggactt gaccaaccaa  3420
cgggccgaac tgcacgcggc cggctgcacc aagctgtttt ccgagaagat caccggcacc  3480
aggcgcgacc gcccggagct ggccaggatg cttgaccacc tacgccctgg cgacgttgtg  3540
acagtgacca ggctagaccg cctggcccgc agcacccgcg acctactgga cattgccgag  3600
cgcatccagg aggccggcgc gggcctgcgt agcctggcag agccgtgggc cgacaccacc  3660
acgccggccg gccgcatggt gttgaccgtg ttcgccggca ttgccgagtt cgagcgttcc  3720
ctaatcatcg accgcacccg gagcgggcgc gaggccgcca aggcccgagg cgtgaagttt  3780
ggcccccgcc ctaccctcac cccggcacag atcgcgcacg cccgcgagct gatcgaccag  3840
gaaggccgca ccgtgaaaga ggcggctgca ctgcttggcg tgcatcgctc gaccctgtac  3900
cgcgcacttg agcgcagcga ggaagtgacg cccaccgagg ccaggcggcg cggtgccttc  3960
cgtgaggacg cattgaccga ggccgacgcc ctggcggccg ccgagaatga acgccaagag  4020
gaacaagcat gaaaccgcac caggacggcc aggacgaacc gtttttcatt accgaagaga  4080
tcgaggcgga gatgatcgcg gccgggtacg tgttcgagcc gccccgcgcac gtctcaaccg  4140
tgcggctgca tgaaatcctg gccggtttgt ctgatgccaa gctggcggcc tggccggcca  4200
gcttggccgc tgaagaaacc gagcgccgcc gtctaaaaag gtgatgtgta tttgagtaaa  4260
acagcttgcg tcatgcggtc gctgcgtata tgatgcgatg agtaaataaa caaatacgca  4320
aggggaacgc atgaaggtta tcgctgtact taaccagaaa ggcgggtcag gcaagacgac  4380
catcgcaacc catctagccc gcgccctgca actcgccggg gccgatgttc tgttagtcga  4440
ttccgatccc cagggcagtg cccgcgattg ggcggccgtg cgggaagatc aaccgctaac  4500
cgttgtcggc atcgaccgcc cgacgattga ccgcgacgtg aaggccatcg gccggcgcga  4560
cttcgtagtg atcgacggag cgccccaggc ggcggacttg gctgtgtccg cgatcaaggc  4620
agccgacttc gtgctgattc cggtgcagcc aagcccttac gacatatggg ccaccgccga  4680
cctggtggag ctggttaagc agcgcattga ggtcacggat ggaaggctac aagcggcctt  4740
tgtcgtgtcg cgggcgatca aaggcacgcg catcggcggt gaggttgccg aggcgctggc  4800
cgggtacgag ctgcccattc ttgagtcccg tatcacgcag cgcgtgagct acccaggcac  4860
tgccgccgcc ggcacaaccg ttcttgaatc agaacccgag ggcgacgctg cccgcgaggt  4920
ccaggcgctg gccgctgaaa ttaaatcaaa actcatttga gttaatgagg taaagagaaa  4980
atgagcaaaa gcacaaacac gctaagtgcc ggccgtccga gcgcacgcag cagcaaggct  5040
gcaacgttgg ccagcctggc agacacgcca gccatgaagc gggtcaactt tcagttgccg  5100
gcggaggatc acaccaagct gaagatgtac gcggtacgcc aaggcaagac cattaccgag  5160
ctgctatctg aatacatcgc gcagctacca gagtaaatga gcaaatgaat aaatgagtag  5220
```

-continued

```
atgaatttta gcggctaaag gaggcggcat ggaaaatcaa gaacaaccag gcaccgacgc  5280
cgtggaatgc cccatgtgtg gaggaacggg cggttggcca ggcgtaagcg gctgggttgt  5340
ctgccggccc tgcaatggca ctggaacccc caagcccgag gaatcggcgt gacggtcgca  5400
aaccatccgg cccggtacaa atcggcgcgg cgctgggtga tgacctggtg gagaagttga  5460
aggccgcgca ggccgcccag cggcaacgca tcgaggcaga agcacgcccc ggtgaatcgt  5520
ggcaagcggc cgctgatcga atccgcaaag aatcccggca accgccggca gccggtgcgc  5580
cgtcgattag gaagccgccc aagggcgacg agcaaccaga tttttcgtt ccgatgctct  5640
atgacgtggg cacccgcgat agtcgcagca tcatggacgt ggccgttttc cgtctgtcga  5700
agcgtgaccg acgagctggc gaggtgatcc gctacgagct tccagacggg cacgtagagg  5760
tttccgcagg gccggccggc atggccagtg tgtgggatta cgacctggta ctgatggcgg  5820
tttcccatct aaccgaatcc atgaaccgat accgggaagg gaagggagac aagcccggcc  5880
gcgtgttccg tccacacgtt gcggacgtac tcaagttctg ccggcgagcc gatggcggaa  5940
agcagaaaga cgacctggta gaaacctgca ttcggttaaa caccacgcac gttgccatgc  6000
agcgtacgaa gaaggccaag aacggccgcc tggtgacggt atccgagggt gaagccttga  6060
ttagccgcta caagatcgta aagagcgaaa ccgggcggcc ggagtacatc gagatcgagc  6120
tagctgattg gatgtaccgc gagatcacag aaggcaagaa cccggacgtg ctgacggttc  6180
accccgatta ctttttgatc gatcccggca tcggccgttt tctctaccgc ctggcacgcc  6240
gcgccgcagg caaggcagaa gccagatggt tgttcaagac gatctacgaa cgcagtggca  6300
gcgccggaga gttcaagaag ttctgtttca ccgtgcgcaa gctgatcggg tcaaatgacc  6360
tgccggagta cgatttgaag gaggaggcgg ggcaggctgg cccgatccta gtcatgcgct  6420
accgcaacct gatcgagggc gaagcatccg ccggttccta atgtacggag cagatgctag  6480
ggcaaattgc cctagcaggg gaaaaaggtc gaaaaggtct ctttcctgtg gatagcacgt  6540
acattgggaa cccaaagccg tacattggga accggaaccc gtacattggg aacccaaagc  6600
cgtacattgg gaaccggtca cacatgtaag tgactgatat aaaagagaaa aaaggcgatt  6660
tttccgccta aaactcttta aaacttatta aaactcttaa aacccgcctg gcctgtgcat  6720
aactgtctgg ccagcgcaca gccgaagagc tgcaaaaagc gcctaccctt cggtcgctgc  6780
gctccctacg ccccgccgct tcgcgtcggc ctatcgcggc cgctggccgc tcaaaaatgg  6840
ctggcctacg gccaggcaat ctaccagggc gcggacaagc cgcgccgtcg ccactcgacc  6900
gccggcgccc acatcaaggc accctgcctc gcgcgtttcg gtgatgacgg tgaaaacctc  6960
tgacacatgc agctcccgga gacggtcaca gcttgtctgt aagcggatgc cgggagcaga  7020
caagcccgtc agggcgcgtc agcgggtgtt ggcgggtgtc ggggcgcagc catgacccag  7080
tcacgtagcg atagcggagt gtatactggc ttaactatgc ggcatcagag cagattgtac  7140
tgagagtgca ccatatgcgg tgtgaaatac cgcacagatg cgtaaggaga aaataccgca  7200
tcaggcgctc ttccgcttcc tcgctcactg actcgctgcg ctcggtcgtt cggctgcggc  7260
gagcggtatc agctcactca aaggcggtaa tacggttatc cacagaatca ggggataacg  7320
caggaaagaa catgtgagca aaaggccagc aaaaggccag gaaccgtaaa aaggccgcgt  7380
tgctggcgtt tttccatagg ctccgccccc ctgacgagca tcacaaaaat cgacgctcaa  7440
gtcagaggtg gcgaaacccg acaggactat aaagatacca ggcgtttccc cctggaagct  7500
ccctcgtgcg ctctcctgtt ccgaccctgc cgcttaccgg atacctgtcc gcctttctcc  7560
cttcgggaag cgtggcgctt tctcatagct cacgctgtag gtatctcagt tcggtgtagg  7620
tcgttcgctc caagctgggc tgtgtgcacg aaccccccgt tcagcccgac cgctgcgcct  7680
tatccggtaa ctatcgtctt gagtccaacc cggtaagaca cgacttatcg ccactggcag  7740
cagccactgg taacaggatt agcagagcga ggtatgtagg cggtgctaca gagttcttga  7800
agtggtggcc taactacggc tacactagaa ggacagtatt tggtatctgc gctctgctga  7860
agccagttac cttcggaaaa agagttggta gctcttgatc cggcaaacaa accaccgctg  7920
gtagcggtgg tttttttgtt tgcaagcagc agattacgcg cagaaaaaaa ggatctcaag  7980
aagatccttt gatcttttct acggggtctg acgctcagtg gaacgaaaac tcacgttaag  8040
ggattttggt catgcatgat atatctccca atttgtgtag ggcttattat gcacgcttaa  8100
aaataataaa agcagacttg acctgatagt ttggctgtga gcaattatgt gcttagtgca  8160
tctaatcgct tgagttaacg ccggcgaagc ggcgtcggct tgaacgaatt tctagctaga  8220
cattatttgc cgactacctt ggtgatctcg cctttcacgt agtggacaaa ttcttccaac  8280
tgatctgcgc gcgaggccaa gcgatcttct tcttgtccaa gataagcctg tctagcttca  8340
agtatgacgg gctgatactg ggccggcagg cgctccattg cccagtcggc agcgacatcc  8400
ttcggcgcga ttttgccggt tactgcgctg taccaaatgc gggacaacgt aagcactaca  8460
tttcgctcat cgccagccca gtcgggcggc gagttccata gcgttaaggt ttcatttagc  8520
gcctcaaata gatcctgttc aggaaccgga tcaaagagtt cctccgccgc tggacctacc  8580
aaggcaacgc tatgttctct tgcttttgtc agcaagatag ccagatcaat gtcgatcgtg  8640
gctggctcga agatacctgc aagaatgtca ttgcgctgcc attctccaaa ttgcagttcg  8700
cgcttagctg gataacgcca cggaatgatg tcgtcgtgca caacaatggt gacttctaca  8760
gcgcggagaa tctcgctctc tccaggggaa gccgaagttt ccaaaaggtc gttgatcaaa  8820
gctcgccgcg ttgtttcatc aagccttacg gtcaccgtaa ccagcaaatc aatatcactg  8880
tgtggcttca ggccgccatc cactgcggag ccgtacaaat gtacggccag caacgtcggt  8940
tcgagatggc gctcgatgac gccaactacc tctgatagtt gagtcgatac ttcggcgatc  9000
accgcttccc ccatgatgtt taactttgtt ttagggcgac tgccctgctg cgtaacatcg  9060
ttgctgctcc ataacatcaa acatcgaccc acggcgtaac gcgcttgctg cttggatgcc  9120
cgaggcatag actgtacccc aaaaaaacat gtcataacaa gaagccatga aaaccgccac  9180
tgcgccgtta ccaccgctgc gttcggtcaa ggttctggac cagttgcgtg acggcagtta  9240
cgctacttgc attacagctt acgaaccgaa cgaggcttat gtccactggg ttcgtgcccg  9300
aattgatcac aggcagcaac gctctgtcat cgttacaatc aacatgctac cctccgcgag  9360
atcatccgtg tttcaaaccc ggcagcttag ttgccgttct tccgaatagc atcggtaaca  9420
tgagcaaagt ctgccgcctt acaacggctc tcccgctgac gccgtcccgg actgatgggc  9480
tgcctgtatc gagtggtgat tttgtgccga gctgccggtc ggggagctgt tggctggctg  9540
gtggcaggat atattgtggt gtaaacaaat tgacgcttag acaacttaat aacacattgc  9600
ggacgttttt aatgtactga attaacgccg aattgctcta gccaatacgc aaaccgcctc  9660
tccccgcgcg ttggccgatt cattaattgc agcgtgaccc ggtcgtgccc ctctctagag  9720
ataatgagca ttgcatgtct aagttataaa aaattaccac atattttttt tgtcacactt  9780
gtttgaagtg cagtttatct atctttatac atatatttaa actttactct acgaataata  9840
taatctatag tactacaata atatcagtgt tttagagaat catataaatg aacagttaga  9900
catggtctaa aggacaattg agtattttga caacaggact ctacagtttt atctttttag  9960
```

```
tgtgcatgtg ttctcctttt tttttgcaaa tagcttcacc tatataatac ttcatccatt  10020
ttattagtac atccatttag ggtttagggt taatggtttt tatagactaa ttttttttagt  10080
acatctattt tattctattt tagcctctaa attaagaaaa ctaaaactct attttagttt  10140
ttttatttaa taatttagat ataaaataga ataaaataaa gtgactaaaa attaaacaaa  10200
taccctttaa gaaattaaaa aaactaagga aacattttc ttgtttcgag tagataatgc  10260
cagcctgtta aacgccgtcg atcgacgagt ctaacggaca ccaaccagcg aaccagcagc  10320
gtcgcgtcgg gccaagcgaa gcagacggca cggcatctct gtcgctgcct ctggacccct  10380
ctcgagagtt ccgctccacc gttggacttg ctccgctgtc ggcatccaga aattgcgtgg  10440
cggagcggca gacgtgagcc ggcacggcag gcggcctcct cctcctctca cggcaccggc  10500
agctacgggg gattcctttc ccaccgctcc ttcgctttcc cttcctcgcc cgccgtaata  10560
aatagacacc ccctccacac cctctttccc caacctcgtg ttgttcggag cgcacacaca  10620
cacaaccaga tctcccccaa atccacccgt cggcacctcc gcttcaaggt acgccgctcg  10680
tcctcccccc ccccccctct ctaccttctc tagatcggcg ttccggtcca tggttagggc  10740
ccggtagttc tacttctgtt catgtttgtg ttagatccgt gtttgtgtta gatccgtgct  10800
gctagcgttc gtacacggat gcgacctgta cgtcagacac gttctgattg ctaacttgcc  10860
agtgtttctc tttggggaat cctgggatgg ctctagccgt tccgcagacg ggatcgatct  10920
aggataggta tacatgttga tgtgggtttt actgatgcat atacatgatg gcatatgcag  10980
catctattca tatgctctaa ccttgagtac ctatctatta taataaacaa gtatgtttta  11040
taattatttt gatcttgata tacttggatg atggcatatg cagcagctat atgtggattt  11100
ttttagccct gccttcatac gctatttatt tgcttggtac tgtttctttt gtcgatgctc  11160
accctgttgt ttggtgttac ttctgcaggg gtaccgccat ggataagaag tactctatcg  11220
gactcgatat cggaactaac tctgtgggat gggctgtgat caccgatgag tacaaggtgc  11280
catctaagaa gttcaaggtt ctcggaaaca ccgataggca ctctatcaag aaaaacctta  11340
tcggtgctct cctcttcgat tctggtgaaa ctgctgaggc taccagactc aagagaaccg  11400
ctagaagaag gtacaccaga agaaagaaca ggatctgcta cctccaagag atcttctcta  11460
acgagatggc taaagtggat gattcattct tccacaggct cgaagagtca ttcctcgtgg  11520
aagaagataa gaagcacgag aggcacccta tcttcggaaa catcgttgat gaggtggcat  11580
accacgagaa gtaccctact atctaccacc tcagaaagaa gctcgttgat tctactgata  11640
aggctgatct caggctcatc tacctcgctc tcgctcacat gatcaagttc agaggacact  11700
tcctcatcga gggtgatctc aaccctgata actctgatgt ggataagttg ttcatccagc  11760
tcgtgcagac ctacaaccag cttttcgaag agaaccctat caacgcttca ggtgtggatg  11820
ctaaggctat cctctctgct aggctctcta agtcaagaag gcttgagaac ctcattgctc  11880
agctccctgg tgagaagaag aacggacttt tcggaaactt gatcgctctc tctctcggac  11940
tcacccctaa cttcaagtct aacttcgatc tcgctgagga tgcaaagctc cagctctcaa  12000
aggataccta cgatgatgat ctcgataacc tcctcgctca gatcggagat cagtacgctg  12060
atttgttcct cgctgctaag aacctctctg atgctatcct cctcagtgat atcctcagag  12120
tgaacaccga gatcaccaag gctccactct cagcttctat gatcaagaga tacgatgagc  12180
accaccagga tctcacactt ctcaaggctc ttgttagaca gcagctccca gagaagtaca  12240
aagagatttt cttcgatcag tctaagaacg gatacgctgg ttacatcgat ggtggtgcat  12300
ctcaagaaga gttctacaag ttcatcaagc ctatcctcga gaagatggat ggaaccgagg  12360
aactcctcgt gaagctcaat agagaggatc ttctcagaaa gcagaggacc ttcgataacg  12420
gatctatccc tcatcagatc cacctcggag agttgcacgc tatccttaga aggcaagagg  12480
atttctaccc attcctcaag gataacaggg aaaagattga gaagattctc accttcagaa  12540
tcccttacta cgtgggacct ctcgctagag gaaactcaag attcgcttgg atgaccagaa  12600
agtctgagga aaccatcacc ccttggaact tcgaagaggt ggtggataag ggtgctagtg  12660
ctcagtcttt catcgagagg atgaccaact tcgataagaa ccttccaaac gagaaggtgc  12720
tccctaagca ctctttgctc tacgagtact tcaccgtgta caacgagttg accaaggtta  12780
agtacgtgac cgagggaatg aggaagcctg cttttttgtc aggtgagcaa aagaaggcta  12840
tcgttgatct cttgttcaag accaacagaa aggtgaccgt gaagcagctc aaagaggatt  12900
acttcaagaa aatcgagtgc ttcgattcag ttgagatttc tggtgttgag gataggttca  12960
acgcatctct cggaacctac cacgatctcc tcaagatcat taaggataag gatttcttgg  13020
ataacgagga aaacgaggat atcttggagg atatcgttct taccctcacc ctctttgaag  13080
atagagagat gattgaagaa aggctcaaga cctacgctca tctcttcgat gataaggtga  13140
tgaagcagtt gaagagaaga agatacactg gttggggaag gctctcaaga aagctcatta  13200
acggaatcag ggataagcag tctggaaaga caatccttga tttcctcaag tctgatggat  13260
tcgctaacag aaacttcatg cagctcatcc acgatgattc tctcaccttt aaagaggata  13320
tccagaaggc tcaggtttca ggacagggtg atagtctcca tgagcatatc gctaacctcg  13380
ctggatctcc tgcaatcaag aagggaatcc tccagactgt gaaggttgtg gatgagttgg  13440
tgaaggtgat gggaaggcat aagcctgaga acatcgtgat cgaaatggct agagagaacc  13500
agaccactca gaagggacag aagaactcta gggaaaggat gaagaggatc gaggaaggta  13560
tcaaagagct tggatctcag atcctcaaag agcaccctgt tgagaacact cagctccaga  13620
atgagaagct ctacctctac tacctccaga acggaaggga tatgtatgtg gatcaagagt  13680
tggatatcaa caggctctct gattacgatg ttgatcatat cgtgccacag tcattcttga  13740
aggatgattc tatcgataac aaggtgctca ccaggtctga taagaacagg ggtaagagtg  13800
ataacgtgcc aagtgaagag gttgtgaaga aaatgaagaa ctattggagg cagctcctca  13860
acgctaagct catcactcag agaaagttcg ataacttgac taaggctgag aggggaggac  13920
tctctgaatt ggataaggca ggattcatca agaggcagct tgtggaaacc aggcagatca  13980
ctaagcacgt tgcacagatc ctcgattcta ggatgaacac caagtacgat gagaacgata  14040
agttgatcag ggaagtgaag gttatcaccc tcaagtcaaa gctcgtgtct gatttcagaa  14100
aggatttcca attctacaag gtgagggaaa tcaacaacta ccaccacgct cacgatgctt  14160
accttaacgc tgttgttgga accgctctca tcaagaagta tcctaagctc gagtcagagt  14220
tcgtgtacgg tgattacaag gtgtacgatg tgaggaagat gatcgctaag tctgagcaag  14280
agatcggaaa ggctaccgct aagtatttct tctactctaa catcatgaat ttcttcaaga  14340
ccgagattac cctcgctaac ggtgagatca gaaagaggcc actcatcgag acaaacggtg  14400
aaacaggtga gatcgtgtgg gataagggaa gggatttcgc taccgttaga aaggtgctct  14460
ctatgccaca ggtgaacatc gttaagaaaa ccgaggtgca gaccggtgga ttctctaaag  14520
agtctatcct ccctaagagg aactctgata agctcattgc taggaagaag gattgggacc  14580
ctaagaaata cggtggtttc gattctccta ccgtggctta ctctgttctc gttgtggcta  14640
aggttgagaa gggaaagagt aagaagctca agtctgttaa ggaacttctc ggaatcacta  14700
```

```
tcatggaaag gtcatctttc gagaagaacc caatcgattt cctcgaggct aagggataca  14760
aagaggttaa gaaggatctc atcatcaagc tcccaaagta ctcactcttc gaactcgaga  14820
acggtagaaa gaggatgctc gcttctgctg gtgagcttca aaagggaaac gagcttgctc  14880
tcccatctaa gtacgttaac tttctttacc tcgcttctca ctacgagaag ttgaagggat  14940
ctccagaaga taacgagcag aagcaacttt tcgttgagca gcacaagcac tacttggatg  15000
agatcatcga gcagatctct gagttctcta aaagggtgat cctcgctgat gcaaacctcg  15060
ataaggtgtt gtctgcttac aacaagcaca gagataagcc tatcagggaa caggcagaga  15120
acatcatcca tctcttcacc cttaccaacc tcggtgctcc tgctgctttc aagtacttcg  15180
atacaaccat cgataggaag agatacacct ctaccaaaga agtgctcgat gctaccctca  15240
tccatcagtc tatcactgga ctctacgaga ctaggatcga tctctcacag ctcggtggtg  15300
attcaagggc tgatcctaag aagaagagga aggtttgagg cgcgccgagc tccaggcctc  15360
ccagctttcg tccgtatcat cggtttcgac aacgttcgtc aagttcaatg catcagtttc  15420
attgcccaca caccagaatc ctactaagtt tgagtattat ggcattggaa aagctgtttt  15480
cttctatcat ttgttctgct tgtaatttac tgtgttcttt cagtttttgt tttcggacat  15540
caaaatgcaa atggatggat aagagttaat aaatgatatg gtccttttgt tcattctcaa  15600
attattatta tctgttgttt ttactttaat gggttgaatt taagtaagaa aggaactaac  15660
agtgtgatat taaggtgcaa tgttagacat ataaaacagt ctttcacctc tctttggtta  15720
tgtcttgaat tggtttgttt cttcacttat ctgtgtaatc aagtttacta tgagtctatg  15780
atcaagtaat tatgcaatca agttaagtac agtataggct tgagctccct aggcctgtta  15840
tccctaacaa gtttgtacaa aaaagcaggc tgagctcgac caagcccgtt attctgacag  15900
ttctggtgct caacacattt atatttatca aggagcacat tgttactcac tgctaggagg  15960
gaatcgaact aggaatattg atcagaggaa ctacgagaga gctgaagata actgccctct  16020
agctctcact gatctgggcg catagtgaga tgcagcccac gtgagttcag caacggtcta  16080
gcgctgggct tttaggcccg catgatcggg ctttgtcggg tggtcgacgt gttcacgatt  16140
ggggagagca acgcagcagt tcctcttagt ttagtcccac ctcgcctgtc cagcagagtt  16200
ctgaccggtt tataaactcg cttgctgcat cagacttgnn nnnnnnnnnn nnnnnnnngt  16260
tttagagcta gaaatagcaa gttaaaataa ggctagtccg ttatcaactt gaaaaagtgg  16320
caccgagtcg gtgctttttt tctagaccca gctttcttgt acaaagttgg cattaaccca  16380
gctttc                                                             16386

SEQ ID NO: 24          moltype = DNA  length = 16792
FEATURE                Location/Qualifiers
source                 1..16792
                       mol_type = other DNA
                       organism = synthetic construct
                       note = Vektor1_ZmU3
misc_difference        16645
                       note = misc_feature - a, c, g, or t
misc_difference        16646
                       note = misc_feature - a, c, g, or t
misc_difference        16647
                       note = misc_feature - a, c, g, or t
misc_difference        16648
                       note = misc_feature - a, c, g, or t
misc_difference        16649
                       note = misc_feature - a, c, g, or t
misc_difference        16650
                       note = misc_feature - a, c, g, or t
misc_difference        16651
                       note = misc_feature - a, c, g, or t
misc_difference        16652
                       note = misc_feature - a, c, g, or t
misc_difference        16653
                       note = misc_feature - a, c, g, or t
misc_difference        16654
                       note = misc_feature - a, c, g, or t
misc_difference        16655
                       note = misc_feature - a, c, g, or t
misc_difference        16656
                       note = misc_feature - a, c, g, or t
misc_difference        16657
                       note = misc_feature - a, c, g, or t
misc_difference        16658
                       note = misc_feature - a, c, g, or t
misc_difference        16659
                       note = misc_feature - a, c, g, or t
misc_difference        16660
                       note = misc_feature - a, c, g, or t
misc_difference        16661
                       note = misc_feature - a, c, g, or t
misc_difference        16662
                       note = misc_feature - a, c, g, or t
misc_difference        16663
                       note = misc_feature - a, c, g, or t
misc_difference        16664
                       note = misc_feature - a, c, g, or t
SEQUENCE: 24
ttgtacaaag tggttcgata attccgatcc agcctaggcc cgggcctgag gacgcgcctt  60
actagtggat cccttcaccg ccattgcaaa aattgtcaat aaatatttag agtgggtggc  120
```

```
atcagaaaaa catctctagt ggactctctt cctatcatag ctactcgggc tgtagataga  180
acgagggcac aagagttggg tggcgtaggt ttactcgtga cctcaactct tttggctgtg  240
tcttacgtct aagatgggtt tggcatgtga gaaacatagg tctaagcaat tcatgttagg  300
gctgttgcat tgttgttgca tcaaccaaat gtccagatag cagttcatgc tacatctagt  360
tgaaaaccct catcattagg cggaacatgt gttcttttt agcatagtca aagtcagatt  420
gcggcactcg ctcatccacg gaaagaattt tccctgtgca ggcatctcga tcaaaagacg  480
caaattaatt tttgaatagc gatataacaa tatctaatta acgtttcttg ttttctgcga  540
aatgtctttc atcataaaat gagtcatctc gatgagccca agtgacatag cccaacaccc  600
caccccacca ataaaagtga agaaaacatg ttgggaaaac tataccaagt aaaatacgag  660
ttgttctaaa gaaaaagtaa agtacgagtt agatcgcacc ctgtcctgga gtgtggcttg  720
atgatccaac tcctagcatt gtatccctgt ttttggatga tgtaactatt atttacaatg  780
aataaagagg tgttttacta gtaaaaaaat cttgagggga ggagaaaata atggaggtct  840
tttttcaaac cgatggacta ttatttttag tgaaagagaa taatattatt ggaaaaatta  900
ttctatccac ttattttata ttggcagaat acaaagaatg gtggggtcca cgcggaactt  960
gcggcccccg aaacctatcg agggcgcggt acccaagcaa ggaacggagg aaacttgcgg  1020
ggcccgaaac ctagtgataa aaggcatatc atccacacga tgaagatctg acggaccata  1080
tctcccacca cggaaagcca tcagacgagg atcagacggc caggaaggaa ccctagcgcc  1140
cgccggtgcc aatataaagc gccactctct ctcgtcttaa gccccagcct ctccattccc  1200
ctctccctct cgattacgag gtgtgttgtt catccgtccc gaatccatcc atcccctctt  1260
cagatgtgtt gttcatggct ctaatagctc tagatctgct tgtttgtgtt gtttagctct  1320
agatctactc gcgcgcgctt ctctctcgat ctcctgtaga acaattttgg ttggtttttt  1380
gtgcatatcc atggtaattt tgtctgcaat atggaggagg ctttctaagc tcctacgtag  1440
catcgatctt tagaattccc tcggtttctg tttatttctt cgcgagggct ctctgttatc  1500
tgtaggagta gctgtaagcg cggttcgtta cggattaatc gtcatgctta gttgaaccta  1560
tcggtcgaag gatttgtgtg ggttgtcgtg tagaattgac accatctact tactgtactg  1620
atatgccgat ctgtaggata ctcttcatta cttttgttta ctgctagttg tggtgtagat  1680
ttagcattct caaacccatg ctgtagcgtt tctaatattg ttacatagat ctaccggtgc  1740
ctgttaattg tattcgatcg ggcgtttcta catctgtccg cccacctagt tttatatgtg  1800
gtaatcaaaa ttgcgttgac ttcgtgatgc tgtctgtgta ctgtttttaa tcgctcttac  1860
ttagatgatc aacatggtga tggttacgat ttactgtttt ctaatccctg ttacttcgat  1920
gctgcagttt gattgatggg cccagaacga cgcccggccg acatccgccg tgccaccgag  1980
gcggacatgc cggcggtctg caccatcgtc aaccactaca tcgagacaag cacggtcaac  2040
ttccgtaccg agccgcagga accgcaggag tggacggacg acctcgtccg tctgcgggag  2100
cgctatccct ggctcgtcgc cgaggtggac ggcgaggtcg ccggcatcgc ctacgcgggc  2160
ccctggaagg cacgcaacgc ctacgactgg acggccgagt cgaccgtgta cgtctccccc  2220
cgccaccagc ggacgggact gggctccacg ctctacaccc acctgctgaa gtccctggag  2280
gcacagggct tcaagagcgt ggtcgctgtc atcgggctgc ccaacgaccc gagcgtgcgc  2340
atgcacgagg cgctcggata tgccccccgc ggcatgctgc gggcggccgg cttcaagcac  2400
gggaactggc atgacgtggg tttctggcag ctggacttca gcctgccggt accgccccgt  2460
ccggtcctgc ccgtcaccga gatctgaatg ccgaatttcc ccgatcgttc aaacatttgg  2520
caataaagtt tcttaagatt gaatcctgtt gccggtcttg cgatgattat catataattt  2580
ctgttgaatt acgttaagca tgtaataatt aacatgtaat gcatgacgtt atttatgaga  2640
tgggttttta tgattagagt cccgcaatta tacatttaat acgcgataga aaacaaaata  2700
tagcgcgcaa actaggataa attatcgcgc gcggtgtcat ctatgttact agatcgctcg  2760
aagatccccc gggctgcagg aattcaagct tggcactggc cgtcgtttta caacgtcgtg  2820
actgggaaaa ccctggcgtt acccaactta atcgccttgc agcacatccc cctttcgcca  2880
gctggcgtaa tagcgaagag gcccgcaccg atcgcccttc ccaacagttg cgcagcctga  2940
atggcgaatg agcttgagct tggatcagat tgtcgtttcc cgccttcagt ttaaactatc  3000
agtgtttgac aggatatatt ggcgggtaaa cctaagagaa aagagcgttt attagaataa  3060
cggatattta aaagggcgtg aaaaggttta tccgttcgtc catttgtatg tgcatgccaa  3120
ccacagggtt cccctcggga tcaaagtact ttgatccaac ccctccgctg ctatagtgca  3180
gtcggcttct gacgttcagt gcagccgtct tctgaaaacg acatgtcgca caagtcctaa  3240
gttacgcgac aggctgccgc cctgcccttt tcctggcgtt ttcttgtcgc gtgttttagt  3300
cgcataaagt agaatacttg cgactagaac cggagacatt acgccatgaa caagagcgcc  3360
gccgctggcc tgctgggcta tgcccgcgtc agcaccgacg accaggactt gaccaaccaa  3420
cgggccgaac tgcacgcggc cggctgcacc aagctgtttt ccgagaagat caccggcacc  3480
aggcgcgacc gcccggagct ggccaggatg cttgaccacc tacgccctgg cgacgttgtg  3540
acagtgacca ggctagaccg cctggcccgc agcacccgcg acctactgga cattgccgag  3600
cgcatccagg aggccggcgc gggcctgcgt agcctggcag agccgtgggc cgacaccacc  3660
acgccggccg gccgcatggt gttgaccgtg ttcgccggca ttgccgagtt cgagcgttcc  3720
ctaatcatcg accgcacccg gagcgggcgc gaggccgcca aggcccgagg cgtgaagttt  3780
ggcccccgcc ctaccctcac cccggcacag atcgcgcacg cccgcgagct gatcgaccag  3840
gaaggccgca ccgtgaaaga ggcggctgca ctgcttggcg tgcatcgctc gaccctgtac  3900
cgcgcacttg agcgcagcga ggaagtgacg cccaccgagg ccaggcggcg cggtgccttc  3960
cgtgaggacg cattgaccga ggccgacgcc ctggcggccg ccgagaatga acgccaagag  4020
gaacaagcat gaaaccgcac caggacggcc aggacgaacc gtttttcatt accgaagaga  4080
tcgaggcgga gatgatcgcg gccgggtacg tgttcgagcc gcccgcgcac gtctcaaccg  4140
tgcggctgca tgaaatcctg gccggtttgt ctgatgccaa gctggcggcc tggccggcca  4200
gcttggccgc tgaagaaacc gagcgccgcc gtctaaaaag gtgatgtgta tttgagtaaa  4260
acagcttgcg tcatgcggtc gctgcgtata tgatgcgatg agtaaataaa caaatacgca  4320
aggggaacgc atgaaggtta tcgctgtact taaccagaaa ggcgggtcag gcaagacgac  4380
catcgcaacc catctagccc gcgccctgca actcgccggg gccgatgttc tgttagtcga  4440
ttccgatccc cagggcagtg cccgcgattg ggcggccgtg cgggaagatc aaccgctaac  4500
cgttgtcggc atcgaccgcc cgacgattga ccgcgacgtg aaggccatcg gccggcgcga  4560
cttcgtagtg atcgacggag cgccccaggc ggcggacttg gctgtgtccg cgatcaaggc  4620
agccgacttc gtgctgattc cggtgcagcc aagcccttac gacatatggg ccaccgccga  4680
cctggtggag ctggttaagc agcgcattga ggtcacggat ggaaggctac aagcggcctt  4740
tgtcgtgtcg cgggcgatca aaggcacgcg catcggcggt gaggttgccg aggcgctggc  4800
cgggtacgag ctgcccattc ttgagtcccg tatcacgcag cgcgtgagct acccaggcac  4860
```

-continued

```
tgccgccgcc ggcacaaccg ttcttgaatc agaacccgag ggcgacgctg cccgcgaggt  4920
ccaggcgctg gccgctgaaa ttaaatcaaa actcatttga gttaatgagg taaagagaaa  4980
atgagcaaaa gcacaaacac gctaagtgcc ggccgtccga gcgcacgcag cagcaaggct  5040
gcaacgttgg ccagcctggc agacacgcca gccatgaagc gggtcaactt tcagttgccg  5100
gcggaggatc acaccaagct gaagatgtac gcggtacgcc aaggcaagac cattaccgag  5160
ctgctatctg aatacatcgc gcagctacca gagtaaatga gcaaatgaat aaatgagtag  5220
atgaatttta gcggctaaag gaggcggcat ggaaaatcaa gaacaaccag gcaccgacgc  5280
cgtggaatgc cccatgtgtg gaggaacggg cggttggcca ggcgtaagcg gctgggttgt  5340
ctgccggccc tgcaatggca ctggaacccc caagcccgag gaatcggcgt gacggtcgca  5400
aaccatccgg cccggtacaa atcggcgcgg cgctgggtga tgacctggtg gagaagttga  5460
aggccgcgca ggccgcccag cggcaacgca tcgaggcaga agcacgcccc ggtgaatcgt  5520
ggcaagcggc cgctgatcga atccgcaaag aatcccggca accgccggca gccggtgcgc  5580
cgtcgattag gaagccgccc aagggcgacg agcaaccaga tttttttcgtt ccgatgctct  5640
atgacgtggg cacccgcgat agtcgcagca tcatggacgt ggccgttttc cgtctgtcga  5700
agcgtgaccg acgagctggc gaggtgatcc gctacgagct tccagacggg cacgtagagg  5760
tttccgcagg gccggccggc atggccagtg tgtgggatta cgacctggta ctgatggcgg  5820
tttcccatct aaccgaatcc atgaaccgat accgggaagg gaagggagac aagcccggcc  5880
gcgtgttccg tccacacgtt gcggacgtac tcaagttctg ccggcgagcc gatggcggaa  5940
agcagaaaga cgacctggta gaaacctgca ttcggttaaa caccacgcac gttgccatgc  6000
agcgtacgaa gaaggccaag aacggccgcc tggtgacggt atccgagggt gaagccttga  6060
ttagccgcta caagatcgta aagagcgaaa ccgggcggcc ggagtacatc gagatcgagc  6120
tagctgattg gatgtaccgc gagatcacag aaggcaagaa cccggacgtg ctgacggttc  6180
accccgatta ctttttgatc gatcccggca tcggccgttt tctctaccgc ctggcacgcc  6240
gcgccgcagg caaggcagaa gccagatggt tgttcaagac gatctacgaa cgcagtggca  6300
gcgccggaga gttcaagaag ttctgtttca ccgtgcgcaa gctgatcggg tcaaatgacc  6360
tgccggagta cgatttgaag gaggaggcgg ggcaggctgg cccgatccta gtcatgcgct  6420
accgcaacct gatcgagggc gaagcatccg ccggttccta atgtacggag cagatgctag  6480
ggcaaattgc cctagcaggg gaaaaaggtc gaaaaggtct ctttcctgtg gatagcacgt  6540
acattgggaa cccaaagccg tacattggga accggaaccc gtacattggg aacccaaagc  6600
cgtacattgg gaaccggtca cacatgtaag tgactgatat aaaagagaaa aaaggcgatt  6660
tttccgccta aaactcttta aaacttatta aaactcttaa aacccgcctg gcctgtgcat  6720
aactgtctgg ccagcgcaca gccgaagagc tgcaaaaagc gcctaccctt cggtcgctgc  6780
gctccctacg ccccgccgct tcgcgtcggc ctatcgcggc cgctggccgc tcaaaaatgg  6840
ctggcctacg gccaggcaat ctaccagggc gcggacaagc cgcgccgtcg ccactcgacc  6900
gccggcgccc acatcaaggc accctgcctc gcgcgtttcg gtgatgacgg tgaaaacctc  6960
tgacacatgc agctcccgga gacggtcaca gcttgtctgt aagcggatgc cgggagcaga  7020
caagcccgtc agggcgcgtc agcgggtgtt ggcgggtgtc ggggcgcagc catgacccag  7080
tcacgtagcg atagcggagt gtatactggc ttaactatgc ggcatcagag cagattgtac  7140
tgagagtgca ccatatgcgg tgtgaaatac cgcacagatg cgtaaggaga aaataccgca  7200
tcaggcgctc ttccgcttcc tcgctcactg actcgctgcg ctcggtcgtt cggctgcggc  7260
gagcggtatc agctcactca aaggcggtaa tacggttatc cacagaatca ggggataacg  7320
caggaaagaa catgtgagca aaaggccagc aaaaggccag gaaccgtaaa aaggccgcgt  7380
tgctggcgtt tttccatagg ctccgccccc ctgacgagca tcacaaaaat cgacgctcaa  7440
gtcagaggtg gcgaaacccg acaggactat aaagatacca ggcgtttccc cctggaagct  7500
ccctcgtgcg ctctcctgtt ccgaccctgc cgcttaccgg atacctgtcc gcctttctcc  7560
cttcgggaag cgtggcgctt tctcatagct cacgctgtag gtatctcagt tcggtgtagg  7620
tcgttcgctc caagctgggc tgtgtgcacg aaccccccgt tcagcccgac cgctgcgcct  7680
tatccggtaa ctatcgtctt gagtccaacc cggtaagaca cgacttatcg ccactggcag  7740
cagccactgg taacaggatt agcagagcga ggtatgtagg cggtgctaca gagttcttga  7800
agtggtggcc taactacggc tacactagaa ggacagtatt tggtatctgc gctctgctga  7860
agccagttac cttcggaaaa agagttggta gctcttgatc cggcaaacaa accaccgctg  7920
gtagcggtgg tttttttgtt tgcaagcagc agattacgcg cagaaaaaaa ggatctcaag  7980
aagatccttt gatcttttct acggggtctg acgctcagtg gaacgaaaac tcacgttaag  8040
ggattttggt catgcatgat atatctccca atttgtgtag ggcttattat gcacgcttaa  8100
aaataataaa agcagacttg acctgatagt ttggctgtga gcaattatgt gcttagtgca  8160
tctaatcgct tgagttaacg ccggcgaagc ggcgtcggct tgaacgaatt tctagctaga  8220
cattatttgc cgactacctt ggtgatctcg cctttcacgt agtggacaaa ttcttccaac  8280
tgatctgcgc gcgaggccaa gcgatcttct tcttgtccaa gataagcctg tctagcttca  8340
agtatgacgg gctgatactg ggccggcagg cgctccattg cccagtcggc agcgacatcc  8400
ttcggcgcga ttttgccggt tactgcgctg taccaaatgc gggacaacgt aagcactaca  8460
tttcgctcat cgccagccca gtcgggcggc gagttccata gcgttaaggt ttcatttagc  8520
gcctcaaata gatcctgttc aggaaccgga tcaaagagtt cctccgccgc tggacctacc  8580
aaggcaacgc tatgttctct tgcttttgtc agcaagatag ccagatcaat gtcgatcgtg  8640
gctggctcga agatacctgc aagaatgtca ttgcgctgcc attctccaaa ttgcagttcg  8700
cgcttagctg gataacgcca cggaatgatg tcgtcgtgca caacaatggt gacttctaca  8760
gcgcggagaa tctcgctctc tccaggggaa gccgaagttt ccaaaaggtc gttgatcaaa  8820
gctcgccgcg ttgtttcatc aagccttacg gtcaccgtaa ccagcaaatc aatatcactg  8880
tgtggcttca ggccgccatc cactgcggag ccgtacaaat gtacggccag caacgtcggt  8940
tcgagatggc gctcgatgac gccaactacc tctgatagtt gagtcgatac ttcggcgatc  9000
accgcttccc ccatgatgtt taactttgtt ttagggcgac tgccctgctg cgtaacatcg  9060
ttgctgctcc ataacatcaa acatcgaccc acggcgtaac gcgcttgctg cttggatgcc  9120
cgaggcatag actgtacccc aaaaaaacat gtcataacaa gaagccatga aaaccgccac  9180
tgcgccgtta ccaccgctgc gttcggtcaa ggttctggac cagttgcgtg acggcagtta  9240
cgctacttgc attacagctt acgaaccgaa cgaggcttat gtccactggg ttcgtgcccg  9300
aattgatcac aggcagcaac gctctgtcat cgttacaatc aacatgctac cctccgcgag  9360
atcatccgtg tttcaaaccc ggcagcttag ttgccgttct tccgaatagc atcggtaaca  9420
tgagcaaagt ctgccgcctt acaacggctc tcccgctgac gccgtcccgg actgatgggc  9480
tgcctgtatc gagtggtgat tttgtgccga gctgccggtc ggggagctgt tggctggctg  9540
gtggcaggat atattgtggt gtaaacaaat tgacgcttag acaacttaat aacacattgc  9600
```

```
ggacgttttt aatgtactga attaacgccg aattgctcta gccaatacgc aaaccgcctc  9660
tccccgcgcg ttggccgatt cattaattgc agcgtgaccc ggtcgtgccc ctctctagag  9720
ataatgagca ttgcatgtct aagttataaa aaattaccac atatttttt tgtcacactt  9780
gtttgaagtg cagtttatct atctttatac atatatttaa actttactct acgaataata  9840
taatctatag tactacaata atatcagtgt tttagagaat catataaatg aacagttaga  9900
catggtctaa aggacaattg agtattttga caacaggact ctacagtttt atctttttag  9960
tgtgcatgtg ttctcctttt tttttgcaaa tagcttcacc tatataatac ttcatccatt  10020
ttattagtac atccatttag ggtttagggt taatggtttt tatagactaa ttttttagt  10080
acatctattt tattctattt tagcctctaa attaagaaaa ctaaaactct attttagttt  10140
ttttatttaa taatttagat ataaaataga ataaaataaa gtgactaaaa attaaacaaa  10200
taccctttaa gaaattaaaa aaactaagga aacatttttc ttgtttcgag tagataatgc  10260
cagcctgtta aacgccgtcg atcgacgagt ctaacggaca ccaaccagcg aaccagcagc  10320
gtcgcgtcgg gccaagcgaa gcagacggca cggcatctct gtcgctgcct ctggacccct  10380
ctcgagagtt ccgctccacc gttggacttg ctccgctgtc ggcatccaga aattgcgtgg  10440
cggagcggca gacgtgagcc ggcacggcag gcggcctcct cctcctctca cggcaccggc  10500
agctacgggg gattcctttc ccaccgctcc ttcgctttcc cttcctcgcc cgccgtaata  10560
aatagacacc ccctccacac cctctttccc caacctcgtg ttgttcggag cgcacacaca  10620
cacaaccaga tctcccccaa atccacccgt cggcacctcc gcttcaaggt acgccgctcg  10680
tcctcccccc ccccccctct ctaccttctc tagatcggcg ttccggtcca tggttagggc  10740
ccggtagttc tacttctgtt catgtttgtg ttagatccgt gtttgtgtta gatccgtgct  10800
gctagcgttc gtacacggat gcgacctgta cgtcagacac gttctgattg ctaacttgcc  10860
agtgtttctc tttggggaat cctgggatgg ctctagccgt tccgcagacg ggatcgatct  10920
aggataggta tacatgttga tgtgggtttt actgatgcat atacatgatg gcatatgcag  10980
catctattca tatgctctaa ccttgagtac ctatctatta taataaacaa gtatgtttta  11040
taattatttt gatcttgata tacttggatg atggcatatg cagcagctat atgtggattt  11100
ttttagccct gccttcatac gctatttatt tgcttggtac tgtttctttt gtcgatgctc  11160
accctgttgt ttggtgttac ttctgcaggg gtaccgccat ggataagaag tactctatcg  11220
gactcgatat cggaactaac tctgtgggat gggctgtgat caccgatgag tacaaggtgc  11280
catctaagaa gttcaaggtt ctcggaaaca ccgataggca ctctatcaag aaaaacctta  11340
tcggtgctct cctcttcgat tctggtgaaa ctgctgaggc taccagactc aagagaaccg  11400
ctagaagaag gtacaccaga agaaagaaca ggatctgcta cctccaagag atcttctcta  11460
acgagatggc taaagtggat gattcattct tccacaggct cgaagagtca ttcctcgtgg  11520
aagaagataa gaagcacgag aggcacccta tcttcggaaa catcgttgat gaggtggcat  11580
accacgagaa gtaccctact atctaccacc tcagaaagaa gctcgttgat tctactgata  11640
aggctgatct caggctcatc tacctcgctc tcgctcacat gatcaagttc agaggacact  11700
tcctcatcga gggtgatctc aaccctgata actctgatgt ggataagttg ttcatccagc  11760
tcgtgcagac ctacaaccag cttttcgaag agaaccctat caacgcttca ggtgtggatg  11820
ctaaggctat cctctctgct aggctctcta agtcaagaag gcttgagaac ctcattgctc  11880
agctccctgg tgagaagaag aacggacttt tcggaaactt gatcgctctc tctctcggac  11940
tcacccctaa cttcaagtct aacttcgatc tcgctgagga tgcaaagctc cagctctcaa  12000
aggataccta cgatgatgat ctcgataacc tcctcgctca gatcggagat cagtacgctg  12060
atttgttcct cgctgctaag aacctctctg atgctatcct cctcagtgat atcctcagag  12120
tgaacaccga gatcaccaag gctccactct cagcttctat gatcaagaga tacgatgagc  12180
accaccagga tctcacactt ctcaaggctc ttgttagaca gcagctccca gagaagtaca  12240
aagagatttt cttcgatcag tctaagaacg gatacgctgg ttacatcgat ggtggtgcat  12300
ctcaagaaga gttctacaag ttcatcaagc ctatcctcga gaagatggat ggaaccgagg  12360
aactcctcgt gaagctcaat agagaggatc ttctcagaaa gcagaggacc ttcgataacg  12420
gatctatccc tcatcagatc cacctcggag agttgcacgc tatccttaga aggcaagagg  12480
atttctaccc attcctcaag gataacaggg aaaagattga gaagattctc accttcagaa  12540
tcccttacta cgtgggacct ctcgctagag gaaactcaag attcgcttgg atgaccagaa  12600
agtctgagga aaccatcacc ccttggaact tcgaagaggt ggtggataag ggtgctagtg  12660
ctcagtcttt catcgagagg atgaccaact tcgataagaa ccttccaaac gagaaggtgc  12720
tccctaagca ctctttgctc tacgagtact tcaccgtgta caacgagttg accaaggtta  12780
agtacgtgac cgaggggaatg aggaagcctg ctttttttgtc aggtgagcaa aagaaggcta  12840
tcgttgatct cttgttcaag accaacagaa aggtgaccgt gaagcagctc aaagaggatt  12900
acttcaagaa aatcgagtgc ttcgattcag ttgagatttc tggtgttgag gataggttca  12960
acgcatctct cggaacctac cacgatctcc tcaagatcat taaggataag gatttcttgg  13020
ataacgagga aaacgaggat atcttggagg atatcgttct taccctcacc ctctttgaag  13080
atagagagat gattgaagaa aggctcaaga cctacgctca tctcttcgat gataaggtga  13140
tgaagcagtt gaagagaaga agatacactg gttggggaag gctctcaaga aagctcatta  13200
acggaatcag ggataagcag tctggaaaga caatccttga tttcctcaag tctgatggat  13260
tcgctaacag aaacttcatg cagctcatcc acgatgattc tctcaccttt aaagaggata  13320
tccagaaggc tcaggtttca ggacagggtg atagtctcca tgagcatatc gctaacctcg  13380
ctggatctcc tgcaatcaag aagggaatcc tccagactgt gaaggttgtg gatgagttgg  13440
tgaaggtgat gggaaggcat aagcctgaga acatcgtgat cgaaatggct agagagaacc  13500
agaccactca gaagggacag aagaactcta gggaaaggat gaagaggatc gaggaaggta  13560
tcaaagagct tggatctcag atcctcaaag agcaccctgt tgagaacact cagctccaga  13620
atgagaagct ctacctctac tacctccaga acggaaggga tatgtatgtg gatcaagagt  13680
tggatatcaa caggctctct gattacgatg ttgatcatat cgtgccacag tcattcttga  13740
aggatgattc tatcgataac aaggtgctca ccaggtctga taagaacagg ggtaagagtg  13800
ataacgtgcc aagtgaagag gttgtgaaga aaatgaagaa ctattggagg cagctcctca  13860
acgctaagct catcactcag agaaagttcg ataacttgac taaggctgag aggggaggac  13920
tctctgaatt ggataaggca ggattcatca agaggcagct tgtggaaacc aggcagatca  13980
ctaagcacgt tgcacagatc ctcgattcta ggatgaacac caagtacgat gagaacgata  14040
agttgatcag ggaagtgaag gttatcaccc tcaagtcaaa gctcgtgtct gatttcagaa  14100
aggatttcca attctacaag gtgagggaaa tcaacaacta ccaccacgct cacgatgctt  14160
accttaacgc tgttgttgga accgctctca tcaagaagta tcctaagctc gagtcagagt  14220
tcgtgtacgg tgattacaag gtgtacgatg tgaggaagat gatcgctaag tctgagcaag  14280
agatcggaaa ggctaccgct aagtatttct tctactctaa catcatgaat ttcttcaaga  14340
```

```
ccgagattac cctcgctaac ggtgagatca gaaagaggcc actcatcgag acaaacggtg  14400
aaacaggtga gatcgtgtgg gataagggaa gggatttcgc taccgttaga aaggtgctct  14460
ctatgccaca ggtgaacatc gttaagaaaa ccgaggtgca gaccggtgga ttctctaaag  14520
agtctatcct ccctaagagg aactctgata agctcattgc taggaagaag gattgggacc  14580
ctaagaaata cggtggtttc gattctccta ccgtggctta ctctgttctc gttgtggcta  14640
aggttgagaa gggaaagagt aagaagctca agtctgttaa ggaacttctc ggaatcacta  14700
tcatggaaag gtcatctttc gagaagaacc caatcgattt cctcgaggct aagggataca  14760
aagaggttaa gaaggatctc atcatcaagc tcccaaagta ctcactcttc gaactcgaga  14820
acggtagaaa gaggatgctc gcttctgctg gtgagcttca aaagggaaac gagcttgctc  14880
tcccatctaa gtacgttaac tttctttacc tcgcttctca ctacgagaag ttgaagggat  14940
ctccagaaga taacgagcag aagcaacttt tcgttgagca gcacaagcac tacttggatg  15000
agatcatcga gcagatctct gagttctcta aaagggtgat cctcgctgat gcaaacctcg  15060
ataaggtgtt gtctgcttac aacaagcaca gagataagcc tatcagggaa caggcagaga  15120
acatcatcca tctcttcacc cttaccaacc tcggtgctcc tgctgctttc aagtacttcg  15180
atacaaccat cgataggaag agatacacct ctaccaaaga agtgctcgat gctaccctca  15240
tccatcagtc tatcactgga ctctacgaga ctaggatcga tctctcacag ctcggtggtg  15300
attcaagggc tgatcctaag aagaagagga aggtttgagg cgcgccgagc tccaggcctc  15360
ccagctttcg tccgtatcat cggtttcgac aacgttcgtc aagttcaatg catcagtttc  15420
attgcccaca caccagaatc ctactaagtt tgagtattat ggcattggaa aagctgtttt  15480
cttctatcat ttgttctgct tgtaatttac tgtgttcttt cagtttttgt tttcggacat  15540
caaaatgcaa atggatggat aagagttaat aaatgatatg gtccttttgt tcattctcaa  15600
attattatta tctgttgttt ttactttaat gggttgaatt taagtaagaa aggaactaac  15660
agtgtgatat taaggtgcaa tgttagacat ataaaacagt ctttcacctc tctttggtta  15720
tgtcttgaat tggtttgttt cttcacttat ctgtgtaatc aagtttacta tgagtctatg  15780
atcaagtaat tatgcaatca agttaagtac agtataggct tgagctccct aggcctgtta  15840
tccctaacaa gtttgtacaa aaaagcaggc tgagctcgaa ttccatctaa gtatcttggt  15900
aaagcatgga ttaatttgga tgcccacttc aggtctatgc agctccggtg ccttgtgatt  15960
gtgagttgtg accgatgctc atgctattct gcatttctgc gatgtatgta gctagtagat  16020
cttcaaaact aacaccgcat gccatcatca tccactgctt gattttagtc tcaccgctgg  16080
ccaaaaatgt gatgatgcca gaaacctcaa ctaccttgaa tcaacacggg cccaacagtg  16140
tgatgacgac agaaacaaaa aaaaatgagc caatagttca gaaggaggca ctatgcagaa  16200
actacatttc tgaaggtgac taaaaggtga gcgtagagtg taattactag tagtttagcc  16260
accattaccc aaatgctttc gagcttgtat taagatttcc taagctgagc atcatcactg  16320
atctgcaggc caccctcgct tcgctgccaa gatcaacagc aaccatgtgg cggcaacatc  16380
cagcattgca catgggctaa agattgagct ttgtgcctcg tctagggatc agctgaggtt  16440
atcagtcttt ccttttttc atccaggtga ggcatcaagc tactactgcc tcgattggct  16500
ggacccgaag cccacatgta ggataccaga atgggccgac ccaggacgca gtatgttggc  16560
cagtcccacc ggttagtgcc atctcggttg ctcacatgcg tagaagccag cttaaaaatt  16620
tagctttggt gactcacagc attgnnnnnn nnnnnnnnnn nnnngtttta gagctagaaa  16680
tagcaagtta aaataaggct agtccgttat caacttgaaa aagtggcacc gagtcggtgc  16740
tttttttcta gacccagctt tcttgtacaa agttggcatt aacccagctt tc          16792
```

```
SEQ ID NO: 25          moltype = DNA  length = 3256
FEATURE                Location/Qualifiers
source                 1..3256
                       mol_type = genomic DNA
                       organism = Brome mosaic virus
misc_feature           1..3256
                       note = Fescue segment RNA1, complete sequence cDNA DQ530423
SEQUENCE: 25
gagcgttaac gtagaccacg gaacgaggtt caatcccttg tcgaccacgg ttctactact  60
tgttctttgt ttttcaccaa caaaatgtca agttctatcg atttgctgaa gttgattgct  120
gagaagggtg ctgccagcca gagtgcccaa gacatcgtag acaatcaggt cgcgcaacag  180
ttatctgcgc agattgaata cgcgaaaagg tctaagaaaa tcaacgttcg caataagctc  240
tctattgagg aggctgacgc cttccgtgac cgttatggtg gtgcctttga tttaaatttg  300
actcagcagt atcatgcacc ccatagcctg gctggtgctc tgcgtgtagc ggagcattac  360
gactgtctcg acagttttcc ccctgaagac cccgttatag atttcggagg gtcttggtgg  420
catcactttt caagaaggga taaaagggtg cacagttgtt gtcctgtgtt gggtgttaga  480
gacgctgccc gacatgagga gaggatgtgc cgcatgcgga aaattttgca agaaagcgat  540
gatttcgatg aagtcccgaa cttttgtctt aaccgagctc aagattgtga tgtccaagct  600
gattgggcta tctgtatcca tggcggttat gatatgggct tccaaggtct gtgtgacgcc  660
atgcattcgc atggagtacg cgtactacgt ggtaccgtta tgttcgacgg cgccatgttg  720
tttgaccgcg agggttttct tcccttgctt aaatgtcact ggcaacgtga cgggtcaggc  780
gcggatgagg tgatcaaatt cgactttgaa aatgaaagca cattatctta catccatgga  840
tggcaagatt tgggctcctt tttcaccgag tcggtgcatt gcatcgatgg aaccacctat  900
ctgttggagc gcgaaatgct gaaatgtaac atcatgacct ataagatcat cgctacaaat  960
ttacgctgcc cccgggagac actacgtcac tgtgtatggt ttgaagacat atctaagtac  1020
gtgggagtct caatacctga agactggagt ctcaatcgct ggaaatgtgt gcgcgtcgcc  1080
aaaaccacag tgagagaggt agaggagata gctttcagat gtttcaagga aaataaagaa  1140
tggaccgaga acatgaaagc tgtcgcatct atcttatccg ccaagtcgtc gactgttatt  1200
attaacggtc aggctatcat ggctggtgag cgcttagaca ttgaagatta tcatctagtg  1260
gcctttgctt tgactttgaa tctgtatcaa aagtacgaaa agcttacggc cctccgcgat  1320
gggatggaat ggaaaggttg gtgccatcac ttcaaaacta ggttttggtg gggtggagat  1380
tcatccaggg cgaaagtagg atggctgaga acattggcta gcagatttcc cctactacgt  1440
ctggattctt atgcggacag ttttaagttt ctgactcgtc tctcaaacgt tgaagaattt  1500
gagcaagatt ctgtaccaat atcacgtttg agaacgtttt ggactgaaga ggacttattc  1560
gaccggctgg agcatgaagt gcagacagcc aagaccaagc gctcgaagaa gaaggcgata  1620
gtcccgccag ctgctgagat acctcaggag gagtttcatg atgcccctga gagttcgagc  1680
cctgagtccg tcagtgatga cgttaaaccg gtgactgatg tggtcccgga tgccgaggtg  1740
```

```
tctgttgagg taccaacgga ccctcgtggc atatctagac acggagccat gaaggaattt  1800
gtgcgttatt gtaagagatt acataacaac tccgagtcta atcttcgtca cctatgggac  1860
atttccggcg gtcgcggaag tgagatcgca aataagagca tcttcgagac ctaccatcgc  1920
atagacgata tggtgaatgt ccatttggcc aacggtaact ggttgtatcc taaaaaatac  1980
gattacaccg ttggatataa tgagcatggt ttaggtccga agcacgcaga tgaaacgtac  2040
attgttgata aaacatgtgc atgctctaac ttgagggaca ttgcagaagc tagcgccaaa  2100
gtttctgtcc ctacatgcga tatttccatg gttgatggag ttgcgggatg cggtaaaacc  2160
actgccataa aagatgcatt ccgtatggga gaggacctaa ttgtgacggc gaatcgtaaa  2220
tcggccgagg acgtcaggat ggctttattc cctgacactt ttaattccaa ggtagctttg  2280
gatgttgtgc gcaccgcgga ttctgcgatc atgcacggtg taccgtcctg tcataggctg  2340
cttgttgatg aggctggttt actacattac ggtcaactcc tggtggtggc tgctctgtct  2400
aaatgttcac aagttcttgc ctttggggac acagagcaga tttcgttcaa gtctcgtgac  2460
gcgggtttta aattgctcca cggtaatctg aaatatgatc gccgtgacgt tgttcacaag  2520
acttaccggt gtccgcaaga tgttatcgct gctgttaatc tgctgaagcg taaatgcggt  2580
aatagggaca cgaagtatca atcctggaca tctgagtcca aagtttctag aagtctcacg  2640
aagcgtcgta ttacttctgt tttgcaggtc actattgatc cgaacagaac gtatcttacg  2700
atgactcaag ctgataaagc ggcccttcaa acgagggcta aggactttcc cgtgagcaag  2760
gactggattg atggacatat aaaaacagta cacgaagcgc aagggatctc tgttgacaat  2820
gtcgctttgg ttcggcttaa gtcgaccaaa tgtgatttgt ttaaacatga ggagtactgt  2880
ttggttgcct taacacgaca caagaagtcc tttgagtatt gctttaacgg cgagctcgct  2940
ggtgatttga tctttaattg tgttaagtga tgcgcttgtc tctgtgtgag acctctgctc  3000
gaggagagcc ctgttccagg taggaacgtt gtggtctaac ttaagactag ctgaatcggt  3060
gctataaccg atagtcgtgg ttgacacgca gacctcttac aagagtgtct aggcgccttt  3120
gagagttact ctttgctctc ttcggaagaa cccctagggg ttcgtgcatg ggcttgcata  3180
gcaagtctta gaatgcgggt gccttacagt gttgaaaaac actgtaaatc tctaaaagag  3240
accattaatt aagctc                                                  3256

SEQ ID NO: 26          moltype = DNA  length = 2895
FEATURE                Location/Qualifiers
source                 1..2895
                       mol_type = genomic DNA
                       organism = Brome mosaic virus
misc_feature           1..2895
                       note = Fescue segment RNA2, complete sequence cDNA DQ530424
SEQUENCE: 26
gagcgttaac acgcgtgtaa accacggaac gaggttcaat cccttgtcga cccacggttt  60
gcgcaacaca catctaacct tgttgttgtt gtgttttgtt tctttctact atcaccaaga  120
tgtcttcgaa aacctgggat gatgatttcg ttcgccaggt cccgtctttc caatggatca  180
tagatcaatc cttagaagac gaggtggagg ctgctagcct tcaggtgcag gagccggcag  240
acggagttgc cattgacgga tctctcgcga gttttaaatt agctatagcg cccttggaga  300
taggaggggt gttcgatccc ccttttgacc gagtgcgctg gggctctatt tgcgataccg  360
tccagcaaat ggttcaacag ttcaccgata gaccactgat tcctcaggct gaaatggcac  420
ggatgttata tcttgacatt ccgggctctt ttgtgctcga agatgaaatc gatgactggt  480
atcctgagga tactagtgac ggttacggtg tatcgtttgc cgccgatgaa gatcatgcga  540
gcgatctaaa actcgccagt gattcctcga actgtgaaat tgaggaagtt cgtgttactg  600
gagatacccc caaggagctg acccttggag ataggtacat gggcattgac gaagagtttc  660
agactaccaa tactgattac gacatcactc ttcagatcat gaatcctatt gaacataggg  720
tttcgcgcgt tattgatacg cactgccatc cagataaccc tgacatctcc actgggccaa  780
tttatatgga gagagtcagc cttgctagaa cagaagcaac cagtcattcc atactgccaa  840
cccatgctta tttcgatgat tcgtaccatc aagcccttgt tgagaatggt gattattcca  900
tggactttga taggatcaga cttaagcaaa gtgatgtaga ctggtacagg gaccccgata  960
aatattttca accaaaaatg aatatcggga gtgctcagcg aagagttggt actcagaaag  1020
aagtcttaac cgcacttaaa aagcgaaacg cggatgttcc agaaatggga gacgcgatta  1080
acatgaagga aactgcgaag gctatagcaa agcgctttcg tagcacattc cttaatgttg  1140
acggtgaaga ctgtctgaga gcttctatgg atgtcatgac taagtgtctt gagtaccata  1200
agaagtgggg taagcacatg gacttacaag gtgtgaatgt ggcagcagag actgatttac  1260
gtcggtacca gcatatgctg aagtctgatg taaaacctgt tgtaactgac acccttcact  1320
tggaacgagc agtagcagct actataacat ttcatagtaa aggtgtgact agtaattttt  1380
caccctttttt cactgcttgt ttcgagaagt tatcattggc cctgaaatcc aggttcattg  1440
tgcctatcgg aaagatatcc tctctggagc ttaagaatgt ccgcttgaat aacagatact  1500
ttcttgaagc ggacctaagc aaatttgata aatctcaggg tgagctgcac ctagagtttc  1560
agagagagat acttcttgcg ctgggctttc cagcgccgct gacgaattgg tggtctgatt  1620
ttcatcgcga ttcttattta tcagaccctc atgccaaggt gggaatgtcc gtttccttcc  1680
aacgcagaac tggtgatgcg tttacatatt tcgggaatac tcttgtcact atggctatga  1740
ttgcatatgc ctctgatcta agtgactgtg actgtgcaat attctcagga gatgattctt  1800
taatcatttc taaagttaaa ccagtcttgg ataccgatat gttcacgtct ctctttaata  1860
tggagataaa agttatggac cctagtgtgc cctacgtttg tagtaagttt cttgttgaaa  1920
ctgaaatggg caattgggtg tctataccag accctatgag agagatccag cgcttagcta  1980
agcgaaagat tctgcgtgaa gaacagatgc tcagagcaca tttcgtttcc ttctgcgatc  2040
gaatgaagtt tattaatcaa cttgatgaga agatgattac gatgctctgt cattttgttt  2100
atctgaaata tgggaaagaa aaaccttgga ttttcgagga ggttagagct gctcttgcgg  2160
ctttttcttt atactccgag aatttcctga ggttctctga ttgctactgt accgaaggca  2220
tcagagttta tcagatgagc gatcctgtat gtaagttcaa acgcactatg gaagagcgta  2280
aaactgatgg tgactggttt cacaactgga agaatccaaa gtttcctggt gtgttagaca  2340
aagtctacag aacccttgga atttattcct cggactgtag tactaaggag ctccctgtca  2400
aacggatcgg acgtttacat gaggcccttg agcgtgagtc actcagatta gcgaatgatc  2460
gtaggaccac acaacgcttg aaaaagaagg tcgacgatta cgctaccggt agaggaggcc  2520
taacgtcagt tgatgctttg ctcttgaagt cccattgtga gactttaag ccctctgatc  2580
tgagatgatc ggttctatat gatatatgaa cctaagctgt gagcagccct ttggttaagg  2640
```

```
ttaaaaactc ctggtcaggt agaccacttt ggctaagttt aaaagcttgt tgaatcagta  2700
caataactga tagtcgtggt tgacacgcag acctcttaca agagtgtcta ggtgcctttg  2760
agagttactc tttgctctct tcggaagaac ccttaggggt tcgtgcatgg gcttgcatag  2820
caagtcttag aatgcgggta ccgtacagtg ttgaaaaaca ctgtaaatct ctaaaagaga  2880
ccattaatta agctc                                                   2895

SEQ ID NO: 27          moltype = DNA  length = 2148
FEATURE                Location/Qualifiers
source                 1..2148
                       mol_type = genomic DNA
                       organism = Brome mosaic virus
misc_feature           1..2148
                       note = Fescue segment RNA3 T1025C cDNA
SEQUENCE: 27
gagcccatgg gttaacgtaa aataccaact aattctcgtt cgattccggc gaacattcta  60
ttttaccaac atcggttttt tcagtagtga tactgttttt gttcccgatg tctaacatag  120
tttctccctt cagtggttcc tcacgaacta cgtctgacgt tggcaagcaa gcgggaggta  180
ctagcgacga gaagctcatt gagtcgctgt tctctgaaaa ggctgtgaaa gagatagctg  240
ccgagtgtaa actcggatgt tataactatc tgaagtctaa tgaaccccgc aactatatag  300
acctggtgcc aaagtcacac gtatctgctt ggctctcatg ggctacaccc aagtatgata  360
aaggagagtt accttccagg ggattcatga acgttccacg catcgtttgt tttctcgttc  420
gtaccacaga tagcgcagag tccggttcta taaccgtgag cctgtgcgat tctggtaagg  480
ctgctcgtgc tggagtactc gaagccattg ataatcagga ggccacaatt cagttgtcgg  540
ctttacctgc tttgatagct ttgacgccta gctatgattg tccgatggaa gtcatcggcg  600
gtgatagcgg taggaatcga tgttttggga tagcaaccca acttagcggt gtggtgggga  660
caacaggttc cgttgcagtt actcatgctt attggcaagc taatttcaaa gcgaagccca  720
acaactataa gttgcatggt cccgctacaa ttatggtaat gccatttgac agactgagac  780
aactcgataa gaaaagcctc aaaaattaca tcagaggtat ttctaaccag tctgtggatc  840
atgggtatct tctcggaaga ccgttacaat ctgttgatca ggttgcccag gaagatttgt  900
tagttgagga atccgagtct ccttccgctc tcggcagagg tgtgaaggat agtaagtctg  960
tatccgcgtc atctgtcgct ggacttcctg tgtccagtcc ttcgcttaga attaaatagg  1020
taaatccggt ctaacaagct cggtccattt cgtggagtta agcaagctgg ggagaccccc  1080
gacagccgtt tggatcagcg ctcgcgtctc gtttgggttc aattccctta ccttacaacg  1140
gcgtgttgag ataggtcctc gggggaggtt atccatgttt gtggatattc tatgttgtgt  1200
gtctgagtta ttaaaaaaaa aaaaaaaaaa aaaagatcta tgtcctaatt cagcgtatta  1260
ataatgtcga cttcaggaac tggtaagatg actcgcgcgc agcgtcgagc tgccgctcgt  1320
agaaatcgtc ggaccgctac ggtccaaccg gtaattgtcg aaccattcgc tgctggccaa  1380
ggcaaggcca ttaaagcgat tgcaggatac agcatatcaa agtgggaggc gtcttcggac  1440
gcgattacag cgaaagccac caatgccatg agtatcactc tgccccatga gctctcttct  1500
gaaaagaata aggagcttaa ggtcggcagg gtgctgcttt ggttgggact tcttcctagc  1560
gttgctggga ggattaaggc ttgtgttgct gagaaacagg cacaggccga ggccgctttt  1620
caagtagcct tggcggttgc tgactcctcg aaagaggtgg tcgcggccat gtatacggac  1680
gcctttcgag ggcgactctt gggggatttg cttaatctcc agatttatct gtatgcatct  1740
gaagcagtgc ctgctaaggc ggtcgttgta catctagaag ttgagcacgt aaggcctacg  1800
ttcgatgact tcttcacccc ggtttatagg tagtgcccct gctcggagag cccctgactg  1860
ggttaaagtc acaggcccct tgtctcaggt agagaccctg tccaggtagg acactttggc  1920
taaggttaaa agcttgttga atcagtacaa taactgatag tcgtggttga cacgcagacc  1980
tcttacaaga gtgtctaggt gcctttgaga gttactcttt gctctcttcg gaagaaccct  2040
taggggttcg tgcatgggct tgcatagcaa gtcttagaat gcgggtaccg tacagtgttg  2100
aaaaacactg taaatctcta aaagagacca ttaattaact gcaggctc               2148

SEQ ID NO: 28          moltype = DNA  length = 2114
FEATURE                Location/Qualifiers
source                 1..2114
                       mol_type = genomic DNA
                       organism = Brome mosaic virus
misc_feature           1..2114
                       note = Fescue segment RNA3 cDNA DQ530425
SEQUENCE: 28
gtaaaatacc aactaattct cgttcgattc cggcgaacat tctattttac caacatcggt  60
tttttcagta gtgatactgt tttgttcccg atgtctaac atagtttctc ccttcagtgg  120
ttcctcacga actacgtctg acgttggcaa gcaagcggga ggtactagcg acgagaagct  180
cattgagtcg ctgttctctg aaaaggctgt gaaagagata gctgccgagt gtaaactcgg  240
atgttataac tatctgaagt ctaatgaacc ccgcaactat atagacctgg tgccaaagtc  300
acacgtatct gcttggctct catgggctac acccaagtat gataaaggag agttaccttc  360
caggggattc atgaacgttc cacgcatcgt ttgttttctc gttcgtacca cagatagcgc  420
agagtccggt tctataaccg tgagcctgtg cgattctggt aaggctgctc gtgctggagt  480
actcgaagcc attgataatc aggaggccac aattcagttg tcggctttac ctgctttgat  540
agctttgacg cctagctatg attgtccgat ggaagtcatc ggcggtgata gcggtaggaa  600
tcgatgtttt gggatagcaa cccaacttag cggtgtggtg gggacaacag gttccgttgc  660
agttactcat gcttattggc aagctaattt caaagcgaag cccaacaact ataagttgca  720
tggtcccgct acaattatgg taatgccatt tgacagactg agacaactcg ataagaaaag  780
cctcaaaaat tacatcagag gtatttctaa ccagtctgtg gatcatgggt atcttctcgg  840
aagaccgtta caatctgttg atcaggttgc ccaggaagat ttgttagttg aggaatccga  900
gtctccttcc gctctcggca gaggtgtgaa ggatagtaag tctgtatccg cgtcatctgt  960
cgctggactt cctgtgtcca gtccttcgct tagaattaaa taggtaaatc cggtctaaca  1020
agcttggtcc atttcgtgga gttaagcaag ctggggagac ccccgacagc cgtttggatc  1080
agcgctcgcg tctcgtttgg gttcaattcc cttaccttac aacggcgtgt tgagataggt  1140
cctcggggga ggttatccat gtttgtggat attctatgtt gtgtgtctga gttattaaaa  1200
```

```
aaaaaaaaaa aaaaaaaaga tctatgtcct aattcagcgt attaataatg tcgacttcag  1260
gaactggtaa gatgactcgc gcgcagcgtc gagctgccgc tcgtagaaat cgtcggaccg  1320
ctacggtcca accggtaatt gtcgaaccat tcgctgctgg ccaaggcaag gccattaaag  1380
cgattgcagg atacagcata tcaaagtggg aggcgtcttc ggacgcgatt acagcgaaag  1440
ccaccaatgc catgagtatc actctgcccc atgagctctc ttctgaaaag aataaggagc  1500
ttaaggtcgg cagggtgctg ctttggttgg gacttcttcc tagcgttgct gggaggatta  1560
aggcttgtgt tgctgagaaa caggcacagg ccgaggccgc ttttcaagta gccttggcgg  1620
ttgctgactc ctcgaaagag gtggtcgcgg ccatgtatac ggacgccttt cgagggggcga  1680
ctctggggga tttgcttaat ctccagattt atctgtatgc atctgaagca gtgcctgcta  1740
aggcggtcgt tgtacatcta gaagttgagc acgtaaggcc tacgttcgat gacttcttca  1800
ccccggttta taggtagtgc ccctgctcgg agagcccctg actgggttaa agtcacaggc  1860
cccttgtctc aggtagagac cctgtccagg taggacactt tggctaaggt taaaagcttg  1920
ttgaatcagt acaataactg atagtcgtgg ttgacacgca gacctcttac aagagtgtct  1980
aggtgccttt gagagttact ctttgctctc ttcggaagaa cccttagggg ttcgtgcatg  2040
ggcttgcata gcaagtctta gaatgcgggt accgtacagt gttgaaaaac actgtaaatc  2100
tctaaaagag acca                                                    2114

SEQ ID NO: 29          moltype = DNA  length = 2145
FEATURE                Location/Qualifiers
source                 1..2145
                       mol_type = genomic DNA
                       organism = Brome mosaic virus
misc_feature           1..2145
                       note = RNA3 R-BMV cDNA
SEQUENCE: 29
gagcccatgg gttaacgtaa aataccaact aattctcgtt cgattccggc gaacattcta  60
ttttaccaac atcggttttt tcagtagtga tactgttttt gttcccgatg tctaacatag  120
tttctccctt cagtggttcc tcacgaacta cgtctgacgt tggcaagcaa gcgggaggta  180
ctagcgatga gaagctcatt gagtcgctgt tctctgaaaa ggctgtgaaa gagatagctg  240
ccgagtgtaa actcggatgt tataactatc tgaagtctaa tgaaccccgc aactatatag  300
acctggtgcc aaagtcacac gtatctgctt ggctctcatg ggctacatcc aagtatgata  360
aaggagagtt accttccagg ggattcatga acgttccacg catcgtttgt tttctcgttc  420
gtaccacaga tagcgcagag tccggttcta taaccgtgag cctgtgcgat tctggtaagg  480
ctgctcgtgc tggagtactc gaagccattg ataatcagga ggccacaatt cagttgtcgg  540
ctttacctgc tttgatagct ttgacgccta gctatgattg tccgatggaa gtcatcggcg  600
gtgatagcgg taggaatcga tgttttggga tagcaaccca acttagcggt gtggtgggga  660
caacaggttc cgttgcagtt actcatgcgt attggcaagc taatttcaaa gcgaagccca  720
acaactataa gttgcatggt cccgctacaa ttatggtaat gccatttgac agactgagac  780
aactcgataa gaaaagcctc aaaaattata ttagaggtat ttctaaccag tctgtggatc  840
atgggtatct tctcggaaga ccgttacaat ctgttgatca ggttgcccag gaagatttgt  900
tagttgagga atccgagtct ccttccgctc tcggcagagg tgtgaaggat agtaagtctg  960
tatccgcgtc atctgtcgct ggacttcctg tgtccagtcc tacgcttaga attaaatagg  1020
taaatccggt ctaacaagct cggtccattt cgtagagtta agcaagctgg ggagaccccc  1080
gacagccgtt tggatcagcg ctcgcgtctc gtttgggttc aattccctta ccttacaacg  1140
gcgtgttgag ataggtcctc gggggaggtt atccatgttt gtggatattc tatgttgtgt  1200
gtctgagtta ttattaaaaa aaaaaaaaaa agatctatgt cctaattcag cgtattaata  1260
atgtcgactt caggaactgg taagatgact cgcgcgcagc gtcgtgctgc cgctcgcaga  1320
aatcgttgga ccgctagggt ccaaccagta attgtcgaac cactcgctgc tggccaaggc  1380
aaggccatta aagcgattgc aggatacagc atatcaaagt gggaggcgtc ttcggacgcg  1440
attacagcga aagccaccaa tgccatgagt atcactctgc cccatgagct ctcttctgaa  1500
aagaataagg agcttaaggt cggcagggtg ctgctttggt tgggacttct tcctagcgtt  1560
gctgggagga ttaaggcttg tgttgctgag aaacaggcac aggccgaggc tgcttttcaa  1620
gtagccttgg cggttgcaga ctcctcgaaa gaggtggtcg cggccatgta tacggacgcc  1680
tttcgagggg cgactctggg ggatttgctt aatctccaga tttatctgta tgcatctgaa  1740
gcagtgcctg ctaaggcggt cgttgtacat ctagaagttg agcacgtaag gcctacgttc  1800
gatgacttct tcaccccggt ttataggtag tgcccctgct cggagagccc ctgactgggt  1860
taaagtcaca ggccccttgt ctcaggtaga gaccctgtcc aggtaggaca ctttggctaa  1920
ggttaaaagc ttgttgaatc agtacaataa ctgatagtcg tggttgacac gcagacctct  1980
tacaagagtg tctaggtgcc tttgagagtt actctttgct ctcttcggaa gaacccttag  2040
gggttcgtgc atgggcttgc atagcaagtc ttagaatgcg ggtaccgtac agtgttgaaa  2100
aacactgtaa atctctaaaa gagaccatta attaactgca ggctc                  2145

SEQ ID NO: 30          moltype = DNA  length = 2111
FEATURE                Location/Qualifiers
source                 1..2111
                       mol_type = genomic DNA
                       organism = Brome mosaic virus
misc_feature           1..2111
                       note = RNA3 gi[33]1498β2042.1⁄RCG3Z Brome mosaic
                        virus 3a and coat protein genes, complete cds
SEQUENCE: 30
gtaaaatacc aactaattct cgttcgattc cggcgaacat tctattttac caacatcggt  60
tttttcagta gtgatactgt tttgttcccc gatgtctaac atagtttctc ccttcagtgg  120
ttcctcacga actacgtctg acgttggcaa gcaagcggga ggtactagcg atgagaagct  180
cattgagtcg ctgttctctg aaaaggctgt gaaagagata gctgccgagt gtaaactcgg  240
atgttataac tatctgaagt ctaatgaacc ccgcaactat atagacctgg tgccaaagtc  300
acacgtatct gcttggctct catgggctac atccaagtat gataaaggag agttaccttc  360
caggggattc atgaacgttc cacgcatcgt ttgttttctc gttcgtacca cagatagcgc  420
agagtccggt tctataaccg tgagcctgtg cgattctggt aaggctgctc gtgctggagt  480
```

```
actcgaagcc attgataatc aggaggccac aattcagttg tcggctttac ctgctttgat  540
agctttgacg cctagctatg attgtccgat ggaagtcatc ggcggtgata gcggtaggaa  600
tcgatgtttt gggatagcaa cccaacttag cggtgtggtg gggacaacag gttccgttgc  660
agttactcat gcgtattggc aagctaattt caaagcgaag cccaacaact ataagttgca  720
tggtcccgct acaattatgg taatgccatt tgacagactg agacaactcg ataagaaaag  780
cctcaaaaat tatattagag gtatttctaa ccagtctgtg gatcatgggt atcttctcgg  840
aagaccgtta caatctgttg atcaggttgc ccaggaagat ttgttagttg aggaatccga  900
gtctccttcc gctctcggca gaggtgtgaa ggatagtaag tctgtatccg cgtcatctgt  960
cgctggactt cctgtgtcca gtcctacgct tagaattaaa taggtaaatc cggtctaaca  1020
agctcggtcc atttcgtaga gttaagcaag ctggggagac cccgacagc cgtttggatc  1080
agcgctcgcg tctcgtttgg gttcaattcc cttaccttac aacggcgtgt tgagataggt  1140
cctcgggggga ggttatccat gtttgtggat attctatgtt gtgtgtctga gttattatta  1200
aaaaaaaaaa aaaaagatct atgtcctaat tcagcgtatt aataatgtcg acttcaggaa  1260
ctggtaagat gactcgcgcg cagcgtcgtg ctgccgctcg cagaaatcgt tggaccgcta  1320
gggtccaacc agtaattgtc gaaccactcg ctgctggcca aggcaaggcc attaaagcga  1380
ttgcaggata cagcatatca aagtgggagg cgtcttcgga cgcgattaca gcgaaagcca  1440
ccaatgccat gagtatcact ctgccccatg agctctcttc tgaaaagaat aaggagctta  1500
aggtcggcag ggtgctgctt tggttgggac ttcttcctag cgttgctggg aggattaagg  1560
cttgtgttgc tgagaaacag gcacaggccg aggctgcttt tcaagtagcc ttggcggttg  1620
cagactcctc gaaagaggtg gtcgcggcca tgtatacgga cgcctttcga ggggcgactc  1680
tgggggattt gcttaatctc cagatttatc tgtatgcatc tgaagcagtg cctgctaagg  1740
cggtcgttgt acatctagaa gttgagcacg taaggcctac gttcgatgac ttcttcaccc  1800
cggtttatag gtagtgcccc tgctcggaga gcccctgact gggttaaagt cacaggcccc  1860
ttgtctcagg tagagaccct gtccaggtag gacactttgg ctaaggttaa aagcttgttg  1920
aatcagtaca ataactgata gtcgtggttg acacgcagac ctcttacaag agtgtctagg  1980
tgcctttgag agttactctt tgctctcttc ggaagaaccc ttaggggttc gtgcatgggc  2040
ttgcatagca agtcttagaa tgcgggtacc gtacagtgtt gaaaaacact gtaaatctct  2100
aaaagagacc a                                                     2111

SEQ ID NO: 31          moltype = DNA  length = 2150
FEATURE                Location/Qualifiers
source                 1..2150
                       mol_type = genomic DNA
                       organism = Brome mosaic virus
                       note = Brome mosaic virus C-BMVA/G
SEQUENCE: 31
gagcccatgg gttaacgtaa aataccaact aattctcgtt cgattccggc gaacattcta  60
ttttaccaac atcggttttt tcagtagtga tactgttttt gttcccgatg tctaacatag  120
tttctccctt cagtggttcc tcacgaacta cgtctgacgt tggcaagcaa gcgggaggta  180
ctagcgacga gaagctcatt gagtcgctgt tctctgaaaa ggctgtgaaa gagatagctg  240
ccgagtgtaa actcggatgt tataactatc tgaagtctaa tgaaccccgc aactatatag  300
acctggtgcc aaagtcacac gtatctgctt ggctctcatg ggctacaccc aagtatgata  360
aaggagagtt accttccagg ggattcatga acgttccacg catcgtttgt tttctcgttc  420
gtaccacaga tagcgcagag tccggttcta taaccgtgag cctgtgcgat tctggtaagg  480
ctgctcgtgc tggagtactc gaagccattg ataatcagga ggccacaatt cagttgtcgg  540
ctttacctgc tttgatagct ttgacgccta gctatgattg tccgatggaa gtcatcggcg  600
gtgatagcgg taggaatcga tgttttggga tagcaaccca acttagcggt gtggtgggga  660
caacaggttc cgttgcagtt actcatgctt attggcaagc taatttcaaa gcgaagccca  720
acaactataa gttgcatggt cccgctacaa ttatggtaat gccatttgac agactgagac  780
aactcgataa gaaaagcctc aaaaattaca tcagaggtat ttctaaccag tctgtggatc  840
atgggtatct tctcggaaga ccgttacaat ctgttgatca ggttgcccag gaagatttgt  900
tagttgagga atccgagtct ccttccgctc tcggcagagg tgtgaaggat agtaagtctg  960
tatccgcgtc atctgtcgct ggacttcctg tgtccagtcc tacgcttaga attaaatagg  1020
taaatccggt ctaacaagct cggtccattt cgtagagtta agcaagctgg ggagaccccc  1080
gacagccgtt tggatcagcg ctcgcgtctc gtttgggttc aattccctta ccttacaacg  1140
gcgtgttgag ataggtcctc gggggaggtt atccatgttt gtggatattc tatgttgtgt  1200
gtctgagtta ttattaaaaa aaaaaaaaaa agatctatgt cctaattcag cgtattaatt  1260
taacaatgtc gacttcagga actggtaaga tgactcgcgc gcagcgtcga gctgccgctc  1320
gtagaaatcg tcggaccgct acggtccaac cggtaattgt cgaaccattc gctgctggcc  1380
aaggcaaggc cattaaagcg attgcaggat acagcatatc aaagtgggag gcgtcttcgg  1440
acgcgattac agcgaaagcc accaatgcca tgagtatcac tctgccccat gagctctctt  1500
ctgaaaagaa taaggagctt aaggtcggca gggtgctgct ttggttggga cttcttccta  1560
gcgttgctgg gaggattaag gcttgtgttg ctgagaaaca ggcacaggcc gaggccgctt  1620
ttcaagtagc cttggcggtt gctgactcct cgaaagaggt ggtcgcggcc atgtatacgg  1680
acgcctttcg aggggcgact ctgggggatt tgcttaatct ccagatttat ctgtatgcat  1740
ctgaagcagt gcctgctaag gcggtcgttg tacatctaga agttgagcac gtaaggccta  1800
cgttcgatga cttcttcacc ccggtttata ggtagtgccc ctgctcggag agcccctgac  1860
tgggttaaag tcacaggccc cttgtctcag gtagagaccc tgtccaggta ggacactttg  1920
gctaaggtta aaagcttgtt gaatcagtac aataactgat agtcgtggtt gacacgcaga  1980
cctcttacaa gagtgtctag gtgcctttga gagttactct ttgctctctt cggaagaacc  2040
cttaggggtt cgtgcatggg cttgcatagc aagtcttaga atgcgggtac cgtacagtgt  2100
tgaaaaacac tgtaaatctc taaaagagac cattaattaa ctgcaggctc            2150

SEQ ID NO: 32          moltype = DNA  length = 3787
FEATURE                Location/Qualifiers
source                 1..3787
                       mol_type = genomic DNA
                       organism = Barley stripe mosaic virus
misc_feature           1..3787
```

```
                        note = BSMV ND18 RNA1 U35767
SEQUENCE: 32
gtatgtaagt tgcctttggg tgtaaaattt cttgcatgca cataatcgta atcgattctt  60
cttgatctct aaacaacact ttcccgttag catggctagc gatgagattg tccgcaatct  120
gatctcccgt gaggaggtga tgggtaattt gattagcaca gcttctagct cagtaaggtc  180
acccttacat gacgtactgt gctcgcacgt aaggaccatc gtcgattccg tggataagaa  240
agcggtcagt cgcaagcatg ttgatgtacg gcgcaacatc tcctctgaag agttacagat  300
gttgataaat gcatatcctg aatatgccgt ttcatcctca gcttgtgaat ctggtactca  360
tagcatggcg gcttgttttc gatttctgga gacagaatac ctcttagata tggttccaat  420
gaaagagact tttgtttatg acattggtgg taactggttt tctcatatga agtttcgtgc  480
tgatagagaa attcattgtt gctgtccgat cttatctatg agagattctg aaagactgga  540
aacacgcatg atggcaatgc aaaaatatat gcgtggatcg aaagacaaac cgttacgctt  600
gttaagccgt tatcaaaata tcctgcgtga acaagcggcg agaacaactg cctttatggc  660
aggtgaggtg aatgcgggtg ttctcgatgg agatgtgttt tgtgagaaca cttttcaaga  720
ctgtgtgaga caggtgcccg aaggtttttt gaagacagct atagcagttc atagcatcta  780
cgatatcaaa gtggaagaat ttgcgtctgc attgaaaaga aaaggtataa cacaggctta  840
tgggtgcttc ctgtttcctc ctgctgtatt gataggtcag aaggaaggta ttttaccttc  900
cgtggacggt cattacttgg tggagaatgg caggattaag ttcttctttg cgaatgatcc  960
gaatgccggt tactctcatg accttaagga ttatctgaag tatgtggaaa aaacctacgt  1020
ggatataaag gatggagtgt ttgctattga gctgatgcaa atgcgaggtg ataccatgtt  1080
ctttaagatc acggatgtca ccgcagcaat gtatcatatg aaatacagag gtatgaaacg  1140
tgatgaaaca ttcaaatgca ttccgttgct aaaaaattca tccgttgtcg tacctctatt  1200
ttcgtgggac aaccgttctt taaagatcac aagtggttta ttaccacgaa ctttggtcga  1260
gcaaggtgcg gcgtttatta tgaaaaacaa ggagaaggac ttgaacgttg ctgtgttgaa  1320
gaactatctt tccgctgtga acaactcata cattttcaac ggatcccagg ttagagatgg  1380
tgtgaaaatt gccccggatt taatctccaa attggcagtg actctgtacc tgagagaaaa  1440
ggtctatcga caaagagaaa attcaatcat aagttatttc gagcaagaaa tgcttcacga  1500
tcccaacttg aaagccatgt ttggagactt tctgtggttt gttccaaata ctctctcgag  1560
tgtctggaag aacatgcgaa aatcactgat ggaatggttt ggctacgcag aatttgactt  1620
gactactttt gatatttgcg atcccgttct ctacgtagag atagtggatc ggtataagat  1680
cattcaaaaa gggcgaattc cacttggtga gttttttgat tgtcatgaag aatgcgagaa  1740
ttacgaactg cgtgagaagg agaaaaatga cctagcggtg aaaatggccc agaaggtaac  1800
agggacggtg accgaatgcg agaaggacct gggacctctt gttcaaccga taaaacagat  1860
attggttcaa cttgtgatgc ccaatttggt cagagcgctg tgtagacctc gtagcccaac  1920
gtctcctttg gacttaaata tcccagggtc aactccatca cactcaagtt cagattctga  1980
acaatctatg actgaagaag cgagctgcgc cattgcgggt agcgtaccaa catgggaaat  2040
tgcgactaag aaagatctaa cctttcagcg aattgatgaa gatatgtctc gacgaactgg  2100
tatgcctcca agaccaaaag taacttctag ttacaacatg aatgccagag ctgagtttct  2160
ctactatcaa ctgtgtagcg tgatttgtga aagggctcag attttgagtg tcatcgaaga  2220
ctttcgtcag aatttgatat tctcagataa agtggccgtt ccattgaacg ctagattcta  2280
cagttttcag tcattgcaac ccggatgggt gttcaagact ccatcgcata gtgaagtagg  2340
ccacagttat gcagtacatt ttgacttcaa gacagttgga accgatttgg aagagagcct  2400
agctttttgc cgaatggtac cgatttcatg ggataaaagc ggcaaataca tcgcgacaac  2460
tcctcatttt cccgagagac atggttacta cgtgatttgt gacaacacta aattgtgtaa  2520
caattggctt atttacaata agttagttga tgtctacgca cgagtggctg atagacctct  2580
gagatttgag ttgattgacg gagttcctgg ctgcggaaag tcaaccatga ttttaaacag  2640
ctgtgatatt cgacgcgaag ttgttgttgg tgaaggaagg aatgcaactg atgacttaag  2700
ggagaggttc aagcgtaaga aaaatttgaa tagtaagact gctaatcata gagttcgaac  2760
gcttgacagc ttattacttg ctgaaggacc ttgtgtaccg caagctgata ggtttcattt  2820
tgatgaagct ctaaaagttc attacggcgc cataatgttc tgtgctgata agcttggtgc  2880
ctcagaaatt ctcgctcagg gagatagggc tcaactgccg atgatctgtc gtgtagaagg  2940
tattgaactt caatttcaat ctcctgatta cacgaagacg atcataaatc ctaagctacg  3000
atcataccgt atccctggag atgttgcctt ctatttgagt gctaaggaat tttacaaagt  3060
taaaggaata cctcaaaagg ttacaacttc taacagtgtg aaacgttccc tgtacgctag  3120
aggcgaaaca actccggaaa gattcgtgag tttgcttgat gttccggtga gaaaaaacac  3180
ccattatcta accttcttac aagctgagaa ggaaagtttg atgagtcatt tgattccaaa  3240
gggtgtgaag aaagagtcta tttcaacgat tcatgaggcg cagggtggta cctatgaaaa  3300
tgtgattctg gtccgtttgc aacggacgcc caatgaaatt tatccgggtg gacctaggtc  3360
cgccccttac attgtggttg ggacttcaag gcatacaaaa actttcactt attgtagtgt  3420
tacggacgat aagttgcttt tagatatcgc cgacgtcggt ggtattgcac atacacctat  3480
tcgtactttt gaatctcata tagtttaaaa aaaaaaaaaa aaaaaaaaaa aaaaaaaaaa  3540
aaaaaaaaat gtttgatcag atcattcaaa tctgatggtg cccatcaacc atatgatggg  3600
agtgtttgca agtccactat aatcgaactt gaaaacgatg cctgaattgg aaaccatgaa  3660
tcttaacgga ttctggagag aaaatttagg aattggtatg taagctacaa cttccggtag  3720
ctgcgtcaca ctttaagagt gtgcatactg agccgaagct cagcttcggt cccccaaggg  3780
aagacca                                                            3787

SEQ ID NO: 33           moltype = DNA  length = 3239
FEATURE                 Location/Qualifiers
source                  1..3239
                        mol_type = genomic DNA
                        organism = Barley stripe mosaic virus
misc_feature            1..3239
                        note = BSMV ND18 RNA2 U35770
SEQUENCE: 33
gtaaaagaaa aggaacaacc ctgttgttgt tcgacgctat actaaatata tattatctta  60
ttagtgcatt tcttttacca cttcacagta tgccgaacgt ttctttgact gctaagggtg  120
gaggacacta caacgaggat caatgggata cacaagttgt ggaagccgga gtatttgacg  180
attggtgggt ccacgtagaa gcctggaata aatttctaga caatttacgt ggtatcaact  240
```

```
ttagcgttgc ttcctctcgg tcgcaagtcg ctgaatgctt agctgcgtta gatcgtgatc  300
tacctgctga tgtagacaga cggtttgcag gtgctagagg acaaattggt ttacccaatt  360
atcttcctgc gccaaaattc tttcgtctcg ataagcgaac tatcgctgaa ctgactagac  420
tctctcgtct tacggatcag ccgcacaaca atcgtgatat agagcttaac cgagcgaaaa  480
gagccacaac taacccatct cccccggcgc aggcaccgtc ggagaatctt actcttcgtg  540
atgttcaacc gttaaaggat agtgcgttgc attatcaata cgtgttgatt gacctacaga  600
gtgcgagact cccagtgtat accaggaaga ctttcgaacg tgaactcgct ttggaatgga  660
tcattccaga tgccgaggaa gcgtgacctg ctgttgaagc ggtaaaagga tgtacatatg  720
tatcttattt attttgttta tctattttct tttactttta gtttttgctt tttacgcgtt  780
aactagatgt attgacttta gccatggaca tgacgaaaac tgttgaggaa aagaaaacaa  840
atggaactga ttcagtgaaa ggtgtttttg aaaactcgac gattcccaaa gttccgactg  900
gacaggaaat gggtggtgac gattcttcta cttctaaatt aaaggaaact ctaaaagttg  960
ccgatcagac tccattgtcc gttgacaacg gtgccaaatc caaattggat tcttctgata  1020
gacaagttcc tggtcctaag ttggcaacaa ctgtggaaaa ggaacctgag ttgaaaccca  1080
acgttaagaa gtccaagaag aaaagaatcc aaaaacctgc tcaaccgagt aggcccaatg  1140
accttaaagg cgggactaag ggatcatctc aagtgggtga aaatgtgagt gagaactata  1200
ctgggatttc taaggaagca gctaagcaaa agcagaagac acccaagtct gtgaaaatgc  1260
aaagcaatct ggccgataag ttcaaagcga atgatactcg tagatcggaa ttaattaaca  1320
agtttcagca atttgtgcat gaaacctgtc ttaaatctga ttttgagtac actggtcgac  1380
agtatttcag agctagatca aatttctttg aaatgattaa gctcgcatcc ttgtatgaca  1440
aacatctaaa ggaatgtatg gcgcgagcct gcaccctaga acgagaacga ttgaagcgta  1500
agttactcct agtacgagct ttgaaaccag cagttgactt ccttacggga atcatctctg  1560
gagttcctgg ctcaggaaaa tcaaccattg tgcgtacttt gctcaaaggt gaatttccgg  1620
ctgtttgtgc tttggccaat cctgccttaa tgaacgacta ttctggtatt gaaggcgttt  1680
acgggttaga tgacctgttg ctttctgcag ttccgataac gtctgattta ttgatcatag  1740
atgaatatac acttgctgag agcgcggaaa tcctgttgtt acaacgaaga ctcagagcct  1800
ctatggtgtt gttagtcggg gatgtagctc aaggaaaagc caccactgct tccagtattg  1860
agtatttaac tctgccggtg atctacagat cagagacgac ttatcgtttg ggacaagaga  1920
ctgcttcgct ttgcagcaag cagggtaaca gaatggtttc aaagggtgga agggacacag  1980
tgatcattac tgattacgat ggcgaaacag atggaacgga gaaaaatatc gcttttactg  2040
tcgatacagt tcgagatgtg aaagattgcg ggtacgattg tgccctggca attgatgtgc  2100
aagggaaaga attcgattca gtgactttat tcctaaggaa cgaagaccgg aaagctttag  2160
cagataagca tttgcgttta gtcgctttga gcagacataa gtcgaagtta atcatcaggg  2220
ccgacgcgga aattcgtcaa gcattcctga caggtgatat tgacttgagc tctaaggcga  2280
gtaactctca tcgttattct gcaaaaccgg atgaagacca cagttggttc aaggccaaat  2340
aagtattggc caattgtcgc cggaatcggt gtcgttggat tgtttgcgta tttgatcttt  2400
tcaaatcaaa aacattctac ggaatccggc gataatattc acaaattcgc caacggaggt  2460
agttacaggg acgggtcaaa gagtataagt tataatcgta atcatccttt tgcctatggc  2520
aatgcctcat cccctggaat gttgttgccc gcaatgctta ccatcatcgg aatcatttcc  2580
tatttatggc gaacaagaga ttccgtgctc ggagactcag gcggaaacaa ttcctgcgga  2640
gaagactgtc agggcgaatg tcttaacgga cattctcgac gatcattact atgcgatatt  2700
ggctagtctt tttatcattg ctctatggtt attgtatata tatctaagca gtatacctac  2760
ggagactggt ccctacttct atcaagatct gaactctgtg aagatctatg gaataggggc  2820
tacgaatcca gaagttattg cggccatcca ccattggcag aagtaccctt ttggggaatc  2880
tccgatgtgg ggaggtttag tcagtgtttt gagcgttctt cttaaaccgc tgacgttagt  2940
ttttgcgtta agctttttc tcttactttc ttcaaaaagg taaaaaaaaa aaaaaaaaaa  3000
atgtttgatc agatcattca aatctgatgg tgcccatcaa ccatatgatg ggagtgtttg  3060
caagtccact ataatcgaac ttgaaaacga tgcctgaatt ggaaaccatg aatcttaacg  3120
gattctggag agaaaattta ggaattggta tgtaagctac aacttccggt agctgcgtca  3180
cactttaaga gtgtgcatac tgagccgaag ctcagcttcg gtcccccaag ggaagacca   3239
```

```
SEQ ID NO: 34          moltype = DNA  length = 2790
FEATURE                Location/Qualifiers
source                 1..2790
                       mol_type = genomic DNA
                       organism = Barley stripe mosaic virus
misc_feature           1..2790
                       note = BSMV ND18 RNA3 U13917
SEQUENCE: 34
gtatagcttg agcattaccg tcgtgtaatt gcaacacttg gcttgccaaa taacgctaaa  60
gcgttcacga aacaaacaac acttcggcat ggatgttgtg aagaaattcg ccgtcatgtc  120
agtgactgta gtagcaggtc ccgtccttac gctttcatca cctgtggtgg tgacgtttgg  180
aacaggctta attgccgtat ctttggtgaa acggttgcta caggaacaac cccgtgtaat  240
tgctcacgat cacgaacatt acccaggtgg ttctgagagc agttctagct cttgtgctac  300
cgcgcctatt ttacgtaatc tttcgcgaga tcagtgcgat tcagagaata ttggatgcag  360
ttctagcgcc tgttctccgt ctgaaattgt gaaagttaca aggcaggtag tgggagttga  420
acgtggtctt taccgggaca tttttcagga caacgaaatc ccatcagtca tggaagagaa  480
actgcagaaa ctcctttact ctgagggtga gaagattcga agacgttgcc aatttgaagc  540
atcaacgatg cactcacgca aagtaaaggt tccggaggta ggtactatcc cagatatcca  600
aacttggttc gatgctacgt ttcctggtaa ctccgttagg ttttctgatt tcgacggtta  660
tactgttgct acggaggaca ttaacatgga tgttcaggat tgtagactta agttcgggaa  720
gacttttcga ccttatgaat ttaaggaatc actgaaacca gtactgagga cagcaatgcc  780
agaaaaacga cagggtagtt tgattgaaag tgtgctggcc tttcgtaaaa gaaatttggc  840
tgcgcccaga ttacaaggag ctttgaatga atggcacaca attgagaatg tgctaacgaa  900
ggcgttaaag gtattcttct ttgaagattt aattgatcga acggatcact gcacttacga  960
gtcagcgctc agatggtggg ataaacaatc agtgacagct cgagcgcagc tcgtggcgga  1020
tcagcggagg ttatgtgatg ttgacttcac gacttataac ttcatgataa aaaatgatgt  1080
aaagccgaag ttagatctaa cacctcaagt tgaatatgca gctttgcaga ctgttgtata  1140
tcctgataag atagtcaatg ctttctttgg tccgatcata aaggagatta atgaacggat  1200
```

```
catcagagcg cttagacctc atgtggtctt taattctcgt atgactgctg atgaactgaa  1260
tgaaacagct gcctttttga cacctcataa gtacagagcc ttagagattg atttttcaaa  1320
atttgataaa tcaaagactg ggcttcatat caaagctgtc attggactct ataagctctt  1380
tggcctagat ggcctgttaa aagtgctctg ggaaaaatcg caatatcaga cttacgtgaa  1440
agatagaaac ttcggtctcg aggcatatct attgtatcag caaaagtcag gaaattgtga  1500
cacttacggt tcgaacacct ggtctgccgc cttggcgttg ttagattgtc ttcctttgga  1560
agatgcacat ttctgtgtat ttggtggtga tgattcattg atattgtttg atcagggata  1620
cataatttcc gacccatgcc ggcaacttgc cggtacttgg aatcttgaat gtaaagtgtt  1680
cgacttcaag taccccgcat tttgtggtaa atttctgctg tgcatagatg gaaaatatca  1740
atttgttcca gatgcggcaa aatttatcac aaaattaggt agaactgatg tgagagatgt  1800
agaagttttg agtgagattt atatctctat caatgacaat tacaaatctt acaaagactt  1860
taaggtgctt gatgctttgg ataaggcttt agtggataga tatcgatccc cttatagtgc  1920
tatttctgct ttggtttctt tatgttatca tatctttgac tttaataagt ttaagttgct  1980
gtttaattgt gaagggaaat ttgtggataa gaagctgaga aaagacttcg agtggtgaac  2040
tctaggtcct gatgtttaaa tctactgtat ttaccttcgc atgatggcta ctttctcttg  2100
tgtgtgttgt ggtaccttaa ctacaagtac ttactgtggt aagagatgtg agcgaaagca  2160
tgtatattct gaaacaagaa ataagagatt ggaactttac aagaagtatc tattggaacc  2220
gcaaaaaatgc gccctgaatg gaatcgttgg acacagttgt ggaatgccat gctccattgc  2280
ggaagaggct tgtgatcaac tgccaatcgt gagtaggttc tgtggccaaa agcatgcgga  2340
tctgtatgat tcacttctga aacgttctga acaggagtta cttcttgaat ttctccagaa  2400
gaagatgcag gagctgaaac tttctcatat cgtaaaaatg gctaagcttg aaagtgaggt  2460
taacgcaata cgtaagtccg tagcttcttc ttttgaagat tctgttggat gtgatgattc  2520
ttcttccgtt tctaagtaaa aaaaaaaaaa aatgtttgat cagatcattc aaatctgatg  2580
gtgcccatca accatatgat gggagtgttt gcaagtccac tataatcgaa cttgaaaacg  2640
atgcctgaat tggaaaccat gaatcttaac ggactctgga gagaaaattt aggaattggt  2700
atgtaagcta caacttccgg tagctgcgtc acactttaag agtgtgcata ctgagccgaa  2760
gctcagcttc ggtcccccaa gggaagacca                                   2790

SEQ ID NO: 35          moltype = DNA  length = 3768
FEATURE                Location/Qualifiers
source                 1..3768
                       mol_type = genomic DNA
                       organism = Barley stripe mosaic virus
misc_feature           1..3768
                       note = BSMV_RNA1_gi[19]744917f∮_003469.1[0anc]Tr;;63SEQUENCE: 35
gtatgtaagt tgcctttggg tgtaaaattt cttgcatgca cataatcgta atcgattctt  60
cttgatctct aaacaacact ttcccgttag catggctagc gatgagattg tccgcaatct  120
gatctcccgt gaggaggtga tgggtaattt gattagcaca gcttctagct cagtaaggtc  180
acccttacat gacgtactgt gctcgcacgt aaggaccatc gtcgattccg tggataagaa  240
agcggtcagt cgcaagcatg aagatgtacg gcgcaacatc tcctctgagg aattgcagat  300
gttgataaat gcatatcctg aatatgccgt ttcatcctca gcttgtgaat ctggtactca  360
tagcatggcg gcttgttttc gatttctgga gacagaatat ctcttagata tggttccaat  420
gaaagagact tttgtttatg acattggtgg caactggttt tctcatatga agtttcgtgc  480
tgatagagaa attcattgtt gctgtccgat cttatctatg agagattctg aaagactgga  540
aacacgcatg atggcaatgc aaaaatatat gcgtggatcg aaagacaaac cgttacgctt  600
gttaagccgt tatcaaaata tcctgcgtga acaagcggcg agaacaactg cctttatggc  660
aggtgaggtg aatgcgggtg ttctcgatgg agatgtgttt tgtgagaaca cttttcaaga  720
ctgtgtgaga cgagtgcccg aaggtttttt gaagacagct atagcagttc atagcatcta  780
cgatatcaaa gtggaggaat ttgcgtctgc attgaaaaga aaaggtataa cacaggctta  840
tgggtgtttc ctgtttcctc ctgctgtatt gataggtcag aaggaaggca ttttaccttc  900
cgtggacggt cattacttgg tggagaatgg caggattaag ttcttctttg cgaatgatcc  960
gaatgccggt tactctcatg accttaagga ttatctgaag tatgtggaaa agacctatgt  1020
ggatatagag gatggagtgt ttgctattga gctgatgcaa atgcgaggtg ataccatgtt  1080
ctttaagatc acggatgtca ccgcagcaat gtatcatatg aaatacagag gtatgaaacg  1140
cgatgaaaca ttcaaatgca ttccgttgct aaagaattca tctgttgtcg tacctctatt  1200
ttcgtgggac aaccgttctt taaagatcac aagtggttta ctaccacgaa ctttggtcga  1260
gcagggtgcg gcttttatta tgaaaaacaa ggagaaggac ttgaacgttg ctgtgttgaa  1320
gaactatctt tccgctgtga acaactcata cattttcaac ggatcccagg ttagagatgg  1380
cgtgaaaatt gccccggatt taatctccaa gttggcagtg actctgtacc tgagagaaaa  1440
agtctatcga caaagagaaa attcaatcat aagttatttc gagcaagaaa tgcttcacga  1500
tcccaacttg aaagccatgt ttggagactt tctgtggttt gttccaaata ctctctcgag  1560
tgtctggaag aacatgcgaa aatcactgat ggaatggttt ggctacgcag aatttgactt  1620
gactactttt gatatttgcg atcccgttct ctatgtagag atagtggatc ggtataagat  1680
cattcaaaaa gggcgaattc cacttggtga gttctttgat tgtcatgaag aatgcgagaa  1740
ttacgaactg cgtgagaagg agaaaaacga cctagcggtg aaaatggccc agaaggtaac  1800
agggacggtg accgaatgcg agaaggacct gggacctctt gttcaaccga taaaagagat  1860
attggttcaa cttgtgatgc ccaatttggt cagagcgctg tgtagacctc gtagcccaac  1920
gtctcctttg gacttaaaaa gtatcccagg gtcaactcca tcacactcaa gttcagattc  1980
tgaacactct atgactgaag aagcgagctg caccattgcg ggtagcgtac caacatggga  2040
aattgcgact aggaaagatc taacctttca gcgaattgat gaagatatgt ctcgacgaac  2100
tggtatgcct ccaagaccaa aagtaacttc tagttacaac atgaatgcca gagctgagtt  2160
tctctactat caactgtgta gcgtgatttg tgaaagggct cagattttga gtgtcatcga  2220
agactttcgt cagaatttga tattctcaga taaagtggcc gttccattga acgctagatt  2280
ctacagtttt cagtcattga gacccggatg ggtgttcaaa actccatcgc atagtgaagt  2340
aggccacagt tatgcagtac attttgactt caagacaatt ggaaccgatt tggaagagag  2400
cctagctttt tgccgaatgg taccgatttc atgggataaa agcggcaaat acatcgcgac  2460
aactcctcat tttcccgaga gacatggtta ctacgtgatt tgtgacaaca ctaaattgtg  2520
taacaattgg cttatttaca ataagttagt tgacgtctac gcactagtgg ctgatagacc  2580
tctgagattc gagttgattg acggagttcc tggctgcgga aagtcaacca tgattttaaa  2640
```

-continued

```
cagctgtgat attcgacgcg aagttgttgt tggtgaagga cggaatgcaa ctgatgactt  2700
aagggagagg ttcaagcgta agaaaaattt gaatagtaag actgctaatc acagagttcg  2760
aacgcttgac agcttattac ttgctgaagg accttgtgta ccgcaagctg ataggtttca  2820
ttttgatgaa gctctaaaag ttcattacgg cgccataatg ttctgtgctg ataagcttgg  2880
tgcctcagaa attctcgctc agggagatag ggctcaattg ccaatgatct gtcgtgtaga  2940
aggtattgaa cttcaatttc aatctcctga ttacacgaag acgatcataa atcctaagct  3000
acggtcatac cgtatccctg gagatgttgc cttctatttg agtgctaagg aattttacaa  3060
agttaaagga atacctcaaa aggttataac ttctaacagt gtgaaacgtt ccttgtacgc  3120
tagaggcgaa acgactccgg aaagattcgt gagtttgctt gatgttccgg tgagaaaaga  3180
cacccactat ctaaccttct tacaagctga gaaggaaagt ttgatgagtc atttgattcc  3240
aaagggtgtg aagaaagagt ctatttcaac gattcatgag gcgcagggtg gtacctatga  3300
aaatgtgatt ctggtccgtt tgcaacggac gcccaatgaa atttatccgg gtggacctag  3360
gtccgcccct tacattgtgg ttgggacttc aaggcataca aaaactttca cttattgtag  3420
tgttacggac gataagttgc ttttagatat cgccgacgtc ggtggtattg cacatacacc  3480
tattcgtact tttgaatctc atatagttta aaaaaaaaaa aaaaaaaaaa tgtttgatca  3540
gatcattcaa atctgatggt gcccatcaac catatgatgg gagtgtttgc aagtccacta  3600
taatcgaact tgaaaacgat gcctgaattg gaaaccatga atcttaacgg attctggaga  3660
gaaaatttag gaattggtat gtaagctaca acttccggta gctgcgtcac actttaagag  3720
tgtgcatact gagccgaagc tcagcttcgg tcccccaagg gaagacca              3768

SEQ ID NO: 36          moltype = DNA  length = 3289
FEATURE                Location/Qualifiers
source                 1..3289
                       mol_type = genomic DNA
                       organism = Barley stripe mosaic virus
misc_feature           1..3289
                       note = BSMV_RNA2_gi[19]744922f∮_003481.1[0anc]Tr;;63SEQUENCE: 36
gtaaaagaaa aggaacaacc ctgttgttgt tcgacgctat actaaatata tattatctta  60
ttagtgcatt tcttttaccg cttcacagta tgccgaacgt ttctttgact gctaagggtg  120
gaggacacta catcgaggat caatgggata cacaagttgt ggaagccgga gtatttgacg  180
attggtgggt ccacgtagaa gcctggaata aatttctaga caatttacgt ggtatcaact  240
ttagcgttgc ttcctctcgg tcgcaagtcg ctgaatactt agctgcgtta gatcgtgatc  300
tacctgctga tgtagacaga cggtttgcag gtgctagggg acaaattggt tcacccaatt  360
atcttcctgc gccaaaattc tttcgtctcg ataagcgaac tatcgctgaa ctgactagac  420
tctctcgtct tacggatcag ccgcacaaca atcgcgatat agaacttaac cgagcgaaaa  480
gagccacaac taacccatct cccccggcgc aggcaccgtc ggagaatctc actcttcgtg  540
atgttcaacc gttaaaggat agtgcgttgc attatcaata cgtgttgatt gacctacaga  600
gtgcgagact cccggtgtat accaggaaga ctttcgaacg tgaactcgct ttggaatgga  660
tcattccaga tgccgaggaa gcgtgacctg ctgtcgaagc ggtaaaagga tgtacatatg  720
tatcttattt attttgttta tctattttct tttgctttta gtttttgctt tttacgcatt  780
aactagatgt attgacttta gccatggaca tgacgaaaac tgttgaggaa aagaaaacaa  840
atggaactga ttcagtgaaa ggtgtttttg aaaactcgac gattcccaaa gttccgactg  900
gacaggaaat gggtggtgac ggttcttcta cttctaaatt aaaggaaact ctgaaagttg  960
ccgatcagac tccattgtcc gttgacaatg gtgccaaatc caaattggat tcctctgata  1020
gacaagttcc tggagttgcc gatcagactc cattgtccgt tgacaatggt gccaaatcca  1080
aattggattc ctctgataga caagttcctg gacctgagtt gaaacccaac gttaagaagt  1140
ccaagaagaa aagaatccaa aaacctgctc aaccgagtgg gcccaatgac cttaaaggcg  1200
ggactaaggg atcatctcaa gtgggtgaaa atgtgagtga gaactatact gggatttcta  1260
aggaagcagc taagcaaaag cagaagacgc ccaagtctgt gaaaatgcaa agcaatctgg  1320
ccgataagtt caaagcgaat gatactcgta gatcggaatt aattaacaag tttcagcaat  1380
ttgtgcatga aacctgtctt aaatctgatt ttgagtacac tggtcgacag tatttcagag  1440
ctagatcaaa tttctttgaa atgattaagc tcgcatcctt gtatgacaaa catctaaagg  1500
aatgtatggc gcgagcctgc accctagaac gtgaacgatt gaagcgtaag ttactcctag  1560
tacgagcttt gaaaccagca gttgacttcc ttacgggaat catctctgga gttcctggct  1620
caggaaaatc aaccattgtg cgtactttgc tcaaaggtga atttccggct gtttgtgctt  1680
tggccaatcc tgccttaatg aacgactatt ctggtattga aggcgtttac gggttagatg  1740
acctgttgct ttctgcagtt ccgataacgt ctgatttatt gatcatagat gaatatacac  1800
ttgctgagag cgcggaaatc ctgttgttac aacgaagact cagagcctct atggtgttgt  1860
tagtcgggga tgtagctcaa ggaaaagcca ccactgcttc cagtattgag tatttaactc  1920
tgccggtgat ctacagatca gagacgactt atcgtttggg acaagagact gcttcgcttt  1980
gcagcaagca gggtaacaga atggtttcaa agggtggaag ggacacagtg atcattactg  2040
attacgatgg cgaaacagat gaaacggaga aaaatatcgc ttttactgtc gatacagttc  2100
gagatgtgaa agattgcggg tacgattgtg ccctggcaat tgatgtgcaa gggaaagaat  2160
tcgattcagt gactttattc ctaaggaacg aagaccggaa agctttagca gataagcatt  2220
tgcgtttagt cgctttgagc agacataagt cgaagttaat catcagggcc gacgcggaaa  2280
ttcgtcaagc attcctgaca ggtgatattg acttgagctc taaggcgagt aactctcatc  2340
gttattctgc aaaaccggat gaagaccaca gttggttcaa ggccaaataa gtattggcca  2400
attgtcgccg gaatcggtgt cgttggattg tttgcgtatt tgatcttttc aaatcaaaaa  2460
cattctacgg aatccggtga taatattcac aaattcgcca acggaggtag ttacagagac  2520
gggtcaaaga gtataagtta taatcgtaat catccttttg cctatggcaa tgcctcatcc  2580
cctggaatgt tgttgcccgc aatgcttacc atcatcggaa tcatttccta tttatggcga  2640
acaagagatt ccgtgctcgg agactcaggc ggaaacaact cctgtggaga agactgtcag  2700
ggcgaatgtc ttaacggaca ttctcgacga tcattactat gcgatattgg ctagtctttt  2760
tatcattgct ctatggctat tgtatatata tctaagcagt atacctacgg agactggtcc  2820
ctacttctat caagatctga actctgtgaa gatctatgga ataggggcta cgaacccaga  2880
agttattgcg gccatccacc attggcagaa gtaccctttt ggggaatctc cgatgtgggg  2940
aggtttaatc agtgttttga gtattcttct taaaccgctg acattagttt ttgcgttaag  3000
ctttttctc ttactttctt caaaaaggta aaaaaaaaaa aaaaaaaaaa atgtttgatc  3060
agatcattca aatctgatgg tgcccatcaa ccatatgatg ggagtgtttg caagtccact  3120
```

```
ataatcgaac ttgaaaacaa tgcctgaatt ggaaaccatg aatcttaacg gattctggag  3180
agaaaattta ggaattggta tgtaagctac aacttccggt agctgcgtca cactttaaga  3240
gtgtgcatac tgagccgaag ctcagcttcg gtcccccaag ggaagacca              3289

SEQ ID NO: 37          moltype = DNA  length = 3164
FEATURE                Location/Qualifiers
source                 1..3164
                       mol_type = genomic DNA
                       organism = Barley stripe mosaic virus
misc_feature           1..3164
                       note = BSMV_RNA3_gi[19]744919f|_003478.1[0anc]Tr;;63SEQUENCE: 37
gtatagcttg agcattaccg tcgtgtaatt gcaacacttg gcttgccaaa taacgctaaa  60
gcgttcacga aacaaacaac aattcggcat ggatgttgtg aagaaattcg ccgtcatgtc  120
agtgactgta gtagcaggtc ccgtccttac gctttcatca cctgtggtgg tgacgtttgg  180
aacaagctta attgccgtat ctttggtgaa acggttgcta caggaacaac cccgtgtaat  240
tgctcacgat cacgaacatt acccaggtgg ttctgagagc agttctagct cttgtgctac  300
cgcgcctatt ttacgtaatc tttcgcgaga tcagtgcgat tcagagaata ttggatgcag  360
ttctagcgcc tgttctccgt ctgaaattgt gaaagttaca aggcaggtag tggaagttga  420
acgtggtctt taccgggaca aacaacaatt cggcatggat gttgtgaaga aattcgccgt  480
catgtcagtg actgtagtag caggtcccgt ccttacgctt tcatcacctg tggtggtgac  540
gtttggaaca agcttaattg ccgtatcttt ggtgaaacgg ttgctacagg aacaaccccg  600
tgtaattgct cacgatcacg aacattaccc aggtggttct gagagcagtt ctagctcttg  660
tgctaccgcg cctattttac gtaatctttc gcgagatcag tgcgattcag agaatattgg  720
atgcagttct agcgcctgtt ctccgtctga aattgtgaaa gttacaaggc aggtagtgga  780
agttgaacgt ggtctttacc gggacatttt tcaggacaac gaaatcccat cagtcatgga  840
agagaaactg cagaaactcc tttactctga gggtgagaag attcgaagac gttgccaatt  900
tgaagcatca acgatgcact cacgcaaagt aaaggttccg gaggtaggta ctatcccaga  960
tatccaaact tggttcgatg ctacgtttcc tggtaactcc gttaggtttt ctgatttcga  1020
cggttatact gttgctacgg aggacattaa catggatgtt caggattgta gacttaagtt  1080
cgggaagact tttcgacctt atgaatttaa ggaatcactg aaaccagtac tgaggacagc  1140
aatgccagaa aagcgacagg gtagtttgat tgaaagtgtg ctggcctttc gtaaaagaaa  1200
tttggctgcg cccagattac aaggggcttt gaatgaatgg cacacaattg agaatgtgct  1260
gaagaaggcg ttaaaggtat tcttctttga agatttaatt gatcgaacgg atcattgcac  1320
ttacgagtca gcgctcagat ggtgggataa acaatcagtg acggctcgag cgcagctcgt  1380
ggcggaccaa cggaggttat gtgatgttga cttcacgact tataacttca tgataaaaaa  1440
tgatgtaaaa ccgaagttag atctaacacc tcaagttgaa tatgcagctt tgcagactgt  1500
tgtgtatcct gataagatag tcaatgcttt ctttggtccg atcataaagg agattaatga  1560
acggatcatc agagcgctta gacctcatgt ggtctttaat tctcgtatga ctgctgatga  1620
actgaatgaa acagttgcct tttgacacc tcacaagtac agagccttag agattgactt  1680
ttcaaaattt gataaatcaa agactgggct tcatatcaaa gctgtcattg gactctataa  1740
gctctttggt ctagatggcc tgttaaaagt actctgggaa aaatcgcaat atcagactta  1800
cgtgaaagat agaaacttcg gtctcgaggc atatctatta tatcagcaaa agtcaggaaa  1860
ttgtgacact tacggttcga acacctggtc tgccgccttg gcgttgttag attgtcttcc  1920
tttggaagat gcacatttct gtgtatttgg tggtgatgat tcattgatat tgtttgatca  1980
gggatacata atttccgacc catgccggca acttgccggt acttggaatc ttgaatgtaa  2040
agtgttcgac ttcaagtacc ccgcattttg tggtaaattt ctgctgtgca tagatggaaa  2100
atatcagttt gttccagatg cggcaaaatt tatcacaaaa ttaggtagaa ctgatgtgag  2160
agatgtagaa gttttgagtg agatttatat ctctatcaat gacaattaca aatcttacaa  2220
agactttaag gtgcttgatg ctttggataa ggctttagtg gacagatatc gatcccctta  2280
tagtgctatt tctgctttgg tttctttatg ttatcatatc tttgacttta ataagtttaa  2340
gttgctgttt aattgtgaag ggaaatttgt ggataagaag ctgagaaagg acttcgagtg  2400
gtgaactctg ggtcctgatg tttaaatcta ctgtatttac cttcgcatga tggctacttt  2460
ctcttgtgtg tgttgtggta cctcaactac aagtacttac tgtggtaaga gatgtgagcg  2520
aaagcatgta tattctgaaa caagaaataa gagattggaa ctttacaaga agtatctatt  2580
ggaaccgcaa aaatgcgccc tgaatggaat cgttggacac agttgtggaa tgccatgctc  2640
cattgcggaa gaggcttgtg atcaactgcc aatcgtgagt aggttctgtg gccaaaagca  2700
tgcggatctg tatgattcac ttctgaaacg ttctgaacag gagttacttc ttgaatttct  2760
ccagaagaag atgcaggagc tgaaactttc tcatatcgta aaaatggcta agcttgaaag  2820
tgaggttaac gcaatacgta agtccgtagc ttcttctttt gaagattctg ttggatgtga  2880
tgattcttct tccgtttcta agttgtaaaa aaaaaaaaaa aaaaaatgtt tgatcagatc  2940
attcaaatct gatggtgccc atcaaccata tgatgggagt gtttgcaagt ccactataat  3000
cgaacttgaa aacgatgcct gaattggaaa ccatgaatct taacggattc tggagagaaa  3060
atttaggaat tggtatgtaa gctacaactt ccggtagctg cgtcacactt taagagtgtg  3120
catactgagc cgaagctcag cttcggtccc ccaagggaag acca                  3164

SEQ ID NO: 38          moltype = DNA  length = 2360
FEATURE                Location/Qualifiers
source                 1..2360
                       mol_type = unassigned DNA
                       organism = unidentified
                       note = Maize stripe virus
misc_feature           1..2360
                       note = segment 3, complete sequence GenBank: AJ969410.1
SEQUENCE: 38
acacaaagtc ctgggtaaaa aatattattt tttatcaata tatatattac ttctgtccat  60
cgaagcatga acttttacac atcatctgtt ggagtgcgac aatacgacca ctctttattg  120
gtcttgaatg atctcaccaa cattcatatc acttgtgagg atgtccactg ctctgcaaag  180
ctcctctgct acatatatga tatctacaag tctaggtacc catcaatgga tgagcattct  240
ttcttgcgct tgctaaaagg tccagatgat gctgagatac ttagcacctt tttgagaaca  300
```

```
atcatttgga tactgtctca tgacagagac ttcccagatg agttcaggat tccagctaca  360
gcacttgctt cagtttatat aaaatattac tctgaattga aaccaagagc tcctaccacc  420
aattgttgga catgcagaat gtccaaaaac aatctacctt tccaagtccc ctcaataaag  480
ggattccctg ctgaagcaga gctatatata gttccaatct ctgatcatga tggaaagaca  540
atagagtttt caggaatgaa aacactgtac aagtctccaa gcaagaagaa acacaattat  600
gtcatttcat cagatatgcc cccacttagt gctagataca ctgtctggga tggcaaatag  660
agtagtatct gtagaatccc ctttctagga gtgtacggat aatgtaacta agttacattt  720
taagaataaa aaagtgtgct aagcacacta tccgaatagc aatcggatga aggccttaac  780
ctaatttttt gtttttttgc ttttttgttt tttatttgtt tttttgtttt ttcatttttt  840
tggttttttt aatatattat aagattttga gcactctaaa agctcaattt attatacaca  900
ctatatgtac atatcaataa tagtgaacta aaaagcacaa gcactaaaat ataatagaag  960
caaaagcaaa gcataataaa catcataaac tataataaga taatattgtt aaaccataat  1020
aataatgaca cacaaacact caatactaat attatcatac tctcattcat acttgttttt  1080
gattttccat tttcccattt ttttgttttt ttgtataatc taatttttat ggtttttcttg  1140
attttttga ttttttgtt tttttgttta aaacacacaa tacaataata taacacaaac  1200
aacacactta aatagaatat catgacacaa tgtgagcact tcccctgctc agtgccagac  1260
cgtcttatcc aacgcattct tccactttat gatgatatca tcatagtatg aggaactcac  1320
tcctcctcga agaactcaat gatcaatgcc ttcatctcat cctgagtctt tgagctgttg  1380
tctacaatgg ttttcatcaa gctgcactgt tctgccaaaa attgcttgac ctgagtacca  1440
taggagcaga caacattctt tccgaatgat gcaagcaagg ccaagaatga ctccttgaat  1500
ttctcattaa catagtatgg ctcacatact ttggtcctcc cagatttctt cttcgcttcg  1560
ttgaggtttt tggattgaca ggtgatgacc agcaaaccag tggtatactt tatcatgtct  1620
atgtctttga gcaatcctct ctccttcttt tttgtctctg gcattgtttt cttagtgacc  1680
aagaaagcat gaatcacatg aatgctgaaa agaatgtggt tgacactctt agttgtgcag  1740
tatggtgcag atgagctgtc aagtgtaata tattggggaa caaagtccca cagcagggaa  1800
tcagtcccag acatgctaag atcagatgaa tcaatagcca ttttcagacc agtgaactgt  1860
ttggtcacct cataggatac atttggaaag agttgagcta cccttcccag tgtaatagca  1920
tttgcgttgc tacccacaga tgaaactaat ccatagcggg caaccaatgc cgctgcttcc  1980
tcactgccag cagttgcctt ggttttctta gtgacatcct taacaaagcc agtccctcgg  2040
acatacctca tcacaatcat cttgacaaca tcttgagcaa gagttgcccc acccttgtct  2100
ttgagaatac caatcaaagt agccgcatca tagcctgcat accctatctg atcatgaaag  2160
gtggtcacag acgccttgtt atcagtgaga tacttcaaag catctttgga gatatcattg  2220
atagctttct ggagatcatt aagatttgca ggcttattag tggccatttt cttcaagggt  2280
attggtgcaa tggttatgat ttagaccttt ctttagttga tcaatacgaa atcgattaaa  2340
cgattaccca gactttgtgt                                              2360

SEQ ID NO: 39           moltype = AA  length = 1368
FEATURE                 Location/Qualifiers
source                  1..1368
                        mol_type = protein
                        organism = Streptococcus pyogenes
SEQUENCE: 39
MDKKYSIGLD IGTNSVGWAV ITDEYKVPSK KFKVLGNTDR HSIKKNLIGA LLFDSGETAE  60
ATRLKRTARR RYTRRKNRIC YLQEIFSNEM AKVDDSFFHR LEESFLVEED KKHERHPIFG  120
NIVDEVAYHE KYPTIYHLRK KLVDSTDKAD LRLIYLALAH MIKFRGHFLI EGDLNPDNSD  180
VDKLFIQLVQ TYNQLFEENP INASGVDAKA ILSARLSKSR RLENLIAQLP GEKKNGLFGN  240
LIALSLGLTP NFKSNFDLAE DAKLQLSKDT YDDDLDNLLA QIGDQYADLF LAAKNLSDAI  300
LLSDILRVNT EITKAPLSAS MIKRYDEHHQ DLTLLKALVR QQLPEKYKEI FFDQSKNGYA  360
GYIDGGASQE EFYKFIKPIL EKMDGTEELL VKLNREDLLR KQRTFDNGSI PHQIHLGELH  420
AILRRQEDFY PFLKDNREKI EKILTFRIPY YVGPLARGNS RFAWMTRKSE ETITPWNFEE  480
VVDKGASAQS FIERMTNFDK NLPNEKVLPK HSLLYEYFTV YNELTKVKYV TEGMRKPAFL  540
SGEQKKAIVD LLFKTNRKVT VKQLKEDYFK KIECFDSVEI SGVEDRFNAS LGTYHDLLKI  600
IKDKDFLDNE ENEDILEDIV LTLTLFEDRE MIEERLKTYA HLFDDKVMKQ LKRRRYTGWG  660
RLSRKLINGI RDKQSGKTIL DFLKSDGFAN RNFMQLIHDD SLTFKEDIQK AQVSGQGDSL  720
HEHIANLAGS PAIKKGILQT VKVVDELVKV MGRHKPENIV IEMARENQTT QKGQKNSRER  780
MKRIEEGIKE LGSQILKEHP VENTQLQNEK LYLYYLQNGR DMYVDQELDI NRLSDYDVDH  840
IVPQSFLKDD SIDNKVLTRS DKNRGKSDNV PSEEVVKKMK NYWRQLLNAK LITQRKFDNL  900
TKAERGGLSE LDKAGFIKRQ LVETRQITKH VAQILDSRMN TKYDENDKLI REVKVITLKS  960
KLVSDFRKDF QFYKVREINN YHHAHDAYLN AVVGTALIKK YPKLESEFVY GDYKVYDVRK  1020
MIAKSEQEIG KATAKYFFYS NIMNFFKTEI TLANGEIRKR PLIETNGETG EIVWDKGRDF  1080
ATVRKVLSMP QVNIVKKTEV QTGGFSKESI LPKRNSDKLI ARKKDWDPKK YGGFDSPTVA  1140
YSVLVVAKVE KGKSKKLKSV KELLGITIME RSSFEKNPID FLEAKGYKEV KKDLIIKLPK  1200
YSLFELENGR KRMLASAGEL QKGNELALPS KYVNFLYLAS HYEKLKGSPE DNEQKQLFVE  1260
QHKHYLDEII EQISEFSKRV ILADANLDKV LSAYNKHRDK PIREQAENII HLFTLTNLGA  1320
PAAFKYFDTT IDRKRYTSTK EVLDATLIHQ SITGLYETRI DLSQLGGD              1368

SEQ ID NO: 40           moltype = DNA  length = 1880
FEATURE                 Location/Qualifiers
source                  1..1880
                        mol_type = genomic DNA
                        organism = Brachypodium distachyon
SEQUENCE: 40
cttcaccgcc attgcaaaaa ttgtcaataa atatttagag tgggtggcat cagaaaaaca  60
tctctagtgg actctcttcc tatcatagct actcgggctg tagatagaac gagggcacaa  120
gagttgggtg gcgtaggttt actcgtgacc tcaactcttt tggctgtgtc ttacgtctaa  180
gatgggtttg gcatgtgaga aacataggtc taagcaattc atgttagggc tgttgcattg  240
ttgttgcatc aaccaaatgt ccagatagca gttcatgcta catctagttg aaaaccctca  300
tcattaggcg gaacatgtgt tctttttag catagtcaaa gtcagattgc ggcactcgct  360
catccacgga aagaatttc cctgtgcagg catctcgatc aaaagacgca aattaatttt  420
```

```
tgaatagcga tataacaata tctaattaac gtttcttgtt ttctgcgaaa tgtctttcat  480
cataaaatga gtcatctcga tgagcccaag tgacatagcc caacacccca ccccaccaat  540
aaaagtgaag aaaacatgtt gggaaaacta taccaagtaa aatacgagtt gttctaaaga  600
aaaagtaaag tacgagttag atcgcaccct gtcctggagt gtggcttgat gatccaactc  660
ctagcattgt atccctgttt ttggatgatg taactattat ttacaatgaa taaagaggtg  720
ttttactagt aaaaaaatct tgaggggagg agaaaataat ggaggtcttt tttcaaaccg  780
atggactatt atttttagtg aaagagaata atatttattgg aaaaattatt ctatccactt  840
attttatatt ggcagaatac aaagaatggt ggggtccacg cggaacttgc ggcccccgaa  900
acctatcgag ggcgcggtac ccaagcaagg aacggaggaa acttgcgggg cccgaaacct  960
agtgataaaa ggcatatcat ccacacgatg aagatctgac ggaccatatc tcccaccacg  1020
gaaagccatc agacgaggat cagacggcca ggaaggaacc ctagcgcccg ccggtgccaa  1080
tataaagcgc cactctctct cgtcttaagc cccagcctct ccattcccct ctccctctcg  1140
ccgccgccgt ctccttctcc tactcccttc gaggtgtgtt gttcatccgt cccgaatcca  1200
tccatcccct cttcagatgt gttgttcatg gctctaatag ctctagatct gcttgtttgt  1260
gttgtttagc tctagatcta ctcgcgcgcg cttctctctc gatctcctgt agaacaattt  1320
tggttggttt tttgtgcata tccatggtaa ttttgtctgc aatatggagg aggctttcta  1380
agctcctacg tagcatcgat ctttagaatt ccctcggttt ctgtttattt cttcgcgagg  1440
gctctctgtt atctgtagga gtagctgtaa gcgcggttcg ttacggatta atcgtcatgc  1500
ttagttgaac ctatcggtcg aaggatttgt gtgggttgtc gtgtagaatt gacaccatct  1560
acttactgta ctgatatgcc gatctgtagg atactcttca ttacttttgt ttactgctag  1620
ttgtggtgta gatttagcat tctcaaaccc atgctgtagc gtttctaata ttgttacata  1680
gatctaccgg tgcctgttaa ttgtattcga tcgggcgttt ctacatctgt ccgcccacct  1740
agttttatat gtggtaatca aaattgcgtt gacttcgtga tgctgtctgt gtactgtttt  1800
taatcgctct tacttagatg atcaacatgg tgatggttac gatttactgt tttctaatcc  1860
ctgttacttc gatgctgcag                                              1880

SEQ ID NO: 41          moltype = DNA  length = 17
FEATURE                Location/Qualifiers
source                 1..17
                       mol_type = other DNA
                       organism = synthetic construct
                       note = Protospacer Region guide RNA 14
SEQUENCE: 41
tggttctgcc tctggtc                                                 17

SEQ ID NO: 42          moltype = DNA  length = 20
FEATURE                Location/Qualifiers
source                 1..20
                       mol_type = other DNA
                       organism = synthetic construct
                       note = Protospacer Region guide RNA 16
SEQUENCE: 42
taacggatag cgctcctcgt                                              20

SEQ ID NO: 43          moltype = DNA  length = 20
FEATURE                Location/Qualifiers
source                 1..20
                       mol_type = other DNA
                       organism = synthetic construct
                       note = Protospacer Region guide RNA 37
SEQUENCE: 43
tggagcttac cgactcgctc                                              20

SEQ ID NO: 44          moltype = DNA  length = 20
FEATURE                Location/Qualifiers
source                 1..20
                       mol_type = other DNA
                       organism = synthetic construct
                       note = Protospacer Region guide RNA 38
SEQUENCE: 44
ggagcttacc gactcgctca                                              20

SEQ ID NO: 45          moltype = DNA  length = 20
FEATURE                Location/Qualifiers
source                 1..20
                       mol_type = other DNA
                       organism = synthetic construct
                       note = Protospacer Region guide RNA 39
SEQUENCE: 45
ggaaagctgc tggcgacagg                                              20

SEQ ID NO: 46          moltype = DNA  length = 20
FEATURE                Location/Qualifiers
source                 1..20
                       mol_type = other DNA
                       organism = synthetic construct
                       note = Protospacer Region guide RNA 43
SEQUENCE: 46
tcctggtcga acttttcagg                                              20
```

```
SEQ ID NO: 47          moltype = DNA  length = 20
FEATURE                Location/Qualifiers
source                 1..20
                       mol_type = other DNA
                       organism = synthetic construct
                       note = Protospacer Region guide RNA 18
SEQUENCE: 47
taattctagt acatggatat                                          20

SEQ ID NO: 48          moltype = DNA  length = 20
FEATURE                Location/Qualifiers
source                 1..20
                       mol_type = other DNA
                       organism = synthetic construct
                       note = Protospacer Region guide RNA 52
SEQUENCE: 48
cggtcataaa gcagctctca                                          20

SEQ ID NO: 49          moltype = AA  length = 9
FEATURE                Location/Qualifiers
source                 1..9
                       mol_type = protein
                       organism = Simian virus 40
SEQUENCE: 49
MAPKKKRKV                                                      9

SEQ ID NO: 50          moltype = AA  length = 18
FEATURE                Location/Qualifiers
source                 1..18
                       mol_type = protein
                       organism = unidentified
                       note = Agrobacterium tumefaciens
SEQUENCE: 50
KRPRDRHDGE LGGRKRAR                                            18

SEQ ID NO: 51          moltype = AA  length = 18
FEATURE                Location/Qualifiers
source                 1..18
                       mol_type = protein
                       organism = unidentified
                       note = Agrobacterium tumefaciens
SEQUENCE: 51
KRPREDDDGE PSERKRER                                            18

SEQ ID NO: 52          moltype = AA  length = 17
FEATURE                Location/Qualifiers
source                 1..17
                       mol_type = protein
                       organism = unidentified
                       note = Agrobacterium tumefaciens
SEQUENCE: 52
KLRPEDRYVQ TERYGRR                                             17

SEQ ID NO: 53          moltype = AA  length = 17
FEATURE                Location/Qualifiers
source                 1..17
                       mol_type = protein
                       organism = unidentified
                       note = Agrobacterium tumefaciens
SEQUENCE: 53
KLRPEDRYIQ TEKYGRR                                             17

SEQ ID NO: 54          moltype = AA  length = 15
FEATURE                Location/Qualifiers
source                 1..15
                       mol_type = protein
                       organism = unidentified
                       note = Agrobacterium tumefaciens
SEQUENCE: 54
KRRYGGETEI KLKSK                                               15

SEQ ID NO: 55          moltype = AA  length = 15
FEATURE                Location/Qualifiers
source                 1..15
                       mol_type = protein
                       organism = unidentified
                       note = Agrobacterium tumefaciens
SEQUENCE: 55
```

```
KTKYGSDTEI KLKSK                                                15

SEQ ID NO: 56           moltype = AA  length = 20
FEATURE                 Location/Qualifiers
source                  1..20
                        mol_type = protein
                        organism = unidentified
                        note = Agrobacterium rhizogenes
SEQUENCE: 56
KRKRAAAKEE IDSRKKMARH                                           20

SEQ ID NO: 57           moltype = AA  length = 20
FEATURE                 Location/Qualifiers
source                  1..20
                        mol_type = protein
                        organism = unidentified
                        note = Agrobacterium rhizogenes
SEQUENCE: 57
KRKRVATKEE IEPHKKMARR                                           20

SEQ ID NO: 58           moltype = AA  length = 18
FEATURE                 Location/Qualifiers
source                  1..18
                        mol_type = protein
                        organism = unidentified
                        note = Agrobacterium rhizogenes
SEQUENCE: 58
KRPRVEDDGE PSERKRAR                                             18

SEQ ID NO: 59           moltype = DNA  length = 3738
FEATURE                 Location/Qualifiers
source                  1..3738
                        mol_type = other DNA
                        organism = synthetic construct
                        note = pEn Chimera Vector
SEQUENCE: 59
gggcgaattg ggcccgacgt cgcatgctcc cggccgccat ggcggccgcg ggaattcgat  60
caaataatga ttttattttg actgatagtg acctgttcgt tgcaacaaat tgatgagcaa  120
tgctttttta taatgccaac tttgtacaaa aaagcaggct ctttttttct tcttcttcgt  180
tcatacagtt ttttttgtt tatcagctta cattttcttg aaccgtagct ttcgttttct  240
tctttttaac tttccattcg gagtttttgt atcttgtttc atagtttgtc ccaggattag  300
aatgattagg catcgaacct tcaagaattt gattgaataa aacatcttca ttcttaagat  360
atgaagataa tcttcaaaag gcccctggga atctgaaaga agagaagcag gcccatttat  420
atgggaaaga acaatagtat ttcttatata ggcccattta agttgaaaac aatcttcaaa  480
agtcccacat cgcttagata agaaaacgaa gctgagttta tatacagcta gagtcgaagt  540
agtgattggg gtcttcgaga agacctgttt tagagctaga aatagcaagt taaaataagg  600
ctagtccgtt atcaacttga aaaagtggca ccgagtcggt gctttttttc tagacccagc  660
tttcttgtac aaagttggca ttaacccagc tttcttgtac aaagttggca ttataaaaaa  720
taattgctca tcaatttgtt gcaacgaaca ggtcactatc agtcaaaata aaatcattat  780
ttgatcacta gtgaattcgc ggccgcctgc aggtcgacca tatgggagag ctcccaacgc  840
gttggatgca tagcttgagt attctatagt gtcacctaaa tagcttggcg taatcatggt  900
catagctgtt tcctgtgtga aattgttatc cgctcacaat tccacacaac atacgagccg  960
gaagcataaa gtgtaaagcc tggggtgcct aatgagtgag ctaactcaca ttaattgcgt  1020
tgcgctcact gcccgctttc cagtcgggaa acctgtcgtg ccagctgcat taatgaatcg  1080
gccaacgcgc ggggagaggc ggtttgcgta ttgggcgctc ttccgcttcc tcgctcactg  1140
actcgctgcg ctcggtcgtt cggctgcggc gagcggtatc agctcactca aaggcggtaa  1200
tacggttatc cacagaatca ggggataacg caggaaagaa catgtgagca aaaggccagc  1260
aaaaggccag gaaccgtaaa aaggccgcgt tgctggcgtt tttccatagg ctccgccccc  1320
ctgacgagca tcacaaaaat cgacgctcaa gtcagaggtg gcgaaacccg acaggactat  1380
aaagatacca ggcgtttccc cctggaagct ccctcgtgcg ctctcctgtt ccgaccctgc  1440
cgcttaccgg atacctgtcc gcctttctcc cttcgggaag cgtggcgctt tctcatagct  1500
cacgctgtag gtatctcagt tcggtgtagg tcgttcgctc caagctgggc tgtgtgcacg  1560
aaccccccgt tcagcccgac cgctgcgcct tatccggtaa ctatcgtctt gagtccaacc  1620
cggtaagaca cgacttatcg ccactggcag cagccactgg taacaggatt agcagagcga  1680
ggtatgtagg cggtgctaca gagttcttga agtggtggcc taactacggc tacactagaa  1740
gaacagtatt tggtatctgc gctctgctga agccagttac cttcggaaaa agagttggta  1800
gctcttgatc cggcaaacaa accaccgctg gtagcggtgg tttttttgtt tgcaagcagc  1860
agattacgcg cagaaaaaaa ggatctcaag aagatccttt gatcttttct acggggtctg  1920
acgctcagtg gaacgaaaac tcacgttaag ggattttggt catgagatta tcaaaaagga  1980
tcttcaccta gatcctttta aattaaaaat gaagttttaa atcaatctaa agtatatatg  2040
agtaaacttg gtctgacagt taccaatgct taatcagtga ggcacctatc tcagcgatct  2100
gtctatttcg ttcatccata gttgcctgac tccccgtcgt gtagataact acgatacggg  2160
agggcttacc atctggcccc agtgctgcaa tgataccgcg agacccacgc tcaccggctc  2220
cagatttatc agcaataaac cagccagccg gaagggccga gcgcagaagt ggtcctgcaa  2280
ctttatccgc ctccatccag tctattaatt gttgccggga agctagagta agtagttcgc  2340
cagttaatag tttgcgcaac gttgttgcca ttgctacagg catcgtggtg tcacgctcgt  2400
cgtttggtat ggcttcattc agctccggtt cccaacgatc aaggcgagtt acatgatccc  2460
ccatgttgtg caaaaaagcg gttagctcct tcggtcctcc gatcgttgtc agaagtaagt  2520
tggccgcagt gttatcactc atggttatgg cagcactgca taattctctt actgtcatgc  2580
```

```
catccgtaag atgcttttct gtgactggtg agtactcaac caagtcattc tgagaatagt  2640
gtatgcggcg accgagttgc tcttgcccgg cgtcaatacg ggataatacc gcgccacata  2700
gcagaacttt aaaagtgctc atcattggaa aacgttcttc ggggcgaaaa ctctcaagga  2760
tcttaccgct gttgagatcc agttcgatgt aacccactcg tgcacccaac tgatcttcag  2820
catcttttac tttcaccagc gtttctgggt gagcaaaaac aggaaggcaa aatgccgcaa  2880
aaaagggaat aagggcgaca cggaaatgtt gaatactcat actcttcctt tttcaatatt  2940
attgaagcat ttatcagggt tattgtctca tgagcggata catatttgaa tgtatttaga  3000
aaaataaaca aataggggtt ccgcgcacat ttccccgaaa agtgccacct gatgcggtgt  3060
gaaataccgc acagatgcgt aaggagaaaa taccgcatca ggaaattgta agcgttaata  3120
ttttgttaaa attcgcgtta aatttttgtt aaatcagctc attttttaac caataggccg  3180
aaatcggcaa aatcccttat aaatcaaaag aatagaccga gatagggttg agtgttgttc  3240
cagtttggaa caagagtcca ctattaaaga acgtggactc caacgtcaaa gggcgaaaaa  3300
ccgtctatca gggcgatggc ccactacgtg aaccatcacc ctaatcaagt tttttggggt  3360
cgaggtgccg taaagcacta aatcggaacc ctaaagggag cccccgattt agagcttgac  3420
ggggaaagcc ggcgaacgtg gcgagaaagg aagggaagaa agcgaaagga gcgggcgcta  3480
gggcgctggc aagtgtagcg gtcacgctgc gcgtaaccac cacacccgcc gcgcttaatg  3540
cgccgctaca gggcgcgtcc attcgccatt caggctgcgc aactgttggg aagggcgatc  3600
ggtgcgggcc tcttcgctat tacgccagct ggcgaaaggg ggatgtgctg caaggcgatt  3660
aagttgggta acgccagggt tttcccagtc acgacgttgt aaaacgacgg ccagtgaatt  3720
gtaatacgac tcactata                                               3738
```

```
SEQ ID NO: 60          moltype = DNA  length = 1023
FEATURE                Location/Qualifiers
source                 1..1023
                       mol_type = genomic DNA
                       organism = Zea mays
SEQUENCE: 60
ctttgacttt tcccttaatg acgacttatt atttaattta ctcgtcacga ttcccctctc  60
ctggtcgaac ttttcaggtg gggaaagctg ctggcgacag gtggaaatcc ctgagcgagt  120
cggtaagctc catcttctgt actaaagtag tagttgattg gactagaaat ctcgtgctga  180
ttaattgttt tacgcgtgcg tttgtgtgga ttgtaggaca aggctcccta tgtagccaag  240
gctaacaagc tcaagctcga gtacaacaag gccatcgctg cctacaacaa gggcgaggta  300
gggaaactga tgcttcaatt gcgttgttac ttaatgtgta tatagactgc tcctgctggt  360
catttattca aatacgtatg cttactgaac catgtgttgt ttgttcagag cactgcagct  420
aagaaggctc ctgccaagga ggaagaggag gaagatgaag aggagtctga caagtccaag  480
tcggaggtca atgacgagga tgatgaagag ggtagtgagg aggtatacaa aatctattcc  540
tgtcttctcc atattttttc cttagacaaa ataccaatta atccaggata catagcatgt  600
tcatgcatta agcaagttgc taaatttatc ttcgaccaca atgtagacct agtagtattg  660
tattggattc catcaatgca aaacatatgc agatttgcat atgcaaccct cttttgcaag  720
tcctcaatat gagcatttgt ttggaacacg gtgcattggc cttaggaagt ctttaaaaat  780
atgtcttccc tctgcttgca ggatgaagat gatgacgagt gatggagctc ctcgagacaa  840
tggaccgtgc ttcatccaac aatggagcgg ctacacaagg ccccgtggcg atcacaaaaa  900
aggagcctat atccatgtac tagaattatt cagtttcact ccacatcgtg atgttttatt  960
tttacttttg tcgtgctata acggatagcg ctcctcgttg gcgccactgg cgggtggttc  1020
tgc                                                                1023
```

```
SEQ ID NO: 61          moltype = DNA  length = 210
FEATURE                Location/Qualifiers
source                 1..210
                       mol_type = other DNA
                       organism = synthetic construct
                       note = genome edited hmg13 gene
SEQUENCE: 61
ctttgacttt tcccttaatg acgacttatt atttaattta ctcgtcacga ttcccctctc  60
ctggtcgaac ttttcaggtg gggaaagctg ctggcgactc catgtactag aattattcag  120
tttcactcca catcgtgatg ttttattttt acttttgtcg tgctataacg gatagcgctc  180
ctcgttggcg ccactggcgg gtggttctgc                                   210
```

```
SEQ ID NO: 62          moltype = AA  length = 16
FEATURE                Location/Qualifiers
source                 1..16
                       mol_type = protein
                       organism = unidentified
                       note = Agrobacterium tumefaciens
SEQUENCE: 62
KLRPEDRYVQ TERGRR                                                  16
```

METHODS AND HYBRIDS FOR TARGETED NUCLEIC ACID EDITING IN PLANTS USING CRISPR/CAS SYSTEMS

CROSS-REFERENCE TO RELATED APPLICATIONS

This application is a continuation of U.S. patent application Ser. No. 15/575,167, filed Apr. 16, 2018, now issued as U.S. Pat. No. 11,492,630 on Nov. 8, 2022, which is a U.S. National Phase of International Patent Application No. PCT/EP2016/061237, filed May 19, 2016, which claims priority to German Patent Application Nos. 102015006335.9, filed on May 19, 2015, and 102015014252.6, filed on Nov. 5, 2015, all of which are herein incorporated by reference in their entireties.

SEQUENCE LISTING

The instant application contains a Sequence Listing which has been filed electronically in XML format and is hereby incorporated by reference in its entirety. Said XML copy, created on Sep. 20, 2022, is named 245761_000185_SL.xml and is 219,680 bytes in size.

TECHNICAL FIELD

The present invention relates in particular to methods for the manufacture of a plant, a plant material or a plant cell, comprising providing and introducing at least one gRNA as well as a CRISPR nuclease or a catalytically active fragment thereof and/or an effector domain or at least one recombinant construct, comprising a gRNA as well as a CRISPR nuclease or a catalytically active fragment and/or an effector domain or the sequences coding therefor, as well as at least one regulatory sequence and/or a localization sequence, into a target plant structure comprising at least one meristematic cell, whereupon a plant, a plant material or a plant cell comprising a targeted modification of a nucleic acid in a target region, can be obtained directly, wherein the at least one recombinant construct is preferably not integrated chromosomally or extrachromosomally. In addition, appropriate recombinant constructs and vectors as well as methods for introducing these constructs and vectors into a target plant structure of interest are disclosed. Finally, the use of a recombinant construct for the specific modification of a target nucleic acid region in a plant cell is disclosed, as well as plants, plant material or a plant cell which can be obtained or is obtained by the method in accordance with the invention. Furthermore, an in vitro screening method is disclosed as a preliminary test, in order to readily determine, with a high output, the functionality of a gRNA or an encoding sequence for a gRNA with respect to the targeted modification of a specific nucleic acid target region in a plant cell, together with a CRISPR nuclease, comprising a Cas and/or Cpf1 nuclease, or variations or catalytically active fragments thereof, or a catalytically active fragment thereof. The methods disclosed herein are suitable in particular for the targeted introduction, modification, or elimination of a desired trait in a plant, in particular in the framework of the targeted trait development, in order to ensure a highly specific and efficient genome editing.

BACKGROUND OF THE INVENTION

Genome editing constitutes a molecular biological method by means of which specific modifications such as insertions, deletions or point mutations or combinations thereof can be introduced into the genome of a living organism. To this end, specific molecular instruments are required which firstly have nuclease activity, but above all can be guided to the target sequence to be modified with sufficient specificity to programme and carry out a specific and site-directed mutagenesis. In the past few years in plant biotechnology, specific genome editing has developed into an alternative to conventional cultivation and to transgenic strategies. However, tools which are currently available, such as zinc finger nucleases (ZFNs) or "transCRISPR ption activator-like effector nucleases" (TALENs) are only used in plant biotechnology to a limited extent because of occasional low efficiency and also because of the complex and costly design of the constructs.

A further molecular tool which has been widely used in recent years for precise and site-directed genome modification is the CRISPR nuclease-based system. These nucleases, including inter alia Cas (CRISPR associated gene) nuclease or Cpf1 nucleases, form part of the system desCRISPR bed now in the literature as "CRISPR SPR" systems (clustered regularly interspaced short palindromic repeat). This system was originally identified in 1987 when the iap gene of *E. coli* was analysed, when naturally occurring repeat sequences in the bacterial genome were identified. Later on it was discovered that these palindromic DNA repeat sequences of 20 to 50 nucleotides followed a pattern. The acronym CRISPR was then adopted (Jansen, R. et al, "Identification of genes that are associated with DNA repeats in prokaryotes", *Mol. Microbiol.,* 2002, 43(6), 1565-1575), whereupon research focused even more closely upon bacteria. Finally, it was reported that the CRISPR locus constitutes a type of bacterial immune system and could confer immunity against phages (Barrangou et al "CRISPR provides acquired resistance against viruses in prokaryotes" *Science* 2007, 315: 1709.1712), wherein the invading phage DNA was initially installed as a protospacer into a CRISPR locus, the locus was then transCRISPR bed and finally the CRISPR SPR-mediated silencing mechanism was activated.

Functional characterization gradually led to the system being exploited as a universal tool for genome modification of higher organisms. In the meantime, a large number of CRISPR SPR/Cas systems have been desCRISPR bed (see, for example Van der Oost et al "Unravelling the structural and mechanistic basis of CRISPR SPR-Cas systems" *Nature* 2014, 482:331-338, Makarova et al., "An updated evolutionary classification of CRISPR SPR-Cas systems ", Nature Reviews Microbiology 13, 722-736); as yet, the analyses are still far from completed.

A further genome editing system with huge potential is now available thanks to the discovery and exploitation of the bacterial type II CRISPR system.

Five types (I-V) of CRISPR systems have been desCRISPR bed so far (Barrangou et al., 2007, Science, 315(5819):1709-12; Bouns et al., 2008, Science, 321(5891): 960-4; Marraffini and Sontheimer, 2008, Science, 322 (5909): 1843-5; Makarova et al., Nature Rev. Microbiol., 13, 722-736, 2015), wherein each system comprises a cluster of CRISPR SPR-associated genes (Cas or others) and a CRISPR array belonging thereto. These characteristic CRISPR arrays are composed of repetitive sequences (direct repetitions, so-called repeats), in which short sections of non-repetitive sequences ("spacers") are embedded, wherein the spacers originate from short fragments of foreign genetic material (protospacers). The CRISPR arrays are subsequently transCRISPR bed into short CRISPR RNAs (crRNAs), wherein the crRNAs direct the Cas proteins or other effector nucleases of a CRISPR system to the respective target nucleic acid molecules, where cleavage occurs by means of Watson-CRISPR ck base pairing. The Type I and Type III CRISPR systems use complexes of Cas proteins and crRNAs for the recognition and subsequent cleaving of target nucleic acids (Wiedenheft et al., 2011, Nature, 477 (7365):486-9). On the contrary, Type II CRISPR systems are recognized and cleaved in their natural form, their target DNA interacting with the RNA-directed nuclease Cas9 with two non-encoded RNAs, the crRNA, and a trans-activating RNA (tracrRNA) (Garneau et al., 2010; Sapranauskas et al., 2011, Nucleic Acids Res., 39(21); 9275-82; Deltcheva et al., 2011, Nature, 471(7340); 602-7). A possible Type IV CRISPR system has also been proposed (Makarova et al., Biol. Direct, 6(38), 2011).

The immune response mediated by CRISPR SPR/Cas in natural systems requires CRISPR SPR-RNA (crRNA), wherein the maturation of this guide RNA, which controls the specific activation of the Cas nuclease, varies significantly between the various CRISPR systems which have been characterized so far. Firstly, the invading DNA, also known as a spacer, is integrated between two adjacent repeat regions at the proximal end of the CRISPR locus. Type II CRISPR systems code for a Cas9 nuclease as a key enzyme for the interference step, which contains both a crRNA and also a trans-activating RNA (tracrRNA) as the guide motif. These hybridize and form double-stranded (ds) RNA regions which are recognized by RNAseIII and can be cleaved in order to form mature crRNAs. These then in turn associate with the Cas molecule in order to direct the nuclease specifically to the target nucleic acid region.

A recombinant CRISPR SPR/Cas system, or in general, a CRISPR SPR/nuclease system, enables a targeted DNA recognition and/or bonding through a small, individually tailored, non-encoding RNA (guide RNA or gRNA) in combination with a possibly modified nuclease, and the optional generation of a single- or double-strand break. Recombinant gRNA molecules can comprise both the variable DNA recognition region and also the nuclease interaction region and thus can be specifically designed, independently of the specific target nucleic acid and the desired nuclease (Jinek et. al., 2012, supra). As a further safety mechanism, PAMs (protospacer adjacent motifs) must be present in the target nucleic acid region; these are DNA sequences which in type II CRISPR system follow on directly from the Cas9/RNA complex-recognized DNA. The PAM sequence for the Cas9 from *Streptococcus pyogenes* is in fact "NGG" or "NAG" (Standard IUPAC nucleotide code) (Jinek et al, "A programmable dual-RNA-guided DNA endonuclease in adaptive bacterial immunity", Science 2012, 337:816-821). The PAM sequence for Cas9 from *Staphylococcus aureus* is "NNGRRT" or "NNGRR (N)". Further variant CRISPR SPR/Cas9 systems are known. Thus, a *Neisseria meningitidis* Cas9 cleaves at the PAM sequence NNNNGATT. A *Streptococcus thermophilus* Cas9 cleaves at the PAM sequence NNAGAAW. Furthermore, by using modified Cas polypeptides, specific single-stranded breaks can be obtained. The combined use of Cas nickases with various recombinant gRNAs can also induce highly specific DNA double-stranded breaks by means of double DNA nicking. By using two gRNAs, moreover, the specificity of the DNA binding and thus the DNA cleavage can be optimized.

In addition to the CRISPR SPR/Cas system, so-called CRISPR SPR/Cpf1 systems have also been desCRISPR bed recently, which are suitable as tools for the targeted genome editing in a manner analogous to that with CRISPR SPR/Cas systems (see Zetsche et al., "Cpf1 Is a Singel RNA-Guides Endonuclease of a Class 2 CRISPR SPR-Cas System," Cell, 163, pp. 1-13, October 2015). The CRISPR SPR/Cpf1 system is also referred to as a Type V CRISPR system (Makarova et al., Nature Rev. Microbiol., 2015, above). In differing from a Cas9 nuclease of a Type II CRISPR SPR/Cas system, a Cpf1 nuclease requires no additional trans-activating tracr-RNAs. Cpf1 recognizes T-rich PAM sequences, and cleaves the target DNA, producing "sticky ends," i.e. overhangs, while in contrast, Cas9 leaves "blunt ends." As with Cas nucleases, Cpf1 nucleases contain an RuvC-like endonuclease domain, while in contrast, they lack a second HNH endonuclease domain (Makarova & Koonin, Methods Mol. Biol., 1311, 47-75, 2015). While Type I, II and IV CRISPR systems are currently referred to as Class 1 systems, Type II and Type V systems are regarded as Class 2 (cf. Makarova et al., Nature Rev. Microbiol., 2015, above).

A DNA double-strand break inside a plant cell is repaired, either by "non-homologous end joining" (NHEJ) or "homologous recombination ((HR), also referred to as "homology-directed repair" (HDR)). Furthermore, in plants, so-called alternative end joining (AEJ) pathways have been desCRISPR bed (Charbonnel C, Allain E, Gallego M E, White C I (2011) Kinetic analysis of DNA double-strand break repair pathways in *Arabidopsis*. DNA Repair (Amst) 10:611-619).

It is therefore proposed in US 2015/082478 A1 that a separate HDR DNA repair vector be used, in order to introduce a double-strand break, which was previously obtained through a recombinant CRISPR SPR/Cas system. Apart from the genetic modification of bacterial genomes, the modification of complex eukaryotic genomes constitutes a huge challenge since, because of the complexity of this genome, molecular tools have to be provided which can effect a specific genome modification without unwanted off-target effects, i.e. unwanted mutations or modifications within the genome or the non-genomic DNA of the target cell.

U.S. Pat. No. 8,697,359 B1 discloses that using CRISPR SPR/Cas technology, eukaryotic genomes, in particular mammalian genomes can be modified, preferably for therapeutic purposes. In this regard, the expression of a target gene by specific introduction of a Cas9 endonuclease as well as a guide RNA (gRNA) is suppressed in a programmable manner. This gRNA is an essential element of every Cas9 CRISPR system, since it in fact guides the actual Cas nuclease specifically to the (genomic) target DNA. To this end, in addition, a tracr (trans-activating CRISPR RNA) sequence and a tracr mate sequence are disclosed for Cas9-CRISPR systems which can be included in the gRNA, wherein the tracr sequences hybridize and can thus be recognized. The use of CRISPR technology to modify complex plant genomes and the molecular tools required for this were not disclosed, however.

WO 2015/026885 A1, on the other hand, is especially concerned with the application of CRISPR SPR/Cas technology in plants. Here, however, only an overall strategy and appropriate molecular tools are disclosed which necessarily require the subculture, selection and regeneration of plant calluses following the successful introduction of the CRISPR SPR/Cas tools and thus do not allow a plant or plant material containing the desired DNA modification and which contains the desired DNA modification to be obtained directly.

An overview of the actual status of the development of the use of CRISPR SPR/Cas technology for genome editing of plant genomes can be found in Bortesi & Fischer ("*The*

*CRISPR SPR/Cas9 system for plant genome editing and beyond*", Biotechnology Advances, 33, pages 41-52, 20.12.2014). This reports, inter alia, on the problems with providing specific gRNAs for targeting in maize. Further, the problems of the high off-target mutation rates are discussed; these are not only observed when using CRISPR SPR/Cas in mammalian cells, but are also observed when using them in plant cells; here, the design of the individual CRISPR SPR/Cas tools is decisive in order, in the respective target cell/respective target organism, to obtain a site-directed targeted modification without off-target effects. Further, Bortesi & Fischer recognise that the CRISPR SPR/Cas system can also be used for epigenetic modification of DNA since the CRISPR SPR/Cas system can also be used to cleave methylated DNA, but state that as yet, no applications in plants are known.

Furthermore, Guilinger et al desCRISPR be Fokl nucleases which are used in the manner of nickases, and thus produce a higher specificity (Guilinger et al; Fusion of catalytically inactive Cas9 to Fokl nuclease improves the specificity of genome modification, doi: 10.1038/nbt.2909). However, Guilinger et al only present data for human cells, and not for plant cells.

Mali et al 2013 are concerned with the use of the CRISPR SPR/Cas system in human cells, wherein here, nuclease-zero variants of Cas9 or aptamer-coupled gRNAs are used which may be fused to transCRISPR ptional activator domains (Mali, P., et al (2013), "CAS9 transCRISPR ptional activators for target specificity screening and paired nickases for cooperative genome engineering). However, Mali et al do not mention how and to what extent a corresponding system could be used in plant cells.

In summary, many of the strategies used today are only temporary or transient in the plant field, meaning that mutations occur in already differentiated cells, for example in leaves, but these mutations cannot be inherited via the germ line. Further, there are strategies which require a stable integration of the coding sequences including the required regulatory sequences such as promoters and terminators into the genome, via which a stable mutation can then be produced which is inherited from generation to generation. However, the CRISPR SPR/Cas tools are still contained in the genome of the plant and thus also in potential plant products such as fruit and seeds, which is undesirable having regard to the risk assessment of the corresponding products.

Accordingly, the CRISPR SPR/Cas strategy in plant biotechnology is still of low efficiency, but is also characterized by a difficult and expensive design of the construct as well as the frequent appearance of off-target effects. In addition, many of the current strategies are based on either integrating the CRISPR SPR/Cas tools into the genome of a plant cell in a stable manner or introducing the CRISPR SPR/Cas tools into cells of a differentiated tissue, for example into leaves. As a consequence, with the stable strategy, the individual tools such as Cas9 and not just the specific DNA modifications effected by them are inherited by the descendants. Upon transformation into differentiated cells and tissue, the mutation introduced by the CRISPR SPR/Cas tools is only effective in the relevant cells, but cannot be inherited further via the germ line. Specifically with regard to the targeted development of positive traits in plants, comprising resistances, in particular to pests and environmental effects, e.g. cold, drought, saline content, increased yield, or herbicide resistances, the creation of reliable methods for targeted activation and deactivation, or for modification, of genomic material, as well as for silencing RNA inside a plant cell, is of major economical interest.

Regarding the selection of suitable gRNAs, in silico tools already exist, which enable identification of suitable gRNAs, and the subsequent production thereof (see: www.dna20.com/eCommerce/cas9/input), but there are currently no specific tools that could be used in important crop plants, which always have complex genomes. Moreover, the available tools provide no information regarding the actual effectiveness of a gRNA determined in silico, in a subsequent test in vitro or in vivo inside a plant cell.

Thus, there is a continuing need for the establishment of transient and also optionally inducible methods and constructs based, inter alia, on gRNAs and CRISPR nucleases or gRNAs and other effector domains, in order to carry out a desired modification of a target sequence in a target plant cell, wherein only the modification of the target sequence but not the construct is passed on to descendants. In addition, there is a substantial need for a CRISPR SPR-based method which offers the possibility of carrying out a germ line modification directly in a plant cell or a plant tissue, so that the modification can be inherited and seeds can be immediately harvested from the plant resulting from the modified plant cell or tissue which contain the specific genome modification without having to carry out difficult and expensive intermediate steps. Finally, there is a need for specifically broadening RNA-directed DNA modification systems which are provided by the CRISPR SPR/Cas tools, in which not only genomic target structures but any nucleic acid as the target structure can not only be modified in a controlled manner in the genome of a cell but also indeed in the cytosol or in plastids. In this regard, there is currently also a desire for suitable insertion systems, which allow the targeted insertion of CRISPR SPR/Cas tools and thus allow the targeted modification of a target region inside a plant target structure.

Furthermore, there is a desire for efficient in vitro screening methods, by means of which it is possible to check the effectiveness of a gRNA inside a plant cell in an in vitro assay with a high output, and make reliable predictions, in order to avoid costly and lengthy attempts with plant material.

The ultimate goal is to optimize the precision of a genome editing approach, in particular for the modification of larger eukaryotic genomes, comprising plant genomes and genomes from animal organisms, in order to obtain fewer off-target effects, and ideally, to obtain an optimal repair of a targeted, inserted, double strand break, by creating a repair matrix, together with the actual genome modification tools.

SUMMARY OF THE INVENTION

Thus, the object of the present invention is to provide methods and molecular tools which permit the transient transformation of plant tissue or plant cells, especially meristematic cells, and thus allow the controlled modification of any target nucleic acid region in any plant cellular compartment. Likewise, one object is to create suitable insertion methods for the molecular tools in accordance with the present disclosure. In addition, suitable in vitro screening assays or tests should be created, such that suitable functional gRNAs can be identified in vitro in advance, in order to be able to efficiently reduce the subsequent effort in planta or in vitro in plant tissue.

Combining the above advantages in one system with broad application in plant biotechnology is an aim of the invention.

In particular, tools are to be created, which facilitate plant cultivation, such that traits of interest can be inserted in a plant genome, or likewise removed therefrom or modified therein.

This object is accomplished by the method and constructs provided herein as claimed in the accompanying claims and as desCRISPR bed in the desCRISPR ption, the figures and the accompanying sequence listing. In particular, the object is accomplished by the provision of a method comprising the transformation or transfection of at least one meristematic cell. Furthermore, the aim is accomplished by the provision of recombinant constructs which comprise specifically modified CRISPR tools and/or further effector domains. Finally, the aim is accomplished by the provision of appropriate regulatory sequences and localization sequences which allow the recombinant construct of interest to be directed in a controlled manner into any discretionary compartment of a target plant structure of interest.

In this manner, at least one specific modification in any target nucleic acid region can be obtained in any compartment of a plant cell, in particular a meristematic plant cell. Since the thus modified at least one meristematic cell can pass on the specific modification in the target nucleic acid region by subsequent cell division and differentiation to its descendants and/or has the potential for a completely modified plant organism to mature from the meristematic cell, then a plant or plant material or a plant cell can be provided without having to carry out further complex culturing or crossing and selection steps (above all complex back-crossing procedures). Moreover, from the at least one meristematic target cell modified in this manner, a plant, plant material or a plant cell can be immediately and directly obtained. In this manner, it is possible to produce or provide or activate gRNA(s) and/or CRISPR nuclease(s) or one or more catalytically active fragment(s) thereof and/or other effector domain(s) only transiently in the meristems, whereupon these recombinant macromolecules are then preferably degraded, i.e. after the gRNA(s) and/or CRISPR nuclease(s) or catalytically active fragments thereof and/or other effector domain(s) have carried out their desired purpose, since no integration thereof occurs into the genome or endogenous extrachromosomal DNA; this may be of advantage as regards regulatory aspects and risk assessment of the plant product. The CRISPR nucleases or catalytically active fragments thereof used herein may also contain one or more mutation(s) in the catalytic domains responsible for DNA (double-stranded or single strand) cleavage. This results in a broad spectrum of application for the Cas nuclease and, in the case of Cas-based nickases, in a higher binding specificity, since two CRISPR SPR/Cas constructs are used in order to cut both single strands of the DNA double-stranded at the desired site. Even Cas-zero variants are proposed herein, as well as their combined use with other effector domains to optimize a specific nucleic acid edit.

Furthermore, it was found that by exploiting the mechanism of action of the CRISPR tools, other effector domains such as DNA or RNA or histone-modifying or DNA or RNA or histone-binding polypeptides or nucleic acids comprising, for example, any type of monomeric, dimeric or multimeric nucleases, including nickases, transCRISPR ption activators and suppressors, phosphatases, glycosylases or enzymes which can make epigenetic modifications such as methylases, acetylases, methyltransferases or histone deacetylases, aptamers, including single-stranded DNA or RNA sequences as well as peptides, fluorescent proteins, bioluminescence proteins, marker nucleic acid sequences or marker amino acid sequences and the like, and combinations thereof in accordance with the method provided herein, whereupon the spectrum of known specific genome editing can be broadened to general nucleic acid editing which is not per se limited to genomic DNA.

Regarding the aspect of editing genomic DNA disclosed herein, a DNA repair matrix or HDR matrices shall also be created, which can be inserted in a targeted manner, together with the CRISPR tools, into a target cell or target structure of interest, in order to dominate over an error-prone endogenous NHEJ repair system, and to furthermore be able to insert a desired nucleic acid at the location of a double strand break.

The present disclosure thus offers the possibility of using the CRISPR SPR/Cas mechanism in a manner that allows not only the nucleolytic cleavage of DNA, but also any modification of genomic DNA, for example epigenetic modification, as well as RNA, in plant cells (for example mRNA).

By using other regulatory sequences comprising promoters, terminators, transCRISPR ption factor binding sites or introns, and/or localization sequences comprising nuclear, mitochondrial and plastid localization sequences, the present disclosure also offers the possibility of modifying any target nucleic acid region of a target plant structure in a specific manner, whereupon mitochondrial and plastid DNA, for example, can also act as the target for editing. Furthermore, the possibility of specific modification of RNA, for example mRNA, is also raised, wherein here too, gRNA-directed sequence recognition which is the basis of the CRISPR SPR/Cas system can be exploited and "reprogrammed" in accordance with the present disclosure in order to broaden the field of application of CRISPR SPR/Cas technology.

Methods and constructs are also provided herein, by means of which gRNA and/or CRISPR nuclease or the catalytically active fragment thereof already linked to a further effector domain is/are provided on a recombinant construct.

Furthermore, a method is provided in which the at least one gRNA as well as the at least one CRISPR nuclease or the catalytically active fragment thereof and/or the at least one further effector domain are provided separately on different recombinant constructs. In accordance with this method, the gRNA component may be provided as DNA or RNA, the CRISPR nuclease or variant thereof or the catalytically active fragment thereof may be provided as DNA or RNA or as a polypeptide sequence and the effector domain may be provided as DNA or RNA.

An additional object is the possibility of providing specific constructs which may be inducible or tissue or organelle-specific, and of minimizing unwanted off-target effects by establishing plant-specific constructs and methods. Finally, in one aspect, methods and constructs are designed which not only offer the possibility of specific gene knock-ins but also, for example, offer the possibility of specific gene knock-outs, insertions of genetic fragments, specific epigenetic modifications, the introduction of point mutations, acetylations, methylations, phosphorylations, glycosylations, marking by resistance markers or fluorescent proteins, activation or repriming of transCRISPR ption, specific cleavage of double-stranded or single-stranded nucleic acids, binding of nucleic acids and the like, so that the field of application in plant cultivation is broadened. From a cultivation and from a regulatory standpoint, it is desirable to have a stable inheritability of a feature effected by the modification over at least one generation with the simultaneous absence of the constructs of the CRISPR SPR/Cas system required for it in the resulting plant or the resulting plant cells.

Lastly, one of the objects was to create an in vitro screening method for identifying a gRNA or an encoding sequence for a gRNA in an in vitro assay, to identify a gRNA or an encoding sequence for a gRNA, which, together with a CRISPR nuclease or catalytically active fragment thereof, is suitable for targeted modification of a nucleic acid target region in a plant cell.

Specific aspects and embodiments of the present invention will become apparent from the following detailed desCRISPR ption and the examples, the figures, the sequence listing and in particular the accompanying patent claims.

BRIEF DESCRIPTION OF THE DRAWINGS

FIGS. 3A-D (FIG. 3A-D) show prepared meristems in maize seedlings. Since the meristem in seedlings is completely surrounded by leaves, it has to be dissected out in order to be accessible for bombardment, microinjection etc. To this end, the outer tissue structures are completely removed so that the meristem (arrows) is exposed.

FIG. 5 (B) presents the fluorescence (white areas in the b/w image) after the test bombardment. For the test bombardment, a gene coding for a fluorescing protein was used. A clear expression of the protein in the meristematic regions (double ring) can be detected.

FIG. 7 (B) shows fluorescence (white areas in the b/w image) after the test bombardment. For the test bombardment, a gene coding for a fluorescing protein was used. A clear expression of the protein in the meristematic regions can be detected.

FIG. 9(A) shows the bombardment with 1350 psi in six individual illustrations.

FIG. 11(A) shows a microscope recording of the prepared meristem in a side view.

FIG. 12(A) shows a microscope recording of the prepared meristem in a top view. FIG. 12(B) shows the detected fluorescence in this view (white dots). FIG. 12(C) shows the region where fluorescence has been detected, enlarged by a factor of 2. The embryo layers have been dyed with a suitable pigment.

FIG. 17A shows the use of two gRNAs, gRNA-1 and gRNA-2, which activate a region of the genomic DNA with the goal of excising the region lying between them from a genomic DNA region by means of a CRISPR nuclease, e.g. a Cas nuclease or any other CRISPR nuclease. (RE: restriction enzyme). FIG. 17B shows the results of a separation in a 1% gel, with the standard parameter of 100 V and the subsequent visualization via fluorescence obtained with ethidium bromide. Column 5 contains the molecular size indicator (given in base pairs; GeneRuler 50 bp DNA Ladder (Thermo Fisher Scientific Inc., USA; SM0373) 1000, 900, 800, 700, 600, 500, 400, 300, 250, 200, 150, 100, 50 bp). Columns 1 and 2 each show the results for non-edited maize plants, and column 4 shows the results after a successful editing. The PCR product is smaller, because the region between the two gRNA target regions has been excised.

FIG. 19 shows the leaf inoculation of *N. benthamiana* with a red fluorescent protein construct (RFP) and a control construct, using expressions obtained from the tobacco rattle virus (TRV). The construct pZFN-tDT-nptII functions as a control, allowed expressly by the expression of the RFP in the inoculated leaves, but not in the distal leaves. In the black-and-white illustration in FIG. 19, light (er) regions correspond to the originally detected red fluorescence, while black regions indicate those regions in which no fluorescence could be detected.

FIGS. 20C (original in black-and-white) and D (counterpart to C, with contrast/exposure adjustment) show a flower bud. A pistil has been recorded in FIGS. 20E (original in black-and-white) and F (counterpart to E, with contrast/exposure adjustment). FIGS. 20G (original in black-and-white) and H (counterpart to G, with contrast/exposure adjustment) show a prepared pistil with exposed ovaries.

FIGS. 25A-C (FIGS. 25A-C) shows immature embryos (FIG. 25A) of a maize plant, which was isolated and subsequently bombarded with a particle bombardment comprising a CRISPR SPR/Cas 9 construct, and a plasmid expressing a red fluorescent protein. FIG. 25B shows the fluorescent development (white and light regions) on the first day after the bombardment. FIG. 25C shows a mature maize plant that was obtained from the embryos from FIGS. 25A and B, which was bombarded in this manner and subsequently raised to maturity.

FIG. 26 shows an immature *Beta vulgaris* embryo, obtained according to the method desCRISPR bed in detail below.

FIGS. 27A und B (FIGS. 27A und B): FIG. 27A: Immature grains of wheat after meristem transformation. FIG. 27B: corresponds to the fluorescent recording of FIG. 27A. The light regions correspond to the detected fluorescence (light/white regions in the black-and-white recording). After the meristem transformation, germinating wheat plants could be obtained directly from the treated grains of wheat (A and B).

FIG. 28 shows the localization of the immature florescence in wheat in the left-hand image. The middle image and the right-hand image show the further development, from left to right, of the meristematic tissue that has been transformed, as desCRISPR bed below.

DETAILED DESCRIPTION

Definitions

Figures 1A, 1B, 1C, 1D, 1E, 1F:
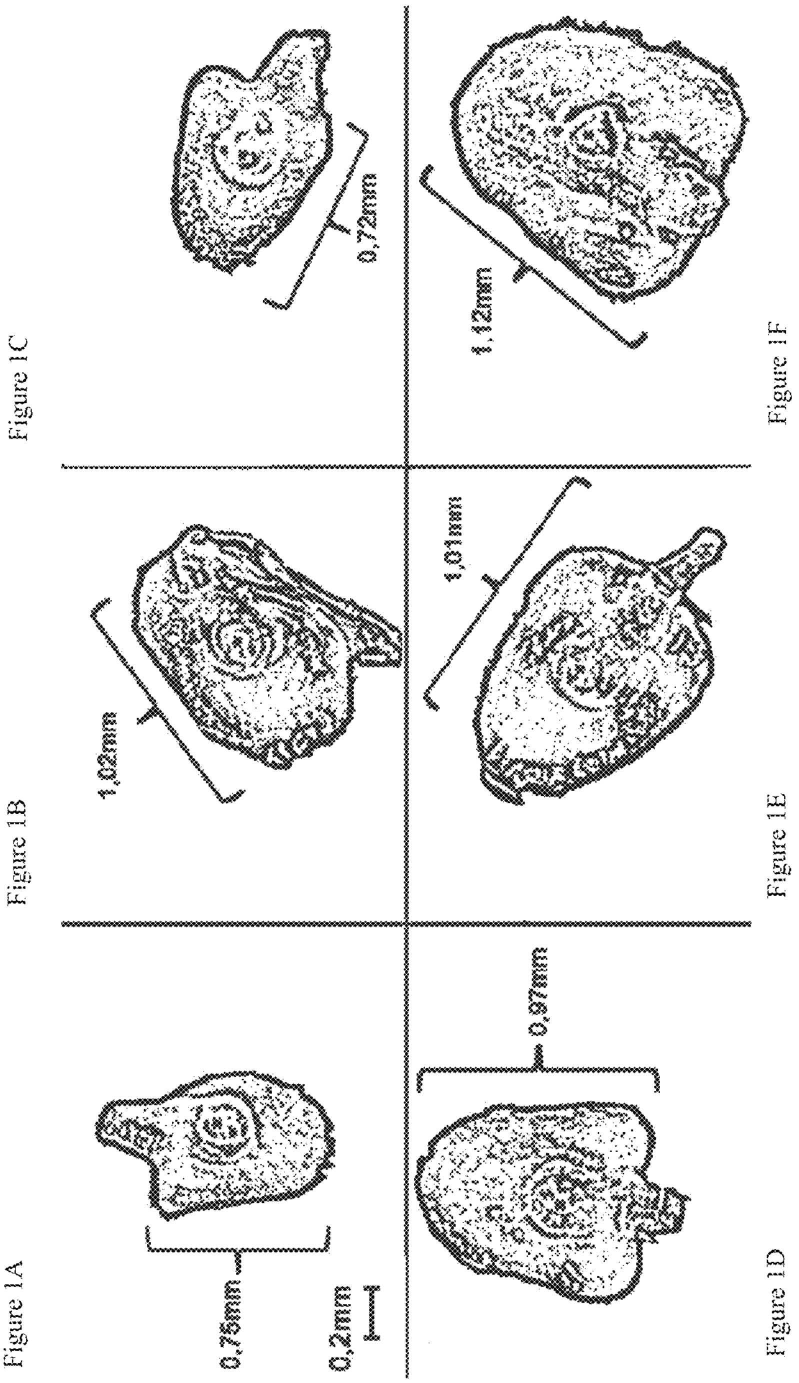
FIGS. 1A-F (FIG. 1A-F) show maize embryos of various sizes. In the embryos analysed here, the meristem can clearly be seen as the discoid structure in the centre of the embryo. Depending on the size and the stage of development of the embryos, the meristem is at different stages of development and easy or hard to detect. In addition, the meristem is also marked with an asterisk (*).

The term "plant" or "plant cell" as used herein refers to plant organisms, plant organs, differentiated and undifferentiated plant tissues, plant cells, seeds and their progeny or descendants. "Plant cells" includes, for example, cells of seeds, mature and immature embryos, meristematic tissues, seedlings, callus tissue, leaves, flowers, roots, plant buds, gametophytes, sporophytes, pollen and microspores, protoplasts, macroalgae and microalgae.

The term "fertile plants" as used herein refers to a fertile plant capable of reproduction, i.e. a fertile plant is a plant that can produce living male and female gametes. A male-sterile plant, accordingly, is a plant that cannot produce living male gametes, but which may be female-fertile. A female-sterile plant is a plant that cannot produce living female gametes, wherein the plant may still be male-fertile.

"Plant material" as used here means any material which can be obtained from a plant in any stage of development. The term thus encompasses plant cells, tissue and organs as well as formed plant structures as well as, if relevant, sub-cellular components such as nucleic acids, polypeptides, as well as all chemical plant substances which are present inside a plant cell and/or can be produced by it.

The term "chromosomally or extrachromosomally integrated" as used herein means the transient introduction and/or the formation of one or more recombinant construct/constructs of the present invention and thus to the subsequent fate of the one or more recombinant construct/constructs in a target plant structure, for example a cell, wherein both the one or more recombinant construct(s) and also the conditions for introduction thereof are maintained in a manner such that no integration of the at least one recombinant construct takes place in the endogenous nucleic acid material of a target plant structure comprising the genome or extrachromosomal nucleic acid of the target plant structure, for example a cell, so that the at least one recombinant construct is not chromosomally or extrachromosomally integrated into the endogenous DNA/RNA of the target cell and thus not passed on to the descendants of the cells. The one or more recombinant construct(s) or its transCRISPR ption or translation products are thus only temporarily active in the target cell, i.e. transient, constitutive or inducible, but cannot be inherited by the descendants of the target cells, i.e. they are also not actively present in the descendants of a target cell.

The term, "homologous recombination," as used herein, indicates a process that takes place in all organisms. This requires homologous, double-strand DNA sections. "Homologous" therefore means that there is a large similarity in the nucleotide sequences of two sequences. With naturally occurring double-strand breaks, damage can be repaired through homologous recombination, in that the data on the intact chromatid in the genome of an organism can be used as a template. If a targeted and precise double-strand break is inserted in a nucleic acid target region of interest in the framework of the genome editing, in accordance with the present disclosure, homologous recombination can also be used here to repair the break, wherein, consequently, the targeted drafting of a DNA repair matrix may be used to obtain the targeted effect on the nucleic acid target regions of interest that are to be repaired. Different organism are differentiated with regard to the ratio of homologous to non-homologous recombinations, as occurs in nature (see above, NHEJ). In general, the length of the homologous region affects the frequency of homologous recombination events, i.e. a longer homologous region results in a greater frequency. The length of the homologous region used to obtain homologous recombination depends on the species. In some cases, it may be necessary to use at least five kilo-bases (kb) of homology, but homologous recombination has also been observed in a homologous region having only approximately 25 base pairs (bp).

"Homology directed repair" (HDR) refers to a cellular mechanism for repairing double-strand as well as single-strand DNA breaks. HDR thus comprises elements of homologous recombination, as well as the so-called single-strand annealing (SSA) (Lieber Michael et al., Annu. Rev. Bichem. 79:181-211, 2010). The most frequent form of HDR in a cell is homologous recombination, wherein this type of repair also requires the highest sequence homology between donor and acceptor DNA. Other forms of HDR comprise single-strand annealing (SSA). SSA is non-conserving, and occurs naturally between direct repetitions of >30 bp, and results in deletions. HDR is obtained with nickings, i.e. with single-strand breaks, via a mechanism other than HDR with double-strand breaks (Davis and Maizels PNAS, 2014 E924-32). Because, in accordance with the present disclosure, CRISPR nucleases are proposed that induce both double-strand breaks as well as single-strand breaks, the term, "HDR," or homologous recombination, therefore refers to repairing a single-strand break or a double-strand break that has been inserted in a targeted manner, with the use of a suitable repair matrix.

"Herbicide resistance" and "herbicide tolerance," as used herein, refer to the resistance or tolerance capacity of a plant or a plant cell to the effects of a herbicide or pesticide. This property is normally obtained through at least one protein or one RNA, which has been either artificially inserted in a plant cell, e.g. as a transgene, or which may be acquired through (targeted) modification of an endogenous gene.

The term "progeny or descendants" as used herein means, in the context of a recombinant microorganism, a plant or a cell in accordance with the present disclosure, the descendants of such an organism or such a cell which derive from the original organism or the original cell from natural reproductive asexual cell division and differentiation processes. The skilled person in this field is aware that mutations in the genome of an organism can be introduced during cell division and differentiation in a natural manner, whereupon the progeny or descendant differs genomically from the parent organism, but can still be assigned to the same (sub) species. Even such progeny modified by natural processes which introduce modifications into other DNA regions in addition to the specifically introduced modification are thus comprised in the term “progeny or descendants” in the present invention.

The term, “CRISPR nuclease,” as used herein, refers in general to a nuclease as it occurs in a naturally occurring CRISPR system, as well as to modifications, mutations, and catalytically active fragments thereof. In a naturally occurring CRISPR locus, the CRISPR nuclease is the molecule that forms the effector molecule, and can recognize and/or cleave a nucleic acid target structure through interaction with a crRNA and, optionally, a tracrRNA, or together with an artificial gRNA. CRISPR nucleases therefore comprise Cas nucleases, Cpf1 nucleases, or other CRISPR effector domains and/or nuclease domains, comprising Csf1 and combinations and variations thereof. Moreover, this term also comprises nucleases that have been modified in a targeted manner, each of which is converted to nicking enzymes for obtaining single-strand breaks, or nuclease-null variations that are converted for bonding and recognition purposes, but not for obtaining a double-strand break. Because the term “CRISPR SPR/Cas has meanwhile become established as a synonym for all types of CRISPR systems in the relevant references, this term shall be used in accordance with the present disclosure for any CRISPR type I-V system, as well as the associated effector proteins, if not specifically indicated otherwise.

The term “vector” or “vector system” as used herein means a transport means which can introduce a recombinant construct, comprising nucleic acids or even polypeptides as well as further sequences such as regulatory sequences or localization sequences directly or indirectly into a desired target cell or target plant structure, into the desired cellular compartment. Direct introduction is carried out directly into a target plant cell or target plant structure which contains nucleic acids which are to be specifically modified in accordance with the present disclosure. The indirect introduction encompasses introducing into a structure cells of leaves or other plant organs and tissues, for example, which do not directly comprise the target plant cells of interest, but which ensure the systematic propagation and transport of the vector comprising a recombinant construct in accordance with the present disclosure into the target plant structure, i.e. meristematic tissues or cells or stem cells. The term “vector” or “vector system” as used herein in the context of transfection of amino acid sequences encompasses suitable agents for peptide or protein transfection such as, for example, ionic lipid mixtures or agents which are suitable for transfection of a nucleic acid such as, for example, carrier materials through which nucleic acid and amino acid sequences can be introduced into a cell by means of particle bombardment, for example using gold and tungsten particles. Furthermore, in particular when applying the method and constructs disclosed herein, this term also encompasses viral vectors, i.e. modified viruses such as, for example, those which derive from one of the following viruses: Maize Streak Virus (MSV), Barley Stripe Mosaic Virus (BSMV), Brome Mosaic virus (BMV, access numbers: X58456; RNA2: X58457; RNA3: X58458), Maize Stripe Virus (MSpV), Maize Rayado Fino virus (MYDV), Maize Yellow Dwarf Virus (MYDV), Maize Dwarf Mosaic Virus (MDMV), Positive strand RNA viruses of the Benyviridae family, e.g. Beet necrotic yellow vein virus (access numbers: RNA1: NC_003514; RNA2: NC_003515; RNA3: NC_003516; RNA4: NC_003517) or the Bromoviridae family, e.g. viruses of the Alfalfa mosaic virus genus (access numbers: RNA1: NC_001495; RNA2: NC_002024; RNA3: NC_002025) or the Bromovirus genus, e.g. BMV (see above), or the Cucumovirus genus, e.g. Cucumber mosaic virus (access numbers: RNA1: NC_002034; RNA2: NC_002035; RNA3: NC_001440), or the Oleavirus genus, dsDNA viruses of the Caulimoviridae family, in particular the Badnavirus or Caulimovirus families, e.g. various Banana streak viruses (see, e.g., access numbers: NC_007002, NC_015507, NC_006955 or NC_003381) or Cauliflower mosaic virus (access number: NC_001497), or viruses of the Cavemovirus, Petuvirus, Rosadnavirus, Solendovirus, Soymovirus or Tungrovirus genus, positive strand RNA viruses of the Closteroviridae family, e.g. the genus Ampelovirus, CRISPR nivirus, e.g. Lettuce infectious yellows virus (access numbers: RNA1: NC_003617; RNA2: NC_003618) or Tomato chlorosis virus (access numbers: RNA1: NC_007340; RNA2: NC_007341), Closterovirus, e.g. Beet yellows virus (access number: NC_001598), or Velarivirus, single-strand DNA (+/−) viruses of the Geminiviridae family, e.g. viruses of the Becurtovirus, Begomovirus family, e.g. Bean golden yellow mosaic virus, Tobacco curly shoot virus, Tobacco mottle leaf curl virus, Tomato chlorotic mottle virus, Tomato dwarf leaf virus, Tomato golden mosaic virus, Tomato leaf curl virus, Tomato mottle virus, or Tomato yellow spot virus, or Geminiviridae of the Curtovirus genus, e.g. Beet curly top virus, or Geminiviridae of the genus Topocuvirus, Turncurtvirus or Mastrevirus, e.g. Maize streak virus (see above), Tobacco yellow dwarf virus, Wheat dwarf virus, positive strand RNA viruses of the Luteoviridae family, e.g. the genus Luteovirus, e.g. Barley yellow dwarf virus-PAV (access number: NC_004750), or the genus Polerovirus, e.g. Potato leafroll virus (access number: NC_001747), single-strand DNA viruses of the Nanoviridae family, comprising the genuses Nanovirus or Babuvirus, double-strand RNA viruses of the Partitiviridae family, comprising inter alia the families Alphapartitivirus, Betapartitivirus or Deltapartitivirus, viroids of the Pospiviroidae family, positive strand RNA viruses of the Potyviridae family, e.g. comprising the genuses Brambyvirus, Bymovirus, Ipomovirus, Macluravirus, Poacevirus, e.g. *Triticum* mosaic virus (access number: NC_012799), or Potyviridae of the genus Potyvirus, e.g. Beet mosaic virus (access number: NC_005304), Maize dwarf mosaic virus (access number: NC_003377), Potato virus Y (access number: NC_001616), or *Zea* mosaic virus (access number: NC_018833), or Potyviridae of the genus Tritimovirus, e.g. Brome streak mosaic virus (access number: NC_003501) or Wheat streak mosaic virus (access number: NC_001886), single-strand RNA viruses of the Pseudoviridae family, e.g. the genuses Pseudovirus, or Sirevirus, double-strand RNA viruses of the Reoviridae family, e.g. Rice dwarf virus (access numbers: RNA1: NC_003773; RNA2: NC_003774; RNA3: NC_003772; RNA4: NC_003761; RNA5: NC_003762; RNA6: NC_003763; RNA7: NC_003760; RNA8: NC_003764; RNA9: NC_003765; RNA10: NC_003766; RNA11: NC_003767; RNA12: NC_003768), positive strand RNA viruses of the Tombusviridae family, e.g. comprising the genuses Alphanecrovirus, Aureusvirus, Betanecrovirus, Carmovirus, Dianthovirus, Gallantivirus, Macanavirus, Machlomovirus, Panicovirus, Tombusvirus, Umbravirus or Zeavirus, e.g. Maize necrotic streak virus (access number: NC_007729), or positive strand RNA viruses of the Virgaviridae family, e.g. viruses of the genus Furovirus, Hordeivirus, e.g. Barley stripe mosaic virus (access numbers: RNA1: NC_003469; RNA2: NC_003481; RNA3: NC_003478), or the genus Pecluvirus, Pomovirus, Tobamovirus or Tobravirus, e.g. Tobacco rattle virus (access numbers: RNA1: NC_003805; RNA2: NC_003811), as well as negative strand RNA viruses of the order Mononegavirales, in particular the Rhabdoviridae family, e.g. Barley yellow striate mosaic virus (access number: KM213865) or Lettuce necrotic yellows virus (access number/specimen: NC_007642/AJ867584), positive strand RNA viruses of the order Picornavirales, in particular the Secoviridae family, e.g. the genuses Comovirus, Fabavirus, Nepovirus, Cheravirus, Sadwavirus, Sequivirus, Torradovirus, or Waikavirus, positive strand RNA viruses of the order Tymovirales, in particular the Alphaflexiviridae family, e.g. viruses of the genus Allexivirus, Lolavirus, Mandarivirus, or Potexvirus, Tymovirales, in particular of the Betaflexiviridae family, e.g. viruses of the genus Capillovirus, Carlavirus, Citrivirus, Foveavirus, Tepovirus, or Vitivirus, positive strand RNA viruses of the order Tymovirales, in particular the Tymoviridae family, e.g. viruses of the genus Maculavirus, Marafivirus, or Tymovirus, and bacterial vectors such as *Agrobacterium* spp., for example, with *Agrobacterium tumefaciens* being an example Finally, the term also encompasses suitable transport means for introducing linear nucleic acids (single-stranded or double-stranded) into a target cell. Knowing the constructs disclosed herein, the skilled person in this field will be aware of all further sequences which a vector must contain in order to be functional in a desired target cell. Conventional production, processing and use of vectors of this type is also known to the skilled person in this field.

The term "vector system" as used here denotes a system which consists of at least one or more vector(s) or contains it (them). Thus, a vector system may comprise a vector which contains/codes for two different recombinant constructs comprising nucleic acid and/or amino acid sequences. Furthermore, a vector system can also contain several vectors which in their turn contain/code for at least one nucleic acid or amino acid sequence in accordance with the present disclosure.

The terms, "quantitative trait locus" or "QTL," as used herein, refer to a DNA region that is associated with the differential expression of a quantitative phenotype trait in at least one defined genetic background, e.g. in at least one cultivation population. The QTL region comprises, or is closely linked to, the gene or genes that affect the trait in question. An allele of a QTL can therefore comprise numerous genes or other genetic factors inside a coherent genomic region, or a linkage group, e.g. a haplotype. An allele of a QTL can indicate a haplotype inside a defined window, wherein this window represents a coherent genomic region, which can be defined and (back) referenced with a set on one or more polymorphic markings. A haplotype can be defined by the unique fingerprints of alleles in each marking within the defined window.

As shall be explained in greater detail below, a number of methods are available to the person skilled in the art for identifying those plant target structures, comprising at least one meristematic cell, or an entire plant or a plant material or a plant cell thereof, which contribute to a targeted modification in their genomic DNA in or close to a nucleic acid target region, without the use of marker phenotypes that can be checked. Such methods are based on the direct analysis of a nucleic acid target region or target sequence of interest, in order to show an arbitrary modification in this nucleic acid region or sequence, and comprise, but are not limited to, PCR processes, sequencing processes, nuclease digestion, southern blots, northern blots, and any arbitrary combination thereof.

The term "nucleic acid" or "nucleic acid sequence" as used herein refers to both natural and synthetic deoxyribonucleic acids (DNA) and ribonucleic acids (RNA) which may also contain synthetic nucleotide analogues. The nucleic acids which are used in accordance with the present invention for the synthesis of a desired product such as protein or RNA or for specific control thereof, for example a CRISPR nuclease, including inter alia a Cas nuclease or a Cpf1 nuclease, or a gRNA, may if relevant be "adapted for use in a target plant structure". In one embodiment, said sequences may be codon-optimized, i.e. the codon use of a gene or a RNA is specifically adapted to the target cell/target organism. The skilled person in the field is familiar with the fact that a desired target gene which codes for a protein of interest can be modified without modification to the translated protein sequence in order to account for the specific species-dependent codon use. Thus, the nucleic acids of the present invention may specifically be adapted to or are adapted to the codon use of *Hordeum vulgare, Sorghum bicolor, Secale cereale, Triticale, Saccharum officinarium, Zea mays, Setaria italic, Oryza sativa, Oryza minuta, Oryza australiensis, Oryza alta, Triticum aestivum, Triticum durum, Hordeum bulbosum, Brachypodium distachyon, Hordeum marinum, Aegilops tauschii, Malus domestica, Beta vulgaris, Helianthus annuus, Daucus glochidiatus, Daucus pusillus, Daucus muricatus, Daucus carota, Eucalyptus grandis, Erythranthe guttata, Genlisea aurea, Nicotiana sylvestris, Nicotiana tabacum, Nicotiana tomentosiformis, Solanum lycopersicum, Solanum tuberosum, Coffea canephora, Vitis vinifera, Cucumis sativus, Morus notabilis, Arabidopsis thaliana, Arabidopsis lyrata, Arabidopsis arenosa, Crucihimalaya himalaica, Crucihimalaya wallichii, Cardamine flexuosa, Lepidium virginicum, Capsella bursa-pastoris, Olmarabidopsis pumila, Arabis hirsuta, Brassica napus, Brassica oleracea, Brassica rapa, Brassica juncacea, Brassica nigra, Raphanus sativus, Eruca vesicaria sativa, Citrus sinensis, Jatropha curcas, Glycine max, Gossypium* ssp. Or *Populus trichocarpa*. Furthermore, in accordance with the present disclosure, the sequence of the gRNA or the sequence coding for the gRNA has to be adapted to the target nucleic acid region within a target plant structure. In a further embodiment, the gRNA or the sequence coding for the gRNA must additionally be adapted in the region which is responsible for interaction or coupling with a Cas nuclease and/or an effector domain.

The term "sequences" as used herein refers to nucleic acid sequences as well as to amino acid sequences wherein the respective sequence, in addition to natural nucleotides and amino acids, may also contain synthetic analogues or synthetic linkages as construction elements.

The terms "polypeptide", "polypeptide sequence", "protein sequence" and "amino acid sequence" are used interchangeably herein.

The term, "catalytically active fragment," as used herein, in particular in reference to CRISPR nucleases or variations thereof, refers to an amino acid nuclei sequence, derived from a given amino acid template sequence, with the condition that the resulting catalytically active fragment comprises all are part of the active centre of the template sequence, and therefore fulfils, as always, the same enzymatic function as the template sequence. These modifications, i.e. truncations, are well known to the skilled person in the field, and are particularly useful with sterically demanding enzymes, for creating multifaceted and more stable truncated enzymes, comprising the catalytically active fragment.

The term "regulatory sequence" as used herein refers to a nucleic acid or a protein sequence which can control cis or trans transCRISPR ption and/or translation of a disclosed nucleic acid sequence.

The term "construct" or "recombinant construct" (used interchangeably herein) as used herein refers to a construct comprising, inter alia, plasmids or plasmid vectors, cosmids, yeast or bacterial artificial chromosomes (YACs and BACs), phagemid, bacteriophage vectors, an expression cassette, single-stranded or linear nucleic acid sequences or amino acid sequences, and viral vectors, i.e. modified viruses, which can be introduced into a target cell in accordance with the present disclosure. A recombinant construct in accordance with the invention may include CRISPR SPR/Cas tools or parts thereof comprising at least one gRNA or at least one CRISPR nuclease variant and/or at least one further effector domain either in the form of a nucleic acid or an amino acid sequence. Furthermore, the recombinant construct may comprise regulatory sequences and/or localization sequences. The recombinant construct may be integrated into a plasmid vector and/or be isolated from a plasmid vector in the form of a polypeptide sequence or as a single-stranded or double-stranded nucleic acid not linked into a plasmid vector. After introduction, the construct is preferably extrachromosomal and not integrated into the genome and usually in the form of a double-stranded or single-stranded DNA, a double-stranded or single-stranded RNA or a polypeptide. "Plasmid vector," as used herein, relates to a construct that was originally obtained from a plasmid. These are normally circular, autonomous, replicating, extrachromosomal elements in the form of a double-strand nucleic acid sequence. In genetic engineering, these original plasmids are modified in a targeted manner, in that resistance genes, target nucleic acids, localization sequences, regulating sequences, etc. are inserted. The structural components of the original plasmid, such as the replication source, are maintained thereby. Numerous plasmid vectors for use in a target cell of interest are commercially available, and the modification thereof for specific cloning strategies is well known to the skilled person in the field. These known plasmid vectors are also referred to as standard vectors herein, wherein this is intended to imply that the basis vector is commercially available, and can be readily adapted to the needs of the respective experiment by a skilled person in the corresponding technological field.

The term, "enhancer" or "enhancer element," refers to a base/nucleotide sequence that has a characteristic sequence. An enhancer is one of the cis-regulatory elements, and can affect the bonding of a transCRISPR ption complex on a promoter, and thus the transCRISPR ption activity of a gene. A promoter, in turn, is a DNA sequence that can regulate the expression of an encoded sequence or a functional RNA. The promoter sequence is composed of both proximal as well as distal elements in relation to a regulated sequence, wherein the latter are frequently referred to as enhancers. Promoters may have a broad activity spectrum, and they may however also be active in tissues, or be development-specifically active, or activatable, e.g. in root cells, seeds, meristematic cells, etc. Likewise, there are constructively active as well as inducible promoters, wherein the induction can be stimulated through numerous environmental effects. There are strong promoters, which can activate a high level of transCRISPR ption of the regulated sequence, as well as weak promoters. Promoters are frequently strongly regulated. A promoter in accordance with the present disclosure can be a promoter containing native endogens, or an artificial (synthetic/chimeric) or transgenic promoter, which has either been obtained from another species, or which is artificial or synthetic/chimeric, i.e. not present in this form in nature, or is comprised of various promoter elements.

The terms "3' non-encoding sequence," "transCRISPR ption terminator," "terminator," or "terminator sequence," as used herein, refer to DNA sequences that are located upstream, i.e. in the 3'-direction of an encoding sequence, and comprise polyadenylation recognition sequences and other sequences that encode regulating sequences, which are capable of affecting the mRNA processing and/or the gene expression. The polyadenylation signal is normally characterized in that it causes poly-A-nucleotides to be added to the 3'-end of an mRNA precursor.

The term, "functionally linked," as used herein, refers to the bonding of nucleic acid sequences to a single nucleic acid fragment, such that the individual fragments of genes or regulating sequences, or other regions, are physically joined, and the individual sequences or segments can regulate, hybridize, or affect one another in a reciprocal manner. A promoter is then functionally linked to an encoding sequence, as long as it is capable of regulating the expression of this encoding sequence, i.e., the encoding sequence is then subject to the transCRISPR ptional regulation of the promoter in question. Moreover, encoding sequences can be functionally linked to regulating sequences, in either a clockwise or counter-clockwise orientation. Complementary RNA regions can basically be linked, directly or indirectly, at 5' with the target mRNA, or 3' with the target mRNA, or inside the target mRNA, or a first region of the complementarity is functionally linked at 5' and its complement is functionally linked at 3' to the target mRNA.

The terms, "stable transformation," or "stable integration," as used herein, refer to the insertion of a nucleic acid sequence of interest, e.g. in the form of a DNA repair matrix or a portion thereof, or a suitable vector, in the genome of a plant target structure of interest, wherein the genome comprises both the nucleic as well as the extra-nucleic genome, basically the genome of organelles, resulting in a genetically stable and thus inheritable modification of the genome. In contrast thereto, the terms, "transient transformation," or "transient insertion," or "transient integration," as used herein, refer to the insertion of a nucleic acid sequence of interest into a plant compartment of interest, comprising the nucleus, organelles or the cytoplasm, or a further compartment inside a plant cell, by means of which, either the transCRISPR ption and/or translation, or, in the case of a direct-effector molecule (DNA, RNA, or protein), the inserted molecule or complexes, can deploy their effects inside the plant cell, but there is no stable integration in the genome of the cell, and thus no inheritance of the corresponding sequences and/or effector molecules.

The term, "genome," as used herein, relates to the totality of the genetic engineering material, comprising genes and non-encoding sequences present in a cell of an organism or a virus or an organelle, and therefore comprises both the nucleic (if present) as well as the extra-nucleic (if present) genome. Furthermore, the term, "genome," as used herein, relates to the entire set of chromosomes that are inherited as a (haploid) unit of an ancestor organism.

One incentive for developing new molecular markers in plant species is the potential for obtaining an increased efficiency in the targeted plant breeding through marker assisted selection (MAS). Gene technology marker-alleles, or alternatively, the quantitative trait loci (QTL) alleles mentioned above, are used for identifying plants or plant material, or a plant cell, which contain a desired genotype at a locus, or at numerous, unlinked or linked, loci, e.g. a haplotype, from which it can be assumed that they can pass on the desired genotype, together with a desired phenotype, to their descendants. With respect to the marker assisted selection, the term, "marker," as used herein, can therefore mean both marker and QTL loci. As soon as it has been determined for a desired phenotype and a polymorphic chromosomal locus, e.g. a marker locus or a QTL, that they segregate collectively, it is possible to use these polymorphic loci to select alleles that correspond to the desired phenotype. This approach is referred to as marker assisted selection (MAS). For this, a nucleic acid sequence corresponding to the marker nucleic acid is detected in a biological sample from a plant that is to be analysed. This can be demonstrated in the form of a hybridization of a nucleic acid probe on a marker, e.g. using allele-specific hybridization, southern blot analysis, northern blot analysis, in situ hybridization, hybridization of primers followed by PCR amplification of a region of the marker, or suchlike, or through any arbitrary combination thereof. Numerous methods for detecting markers are known to the skilled person in the field. After the presence or absence of a specific marker has been confirmed in the biological sample of interest, comprising at least one plant cell, preferably a meristematic cell, the plant is selected, and can be used subsequently for obtaining descendant plants through selective breeding. Likewise, the method according to the invention can be used for analysing an in planta meristematic cell, modified in a targeted manner, for the presence or absence of a specific marker. Preferably either female or male gametes or germ cells can be obtained from these meristematic cells, wherein in particular, the pollen of a plant modified in planta in this manner can be used directly for the subsequent selective breeding. Because there is a desire in classic plant breeding to insert traits of interest into a target plant, which encode a high yield and/or other desirable traits, in order to develop improved plants, there is a large interest in marker assisted selection, in order to reduce the time needed for elaborate and expensive testing of a large number of samples.

In accordance with the method of the present disclosure, phenotype markers can also be inserted in a plant target structure of interest in a targeted manner. A "phenotype marker," as used herein, refers to a marker that can be selected, which facilitates the checking and detectability of a plant cell or target structure of interest. Phenotype markers comprise, in general, either positive or negative selectable markers that can be used in a plant target structure of interest, such as visible markers or (antibiotic) resistant genes. Any type of plant marker that can be used in a plant target structure of interest, in particular a meristematic cell, can be used. Selectable or detectable markers normally comprise DNA segments that allow a cell, or a molecule marked with a "tag" inside a cell of interest, to be identified, often under specific conditions. Such markers can encode an activity, selected from, but not limited to, the production of RNA, peptides, or proteins, or the marker can provide a bonding site for RNA, peptides, proteins, inorganic and organic compounds or composites, etc. By way of example, selectable markers comprise, without being limited thereto, DNA segments that comprise restriction enzyme cleavage points, DNA segments comprising a fluorescent probe, DNA segments that encode products that provide resistance to otherwise toxic compounds, comprising antibiotics, e.g. spectinomycin, ampicillin, kanamycin, tetracycline, BASTA, neomycin-phosphotransferase II (NEO) and hygromycin-phosphotransferase (HPT), DNA segments that encode products that a plant target cell of interest would not have under natural conditions, e.g. tRNA genes, auxotrophic markers and the like, DNA segments that encode products that can be readily identified, in particular optically observable markers, e.g. phenotype markers such as β-galactosidases, GUS, fluorescent proteins, e.g. green fluorescent protein (GFP) and other fluorescent proteins, e.g. blue (CFP), yellow (YFP) or red (RFP) fluorescent proteins, and surface proteins, wherein those fluorescent proteins that exhibit a high fluorescence intensity are of particular interest, because these proteins can also be identified in deeper tissue layers if, instead of a single cell, a complex plant target structure or a plant material or a plant comprising numerous types of tissues or cells is to be analysed, new primer sites for PCR, the recording of DNA sequences that cannot be modified in accordance with the present disclosure by restriction endonucleases or other DNA modified enzymes or effector domains, DNA sequences that are used for specific modifications, e.g. epigenetic modifications, e.g. methylations, and DNA sequences that carry a PAM motif, which can be identified by a suitable CRISPR system in accordance with the present disclosure, and also DNA sequences that do not have a PAM motif, such as is naturally present in an endogenous plant genome sequence.

The methods according to the present invention can be used specifically for the breeding of plants, in order to insert a more transgenic trait in a plant, or the at least one plant target structure of interest, comprising at least one meristematic cell. Currently, transgenic traits are inserted randomly into the plant genome through transformation systems, wherein this takes place with physical/mechanical methods, or biologically, basically comprising the biolistic bombardment of plant material or the transformation with *Agrobacterium* and/or viral vectors. Over the last few years, specific protocols for the targeted insertion of transgenes into the genomes of plant cells have become increasingly more common. One important technology is basically site-specific integration (SSI), which allows for the targeted insertion of a transgene at the same site in a chromosome where a transgene has already been inserted. Moreover, over the last few years target-specific nuclease systems, drafted in a targeted manner, have become increasingly more common for facilitating the cleaving of a chromosomal target point through nucleases. The nucleases currently frequently used for genome editing in eukaryotic genomes comprise, e.g., mega-nucleases, zinc finger mega-nucleases, transCRISPR ption activator-like effector nucleases (TALENs), and a constantly growing family of CRISPR nucleases, as well as variations that have been modified in a targeted manner and catalytically active fragments thereof. Specifically, CRISPR SPR-based nuclease systems have proven to be extremely useful for high precision target-specific and programmable modification of nucleic acid target regions of interest. Because the CRISPR system is guided by a, frequently chimeric, gRNA, and does not allow purely protein-based targeting and target selection, this can result in a high level of reliability, and a reduction in undesired off-target effects. Moreover, the present disclosure offers further advantages for the CRISPR systems intrinsically composed of two components, specifically in that either a gRNA and/or a CRISPR nuclease, or a variation or catalytically active fragment thereof, can be provided with a further effector domain in a targeted manner, by means of which the variability and the range of use of the CRISPR system can be significantly expanded. Through a reprogramming of a CRISPR nuclease, a nuclease-null variation can be generated, which has lost its catalytic activity regarding the cleavage of DNA, but retained its DNA identification function. Through the combination of a molecule modified in this manner with an effector domain, in particular an effector domain that allows the epigenetic modulation of the genome of a target cell of interest, targeted epigenetic modifications, e.g. methylations, demethylations, acetylations, de-acetylations, phosphorylations, de-phosphorylations, or ubiquitinations, can be inserted in a histone protein, or another arbitrary protein inside a nucleosome in the cell nucleus of an eukaryotic cell of interest through the transient insertion of a CRISPR system, comprising at least one gRNA, at least one CRISPR nuclease, and at least one effector domain. As a result, targeted structural adaptations can be acquired in chromosomal regions to obtain modified states of the activation, even when the CRISPR system used for this is only inserted in a transient manner in a plant target structure of interest, and thus cannot be inherited, wherein these structural adaptations can then potentially be inherited.

The CRISPR systems disclosed herein, as well as the methods, in particular for targeted modification of at least one meristematic cell, are suited in particular for genome editing of plant cells or organisms, because off-target cleavage, which is frequently lethal for the target cells, or leads to undesired side effects, can be avoided through the high level of precision.

In one embodiment, the CRISPR nuclease components of the CRISPR system, or a variation, comprising nicking enzymes or nuclease null-variations, or an active fragment thereof, can be stably integrated in a plant genome. The expression of the CRISPR nuclease can be regulated by a plant-specific promoter, wherein the promoter is a constitutive promoter, a tissue-specific promoter, or an inducible promoter, e.g. a temperature, stress, development stage, or chemically, inducible promoter. Without a further essential component of the CRISPR system, i.e. a synthetic gRNA or a crRNA, the Cas nuclease is not capable of cleaving and/or identifying DNA, such that the mere presence of the Cas nuclease has little or no effect on the plant cell of interest and its metabolism. It is therefore an advantage of the method desCRISPR bed herein for plant breeding and development, that cell lines or transgenic plant cells can be produced and propagated, which can express a Cas nuclease in a constitutive or inducible manner, or a variation or catalytically active fragment thereof, without having negative consequences for the cell integrity or viability. In order to acquire the activity of a CRISPR nuclease, whether it is stably integrated or provided in a transient manner, as desCRISPR bed above, the presence of a gRNA or a crRNA is always necessary as a further reliability mechanism, which can be inserted into a plant target structure comprising at least one meristematic cell of interest in a stable or transient manner through a number of methods. The gRNA can be inserted in the cell as a transCRISPR bable DNA construct in the form of a genetic construct, such as a vector, wherein the gRNA transCRISPR bes, in either a constitutive or inducible manner, and can thus be provided in a functional manner. Alternatively, the gRNA can also be directly inserted in a plant target structure of interest as RNA. CRISPR nucleases and gRNA can thus be inserted simultaneously, or offset over time, wherein it is preferred that the gRNA and CRISPR nuclease are provided spatially and temporally such that the less stable RNA and the protein CRISPR nuclease can interact in the cell compartment of interest in a stoichiometrically ideal composition. If the target of the targeted modification is an RNA, then the compartment of interest is the cytoplasm of a target cell. If the nucleic acid target region of interest is genomic DNA or the nucleosome, then the compartment of interest is the cell nucleus of a plant target structure comprising at least one meristematic cell. In this configuration, it may be necessary that the gRNA and/or CRISPR nuclease are functionally linked to suitable nuclear localization sequences, in order that the CRISPR molecules, or the CRISPR complex composed of gRNA and CRISPR nucleases, as well as optional effector domains associated therewith, can reach their workplace. In another embodiment, if the nucleic acid target region is located in an organelle, in particular plastids, the presence of plastid localization sequences, e.g. mitochondrial localization sequences or chloroplast localization sequences, may be necessary for conducting the CRISPR tools to the workplace in accordance with the present disclosure.

A gRNA in accordance with the present disclosure can be a single molecule, or it may be used or present in the form of two separate RNAs, corresponding to crRNA and/or tracrRNA.

The term "recombinant" as used herein means a series of nucleic acids or amino acids, in particular not occurring naturally as a totality. Furthermore, the term, "recombinant" also comprises those nucleic acid or amino acid sequencings that occur naturally with regard to their nucleic acid or amino acid sequences, but can also be obtained through a targeted modification or synthesis, e.g. synthetically obtained nucleic acid or amino acid sequences, or through bio-engineering, e.g. nucleic acid or amino acid sequences that are obtained through a fermentative process, which may exist in nature, but can also be produced in a targeted manner in an organism other than the source organism.

The term, "epigenetics" or "epigenetic," as used herein, desCRISPR bes the structural adaptation of chromosomal regions in order to encode, signalize, conserve, and to potentially pass onto the descendants of a cell, modified states of the activation. Accordingly, potentially inheritable modifications are obtained via modifications that are not encoded in the genomic DNA itself.

When the present disclosure refers to the "sequence homologies" or "sequence identities" of nucleic acid sequences or protein sequences in the form of percentages, these refer to values as can be calculated using EMBOSS Water Pairwise Sequence Alignments (Nucleotide) (www.ebi.ac.uk/Tools/psa/emboss_water/nucleotide.html) for nucleic acid sequences, or EMBOSS Water Pairwise Sequence Alignments (Protein) (www.ebi.ac.uk/Tools/psa/emboss_water/) for amino acid sequences. Tools for local sequence alignments available from the European Molecular Biology Laboratory (EMBL) European Bioinformatics Institute (EBI) use a modified Smith-Waterman algorithm (see www.ebi.ac.uk/Tools/psa/and Smith, T. F. & Waterman, M. S. "Identification of common molecular subsequences" *Journal of Molecular Biology,* 1981 147 (1): 195-197). Furthermore, when carrying out the respective paired alignments of two sequences using the modified Smith-Waterman algorithm, the Default Parameters currently available from EMBL-EBI should be employed. These are as follows: (i) for amino acid sequences: Matrix=BLOSUM62, Gap open penalty=10 and Gap extend penalty=0.5 and (ii) for nucleic acid sequences: Matrix=DNAfull, Gap open penalty=10 and Gap extend penalty=0.5. In the context of the present invention, the term "homologous sequences" or "homologues" or similar terms should be understood to be a reference to nucleic acid sequences which have the same phylogenetic origin. Preferably, proteins which are coded by these nucleic acid sequences have the same function. Homologous nucleic acid sequences exhibit at least 70%, preferably at least 75%, at least 80%, at least 85% or at least 90%, particularly preferably at least 95%, at least 96%, at least 97%, at least 98% or at least 99% sequence identity.

"Nucleic acid target regions" as used herein refer to any genomic as well as extrachromosomal DNA or RNA, in particular mRNA, of a target organism or a target cell which is to be modified and which can be modified by the method and constructs disclosed herein and is definitely not limited to gene regions, i.e. regions which carry the information for transCRISPR ption of a mRNA region. These target regions are thus natural or endogenous target regions, wherein the terms, "endogenous" and "natural" are used interchangeably in this context. Moreover, the term, "nucleic acid target region," is not limited to an endogenous sequence. If an artificial nucleic acid target region has been previously inserted in a target cell of a target structure of interest, the term, "nucleic acid target region," can thus relate to an artificially inserted nucleic acid target region.

"Complementary" or "complementarity" as used herein desCRISPR bes the relationship between two DNA or RNA nucleic acid regions the nucleobases of which fit together like a lock and key and form hydrogen bonds between each other (hybridize). In this regard, Watson-CRISPR ck base pairing of the bases adenine and thymine/uracil or guanine and cytosine are considered to be complementary. Other pairings such as non-Watson-CRISPR ck pairing, reverse Watson-CRISPR ck, Hoogsteen, reverse Hoogsteen and wobble pairing are encompassed by the term "complementary" insofar as the corresponding base pairs form hydrogen bonds together, i.e. two different nucleic acid strands can hybridize together on the basis of their complementarity.

The term "hybridize" or "hybridization" should be understood to mean a procedure during which a single-stranded nucleic acid molecule is applied to by a maximally complementary nucleic acid strand, i.e. undergoes base pairing. Examples of standard methods for hybridization are desCRISPR bed in Sambrook et al, 2001. Preferably, this should be understood to mean at least 65%, 70%, 75%, 80% or 85%, particularly preferably 90%, 91%, 92%, 93%, 94%, 95%, 96%, 97%, 98% or 99% of the bases of the nucleic acid sequence undergo base pairing with the maximally complementary nucleic acid strand. The possibility of such an application depends on the stringency of the hybridization conditions. The term "stringency" refers to the hybridization conditions. High stringency is then when a base pairing is made difficult and low stringency is when base pairing is facilitated. The stringency of the hybridization conditions depends, for example, on the concentration of salt or ionic strength and the temperature. In general, stringency can be increased by increasing the temperature and/or by reducing the salt content. The term "stringent hybridization conditions" should be understood to mean those conditions in which a hybridization primarily only occurs between homologous nucleic acid sequences. The term "hybridization conditions" then refers not only to the conditions prevailing during the actual application of the nucleic acids, but also on the conditions prevailing during the subsequent washing steps. Examples of stringent hybridization conditions are conditions in which overwhelmingly only those nucleic acids hybridize which exhibit at least 70%, preferably at least 75%, at least 80%, at least 85% or at least 90%, particularly preferably at least 95%, at least 96%, at least 97%, at least 98% or at least 99% sequence identity. Examples of stringent hybridization conditions are: hybridization 4×SSC at 65° C. and then washing in 0.1×SSC at 65° C. for a total of approximately 1 hour. The term "stringent hybridization conditions" used here can also mean: hybridization at 68° C. in 0.25 M sodium phosphate, pH 7.2, 7% SDS, 1 mM EDTA and 1% BSA for 16 hours and then washing twice using 2×SSC and 0.1% SDS at 68° C. Preferably, the hybridization is carried out under stringent conditions.

Detailed desCRISPR Ption

In one aspect, the present invention concerns a method for the production of a plant, a plant material or a plant cell, comprising the following steps: (i) providing a target plant structure which comprises at least one meristematic cell, wherein the at least one meristematic cell comprises at least one target nucleic acid region; (ii) providing at least one gRNA or providing one or more recombinant construct/constructs, wherein the recombinant construct(s) comprise at least one gRNA or a sequence coding for a gRNA, and optionally at least one regulatory sequence and/or a localization sequence, and optionally comprise the provision of at least one DNA repair template or HDR template, and the provision of at least one CRISPR nuclease or a catalytically active fragment thereof and/or an effector domain or providing one or more recombinant construct/constructs, wherein the recombinant construct(s) comprise(s) at least one CRISPR nuclease or a catalytically active fragment thereof or a sequence coding for a CRISPR nuclease or a catalytically active fragment thereof and/or at least one effector domain or a sequence coding for an effector domain, and optionally at least one regulatory sequence and/or a localization sequence, wherein the gRNA is both able to hybridize with a section of the target nucleic acid region and also to interact with the CRISPR nuclease or catalytically active fragment thereof and/or the effector domain; wherein, when the gRNA or the sequence coding for the gRNA and the CRISPR nuclease or the catalytically active fragment thereof or the sequence coding for the CRISPR nuclease or the catalytically active fragment thereof and/or the effector domain or the sequence coding for an effector domain is provided by one or more recombinant construct(s), the gRNA or the sequence coding for the gRNA and the CRISPR nuclease or the catalytically active fragment thereof or the sequence coding for the CRISPR nuclease or catalytically active fragment thereof and/or the effector domain or the sequence coding for an effector domain may be located on or in the same or on or in different recombinant constructs; optionally: wherein the gRNA or the sequence coding for the gRNA and/or the Cas nuclease or the sequence coding for the Cas nuclease and/or the effector domain or the sequence coding for an effector domain is adapted to use in a plant cell; (iii) optionally: providing at least one vector for introducing the recombinant construct/constructs; (iv) optionally: providing at least one further recombinant construct comprising a recombinant nucleic acid section for specific homology-directed repair of the target nucleic acid region in the target plant structure or insertion into the target nucleic acid region in the target plant structure preferably comprising at least one regulatory sequence and optionally at least one further vector for introducing the at least one further recombinant construct; (v) introducing the gRNA, the CRISPR nuclease or the catalytically active fragment thereof and/or the effector domain and/or the recombinant construct/constructs into the target plant structure; (vi) culturing the target plant structure under conditions which allow activation of the introduced gRNA, the CRISPR nuclease or catalytically active fragment thereof and/or the effector domain and/or the introduced recombinant construct/constructs and thus a specific modification of the target nucleic acid region in the target plant structure, in order to obtain a target plant structure comprising at least one meristematic cell which comprises the specific modification of the target nucleic acid region; (vii) obtaining a plant, a plant material or a plant cell from the specifically modified at least one meristematic cell; (viii) wherein the plant, the plant material or the plant cell is obtained directly by cell division and differentiation and optionally cross-fertilization or self-fertilization from the specifically modified at least one meristematic cell, and wherein the plant obtained, the plant material obtained or the plant cell obtained comprises the specific modification of the target nucleic acid region, wherein the recombinant construct(s) which comprise(s) at least one gRNA or a sequence coding for a gRNA, and/or at least one CRISPR nuclease or a catalytically active fragment thereof or a sequence coding for CRISPR nuclease or a catalytically active fragment thereof and/or at least one effector domain or a sequence coding for an effector domain is/are preferably not integrated chromosomally or extrachromosomally.

Meristematic cells belong to a tissue type in a plant which is desCRISPR bed as the meristem or formation tissue. In the manner of stem cells in animal organisms, meristematic plant cells, because they are undifferentiated cells, have the ability (depending on environmental influences) of differentiating into any specialized cell type. Meristems in plant organisms are not only present during embryo development, but also throughout the life cycle, so that a specific modification of meristematic cells and tissue in accordance with the present invention is not limited to plant embryos or seedlings, but also in larger seedlings and mature plants, for example in meristems from which generative plant organs (for example in maize the tassel or the cob) can be generated.

In accordance with one embodiment, the meristematic cell is a mature or immature plant cell of a plant embryo or a seedling or a plant comprising at least one meristematic cell or meristematic tissue.

According to one embodiment of the method disclosed herein, the at least one recombinant construct, comprising at least one gRNA, one CRISPR nuclease, optionally at least one effector domain, and optionally at least one DNA repair matrix, can be inserted transiently into a target cell. In another embodiment, the at least one recombinant construct for obtaining at least one targeted modification of at least one nucleic acid target region can be stably inserted in a plant target structure of interest, comprising at least one meristematic cell. In another embodiment, at least one recombinant construct can be used to first stably insert a component of the CRISPR system, preferably a nuclease or a variant or catalytically active fragment thereof, and optionally an effector domain, in the genome of a plant target structure of interest. Subsequently, the other components, i.e. gRNA, are introduced onto at least one further recombinant construct, optionally in an effector domain, and optionally, a DNA repair matrix is inserted transiently into the plant target structure. In all of the embodiments, the individual components can be introduced onto the same of different constructs simultaneously or successively. In some embodiments of the transient introduction it may be advantageous to first insert the construct, which carries one or more product components of the system, i.e. CRISPR nucleases, variations or catalytically active fragments thereof, and optionally, an effector domain. Optionally, if this is a DNA construct, this at least one construct can then be first translated by the cell. The constructs that carry the gRNA and the optional further DNA repair matrices and/or effector domains can then be introduced in a temporally offset manner. As a result, it can be ensured that the less stable gRNA can interact directly with the CRISPR nuclease of interest, and that decomposition of the gRNA will not prevent an effective DNA editing.

In accordance with one embodiment, the meristematic cell is a cell of a monocotyledonous or dicotyledonous plant.

In accordance with the present invention, then, a special method is provided which can either directly or indirectly specifically control the small population of meristematic cells in a plant in all of its stages of development as a target plant structure. The at least one meristematic target cell may be controlled directly or indirectly, i.e. at least one recombinant construct in accordance with the present disclosure may be introduced directly into the at least one meristematic target cell or the at least one recombinant construct may be introduced into any plant cell or any plant tissue with the aid of a suitable vector, wherein the at least one recombinant construct can then be transported to the target plant structure. This is accomplished by means of the systemic propagation of at least one recombinant construct introduced into a plant cell or into a plant tissue by means of a vector.

The term "target plant structure" as used herein encompasses at least one meristematic plant cell which may be present as tissue, plant material, as a whole plant or as isolated cell, wherein the meristematic plant cell also contains at least one nucleic acid target region. The at least one target nucleic acid region contained in the target plant structure comprises DNA and RNA sequences and may be present in the target structure chromosomally or extrachromosomally. The targeted CRISPR SPR-based methods for modifying a nucleic acid target region of interest can thus be used with the modification of genomic DNA, comprising the epigenetic modification of genomic DNA, or the modification of plastid or mitochondrial DNA, as with the modification of RNA in the form of silencing.

In one aspect of the present invention, which concerns the introduction of a specific nucleic acid modification into a non-chromosomal target structure, the term "target plant structure" as used herein encompasses at least one plant cell which may be present as tissue, plant material, as a whole plant or as isolated cells, wherein the plant cell additionally contains at least one target nucleic acid region comprising DNA and RNA.

In accordance with one aspect of the present invention, at least one target nucleic acid region in a meristematic plant cell as the target structure is modified by transiently introduced CRISPR SPR/Cas tools and/or further effector domains if appropriate. Since the at least one meristematic cell modified in this manner can directly and immediately pass on the specific modification in the target nucleic acid region by subsequent cell division and differentiation to its descendants, the method of the present invention does not require any more crossing and selection steps in order to provide a plant, plant material or a plant cell with the desired target modification. Moreover, from embryonal or even from secondary meristems such as pollen or ovaries, for example, optionally with self-fertilization or cross-fertilization, plant organisms or target plant structures may be obtained which carry the specifically introduced modification.

In one embodiment, the method of the present invention has the further advantage that the CRISPR SPR/Cas tools and/or any further effector domains are introduced into the target plant structure, preferably a meristematic cell or a meristematic tissue, in only a transient manner, so that no stable integration of the CRISPR SPR/Cas tools such as CRISPR nuclease and gRNA and possible regulatory sequences as well as other effector domains occurs into the endogenous chromosomal or endogenous extrachromosomal nucleic acids of the target plant structure.

In accordance with the present disclosure it was found that, by exploiting the mechanism of action of RNA-directed DNA modification of the CRISPR SPR/Cas tools, further effector domains in accordance with the method provided herein can be introduced, whereupon the spectrum of specific genome editing can be broadened. Either the CRISPR nuclease variant or the catalytically active fragment thereof or the gRNA or both may be linked with an effector domain.

An "effector domain" as used herein encompasses DNA- or RNA-modified or DNA- or RNA-binding polypeptides or nucleic acids, encompassing all types of monomeric, dimeric or multimeric nucleases, such as TALE nucleases, meganucleases, zinc finger nucleases, ribonucleases, deoxyribonucleases, exonucleases, endonucleases and restriction endonucleases of type I, II, III or IV and the like and including nickases, transCRISPR ption activators and suppressors, phosphatases, glycosylases or enzymes which can cause epigenetic modifications, examples of which are acetylases, methylases, methyl transferases, proteins which can bind methylated DNA, or histone deacetylases, aptamers, comprising single-stranded DNA or RNA sequences as well as peptides, fluorescent proteins, marker nucleic acid sequences or marker amino acid sequences and the like, and combinations thereof. Concerning enzymes or polypeptides in general, the term "effector domain" also means a catalytic domain or nuclear domain of the respective enzyme or polypeptide, for example a binder protein, wherein the catalytic domain or nuclear domain is still capable of carrying out the enzymatic or binding function of the respective native enzyme or polypeptide. The design of such truncated domains and their adaptation to the desired function is known to the skilled person in this field.

In this regard, methods and constructs are provided in which gRNA and/or CRISPR nuclease or the catalytically active fragment thereof already linked to a further effector domain can be provided as or on a recombinant construct. The gRNA and/or the CRISPR nuclease, comprising at least one effector domain, are then introduced onto at least one recombinant construct in a target structure, in order to form a functional complex there, following transCRISPR ption and, optionally, translation.

In a further embodiment, a method is provided in which the at least one gRNA or the at least one CRISPR nuclease or the catalytically active fragment thereof and/or at least one further effector domain is provided separately on different recombinant constructs. In accordance with this method, the gRNA component may be provided as DNA or RNA, the CRISPR nuclease or variant or the catalytically active fragment thereof may be provided as DNA or RNA or as a polypeptide sequence, and the effector domain may be provided as DNA or RNA or as a polypeptide sequence. The gRNA and the CRISPR nucleases, optionally comprising at least one effector domain, can thus be pre-assembled in vitro, and then inserted into a target structure.

According to one embodiment of the present invention, which comprises the simultaneous insertion of at least one gRNA and at least one CRISPR nuclease variation, or a catalytically active fragment thereof, together with at least one effector domain, the effector domain can be linked to the gRNA, or the CRISPR nuclease variation or the catalytically active fragment thereof, by a nucleic acid or amino acid linker, in order to ensure an ideal arrangement of the domains in relation to one another, and as a result, ensure their functionality through adequate flexibility of the domains in relation to one another. According to one embodiment, it is preferred that, in order to produce a plant, plant material, or a plant cell, optimized in a targeted manner, a DNA repair matrix is also provided, in addition to a gRNA and a CRISPR nuclease, a Cas or a Cpf1 nuclease, which can comprise independent effector domains. This embodiment is specifically preferred if a CRISPR nuclease, or a catalytically active fragment thereof, is used, which is capable of catalysing the introduction of a targeted DNA double-strand break in a nucleic acid target region of interest. The additional provision of a DNA repair matrix, either in the form of single-strand or double-strand DNA, can dominate over the natural and error-prone NHEJ repair mechanism of a plant cell, in order to bring about an even greater precision in the genome editing, as well as to provide the possibility of targeted introductions of insertions, mutations or deletions. The DNA repair matrix can be provided thereby in the form of a recombinant construct, either separately or on the same construct that is used for the introduction of the gRNA and/or the CRISPR nucleases. Alternatively, the DNA repair matrix can be inserted directly into a target cell or target structure of interest through transfection or transformation. Normally, a DNA repair matrix is designed such that it comprises left and right homology arms, which flank the position that is cleaved by a CRISPR nuclease. The two homology arms may exhibit a length of numerous hundreds of base pairs (bp), e.g. at least 100, at least 200, at least 300, at least 400, or at least 500 base pairs (bp), up to 1 kilobase (kb) or more. A homology region, i.e. a region where the sequences are aligned, can comprise at least 5-10, 5-15, 5-20, 5-25, 5-30, 5-35, 5-40, 5-45, 5-50, 5-55, 5-60, 5-65, 5-70, 5-75, 5-80, 5-85, 5-90, 5-95, 5-100, 5-200, 5-300, 5-400, 5-500, 5-600, 5-700, 5-800, 5-900, 5-1000, 5-1 100, 5-1200, 5-1300, 5-1400, 5-1500, 5-1600, 5-1700, 5-1800, 5-1900, 5-2000, 5-2100, 5-2200, 5-2300, 5-2400, 5-2500, 5-2600, 5-2700, 5-2800, 5-2900, 5-3000, 5-3100 or more bases, so that the homology region contains enough homologies to permit a homologous recombination with the corresponding genomic region. "Sufficient homologies" in this context means that two polynucleotides exhibit sufficient structural similarity, and thus can serve as a substrate for a homologous recombination. Accordingly, the degree of homology of the respective homology arms of a DNA repair matrix may vary for the corresponding nucleic acid sequences. In general, with shorter homology regions, a higher degree of homology is needed in order to obtain an adequate accumulation of complementary nucleic acid sequences. The degree of homology, i.e. the sequence identity, can accordingly be at least approximately 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%. In addition, the DNA repair matrix comprises a central construct, which carries a sequence, such as a transgene, that is to be introduced, or a modification that is to be introduced. The success of the introduction of a targeted modification in a nucleic acid target structure can be checked subsequently by (quantitative) PCR processes. Such a construct can be amplified via a PCR through primers that are specific for the two homology arms, the sequences of which can thus then be determined in order to establish whether the repair was made by the cells own NHEJ machinery, or by homologous recombination, assisted by the DNA repair matrix.

According to a further embodiment, first, at least one first plant, plant material, or plant cell is provided, which comprises at least one CRISPR nuclease, preferably a Cas nuclease or a Cpf1 nuclease, wherein the CRISPR nuclease is integrated in a stable or transient manner. This embodiment is specifically advantageous as long as the at least one first plant, plant material, or plant cell is later to be crossbred with at least one second plant, wherein the second plant, or at least one plant meristematic cell thereof, comprises a gRNA, with interacts with the Cas nuclease of the first plant, and can thus cause a targeted genome editing. The successful introduction of a targeted modification in a nucleic acid target region of interest in accordance with the present invention can be readily verified by a person skilled in the art using methods comprising polymerase chain reactions and the like, especially if nucleic acid target region of interest, and thus the region where the potential PCR primers can accumulate, is known, and is relevant for the design of a gRNA and/or a DNA repair matrix.

Activators and suppressors which may be used in accordance with the present invention preferably comprise SEQ ID nOs: 1-4 as well as sequences with at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% sequence homology with these sequences, which despite modification still carry out the same function as the sequences with the corresponding SEQ ID nOs.

A targeted modification according to the present disclosure can therefore comprise: (i) the exchange of at least one nucleotide of a nucleic acid target region; (ii) the deletion of at least one nucleotide in a nucleic acid target region; (iii) the insertion of at least one nucleotide in a nucleic acid target region; (iv) the targeted epigenetic modification of the region that regulates at least one nucleic acid target region; (v) the bonding and/or visualization to/of at least one nucleotide in a nucleic acid target region; or (vi) the interaction with and/or the cleavage of at least one RNA nucleic acid target region, or any combination of (i) through (vi). The methods according to the present invention can be used in particular for the precise and rapid trait development in a plant, plant material, or a plant cell.

In another embodiment of the first aspect of the present invention, a method is provided for producing a plant, plant material, or a plant cell, in which at least one plant target structure, comprising at least one meristematic cell, at least one gRNA, at least one CRISPR nuclease, or one catalytically active fragment thereof, and/or an effector domain, as well as at least one DNA repair matrix, is provided, wherein the targeted modification of the nucleic acid target region of interest comprises at least one heterologous sequence, i.e. a non-endogenous sequence, which comprises a gene selected from the group composed of a reporter gene, a selection marker, a gene that provides immunity to a disease, a herbicide resistance gene, a gene providing resistance to insects or nematodes, a gene involved in carbohydrate metabolism, a gene involved in fatty acid metabolism, a gene involved in amino acid metabolism, a gene participating in the plant development, a gene participating in the regulation of the plant growth, a gene participating in improving the yield of a plant material of interest, a gene participating in providing resistance to drought, a gene participating in providing heat resistance, a gene participating in providing resistance to a salt or salts, or a gene that is encoded by a functional RNA, wherein the functional RNA is selected from the group composed of an miRNA, a siRNA, or another RNA that can form an inverted repeat structure, e.g. a ddRNAi construct, that encodes both a clock-wise as well as a counter-clockwise strand, as well as a hairpin loop connecting the clockwise and the counter-clockwise strand, into which the genome of a plant target structure of interest, comprising at least one meristematic cell, is inserted.

Moreover, the methods according to the present disclosure are suitable for the formation of a complex trait locus. A complex trait locus is a chromosomal segment that has at least two modified nucleic acid regions and can be integrated in a nucleic acid target region according to the present disclosure in a single step, or sequentially, wherein the at least two modified nucleic acid regions are genetically linked to one another. The at least two modified nucleic acid regions both come from an endogenous plant locus, or the modification indicates a mutation or deletion of chromosomal DNA, or the at least two modified nucleic acid regions are transgenic sequences, or a combination thereof. Because the DNA repair matrix according to the present disclosure may have a central construct with a length of at least 1, 2, 3, 4, 5, 6, 7, 8, 9, 10, 20, 30, 40, 50, 60, 70, 80, 90, 100, 200, 300, 400, 500, 600, 700, 800, 1000, 2000, 3000, 4000 bp or more, the methods according to the present disclosure are suitable for introducing a complex trait locus in a plant target structure, comprising at least one meristematic cell, and a complex trait can be introduced with greater precision and efficiency, directly into a plant target structure, through the use of a CRISPR system and a DNA repair matrix. Because at least one plant, at least one plant material, or at least one plant cell can be obtained directly according to the methods of the present invention, there is the possibility of obtaining plant cells, plant material, or plants in a short period of time that have been modified in a targeted manner and are suitable for further crossbreeding, breeding, or further targeted modifications. In one embodiment, a first fertile plant, which has a first targeted modification in its genome, can be crossbred with a second plant, which has a second targeted modification in its genome, such that the targeted modifications can be physically linked, i.e. become part of the same nucleic acid molecule, wherein at least the first or the second, or both, plants are obtained according to the methods of the present disclosure. Artificial recognition sites in the form of a modified nucleic acid target region can be inserted in a locus through the intrinsic properties of the CRISPR system and knowledge of PAM motifs, as well as the interaction of an artificial gRNA with a CRISPR nuclease, in order to subsequently generate a nested complex locus, which comprises more than one targeted modification.

In another embodiment, a complex trait locus can also be directly inserted in a single step into a plant target structure comprising at least one meristematic cell. Because the CRISPR system according to the present disclosure can be scaled, in that it comprises numerous CRISPR nucleases, numerous gRNAs, optionally aligned with the CRISPR nucleases and/or a nucleic acid target region of interest, as well as at least one DNA repair matrix, which comprises at least one trait of interest that is to be integrated in the genome of a plant target structure, in addition to suitable homology arms, it is therefore not the case that just one trait can be affected in a targeted manner through the methods disclosed herein. Instead, it is possible to introduce a complex genotype trait in a plant target structure of interest in a stable manner that suppresses at least one phenotype trait.

In one embodiment according to the methods in the present disclosure, a process for producing a complex trait locus in a plant, plant material, or plant cell is therefore disclosed, wherein the method comprises the following steps: (a) selection of a genomic nucleic acid target region of interest in a plant, wherein the genomic nucleic acid target region comprises at least one first and one second nucleic acid target sequence; (b) bringing of at least one plant target structure, comprising at least one meristematic cell in contact with at least one first gRNA, one second gRNA, and optionally, at least one DNA repair matrix, and at least one CRISPR nuclease or a catalytically active fragment thereof, wherein the first and the second gRNAs, and the at least one CRISPR nuclease or the catalytically active fragment thereof, can form a complex, which allows at least one CRISPR nuclease to introduce a double strand break, or a single strand break in the case of a nicking enzyme, in at least one first and one second nucleic acid target region, wherein, optionally, the at least one gRNA or the at least one CRISPR nuclease also comprises an effector domain, or can be associated with at least one effector domain; (c) identification of a cell from step (b), which comprises at least one first targeted modification on the first nucleic acid target sequence, and one second modification on a second nucleic acid target sequence; and optionally, (d) acquiring a first fertile plant from the at least one meristematic cell from step (c), wherein the fertile plant comprises the first targeted nucleic acid modification and the second targeted nucleic acid modification, wherein the first targeted nucleic acid modification and the second targeted nucleic acid modification are physically linked, i.e. located on the same nucleic acid strand.

In another embodiment, the method comprises a process for producing a complex trait locus in which at least two modified nucleic acid target sequences in a genomic nucleic acid target region of interest are modified in a plant, plant material, or plant cell, comprising the following steps: (a) selection of a genomic target region in a plant, plant material, or plant cell, comprising at least one meristematic cell, wherein the genomic target region comprises a first nucleic acid target sequence and a second nucleic acid target sequence; (b) bringing the at least one plant cell, comprising at least one meristematic cell, in contact with a first gRNA, a CRISPR nuclease, or a catalytically active fragment thereof, and optionally, a first donor DNA in the form of a DNA repair matrix, wherein the first gRNA, and the first CRISPR nuclease or the catalytically active fragment thereof, can form a complex that allows the CRISPR nuclease to insert a double strand break in the first nucleic acid target region, wherein the gRNA and/or the CRISPR nuclease can optionally comprise an effector domain, or be associated with an effector domain; (c) identification of the at least one meristematic cell from (b), which comprises the first targeted modification in the first nucleic acid target sequence; (d) acquiring a first fertile plant from the cell from step (c), wherein the first fertile plant comprises the first targeted modification; (e) bringing at least one plant, plant material, or plant cell, comprising at least one meristematic cell, in contact with a second gRNA, a second CRISPR nuclease or a catalytically active fragment thereof, and optionally, a second donor DNA in the form of a DNA repair matrix; (f) identification of a cell from step (e), wherein the cell comprises at least one second targeted modification in a second nucleic acid target sequence; (g) acquiring a second fertile plant from the cell from step (f), wherein the second fertile plant comprises the second targeted modification; and (h) obtaining fertile descendants from the second fertile plant from step (g), wherein the fertile descendant plants comprise both the first and the second targeted modification in a nucleic acid target region of interest, wherein the first targeted modification and the second targeted modification are physically linked.

The tools and methods disclosed herein are therefore valuable tools for targeted and efficient genome editing in higher plant life through the use of CRISPR tools, as well as the targeted homologous recombination, as a repair mechanism. In particular, through the method disclosed herein it is possible to circumvent the natural, error-prone, DNA repair mechanism, "non-homologous end joining" (NHEJ), which repair mechanism frequently leads to mutations or chromosomal deletions.

Selected traits, which, according to the present disclosure, are inserted into a plant, or can be triggered in a plant in the form a targeted modification through genome editing, comprise, without being limited thereto, resistances, comprising resistances to herbicides and pests, comprising prokaryotic and eukaryotic pests and viruses, e.g. bacteria, fungi, protozoa, plant pathogenic viruses, nematodes, insects or other animal organisms, obtaining higher yields, wherein the yields can relate to any desired plant product, e.g. an increased seed, fruit, carbohydrate, protein, or fat yield, or other plant metabolism products, comprising further primary metabolites or secondary metabolites, etc. One aim of the genome editing can be the endogenous 5-enolpyruvylshikimate-3-phosphate (EPSP) synthase gene. EPSP synthase naturally catalyses the conversion of phosphoenolpyruvate (PEP) and 3-phospho-shikimate into phosphate and 5-enolpyruvylshikimate-3-phosphate, and through the introduction of targeted mutations in this endogenous gene, a mutated EPSP synthase encoding gene can be obtained, which displays resistance to the herbicide N-(Phosphonomethyl)glycine, or a salt thereof.

Moreover, the methods according to the present disclosure can be used to introduce traits into a plant or to modify undesired traits in a targeted manner. There thus exists a greater desire for foodstuffs, or food products, that contain a low portion of acrylamide. Acrylamide, which has been categorized as carcinogenic, is an undesired by-product of the Maillard reaction of the amino acids asparagine and glutamine when they react with reduced sugars such as aldoses (e.g. glucose) or acyloines at temperatures above ca. 170° C. In starchy plant products such as potato products, there is therefore a large interest in reducing the content of potential educts that form acrylamides, such as asparagine, in order to create safe foodstuffs. Therefore, a potato plant can be created in a targeted manner through the method disclosed herein, which can be modified in a targeted manner such that the gene is affected in a targeted manner with respect to asparagine metabolism, by influencing an asparagine synthetase gene, or some other gene that is involved in asparagine metabolism.

Another endogenous target gene of interest in the genome of a plant cell, which can be modified such that it exhibits herbicide tolerance or resistance, is the acetohydroxy acid synthase (AHAS) gene. AHAS inhibitor herbicides are important herbicides in agriculture throughout the world. By modifying at least one allele of an endogenous AHAS gene with the method disclosed herein, a herbicide-tolerant, or resistant, plant cell can be generated, from which a fertile plant, plant material, or plant cell can therefore be obtained within a short period of time from the approach disclosed herein for targeting a meristematic cell.

Plants, in particular crop plants for energy and food production that are resistant to various environmental effects, have also become increasingly important. These environmental effects include heat, drought, cold, the condition of the ground and the associated salinity, etc., of the nutrient supply. Consequently, there is a high interest in creating plants that can thrive in changing, and frequently less than optimal, environmental conditions. These traits also include properties, which can be introduced into a plant, in particular a crop plant, in a targeted manner according to the methods of the present invention, or can be induced in at least one plant target structure of interest through the targeted modification of at least one nucleic acid target region.

Specifically with regard to the optimization of traits that are agronomically relevant in a plant, it may also be of interest to modify the endogenous sequences, thus controlling the sequences that function as regulatory sequences, comprising promoters, in a targeted manner.

In one embodiment according to the present invention, a method is therefore proposed for producing a plant, plant material, or a plant cell, which comprises at least one targeted modification in at least one meristematic cell of interest, wherein the targeted modification is the modification of an endogenous promoter. The targeted modification of the promoter can comprise the replacement of the promoter, or a fragment thereof, with another promoter, or a fragment thereof, wherein the promoter exchange results in some arbitrary combination of the following: an increased promoter activity, an increased promoter tissue specificity, an increased pathogen-induced promoter activity, a reduced promoter activity, a reduced promoter tissue specificity, a reduced pathogen-induced promoter activity, a new promoter activity, an inducible promoter activity, a pathogen-induced promoter activity, an expanded spectrum of possible gene expression, which is controlled by the promoter, a modification of the temporal, spatial, or developmental stage gene expression of a nucleic acid target region, in this case a plant gene of interest, by means of which active promoters that are only active in a specific development stage can likewise be active in another development stage, or, regarded spatially, can be active in another tissue, or a mutation of DNA bonding elements, and/or the deletion or addition of DNA bonding elements. The promoter, or the fragment thereof, which is to be modified according to the method of the present disclosure, can be a promoter or fragment thereof, which is endogenous in the plant cell of interest, but it can likewise be an artificial promoter or a transgenic promoter that is present in a plant target structure of interest, which comprises at least one meristematic cell. The promoter or fragment thereof that is to be modified is preferably integrated in the chromosomal or extrachromosomal genome of a plant target structure of interest comprising at least one meristematic cell. The promoter that is to be modified, or the fragment thereof, may also be present on an extrachromosomal, not genomically integrated construct, e.g. a plasmid.

These endogenous genes exhibit further interesting traits that encode relevant metabolism, information, and/or signal transduction proteins, e.g. kinases, transCRISPR ption factors, zinc finger proteins or heat shock proteins. A targeted modification of these genes, and thus the encoded protein, makes it possible to intervene in numerous physiological processes, and thus provides the possibility of controlling metabolism processes in a targeted manner. Furthermore, these genes, and the associated regulatory DNA elements and the regions that encode regulatory proteins, are nucleic acid target regions of interest that are responsible for the fertility and/or sterility of a plant.

Further biotic and abiotic factors, the reaction possibilities, on the basis of which a target plant of interest can be modified according to the method of the present disclosure through targeted modification, comprise nutrient shortages, reactions to exposure to toxic metals, trace elements, quality, in particular the quality of the seeds or grain, optimized nutrient content, starch quality and quantity, the size of the seeds or grains, the overall carbohydrate content, comprising starch, sucrose, and other mono-, di-, and polysaccharides, nitrogen fixation and use, fatty acid and/or oil content and/or the composition of the fat/oil, comprising saturated and unsaturated fats, an increase in the lysine content, or other amino acids, or sulphur in a plant product, or a combination of the aforementioned traits. Exemplary genes that can increase the grain yield include ammonia induced glutamate-dehydrogenases. Genes that affect the amino acid biosynthesis are, e.g. anthranilate synthases (EC 4.1.3.27).

In another embodiment, the nucleic acid target region that is to be modified in a targeted manner can be a promoter, wherein the targeted modification comprises the replacement of a native EPSPS1 promoter with a plant ubiquitin promoter.

In another embodiment, the nucleic acid target region that is to be used in a targeted manner can be a promoter, wherein the targeted modification of the promoter comprises replacement of an endogenous NPK1 promoter from maize with a stress-induced RAB17 maize promoter.

In one embodiment according to the present disclosure, the nucleic acid target region of interest can be a promoter, wherein the promoter that is to be modified in a targeted manner, is selected from the group comprising *Zea mays* PEPC1 promoters (Kausch et al. Plant Molecular Biology, 45:1-15, 2001), a *Zea mays* ubiquitin promoter (UBI1ZM PRO, see Christensen et al., Plant Molecular Biology 18:675-689, 1992), a *Zea mays* root met 2 promoter, an actin promoter from rice (US-ACTIN PRO, McElroy et al. The Plant Cell, Issue 2, 163-171, February 1990), a millet RCC3 promoter, a *Zea mays* GOS2 promoter, a *Zea mays* ACO2 promoter, or an oleosin promoter from *Zea mays*.

Because the methods disclosed herein, as outlined above, are also suitable for introducing targeted insertions into a nucleic acid target region of interest through the combination of a CRISPR system, in particular the combination of at least one specific CRISPR nuclease, or a variation or active fragment thereof, with a specific gRNA and a DNA repair matrix, and a further embodiment of the present disclosure pertains to the creation of a method for inserting a promoter or a promoter element in a genomic nucleic acid target region of interest in a plant target structure, comprising at least one meristematic cell, wherein the promoter insertion may result in any of the following phenotype modifications: an increased promoter activity, i.e., an increased promoter strength, an increased promoter tissue specificity, a new promoter activity, an inducible promoter activity, an expanded spectrum of gene expression for the gene that is regulated by the promoter, or that is set through the introduction of an exogenous promoter under the control of the newly introduced promoter, a modification of the temporal, spatial or developmental stage gene expression, a mutation of DNA bonding elements, and/or the addition of DNA bonding elements. Selected promoter elements that can be introduced according to the method of the present invention into a plant target structure comprising at least one meristematic cell of interest comprise, without being limited thereto, promoter nuclear elements, e.g. a CAAT-box, CCAAT box, Pribnow box, a bonding element that promotes pathogen inducibility, such as a W-box, S-box, or D-box, and/or a TATA box, regulatory sequences that can affect the translation, and/or a repressor system for obtaining an inducible expression, e.g. a Tet-operator/repressor/inducer element, or a sulfonylurea repressor/operator/inducer element. Further promoter/operator systems that can be regulated, which can be introduced into a plant target structure of interest for the purposes of the present disclosure, are known to the skilled person in the field. An exemplary promoter, which can be introduced as an exogenous promoter into a plant target structure of interest is the DRE promoter. This promoter was originally desCRISPR bed by Yamaguchi-Shinozaki and Shinozaki (1994), Plant Cell 6, 251-265, as a cis-operating promoter element in promoters of the drought resistance gene, rd29A, which contains a conserved nuclear sequence comprising new base pairs, TACCGACAT. The introduction of a DRE promoter into an endogenous promoter of an arbitrary plant gene can therefore produce the inducible expression of the gene regulated by this promoter following a drought/aridity stimulus. A further example comprises ABA responsive elements, which contain a (c/T) ACGTGGC consensus sequence, and are found in numerous ABA and/or stress-regulated genes (Busk & Pages (1998), Plant Mol. Biol. 37:425-435). The insertion of 35 S enhancer or MMV enhancer into an endogenous promoter region in a plant cell can likewise increase the expression of the regulated gene. Therefore, through the targeted and precise modification of a promoter, or a portion thereof, in accordance with the present disclosure, the expression of a gene regulated by the promoter can be affected in a targeted manner, and the targeted modification introduced in this manner can be passed down directly to descendants, because the primary target cell is a meristematic cell, in accordance with the present invention, such that a fertile plant or plant material, or a plant cell therefrom, can be obtained, which has the desired promoter modification in its genome, and furthermore has a desired phenotype trait, which is the result of the gene regulated by the promoter through the modified expression.

In another embodiment according to the present disclosure, a method is provided, which relates to the targeted modification of a terminator, using the method disclosed herein. Accordingly, the nucleic acid target region of interest in a plant target structure comprising at least one meristematic cell can be a terminator, wherein the modification comprises the replacement of the terminator, or a fragment thereof, with another terminator, or a fragment thereof, wherein the terminator exchange may involve one or more of the following trait modifications: an increased terminator activity, an increase tissue specificity of the terminator, a reduced terminator activity, a reduced tissue specificity of the terminator, a mutation of DNA bonding elements and/or a deletion or addition of DNA bonding elements. The terminator (or the fragment thereof) that is to be modified in a targeted manner can be a terminator (or fragment thereof) of an endogenous gene, but it can likewise be an artificial, or chimeric or synthetic terminator, or a transgenic terminator. Likewise, the replacement terminator, thus the terminator, or fragment thereof, that is to be introduced through the method disclosed herein into the genome of a plant target structure of interest, can also be an endogenous terminator, an artificial terminator comprising a chimeric terminator, or a transgenic terminator. Exemplary terminators can be selected from the group composed of a maize ARGOS 8 or SRTF18 terminator, a tomato-PIN-II terminator, a millet-actin terminator, a millet-SB-GKAF terminator, a rice T28 terminator, an AT-T9 terminator, or a GZ-W64-A terminator. According to a preferred embodiment of the present invention, the terminator element that is to be replaced is used by the combination of at least one gRNA, aligned with at least one CRISPR nuclease and a nucleic acid target region of interest, together with a DNA repair matrix, wherein the central element of the DNA repair matrix serves as a donor sequence for the insertion of a terminator or terminator element of interest into a genomic nucleic acid target region of a plant target structure comprising at least one meristematic cell.

In another embodiment, the gRNA/CRISPR nuclease/DNA repair matrix system disclosed herein is used in a meristematic cell to specifically delete a terminator, or a terminator element, that is genomically anchored in a plant target structure of interest.

In addition to promoters and terminators, other regulatory sequences exist in the genomes of eukaryotic cells that are important for regulating gene or functional RNA transCRISPR ption. In one embodiment according to the present disclosure, the CRISPR system disclosed herein is used to modify or replace these regulatory sequences in a targeted manner in order to anchor these targeted modifications or replacements in a stable manner in the genome of a plant target structure of interest, to pass them on to the descendants via the initially modified meristematic cell, and thus be able to observe a targeted phenotype modification in the plant material or plant cells thereof obtained in this manner. Exemplary regulatory sequences according to the present disclosure comprise, without being limited thereto, 3'UTR (not translated) regions, 5'UTR regions, transCRISPR ptional activators, transCRISPR ptional enhancers or repressors, translation repressors, splicing factors, miRNAs, siRNAs, artificial miRNAs, incRNAs, promoter elements, CaMV 35S enhancers, MMV enhancer elements, SECIS elements, polyadenylation signals, and polyubiquitination sites.

In some embodiments, the genome editing, i.e. the targeted modification of a nucleic acid target region, comprises the targeted modification of replacement of regulatory elements, resulting in one or more of the following effects and/or phenotype expressions: modified protein translation, RNA cleavage, RNA splicing, and transCRISPR ption or post-translational modification terminations. In one embodiment, the nucleic acid target region of interest, which is to be modified in a meristematic cell in a targeted manner, is a polyubiquitination site, wherein the targeted modification of the polyubiquitination site results in a modified protein degradation rate for a target protein of interest. The ubiquitin tag marks proteins, so that these can subsequently be reduced to proteasomes, or broken down through a process called autophagy. Proteasome inhibitors are known for being able to cause protein overproduction. The targeted modification of a nucleic acid target region of interest that encodes a protein of interest can therefore also lead to at least one amino acid modification of the protein of interest, wherein the modification allows for the subsequent polyubiquitination of the protein, i.e. a post-translational modification, which leads to a modification of the protein degradation, or the rate of protein degradation in the protein of interest.

In one embodiment, the genomic sequence of interest that is to be modified is a polyubiquitination site in a maize EPSP synthase gene, wherein the targeted modification of the polyubiquitination site results in an increased protein content, because the relevant protein is broken down at a lower rate.

In another embodiment, the genomic nucleic acid target sequence inside a meristematic cell that is to be modified in a targeted manner according to the method of the present invention is an intron site, wherein the targeted modification comprises the introduction of an intron-promoting motif into the intron, resulting in a modulation (increase/decrease) of the transCRISPR ption activity of that gene comprising this intron.

In another embodiment, the nucleic acid target region of interest inside the genome of a plant target structure that is to be modified in a targeted manner is an intron site, wherein the targeted modification comprises the replacement of a specific intron, e.g. a soya bean EPSP synthase 1 intron, with another intron, e.g. a soya bean ubiquitin intron 1.

In one embodiment according to the present disclosure, the nucleic acid target sequence of interest that is to be modified in the genome of a meristematic cell of a plant of interest in a targeted manner is an intron or UTR site, wherein the targeted modification comprises the insertion of at least one micro RNA into this intron or UTR site, by means of which the expression of the gene that comprises the intron or UTR site also leads to the expression of this inserted micro RNA, which leads in turn to each target gene of interest being able to be "silenced" by the micro RNA that has been transCRISPR bed in this manner, whether it is an endogenous plant gene or the gene of a plant pest, without affecting the gene expression of the gene that carries the intron. Gene silencing or gene shutdown is a process in which the gene expression is reduced or shut off. The gene regulation in this case comprises the inhibition of the transfer of genetic information from the DNA to the mRNA, or the subsequent translation of the information stored on the mRNA into a protein. The processes that first take place after the transCRISPR ption of the genetic information from the DNA onto the transferring mRNA are referred to as post-transCRISPR ptional gene silencing. These phenomena are frequently referred to as RNA interference or RNAi, which are regulatory processes in which specific RNA molecules participate, such as micro RNAs and siRNA or artificial ddRNAi hairpin constructs. The post transCRISPR ptional gene silencing can result in a concentrated degradation of a target mRNA of interest, impairing the formation of the gene products (protein). As a result, both endogenous as well as foreign products can be silenced or translated at a significantly lower frequency by means of a process called host-induced gene silencing (HIGS).

In one embodiment, the method disclosed herein is used for the targeted modification of a nucleic acid target region inside a plant target structure comprising at least one meristematic cell, using the combination of a CRISPR nuclease and a gRNA, and optionally, at least one effector domain, for the targeted modification of a transCRISPR ption factor, i.e. to mutate or delete a transCRISPR ption factor, or to insert a transCRISPR ption factor into a nucleic acid target region of interest, using a suitable donor construct in the form of a DNa repair matrix. Exemplary transCRISPR ption factors are the zinc finger transCRISPR ption factor or the tapetal development and function factor (TDF; DE 10 2015 004 187 A1). The insertion of a single base pair into the encoding sequence of a transCRISPR ption factor can result in a frameshift mutation, which in turn produces a new protein, which still displays DNA bonding activity, but has nevertheless lost its transCRISPR ption activation capacity. Accordingly, the mutated zinc finger transCRISPR ption factor protein, for example, competes to bond on cytokinin-oxidase gene promoters, and blocks the expression of cytokinin-oxidase. The reduction of the cytokinin-oxidase expression can increase the cytokinin level in rice plants, and promote panicle growth, whereas the ear growth in maize can be increased, and in general, the yield of a plant product of interest can be increased in numerous plants. The mutated TDF, on the other hand, can lead to male sterility in wheat, which can be implemented advantageously for the generation of hybrid wheat plants.

In another embodiment, the methods according to the present disclosure can be used for the targeted modification of splices in a genomic nucleic acid target region of interest in a plant target structure comprising at least one meristematic cell, or alternatively, to introduce splices into the genomic nucleic acid target region of interest. In eukaryotic cells, mRNA that is obtained from pre-mRNA molecules and subsequently subjected to a maturation process is used for the synthesis or expression of proteins. The pre-mRNA molecules are capped, spliced and subsequently stabilized by the addition of a poly-A strand. Eukaryotic cells have developed a complex process for the so-called splicing, which results in alternative variations of an original pre-mRNA molecule. In maize cells, the splicing process can be affected by splicings at the exon-intron bonding sites. One example of a canonical splicing site is AGGT. Sequences that encode genes may contain numerous alternative splicing sites, which can affect the overall efficiency of the pre-mRNA maturation process, and thus decisively limit the protein accumulation in cells. The gRNA/CRISPR nuclease pairs disclosed herein can be used, together with effector domains and a DNA repair matrix, which can be used to introduce a specific modification template into a plant target structure of interest, to modify a genomic nucleic acid target region of interest, such that a canonical splicing site is inserted or created at a specific position with high precision. In one embodiment, a plant EPSP synthase gene can be affected, for example, wherein the targeted modification of the gene comprises the modification of alternative splicing sites such that this targeted genome editing results in an increased production of functional gene transCRISPR ptions and gene products.

If the method disclosed herein has an endogenous plant gene as the nucleic acid target region, one or more of the following effects can be obtained through the targeted modification: an increased protein/enzyme activity, an increased functionality of a protein of interest, a reduced protein activity, a reduced protein functionality, a site-directed mutation, the replacement of a protein domain, a protein knock-out, a new protein functionality, or a modified protein functionality.

In one embodiment, the protein knock-out can comprise the introduction of a stop codon into the encoding sequence of interest.

In another embodiment, the protein knock-out can comprise the deletion of a start codon in an encoding sequence of interest.

In a further embodiment according to the present disclosure, the method disclosed herein can be used for the targeted silencing of a gene of interest.

In one embodiment, the aim is gene silencing of an endogenous plant gene, and in another embodiment, the target gene in which the expression is to be modified is not an endogenous plant gene, but instead, the gene of a plant pathogen, comprising a bacterial gene, a eukaryotic gene, comprising genes from protozoa, nematodes, fungi, insects, or other animal predators or plant pathogens, or a viral gene. The process referred to as RNAi for silencing genes takes place in the cytoplasm of a target structure of interest, because this is where the proteins and protein complexes needed for this are present in their functional form. The methods disclosed herein can thus be used in two different embodiments: (1) inverted gene fragments can be inserted into a nucleic acid target region of interest in a targeted manner through the method disclosed herein. These gene fragments can be subsequently transCRISPR bed, resulting in a double-strand RNA structure, e.g. an RNA hairpin structure, which can subsequently silence an endogenous or exogenous gene. Alternatively, in accordance with this first embodiment, as stated above, a nucleic acid sequence can also be introduced into a genomic nucleic acid target region in a targeted manner, which is encoded as functional RNA for an miRNA or a siRNA, wherein the siRNA or miRNA construct subsequently mediates the gene silencing or gene shut-down; (2) In a second embodiment, the CRISPR nucleases disclosed herein, and the associated gRNAs can be modified such that the artificial CRISPR system is specific to RNA as a nucleic acid target structure. For this, further effector domains can be associated with either the gRNA and/or the modified CRISPR nucleases of interest. This approach is advantageous in particular, when, instead of the targeted modification of a genomic target region, RNA is to be modified directly in the framework of a gene silencing approach.

In another embodiment, the methods disclosed herein are suitable for facilitating the trait mapping in the course of plant breeding. Regarding qualitative traits, the method disclosed herein can be used for the targeted elimination of candidate genes in the identified chromosomal region, in order to determine, on the basis of this, whether or not the deletion of a gene has an effect on the expression of a trait of interest. With quantitative traits, the expression of a trait of interest is controlled by multiple quantitative trait loci ("quantitative trait loci" (QTL)) of different and strongly varying sizes, complexities and statistical significance, which can also be located over numerous chromosomes scattered in the genome of a plant. A QTL is therefore a portion of a chromosome, or a portion of numerous chromosomes, that has an effect on the expression of a specific quantitative phenotype trait of interest. In differing from discrete traits, e.g. blossom colours in plants that are present in numerous different, differentiated states, quantitative or consistent traits can be measured without gradation on a continuous scale. In the case of a negative effect on QTL regions that define a complex trait, the methods desCRISPR bed herein can thus be used in one embodiment in order to eliminate entire chromosomal regions inside a plant target structure comprising at least one meristematic cell of interest through marker assisted mapping, in order to mark specific regions for selective deletion, or redistribution.

In another embodiment of the present disclosure, the methods disclosed herein can be used to modify a genomic region of interest, which is flanked by two different nucleic acid target regions, according to the present disclosure, by two independent gRNA/CRISPR nuclease pairs, optionally using a DNA repair matrix. These modifications can take place simultaneously or successively. The removal preferably takes place simultaneously, and the resulting deletion can be subsequently repaired, optionally using a DNA repair matrix, by linking the two chromosomal ends without the deleted nucleic acid target region of interest.

In an alternative embodiment, a target region of interest can be modified through inversions, mutations in the cleavage sites, or duplication of a region of interest.

Exemplary herbicide resistant proteins or genes according to the present disclosure comprise acetolactate synthase (ALS) inhibitors, in particular if the herbicide is of a sulfonylurea type, and genes that encode a resistance to herbicides that inhibit the effects of glutamine synthases, e.g. phosphinothricin or BASTA, glyphosate, e.g. EPSP synthase genes and GAT genes, HPPD inhibitors, e.g. HPPD genes and suchlike. Thus, the bar gene encodes resistances to the herbicide BASTA, whereas the nptII gene provides resistances to the antibiotics kanamycin and geneticin (G418) and ALS gene mutants encode or provide resistance to the herbicide chlorsulfuron.

Exemplary genes according to the present disclosure that provide resistance to diseases or plant pathogens can provide resistance to plant pests such as the corn rootworm, *Bromius obscurus*, or the larva thereof, the European corn borer, etc. Disease resistance genes and/or insect resistance genes, comprise genes such as lysozymes or cecropins for protecting against microorganisms, or proteins such as defensins, glucanases or chitinases, for protecting against fungi pathogens, or *Bacillus thuringiensis* endotoxins, protease inhibitors, collagenases, lectins or glycosidases for controlling nematodes or insects.

Moreover, the methods according to the present disclosure, as indicated above, can be used for generating male- or female-sterile plants. The creation of male-sterile maize plants is advantageous because such a plant does not require the manual or mechanical removal of the tassel, i.e. the male inflorescence that produces pollen, which may be time consuming and expensive. Exemplary male sterility genes are, e.g. MS26, MS45, or MSCA1. Maize plants can be cultivated through both self-pollination as well as cross-pollination techniques. The maize plant has male flowers located on the tassel, and female flowers located on the ear, wherein the same plant has both male and female flowers. As a result, a maize plant can be reproduced through both self-pollination and cross-pollination. Breeding programs combine desirable traits of two or more strains, or from different sources in so-called breeding pools, from which new inbreeding strains or DH (double-haploid) strains are obtained, which are developed through selfing and subsequent selection of desired phenotypes. A hybrid maize type is a cross between two such inbreeding or DH strains, wherein each of the two parental inbreeding or DH strains carries one or more desirable characteristics that are lacking in the other parental strain, or that can complement the other strain. The new inbreeds or DHs are then crossed with other inbred or DH strains, and the hybrids thereof are examined in order to identify those plants of potential economical and agronomical interest. The hybrid descendants of the first generation (as well as descendants of the first generation in general) are labelled F1. The F1 hybrid is stronger and more robust than its parents. This effect, also referred to as heterosis, can express itself in a variety of ways, such as an increased vegetative growth or an increased yield. Hybrid maize seeds can be generated using a male-sterilization system for manual or mechanical tassel removal. By removing the male tassel, the female flowers of an inbreeding strain can only be pollinated with pollen from a male inbreeding strain of interest. The resulting seeds are therefore hybrids (F1) and produce hybrid plants. It is, however, frequently difficult to prevent self-pollination in female plants, particularly in field tests. As a result, seeds of a female inbreeding strain are then harvested together with hybrid seeds. As explained above, the seeds of a female inbreeding strain or DH strain are not as economically interesting as the F1 seeds, because no heterosis effect occurs. As a result, there is a high demand in plant breeding for male-sterile plants, which can be produced for the production of hybrid seeds for plants of agronomic interest, e.g. maize or wheat, which can be obtained ideally with low labour and production costs. Mutations that cause male-sterility in maize plants or wheat, for example, were obtained in the prior art through numerous methods, e.g. using X-rays or UV radiation, chemical treatment, or through the insertion of transposable elements (Chaubal et al., 2000 AM. J. Bot. 87:1193-1201). There is nevertheless still a strong demand for new genes that affect the male fertility in a plant of interest, and reliable methods for inserting precisely this gene, or a targeted modification of interest, into the genome of a plant of interest. Exemplary genes that are responsible for male sterility comprise the aborted microspores (AMS) gene from *Arabidopsis*, the *Arabidopsis* MS1 gene, the NEF1 gene, the *Arabidopsis* AtGPAT1 gene, the *Arabidopsis* dde2-2-mutation, the *Arabidopsis* faceless pollen-1 gene (flp1), the *Arabidopsis* male meiocyte death 1 gene, the tapetum-specific zinc finger gene (TAZ1), the tapetum determinant 1 gene, and the tapetal development and function (TDF) gene.

Because the methods disclosed herein are suitable for both stable as well as transient integration of a targeted modification in a nucleic acid target region of a plant target structure comprising at least one meristematic cell, a male- or female-sterile plant or plant material can be obtained directly, for example, because the targeted modification, which can be introduced in accordance with the method of the present invention into a meristematic cell, is passed on directly to the descendants of this cell. Using the technologies disclosed herein in vivo, a male- or female-sterile plant, in particular a maize plant, can therefore be obtained without further crossbreeding.

In one embodiment according to the present disclosure, a process is provided that is suitable for selecting or defining a plant, plant material, or a plant cell that comprises the at least one targeted modification in a nucleic acid target region, comprising a genomic target region or an RNA target region, wherein the method comprises the following steps:

a) Obtaining a first plant that comprises at least one CRISPR nuclease, or a variation or catalytically active fragment thereof in at least one meristematic cell, wherein the CRISPR nuclease is capable of inserting a double- or single-strand break in a genomic target region, or RNA nucleic acid target region, of interest;
b) Obtaining a second plant that comprises at least one gRNA, which is capable of forming a complex with the CRISPR nuclease, the variation, or the catalytically active fragment thereof, from step a);
c) Crossbreeding the first plant, from step a), with the second plant, from step b);
d) Checking the descendants from step c), or the cells thereof, for modifications in a nucleic acid target region of interest; and
e) Selection of a descendant plant, a plant material or a plant cell, which comprises the desired targeted modification in at least one nucleic acid target region of interest.

In a further embodiment of this selection process according to the present disclosure, the gRNA and/or the CRISPR nuclease also comprises at least one effector domain, which is associated with, or can be associated with, the gRNA and/or the CRISPR nuclease, and/or, if the gRNA and/or the CRISPR nuclease, as well as the at least one effector domain, are provided on a recombinant construct, an encoding sequence for an effector domain. The effector domain can be associated or linked in a covalent or non-covalent manner to the gRNA and/or the CRISPR nuclease.

In another embodiment according to the present disclosure, a process for selecting a plant, plant material, or a plant cell of interest is provided, which comprises a nucleic acid target region that has been modified in a targeted manner, either in its genome or in its transCRISPR ptome, i.e. the entirety of all of the transCRISPR bed genes or functional RNAs in a cell at a specific point in time, wherein the process comprises the following steps:

(a) Obtaining a first plant that comprises at least one CRISPR nuclease, or a variation or catalytically active fragment thereof, that is capable of causing a double-strand break, single-strand break, and/or specific DNA bond in a nucleic acid target region;
(b) Obtaining a second plant that comprises a gRNA, wherein the gRNA is capable of forming a complex with the CRISPR nuclease, or the variation or catalytically active fragment thereof, wherein the Cas nuclease, the variation, or the catalytically active fragment thereof, as well as the gRNA, are provided directly, or in the form of at least one recombinant construct, and wherein the gRNA and/or the CRISPR nuclease, or the variation or catalytically active fragment thereof, are associated with or can be associated with at least one effector domain or one encoding sequence for an effector domain; and wherein the first plant, from (a), or the second plant, from (b), also comprises a DNA repair matrix, which comprises at least one donor DNA as a central component thereof, wherein the DNA repair matrix is introduced directly, through transformation or transfection, or in a recombinant manner, in the form of at least one recombinant construct, into the first or second plant, plant material, of the plant cell;
(c) Crossbreeding the first plant, from step (a), with the second plant, from step (b) and optionally providing at least one gRNA and/or one DNA repair matrix, as long as this is not stably integrated in the genome of the first and/or second plant;
(d) Assessment of the descendants of the plant from step (c), or the plant cells thereof, with regard to whether a targeted modification can be observed in the at least one nucleic acid target region of interest; and
(e) Selection of a descendant plant, or a plant material or plant cell thereof, which comprises the desired insertion introduced into the at least one nucleic acid region of interest, wherein the insertion is introduced via the donor DNA as part of the DNA repair matrix.

The methods disclosed herein are therefore suitable for obtaining a high precision gene targeting of a transgene of interest, and/or also producing complex transgene trait loci, because, as explained above, according to the method of the present disclosure, multiple transgenes can also be inserted, either simultaneously or successively, into a plant target structure of interest comprising at least one meristematic cell. A more complex transgenic trait locus is a genomic locus that carries numerous transgenes that are genetically linked to one another. By inserting independent transgenes within 0.1, 0.2, 0.3, 0.4, 0.5, 1, 2, or even up to 5 centimorgans (CM) of one another, the transgenes can be configured as individual genetic loci (see, e.g., US 2013/0263324 A1). A centimorgan indicates the distance between two linked genes, markers, nucleic acid target regions, or loci, or an arbitrary pair thereof, wherein 1% of the meiosis products are recombinant. Therefore, 1 centimorgan is equivalent to a distance corresponding to 1% of the mean recombination frequency between the two linked genes, markers, nucleic acid target regions, loci, or an arbitrary pair thereof. After selecting the plant, plant material, or plant cell of interest, which comprises the transgene of interest, those plants that contain at least one transgene can then be crossbred, in order to produce an F1 plant, plant material, or plant cell, that contains both transgenes. One in five hundred of the descendants of these F1 plants would then comprise the two different transgenes, recombined on the same chromosome. The complex locus can then be used for further breeding as the only genetic locus having both transgenic traits. The process can be repeated as often as desired in accordance with the method disclosed herein, in order to collect as many traits as possible, or desired, in a complex locus. Subsequently, the chromosomal intervals that correlate with a phenotype or trait of interest can be identified. There are numerous methods available to the skilled person in this field for identifying chromosomal intervals. The boundaries of such chromosomal intervals are drawn such that they comprise markers that are linked to the gene that controls the trait of interest. In other words, the chromosomal intervals are drawn or defined such that each arbitrary marker lying within an interval, including the terminal markers that define the boundaries of the interval, can be used as a marker. In one embodiment, the chromosomal interval can comprise at least one QTL or more than one QTL. A strongly expressed proximity of the multiple QTLs in the same interval can however obscure the correlation of a specific marker with a specific QTL in the diagnostics, because a marker may indicate a link with more than one QTL. Conversely, it is sometimes unclear, if two markers that are close together display a segregation from the desired phenotype trait, whether each of these markers identifies the same QTL, or two different QTLs.

Furthermore, a plant, plant material, or a plant cell is disclosed, which is or can be obtained in accordance with one of the methods desCRISPR bed above, in accordance with the first aspect of the present invention.

Methods for breeding and cultivating microorganisms and viruses which can be used in accordance with the present disclosure as vectors, are known to the skilled person in this field.

In one embodiment, the recombinant construct of the present invention is introduced into the target plant structure with the aid of at least one vector or vector system.

In another embodiment, the recombinant construct of the present invention is introduced into the target cell directly without an additional vector, preferably by mechanical methods, by transfection or by using endocytosis.

One embodiment of the present invention also envisages the introduction of at least one recombinant construct into a target plant structure.

Vectors and vector systems of the present invention encompass those which are selected from the group consisting of SEQ ID NOs: 12-15 and 25-38, as well as sequences with at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% sequence homology with these sequences which, despite modification, still carry out the same function as the respective unmodified vector or vector system with the corresponding SEQ ID NO. The cited vectors and vector systems may include codon optimized or truncated recombinant constructs, or they may contain specific point mutations in order to ensure their activity in different target cells. The sequence of SEQ ID NO: 31 is a hybrid sequence with which the region between the Bell and the BssHII cleavage sites of the Fescue segment RNA3 of the Brom Mosaic Virus (see NCBI: DQ530425) is replaced with the corresponding section of the R_BMV_RNA3_SI13'A/G (Hema & Kao 2004, Journal of Virology) fragment. Further, in accordance with the present invention, an *Agrobacterium* spp. may be envisaged as a vector and may be used alone or in combination with other introduction means or vectors. In accordance with one embodiment, the vectors and vector systems cited above with SEQ ID NOs: 12-15 and 25-38 or sequences with the sequence homology cited above may be used for this purpose as a framework structure in order to introduce the recombinant constructs of the invention comprising at least one gRNA as well as at least one CRISPR nuclease and/or at least one effector domain into a target plant structure. The molecular biological methods and procedures required in this regard are familiar to the skilled person in this field.

Recombinant constructs of the present invention include those which are selected from the group consisting of SEQ ID NOs: 23 and 24 as well as sequences with at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% sequence homology with these sequences which, despite modification, still fulfil the same function as the respective unmodified recombinant construct with the corresponding SEQ ID NO. The cited recombinant constructs may comprise codon-optimized or truncated sequences or they may comprise specific point mutations in order to ensure or modify their activity or binding properties in various target cells. In SEQ ID NO:23, positions 16239-16258 correspond to the position for the respective gRNA of interest which can be modified depending on the target nucleic acid sequence. In SEQ ID NO:24 positions 16645-16664 correspond to the position of the respective gRNA of interest which can and must be modified depending on the target nucleic acid sequence.

In one aspect, the present invention concerns a method for the production of a plant, a plant material or a plant cell, wherein the recombinant construct is selected from SEQ ID NOs: 23 and 24, as well as sequences with at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% sequence homology with these sequences.

In a further aspect, the present invention concerns a plant, a plant material or a plant cell which can be obtained or is obtained by a method comprising introducing a recombinant construct in accordance with SEQ ID NOs: 23 and 24, as well as sequences with at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% sequence homology with these sequences, into a target plant structure which comprises at least one meristematic cell.

In a yet still further aspect, the present invention concerns the use of at least one recombinant construct in accordance with SEQ ID NOs: 23 and 24, as well as sequences with at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% sequence homology with these sequences, for the specific modification of at least one target nucleic acid region in a plant cell.

All Cas-polypeptide sequences as well as Cas-coding nucleic acid sequences which have been specially optimized for use in a plant cell or for which their coding constructs carry suitable regulatory sequences which can permit adequate transCRISPR ption and/or translation in a plant cell in the cellular compartment provided therefor, including the cell nucleus, the cytosol, a mitochondrion, a plastid, including a chloroplast, are suitable for use in the present invention. Furthermore, in one embodiment the respective CRISPR nucleases must have their intrinsic nuclease function. Therefore, a catalytically active fragment derived from a native CRISPR nuclease can also be used as the CRISPR nuclease according to the present disclosure, as long as the catalytically active fragment still fulfils the same enzymatic catalytic function as the native enzyme from which it is derived.

Alternatively in an aspect of the present disclosure, Cas nickases or catalytically active fragments thereof may be used, i.e. Cas polypeptides which are modified such that they only cleave one DNA and do not produce a DNA double-stranded break, as in a native CRISPR nuclease. This means that firstly there is the possibility of an increased specificity, since in order to carry out a double-stranded break, two recombinant constructs including a Cas nickase have to be used. On the other hand, there is the possibility that a specifically offset double-stranded break can be introduced instead of a blunt cut.

Finally, in accordance with one aspect of the present disclosure, Cas-zero nucleases or catalytically active fragments thereof, i.e. variants which no longer have any nuclease activity, may also be used. In this regard, it raises the possibility that the CRISPR nuclease together with a further effector domain in accordance with the present disclosure, i.e. a further DNA- or RNA-modifying or DNA- or RNA-binding polypeptide or nucleic acids in accordance with the present invention may be used, whereupon the spectrum for introducing specific modifications into a target plant structure is broadened.

The skilled person in the field is aware that specific mutations in the catalytic domains of a CRISPR nuclease are of interest in order to "reprogram" these to a nickase or also a endonuclease-zero variant.

Examples of CRISPR nucleases or catalytically active fragments thereof or sequences coding CRISPR nucleases or catalytically active fragments thereof for application in the present disclosure are disclosed in SEQ ID NOs 16-22 and in UniProtKB/Swiss-Prot database accession no Q99ZW2.1 (SEQ ID NO: 39) and also comprise those sequences with at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% sequence homology with these sequences which, despite modification, still carry out the same function as the respective unmodified sequences with the corresponding SEQ ID NO or which are accessible under the said database accession number.

In a still further aspect of the present invention, the CRISPR SPR/Cas system at the basis of the mechanism of activity of the RNA-controlled DNA modification is used so that an effector domain instead of or together with the CRISPR nuclease is directed by a specific adapted gRNA to the desired position of a target nucleic acid region in a target plant structure, so that the effector domain can be specifically placed in order to carry out the desired nucleic acid edit.

In one embodiment of this aspect, the target nucleic acid region is a genomic DNA.

In a further embodiment of this aspect, the target nucleic acid region is a mitochondrial or plastid DNA, wherein the recombinant construct comprises a localization sequence which comprises the localization of the recombinant construct in the corresponding target compartment, for example in a mitochondrion or a chloroplast.

In one embodiment, the CRISPR nuclease or catalytically active fragments thereof or the sequence coding for the CRISPR nuclease or catalytically active fragments thereof, and/or the effector domain or the sequence coding for the effector domain additionally comprises a sequence selected from a nuclear localization sequence, a plastid localization sequence, preferably a mitochondrial localization sequence and a chloroplast localization sequence. A nuclear localization process can be selected from SEQ ID NO: 49-58, which discloses the following sequences: simian virus 40 (SV40) monopartite: MAPKKKRKV (SEQ ID NO: 49); *A. tumefaciens* VirD2 (pTiA6): KRPRDRHDGELGGRKRAR (SEQ ID NO: 50); *A. tumefaciens* VirD2 (pTiC58): KRPREDDDGEPSERKRER (SEQ ID NO: 51); *A. tumefaciens* VirE2 (pTiA6) #1: KLRPEDRYVQTERGRR (SEQ ID NO: 62); *A. tumefaciens* VirE2 (pTIC58) #1: KLRPEDRYIQTEKYGRR (SEQ ID NO: 53); *A. tumefaciens* VirE2 (pTiA6) #2: KRRYGGETEIKLKSK (SEQ ID NO: 54); A. *Tumefaciens* (PtiC58) #2: KTKYGSDTEIKLKSK (SEQ ID NO: 55); *A. rhizogenes* GALLS (pRil 724): KRKRAAAKEEIDSRKKMARH (SEQ ID NO: 56); *A. rhizogenes* GALLS (pRiA4): KRKRVATKEEIEPHKKMARR (SEQ ID NO: 57); A. *Rhizogenes* GALLS VirD2 (pRiA4): KRPRVEDDGEPSERKRAR (SEQ ID NO: 58).

One or more nuclear localization sequences can be combined with an effector domain, which are preferably united on a plasmid vector.

In a further embodiment, the gRNA or the sequence coding for gRNA additionally comprises a sequence selected from a nuclear localization sequence, a plastid localization sequence, preferably a mitochondrial localization sequence and a chloroplast localization sequence.

In a yet still further embodiment of this aspect, the target nucleic acid region is a ribonucleic acid (RNS) in any plant compartment, for example the cytosol. In accordance with this embodiment, a specifically modified gRNA may be provided which is capable of interacting with a target RNA structure. The gRNA may in addition comprise a further effector domain, for example an aptamer.

The skilled person in the field will be aware that the design of the corresponding at least one gRNA which is used together with at least one CRISPR nuclease and/or with at least one effector domain, is dependent on the specificity and in particular the binding and recognition properties of the CRISPR nuclease and/or the effector domain as well as the target nucleic acid region which is to be specifically modified.

Wild type CRISPR nucleases, in particular of type Cas9, produce a blunt double-stranded break in the target DNA sequence, i.e. without a single-stranded DNA overhang. Moreover, these nucleases can also leave single nucleotide overhangs behind, resulting from offset cleavage of the two individual strands of a DNA double-strand. To this end, the endogenous DNA repair mechanisms of the target cell are activated comprising the so-called non-homologous end joining, NHEJ. This mechanism is prone to errors, however, in particular since hereby insertions and deletions (INDELs) can be introduced at the location of the double strand break. Thus mutations may be established at the sites where the individual DNA strands are re-joined. By means of NHEJ, single or plural gene knock-outs may be mediated, wherein after the specific DNA break, the DNA strands are brought together with a modified sequence that was obtained in a frameshift or another mutation, which can prevent the functional expression of one or more genes of interest, again by endogenous mechanisms. A further repair mechanism is homology-directed repair (HDR) or homologous recombination (HR). These mechanisms use homologous DNA as a template or matrix, from which the sequence information can be copied in order to repair a DNA break. At least one precise editing, insertion, or gene exchange can take place through the targeted provision of a DNA repair matrix, which is homologous over a specific length to a genomic DNA region in which a DNA break is to be induced inside a target cell of interest. The precise modifications obtained in this manner comprise no undesired or uncontrollable mutations, as is always desirable in any gene editing approach. Both repair mechanisms, NHEJ and HDR/HR, constitute naturally occurring mechanisms for DNA repair which are present in every cell disclosed herein.

In one embodiment according to all of the aspects of the present disclosure, a DNA repair matrix, or a repair template, is provided, which repairs a single-strand or double-strand break in a site oriented and precise manner, which was previously inserted by a CRISPR nuclease, or a variation or catalytically active fragment thereof, and/or an effector domain in a nucleic acid region of interest.

What is decisive for the site-directed introduction of the modification of a target nucleic acid region is, in accordance with the above mechanism of the type II CRISPR SPR/Cas system, the specific selection and the specific design of the gRNA sequences in order to avoid cleavage of off-target regions other than the target region. The identification of suitable PAM motifs as a function of the CRISPR SPR/Cas tools used and optional further effector domains and the use of this information for the design of suitable recombinant constructs is known to the skilled person in this field.

In accordance with one embodiment of the present disclosure, the genome or the extrachromosomal target nucleic acid region of a cell is thus initially investigated for suitable PAM sequences in order to be able to specifically design a suitable gRNA.

The term "guide RNA" or "gRNA" as used herein denotes a single stranded or double stranded or partially double stranded nucleic acid molecule which may consist of natural or synthetic RNA and/or of natural or synthetic DNA and has the function of being capable of building a complex with a CRISPR nuclease or a catalytically active fragment thereof, whereupon the CRISPR nuclease or the catalytically active fragment thereof is rendered capable of recognizing a target nucleic acid region. In addition, in addition to the CRISPR nuclease interaction domain, a gRNA functions as a recognition domain for specific hybridization to a complementary target nucleic acid molecule of interest. Thus, a gRNA comprises a crRNA and optionally, a tracrRNA, as explained above. The gRNA can thus be a synthetic dual molecule that unites numerous functionalities, or the gRNA can comprise only one functionality. The length of the crRNA and/or the tracrRNA can lie in a range of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or more nucleotides. Consequently, gRNAs may form an intrinsic hairpin region by complementary base pairing, whereupon the natural tracrRNA/crRNA hairpin structure is imitated (see Jinek et al, 2012, above) and in addition, depending on the desired target structure, comprises a suitable recognition domain. If a Cpf1 nuclease is selected as a CRISPR nuclease, the gRNA can be a crRNA that does not comprise a structure used by tracrRNA (see Zetsche et al., 2015, above). Accordingly, a gRNA according to the present disclosure, can comprise one or more spacer regions, which do not interact with a bonding partner or target molecule, but instead are used for the correct folding and orientation of the gRNA or for the linking of a crRNA and a tracrRNA. These spacers can be composed of DNA and/or RNA, and exhibit a length of at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 78, 79, 80, 81, 82, 83, 84, 85, 86, 87, 88, 89, 90, 91, 92, 93, 94, 95, 96, 97, 98, 99 or 100 nucleotides. A gRNA according to the present invention comprises at least one sub-region composed of RNA, wherein the RNA can be formed by natural or synthetic nucleotides. If desired, a gRNA of interest, preferably at its 5' or 3' ends, may carry a modification, wherein the modification is selected from the addition of a group composed of aCRISPR dine, amine, biotin, Cascade Blue, cholesterol, Cy3 @, Cy5 @, Cy5.5@ daboyl, digoxigenin, dinitrophenyl, EDANS, 6-FAM, fluorescein, or derivatives therefrom, 3'-glyceryl, HEX, IRD-700, IRD-800, JOE, phosphate, psoralen, rhodamine, ROX, Thiol (SH), spacers, TAMRA, TET, AMCA-S", SE, BODIPY<0>, Marina Blue®, Pacific Blue®, Oregon Green®, Rhodamine Green®, Rhodamine Red®, Rhodol Green® und Texas Red®, a locked nucleic acid (LNA), 5-methyl dC, 2,6-Diaminopurin, 2'-Fluor A, 2'-Fluor U, 2'-O-Methyl RNA, one or more phosphorothioate(s) as a spine, a polyethyleneglycol link, or a covalent 5'-3' link, resulting in the circularization, or combinations thereof. For specific embodiments, it may be of interest to reduce the length of the gRNA in a targeted manner, in order to design gRNAs comprising fewer than 100 nucleotides, fewer than 95 nucleotides, fewer than 90 nucleotides, fewer than 85 nucleotides, fewer than 80 nucleotides, fewer than 75 nucleotides, fewer than 70 nucleotides, fewer than 65 nucleotides, fewer than 60 nucleotides, fewer than 55 nucleotides, fewer than 50 nucleotides, fewer than 45 nucleotides, fewer than 40 nucleotides, fewer than 35 nucleotides, or fewer than 30 nucleotides, in order to obtain a higher specificity of the CRISPR nuclease through the shortening. In other embodiments, the gRNA according to the present invention can comprise at least one effector domain, e.g. an aptamer, or a DNA or RNA modified molecule, or a bonding site for a protein or peptide, in order to thus expand the functionality of the gRNA molecule.

In another embodiment according to the present disclosure, the at least one gRNA can also be associated with at least one nucleic acid molecule, in vitro or in vivo, which serves for the specific DNA repair after a double-strand break has been induced by a CRISPR nuclease. This (DNA) repair matrix, or HDR matrix, can be inserted, as a single-stranded and/or double-stranded DNA, directly, or in the form of a recombinant construct, into a target structure of interest. The repair matrix thus allows the targeted homologous recombination, by means of which the specificity, as well as the application range, of the genome editing can be significantly expanded.

In accordance with the present disclosure, gRNAs may be used which are specially adapted for use in a plant cell.

In accordance with the present invention, in addition, any gRNA as desCRISPR bed herein may additionally be introduced to at least one effector domain, such as an aptamer, coupled with or together with the effector domain so that the functionality of the gRNA is broadened. The recombinant construct comprising a gRNA and at least one effector domain may be introduced into the target plant structure as DNA- or RNA-construct using a suitable recombinant construct and/or vector. The effector domain may in addition not only consist of a nucleic acid, but also be a polypeptide or a sequence coding for it.

In one embodiment, the gRNA coupled with the CRISPR nuclease or catalytically active fragments thereof and/or the effector domain, for example the DNA- or RNA-modifying or the DNA- or RNA-binding polypeptide or nucleic acid, is introduced into the target plant structure.

In a further embodiment, the gRNA is introduced into the target plant structure as a separate recombinant construct independently of the CRISPR nuclease and/or the effector domain, for example the DNA- or RNA-modifying or DNA- or RNA-binding polypeptide or nucleic acid.

The gRNA may be introduced into the target plant structure as a DNA- or RNA molecule. Thus, in one embodiment the gRNAs may be introduced directly in the form of a synthetic nucleic acid, for example as RNA, or optionally also in a complex with a CRISPR nuclease or a catalytically active fragment thereof, or in another embodiment into the target cell in the form of an activatable and transCRISPR bable recombinant DNA construct. Furthermore, in accordance with the present disclosure, an individual gRNA may be used or dual or multiple gRNAs in one or more recombinant construct(s) may be introduced into a cell simultaneously, wherein the gRNAs have the same or individual regulatory sequence(s). The selection of suitable gRNAs for insertion in a target cell can take place according to the aspect explained in greater detail below, in accordance with the invention, wherein this aspect provides an in vitro screening process for identifying a gRNA or an encoding sequence for a gRNA.

Since the interaction domain of a conventional CRISPR SPR/Cas gRNA always interacts with the same CRISPR nuclease, individual gRNAs which carry a different recognition sequence as a further component, may be used in a multiplexing strategy, i.e. the specific modification of several target regions in one strategy. In this regard, it may always be necessary for a PAM sequence to be located adjacent to or within the target region. The design of a suitable gRNA may be determined in silico by a skilled person in the field who knows the CRISPR nuclease used, the nucleic acid target region, the type of the desired nucleic acid modification selected from mutation, insertion or deletion, as well as the desired target cell. The effectiveness of these gRNAs in vivo as well as possible off-target effects must, however, be evaluated separately for each gRNA. In addition, for unestablished systems, such as the transient transformation of meristematic plant cells, suitable vectors and methods have to be established for introducing at least one gRNA together with at least one suitable Cas nuclease and/or at least one effector domain, for example a DNA- or RNA-modifying or a DNA- or RNA-binding polypeptide or nucleic acid, so that the concerted activity of both molecules in the target cell can be ensured. In addition to the pure designing and synthesis or provision of the gRNA, the fact that, specifically, plant genomes are very complex, is a further difficulty, and so far no reliable method exists for pre-testing that would allow for a conclusion to be drawn regarding whether a selected gRNA, interacting with the desired CRISPR nuclease or the catalytically active fragment thereof, can actually effectively modify a nucleic acid target region in a plant cell.

In one embodiment of the present invention, the methods of the invention and thus the plants, plant materials or cells produced thereby are based on the naturally occurring DNA repair mechanisms in the target cell.

In another embodiment according to the aspects of the present disclosure, the repair of a single-stranded or double-stranded DNA break which was previously mediated by a CRISPR nuclease or a catalytically active fragment thereof and/or a further effector domain, is repaired by one or more HDR matrix(ces) as DNA repair template which are not naturally present but has/have been introduced into the target cell.

In the context of the present disclosure, then, in one embodiment a DNA repair matrix is disclosed which can optionally be introduced into the target cell together with or at a separate time to the CRISPR constructs and/or a further at least one effector domain, in order to induce a specific HDR mechanism and thus specific nucleic acid sequences at the site of the double-stranded break. In this regard, targeted genome editings comprising both knock-ins and also the specific repair of the DNA lesion to prevent an unwanted mutation at the site of the DNA break may be carried out. A knock-in can mean the specific insertion of at least one nucleotide, at least 2 nucleotides, at least 3 nucleotides, at least 4 nucleotides, at least 5 nucleotides, at least 6 nucleotides, at least 7 nucleotides, at least 8 nucleotides, at least 9 nucleotides, at least 10 nucleotides, at least 15 nucleotides, at least 20 nucleotides, at least 50 nucleotides, at least 100 nucleotides, at least 200 nucleotides, at least 500 nucleotides or at least 1.000 nucleotides into the target nucleic acid in the plant cell. Moreover, a knock-in can also mean the introduction of an entire gene expression cassette, which may comprise up to 10,000 nucleotides. A genome editing can also mean the targeted replacement of at least one nucleotide with another nucleotide. Further, a knock-in may also be obtained by two, three, four or more exchanges or a combination of insertions and exchanges. "Insertions" means the specific insertion of at least one nucleotide, at least 2 nucleotides, at least 3 nucleotides, at least 4 nucleotides, at least 5 nucleotides, at least 6 nucleotides, at least 7 nucleotides, at least 8 nucleotides, at least 9 nucleotides, at least 10 nucleotides, at least 15 nucleotides, at least 20 nucleotides, at least 50 nucleotides, at least 100 nucleotides, at least 200 nucleotides, at least 500 nucleotides, at least 1000 nucleotides, at least 2000 nucleotides, at least 5000 nucleotides, at least 10000 nucleotides or at least 15000 nucleotides into the target nucleic acid of the plant cell. A nucleic acid sequence as an insertion may be a sequence, or a part thereof, of a transCRISPR ption factor binder site, a regulatory sequence, a polypeptide-coding sequence, an intron sequence, a sequence coding for a non-coding RNA (for example lncRNA), an expression cassette, a non-encoding sequence, for use as a marker, in particular a selecting marker, e.g. a marker for marker assisted selection in the framework of the breeding, or a RNAi construct. Furthermore, a knock-in may also be brought about by a deletion of sequence sections which perturb the functionality of a gene (for example the deletion of transposon insertions). The DNA repair matrix may be introduced into the target plant structure of interest as a single-stranded or as a double-stranded nucleic acid.

In one embodiment, a target nucleic acid may be specifically switched off (knock-out), i.e. the transCRISPR ption and optional translation of the nucleic acid is inhibited. This may be carried out by specific insertion, mutation or deletion of a regulatory sequence such as a promoter or terminator sequence of a target nucleic acid or by specific mutation or deletion of the target nucleic acid itself or parts thereof. Furthermore, specific mutation or deletion which changes the reading frame of a target nucleic acid or specific mutation or deletion of potential splice signals may bring about a knock-out. In one embodiment, this knock-out is carried out without the insertion of an HDR matrix via the NHEJ pathway; in another embodiment, in addition to the CRISPR constructs and/or a further effector domain, an HDR matrix or DNA repair matrix is introduced into the target cell. A specific mutation is, for example, an exchange of at least one nucleotide for another nucleotide, preferably with the consequence that the codon concerned then codes for another amino acid. A specific knocked-out target nucleic acid in a plant cell has at least one specific mutation or deletion, but may also comprise two, three, four or more specific mutations and/or deletions.

In embodiments according to which a Cas or a Cpf1 gene, or another effector nuclease in the form of DNA, can be introduced onto a corresponding construct in a target cell of interest, the gene that encodes the nuclease can comprise a suitable promoter that is functionally linked to the sequence encoding the nuclease in order to improve its transCRISPR ption. The promoters can be constitutively active, or they can be inducible promoters, which are first activated after an appropriate stimulus has been added thereto, or has acted thereon (chemical or physical, comprising light, temperature, etc.). Likewise, a construct that encodes a gRNA can comprise a suitable promoter. Suitable promoters for plant cells, in accordance with the present disclosure, can be selected from a group composed of: a maize-ubi-intron promoter (SEQ ID NO: 7), a maize U3 promoter (SEQ ID NO: 10), a plant U6 polymerase III promoter, e.g. a wheat U6 promoter (SEQ ID NO: 8), a U6 promoter derived from rice (see Mikami et al., *Plant Mol. Biol.* 2015, 88 (6), 561-572), or a U6-26 promoter derived from *Arabidopsis thaliana*, a rice U3 promoter (SEQ ID NO: 9), and a Brachypodium EF1 promoter (SEQ ID NO: 40), or a simple or double 35S promoter derived from the cauliflower mosaic virus, comprising, among other items, a 35SPPDK promoter (see Yoo et al. Nature Protocols 2, 1565-1572 (2007)), but the promoters are not limited thereto, because the promoters are selected according to the respective plant cell of interest.

In yet another embodiment, the natural NHEJ mechanism of a plant cell can be deliberately suppressed by adding an appropriate inhibitor or by an targeted knock out or knock down of an endogenous nucleic acid sequence involved in the NHEJ process, whereupon the introduction of a targeted modification in the desired nucleic acid sequence is facilitated, because hereby the NHEJ mechanism of a cell can be reprimed. In one embodiment of the present invention, in which the target plant structure is an isolated meristematic cell of a seedling/plant or a plant embryo or exposed meristematic cells of a plant in a later stage of development, the target plant structures comprising meristematic cells before, during and after introduction of the at least one recombinant construct in accordance with the present disclosure are cultured in a manner such that an oxidation of the isolated structures is prevented. In one embodiment, this involves adding an antioxidant.

Table 1 below shows suitable media for culturing various target plant structures which comprise meristematic cells. Other suitable reaction conditions such as buffers, additives, temperature and pH conditions as well as any required additives can readily be determined by the skilled person in the field knowing the method and construct disclosed herein, in accordance with any aspect of the present disclosure.

TABLE 1

Medium compositions for culturing various target plant structures with meristematic cells (MS Medium = Murashige Skoog medium; MS Salt = Murashige Skoog salt (Toshio Murashige, Folke Skoog: A Revised Medium for Rapid Growth and Bio Assays with Tobacco Tissue Cultures. In: Physiologia Plantarum, issue 15 (1962), Vol 3, p. 473-497, ISSN 0031-9317, doi:10.1111/j.1399-3054.1962.tb08052.x).

| Embryo | Embryo | Embryo bombardment | Embryo bombardment | Agro-embryo | Agro-embryo | Plant meristem exposure |
|---|---|---|---|---|---|---|
| MM1 (MM = maturation medium) 1 | MM2-maturation medium 2 | MM1OSM (osmoticum) | MM1MOD (MOD = modified) | MM1Tim (Tim = timentin) | MM1ACE | Meristem peeling - antioxidant |
| MS salt 30.8 g/l sucrose | MS medium 3.4 g/l sucrose | MS salt 30.8 g/l sucrose 36.4 g/l sorbitol 36.4 g/l mannitol 95 mg L-cysteine 4.25 mg/l L-silver nitrate | MS salt 30.8 g/l sucrose 95 mg/l L-cysteine 4.25 mg/l silver nitrate | MS salt 30.8 g/l sucrose 150 mg/l Timentin | MS salt 30.8 g/l sucrose 19.62 g/l ACE | MS salt 95 mg/L cysteine 100 mg/L ascorbic acid |

The transient introduction of the construct disclosed herein into meristematic cells or tissue has the advantage that they develop from these reproductive tissues, via which the specific modification can then be stably passed on to the next generation, whereby the next generation is free from the constructs which had previously been introduced. The methods and constructs disclosed herein also mean that seeds can be harvested directly from the plant which has been modified in this manner, which carry the stable DNA modification without requiring an intermediate step of cell culture in the form of callus production and regeneration, whereupon also, the necessary selection and regeneration steps and the media and additives required therefor can be dispensed with.

The methods disclosed herein are suitable for the production of specific DNA modifications both in monocotyledonous and also in dicotyledonous plants. Examples of monocotyledons are grasses and cereals such as *Hordeum vulgare, Sorghum bicolor, Secale cereale, Triticale, Saccharum officinarium, Zea mays, Setaria italic, Oryza sativa, Oryza minuta, Oryza australiensis, Oryza alta, Triticum aestivum, Triticum durum, Hordeum bulbosum, Brachypodium distachyon, Hordeum marinum, Aegilops tauschii*. Examples of dicotyledons are *Malus domestica, Beta vulgaris, Helianthus annuus, Daucus glochidiatus, Daucus pusillus, Daucus muricatus, Daucus carota, Eucalyptus grandis, Erythranthe guttata, Genlisea aurea, Nicotiana sylvestris, Nicotiana tabacum, Nicotiana tomentosiformis, Solanum lycopersicum, Solanum tuberosum, Coffea canephora, Vitis vinifera, Cucumis sativus, Morus notabilis, Arabidopsis thaliana, Arabidopsis lyrata, Arabidopsis arenosa, Crucihimalaya himalaica, Crucihimalaya wallichii, Cardamine flexuosa, Lepidium virginicum, Capsella bursa-pastoris, Olmarabidopsis pumila, Arabis hirsuta, Brassica napus, Brassica oleracea, Brassica rapa, Brassica juncacea, Brassica nigra, Raphanus sativus, Eruca vesicaria sativa, Citrus sinensis, Jatropha curcas, Glycine max, Gossypium* ssp, or *Populus trichocarpa.*

In one embodiment, the nucleic acid sequence which is used for the specific modification of a target nucleic acid region comprises at least one or more regulatory sequences.

In one embodiment, the nucleic acid sequence used for specific modification of a target nucleic acid region comprises, as a regulatory sequence, at least one or more promoter(s), optionally a plant and tissue-specific, a phenotypical, a constitutive or inducible promoter, which is suitable for induction of transCRISPR ption in a desired target cell. A promoter is a nucleic acid region which is involved in the recognition and also binding of RNA polymerases as well as other proteins in order to control transCRISPR ption. Suitable promoters for either the gRNAs or the CRISPR nucleases or the sequence coding the catalytically active fragment thereof are well known to the skilled person in the field. Induction of an inducible promoter may be carried out by stimuli such as temperature, chemicals, pH, light, endogenous plant signals for example which are emitted after injuring the plant, and the like. Exemplary promoters are selected from the group consisting of SEQ ID NOs: 5-11, and also includes such sequences with at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% sequence homology with these sequences which, despite modification, still carry out the same function as the respective unmodified sequences with the corresponding SEQ ID NO. Further advantageous promoters are selected from the group consisting of promoters of the Wall-Associated Kinases (WAKs) 1 and 2 (see, for example, Wagner T A, Kohorn B D. Wall-Associated Kinases Are Expressed Throughout Plant Development and Are Required for Cell Expansion. The Plant Cell. 2001; 13 (2): 303-318 as well as, for example NCBI records: NCBI Reference Sequence: NC_003070.9), a promoter for the SCARECROW1 (scr1) gene (see, for example, Tissue Specificity and Evolution of Meristematic WOX3 Function; Rena Shimizu, Jiabing Ji, Eric Kelsey, Kazuhiro Ohtsu, Patrick S. Schnable and Michael J. Scanlon, Plant Physiology February 2009 vol. 149 no. 2 841-850 as well as, for example NCBI records: NCBI Reference Sequence: NC_003070.9), a promoter for the FAF2- and FAF4-gene (see, for example, the FANTASTIC FOUR proteins influence shoot meristem size in *Arabidopsis thaliana*, Vanessa Wahl, Luise H Brand, Ya-Long Guo, Markus Schmid Wahl et al, BMC Plant Biology 2010, 10:285 www.biomedcentral.com/1471-2229/10/285 as well as, for example, NCBI records: NCBI Reference Sequence: NC_003070.9), a promoter of the OSH1 gene (see, for example, Sato et al (1996) Proc. Natl. Acad. Sci. USA, 93:8117-8122 as well as, for example, Genbank records: GenBank: CP002688.1 or GenBank: AP008209.2) or a promoter of a metalloprotein gene, for example from rice (for example GenBank: BAD87835.1). The promoters of the present invention may be naturally occurring, synthetic or chimeric promoters or a combination thereof. A preferred promoter in accordance with the present disclosure is a promoter which is active in a meristematic plant cell or a promoter which is active in plastids of a plant cell. In one embodiment, the nucleic acid sequence which is used for specific modification of a target nucleic acid region also comprises at least one terminator as a regulatory sequence.

In one embodiment, the nucleic acid or amino acid sequence which is used for specific modification of a target nucleic acid region, comprising a gRNA and a CRISPR nuclease or a catalytically active fragment thereof, or a sequence coding for it, comprises one or more nuclear localization sequence(s) (NLS), which brings about nuclear localization of the nucleic acid and polypeptides used for specific modification of a target nucleic acid region.

In one embodiment, the recombinant construct comprising a nucleic acid or amino acid sequence which is used for specific modification of a target nucleic acid region, a gRNA and a CRISPR nuclease or a catalytically active fragment thereof or a sequence coding therefor, comprises one or more plastid localization sequence(s) (PLS), for example a mitochondrial or chloroplast localization sequence (MLS or CLS), which brings about the localization of the specific modification of a target nucleic acid region used nucleic acid and polypeptide in the corresponding plant plastids.

In one embodiment, the nucleic acid sequence which codes for a CRISPR nuclease or a catalytically active fragment thereof disclosed herein or a CRISPR nuclease or a catalytically active fragment thereof disclosed herein also contains a tag sequence. A tag sequence is a nucleic acid or section of protein which may be located upstream and/or downstream and/or within the sequence with respect to the CRISPR nuclease or the gRNA or the nucleic acid sequence coding for the CRISPR nuclease or the gRNA in order optionally, inter alia, to allow its localization and visualization within a target cell. Particularly preferred tag sequences are selected from the following list: polyhistidine (His)-tag, glutathione-S-transferase (GST) tag, thioredoxin tag, FLAG tag, a tag with fluorescent properties selected from the green fluorescing protein tag (GFP), a DsRed tag, a mCherry tag and the like, a streptavidin or strep tag, maltose binder protein (MBP) tag, chloroplast transit peptide, mitochondrial transit peptide, a snap tag and/or a secretion tag.

In another embodiment, fusion constructs are suggested that may be used in the method according to the present invention. These fusion constructs comprise fusion proteins as well as fusion nucleic acids. Fusion proteins can be composed of a CRISPR nuclease, a variation or catalytically active fragment thereof, or the sequence that encodes the CRISPR nuclease or the variation or catalytically active fragment thereof, as an element, as well as, optionally, one of the aforementioned tags and an effector domain, or one of the nucleic acid sequences that encodes the effector domain. As a result, it is possible to introduce the effector domain disclosed herein and/or one or more identical or different CRISPR nucleases, or variations or catalytically active fragments thereof, as a physically linked unit in a plant target structure of interest, or to express them in a plant target structure of interest.

Preferably, the effector domain optionally comprises a left-hand amino acid sequence fused to the N- or C-terminus of the CRISPR nuclease, or the variation or catalytically active fragment thereof. The optionally present left-hand amino acid sequence, or the nucleic acid sequence that encodes this left-hand sequence, allows both the CRISPR nuclease as well as the effector domain to be positioned ideally, without affecting one another sterically, such that both the effector domain as well as the CRISPR nuclease can deploy their activities. A left-hand amino acid sequence can comprise 1, 2, 3, 4, 5, 6, 7, 8, 9, 10, 11, 12, 13, 14, 15, 16, 17, 18, 19, 20, or more, up to 50 or 100 amino acids, and in some cases, it can be even longer. Moreover, fusion nucleic acids are also disclosed, wherein a gRNA of interest is linked in a covalent manner to an effector domain of interest. Moreover, non-covalent fusion nucleic acids are also disclosed, which comprise a gRNA as well as an effector domain and/or DNA repair matrix, wherein the non-covalent link can take place in an association of the respective components through hybridization, i.e. through base pairing of complementary regions. Moreover, fusion constructs are disclosed, in which gRNA and/or a CRISPR nuclease of interest are chemically linked, in vitro/ex vivo, to an effector domain of interest, and subsequently introduced into a plant target structure of interest comprising at least one meristematic cell, whereby these effector molecules are already linked, thus increasing the availability in a plant cell of interest, by means of which the efficiency of the method disclosed herein can be increased. Moreover, the association of a gRNA to an effector molecule and/or a DNA repair matrix can lead to not only the effector domain and/or the DNA repair matrix fulfilling their function in the framework of the genome editing, but also an increase in the stability of a gRNA. Specifically in embodiments in which the gRNA is inserted directly into a plant target structure of interest comprising at least one meristematic target cell through transformation or transfection, this can significantly increase the breakdown of a gRNA by cellular RNAs, before it can exercise its function.

As with the gRNA and/or the CRISPR nuclease, comprising, among other things, a Cas nuclease or a Cpf1 nuclease, the fusion constructs desCRISPR bed above, comprising fusion proteins and fusion nucleic acids, and/or mixed fusion proteins, comprising nucleic acids and proteins, can be introduced into a plant target structure of interest in a stable or transient manner, as recombinant constructs, or at least one of the molecules can be directly introduced, as RNA, DNA, or protein, into a plant target structure of interest, comprising at least one meristematic cell. By way of example, a gene that encodes for a CRISPR nuclease of interest can first be codon-optimized. This gene can then be introduced, in a stable or transient manner, in the form of a recombinant construct, into a plant target structure of interest. Alternatively, the CRISPR nuclease can also be translated in vitro, and subsequently introduced directly into a plant target structure of interest as a protein. In one embodiment, a gRNA can then be inserted directly into a plant target structure of interest as RNA. This can take place, as desCRISPR bed in greater detail below, through particle bombardment or other transfection processes that are known to the skilled person in the field. Likewise, the function constructs desCRISPR bed above are consequently inserted as either recombinant constructs or inserted directly into a nucleic acid target region of interest.

In one embodiment according to the method of the present invention, a transient expression of the CRISPR system disclosed herein, comprising at least one gRNA, one CRISPR nuclease, preferably also at least one effector domain, and optionally one DNA repair matrix, can be introduced in a transient manner, through particle bombardment, into a plant target structure of interest comprising at least one meristematic cell. For this, gold or tungsten particles, for example, can be coated with polyethylenimine (PEI). For this, the gold particles are first washed, and re-suspended in ethanol after centrifuging and optional washing, and stored at −20° C. In order to coat the particles with PEI (Sigma #P3143), the washed mixture of gold particles is centrifuged in ethanol, and the ethanol is discarded. The particles are then washed once in $ddH_2O$ in order to remove alcohol residue, and then added to 250 μl of a 0.25 mM PEI solution, followed by a pulsed ultrasonic treatment, in order to suspend the particles. The sealed containers are then snap-frozen in a dry ice/ethanol mixture, and the suspension is then lyophilised overnight. At this point, the dried, coated gold particles can be stored for at least three weeks at 80° C. Prior to further use, the particles are rinsed three times, in each case with 250 μl of 2.5 mM HEPES buffer, pH 7.1, followed by a pulsed ultrasonic treatment, and then briefly vortexed, before being centrifuged. The particles are then suspended in a final volume of 250 μl HEPES buffer. A 25 μl aliquot of particles is transferred into a clean reaction vessel, before the DNA bonding takes place. In order to bond uncoated DNA to the gold particles, the particles are subjected to a pulsed ultrasonic treatment, and one microgram of DNA (in 5 μl nuclease-free water) is then added, and the mixture is carefully pipetted a few times, before incubation for 10 minutes at room temperature. The particles are spun briefly, normally for 10 seconds, the precipitation is removed, and 60 μl fresh ethanol is added. The particles, which contain DNA precipitated with PEI, are washed twice in 60 μl ethanol. The particles are then centrifuged and the precipitation is discarded, after which the particles are re-suspended in 45 μl water. To bond a second DNA (DNA-2) thereto, a precipitation is used, making use of a water-soluble cationic lipid transfection reagent. 45 μl of the particle-DNA suspension, corresponding to the gold particles to which the first DNA was bonded, are briefly subjected to an ultrasonic treatment, and 5 μl of a 10 nanogram/microliter DNA-2, and 2.5 μl of the water-soluble cationic lipid transfection reagent are then added. The solution is incubated on an orbital shaker for 10 minutes, and subsequently centrifuged at 10,000 g for one minute. Subsequently, the precipitation is removed, and the particles are re-suspended in 60 μl ethanol. The solution can then be transferred to macro-carriers, and the gold particles, to which the first and second DNA were sequentially bonded, are then transfected into a meristematic cell of interest, using a standard protocol for particle bombardment with a PDS-1000 apparatus. Standard protocols for a PDS-1000 apparatus can be obtained from the manufacturer (Bio-Rad).

In one embodiment in accordance with the present invention, the method for the production of a plant, a plant material or a plant cell also comprises a screening step. In this step, by carrying out a method for the analysis of the nucleic acid sequence, a target region is examined, for example by means of a polymerase chain reaction or probes, as to whether the insertion, activation and subsequent reaction of the at least one recombinant construct of the present disclosure has resulted in the desired specific modification of a target nucleic acid region. Methods for carrying out this screening are known to the skilled person in the field in respect of any and all target plant structures and also target nucleic acid regions. There are however, currently no standard methods that would allow the effective interaction of a gRNA, a CRISPR nuclease, or a catalytically active fragment thereof, and a nucleic acid target region of interest for checking the actual efficacy of a gRNA of interest for a specific nucleic acid target region, in particular a nucleic acid target region within a plant cell, in an in vitro screening process, in order to thus monitor the time expenditures and costs with the use of CRISPR SPR/Cas constructs, particularly in a high output process. In addition, most of the available in silico tools (see www.dna20.com/eCommerce/cas9/input), are specialised for *E. coli*, yeast, or animal genomes or model plants, but not for important monocotyledons like dicotyledonous crop plants, which frequently differ significantly from model plants, specifically with regard to the PAM distribution in genomic regions.

In one aspect of the present invention, an in vitro screening method is therefore provided, for identifying a gRNA or an encoding sequence for a gRNA, in an in vitro assay for identifying a gRNA or an encoding sequence for a gRNA, that, together with a CRISPR nuclease or a catalytically active fragment thereof, is suitable for the targeted modification of a nucleic acid target region in a plant cell, comprising the following steps: (i) provision of one or more nucleic acid target region(s) of a plant, plant material, or a plant cell; (ii) insertion of the one or more nucleic acid target region(s) into at least one vector; (iii) provision of at least one gRNA; (iv) provision of at least one CRISPR nuclease or a catalytically active fragment thereof; (v) bringing the at least one CRISPR nuclease or a catalytically active fragment thereof in contact with the at least one vector in vitro, under suitable reaction conditions, which allows the interaction of a gRNA with a CRISPR nuclease and thereby the catalytic activity of the CRISPR nuclease or the catalytically active fragment thereof, wherein the at least one vector is brought into contact, in each case, with exactly one gRNA and exactly one CRISPR nuclease or a catalytically active fragment thereof, in a separate reaction preparation; (vi) analysis of the reaction products from step (v); and (vii) identification of a gRNA or an encoding sequence for a gRNA, which is capable, together with a specific CRISPR nuclease or a catalytically active fragment thereof, of the targeted modification of a nucleic acid target region in a plant cell.

According to this aspect of the present invention, the term in vitro is to be understood such that the at least one nucleic acid target region is not in its natural environment, i.e. a plant cell, but instead is first transferred into a suitable vector for the purpose of the in vitro screenings. Numerous results can then be generated from this pre-screening within a short time, which indicate the suitability of at least one gRNA, in interacting with the corresponding CRISPR nuclease or catalytically active fragment thereof, for the targeted modification of a nucleic acid target region in an intact plant cell. The candidates that have been established in this manner can then be used with a significantly higher success rate, both in vitro as well as in vivo, comprising in planta.

In one embodiment, the PCR amplifier of the nucleic acid target region is derived in accordance with this aspect from genomic DNA, wherein the genomic DNA also comprises, in addition to the nuclear genome, the genomes from plastids, such as mitochondria and chloroplasts. In another embodiment, the PCR amplifier of the nucleic acid target region is derived in accordance with this aspect from plant RNA.

The at least one vector according to this aspect of the present invention is preferably a plasmid vector, although any of the other vectors disclosed herein, that are suitable for the cloning and stable preservation of a PCR amplifier in a nucleic acid target region of interest, can also be used. The cloning of one or more nucleic acid target region(s) in at least one vector is known to the skilled person in the field. The vector can ideally comprise more than one target region of interest, such that numerous target regions of interest can be analysed. Alternatively, numerous vectors that comprise at least one nucleic acid target region of interest could also be provided.

The gRNA for use according to this aspect must be applied in an active ribonucleic acid form, i.e. the gRNA can be created synthetically, and optionally also modified. Alternatively, the gRNA can also be produced in a recombinant manner, i.e. through in vitro or in vivo transCRISPR ption, and optionally through a purification step.

The CRISPR nuclease or the catalytically active fragment thereof is provided as an amino acid sequence. A commercially available CRISPR nuclease or a variation thereof can be used for this. Alternatively, the CRISPR nuclease or the active fragment thereof can be produced in another embodiment in a recombinant manner, and optionally isolated and/or purified, before it is used in the in vitro screening process according to the present invention.

In another embodiment, the CRISPR nuclease or the active fragment thereof that has been provided is coupled to at least one effector domain. Regarding the possible effector domains and their potential advantages and fields of application, the corresponding earlier statements in this disclosure apply accordingly. By already including the effector domains/Cas constructs in an in vitro screening process, there is the advantage that possible undesired positive or synergistic effects of the respective effector domains, which have a steric as well as chemical/physical effect on the Cas or Cpf1 constructs, can already be analysed in the pre-testing phase. This also relates to one possible effect of the at least one effector domain on the gRNA-Cas interaction, as well as the subsequent bonding to and modification of the nucleic acid target region of interest, in addition, or alternatively, to the actual field of application for the respective effector domain.

Bringing the at least one gRNA and the at least one CRISPR nuclease, or the catalytically active fragment thereof, in contact with the at least one vector in vitro takes place under suitable reaction conditions. In this context, these conditions are to be understood as those that allow both the bonding of the gRNA to the respective CRISPR nuclease or the catalytically active fragment thereof, as well as the interaction of the gRNA/Cas complex with the target region of interest and the catalytic activity of the CRISPR nuclease, or catalytically active fragment thereof. Suitable reaction conditions such as buffers, additives, and special cofactors that are needed, including temperature and pH conditions, as well as, if applicable, further additives, can be easily determined by the skilled person in the field with knowledge of a method disclosed herein and a construct disclosed herein, in accordance with any aspect of the present disclosure.

According to one embodiment, the reaction products are analysed in a qualitative manner in accordance with the in vitro screening process. According to another embodiment, the reaction products are analysed in a quantitative manner in accordance with the in vitro screening process. According to yet another embodiment, the reaction products are analysed in both a qualitative as well as quantitative manner in accordance with the in vitro screening process.

In one embodiment of this aspect, the in vitro screening process is a high output process, i.e. numerous gRNAs and/or numerous CRISPR nucleases or catalytically active fragments thereof, and/or numerous nucleic acid target regions on one or more vectors in separate reaction vessels can be tested simultaneously. This upscaling is of particular advantage for quickly acquiring a plurality of data regarding suitable gRNA/Cas candidate pairs for the respective at least one nucleic acid target region of interest. Alternatively, the question of which gRNA/Cas candidate pairs interact particularly efficiently can be analysed as a variable, particularly when the use of new CRISPR nucleases or catalytically active fragments thereof are examined. As a further problem, it is possible to check whether the addition of an effector domain to a CRISPR nuclease or catalytically active fragment thereof has an effect on the gRNA/Cas interaction, or the subsequent catalytic activity of the CRISPR nuclease or catalytically active fragment thereof.

In accordance with the present disclosure, the vectors and/or recombinant constructs may be used for the specific modification of a target nucleic acid region in a plant cell by mechanical methods, including particle bombardment, microinjection and electroporation, or by induced endocytosis, suitable vectors, direct transfection and the like. In one embodiment of the present disclosure, the vectors and/or the recombinant constructs are introduced into the target zones or target plant structure by particle bombardment. To this end, the vectors are initially precipitated onto gold or tungsten particles, for example, and the target cell/target plant structure is then bombarded with the particles obtained thereby or with further processed particles using suitable equipment. In a further embodiment of the present disclosure, the vectors and/or recombinant constructs are introduced directly or indirectly into the target cell or target plant structure by microinjection. In another embodiment of the present disclosure, the vectors and/or recombinant constructs are introduced by spraying with subsequent take-up, for example during a viral infection, or infiltration into the target cell or target plant structure.

In accordance with one embodiment, the vectors and/or recombinant constructs are introduced into a meristematic cell by particle bombardment. This method is suitable both for introducing recombinant constructs comprising double-stranded plasmid DNA, linear single-stranded or double-stranded DNA, single-stranded or double-stranded RNA and polypeptides, as well as combinations thereof in all types of plant meristems in different stages of the development of a plant. Gold and tungsten may, inter alia, be used as the carrier material for the recombinant constructs.

In a further embodiment of the present disclosure, the vectors of the invention and/or the recombinant constructs are introduced directly into the target cell or the desired compartment of a target cell by microinjection.

In accordance with this further embodiment, the vectors and/or recombinant constructs are introduced into a meristematic cell by microinjection. This type of introduction is suitable for all types of meristems (see Example 2 below). In addition, introduction using this embodiment is suitable both for introducing recombinant constructs comprising double-stranded plasmid DNA, linear single-stranded or double-stranded DNA, single-stranded or double-stranded RNA and polypeptides as well as combinations thereof.

In a still further embodiment of the present disclosure, the vectors of the invention are introduced by means of electroporation using high voltage pulses.

In a still further embodiment of the present disclosure, the vectors of the invention are introduced by endocytosis, i.e. an endogenous mechanism by means of which exogenous material can be taken up into the cell.

In one embodiment, the vector is a viral vector which comprises the at least one recombinant construct. Introduction using a viral vector means that the vector and its included at least one recombinant construct can propagate. Suitable viral vectors which may be used or modified for application in accordance with the present disclosure are selected from the group comprising but not limited to SEQ ID NOs: 12-15 and 25-38 and also include sequences with at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% sequence homology with these sequences. The skilled person in this field is aware that the sequence of a naturally occurring virus which might be used as the viral vector, corresponding to the desired recombinant construct to be introduced, as well as the target plant structure of interest, have to be adapted.

In a further embodiment, the recombinant construct is introduced by *Agrobacterium* spp.-mediated transformation, in particular *Agrobacterium tumefaciens*- or *Agrobacterium rhizogenes*-mediated transformation, into a target plant structure. This type of introduction is well known to the skilled person in the field for various target plants as well as various target plant structures thereof.

The skilled person in the field knows that the choice of introduction type may, inter alia, depend on the appropriate target plant cell as well as on the construct to be introduced; thus, depending on the target cell, a different mode of introduction might be necessary.

In a further embodiment of the present disclosure, the vectors of the invention and/or recombinant constructs are introduced by means of a combination of the introduction methods mentioned above. Thus, for example, a viral vector which contains the at least one recombinant construct of interest may be introduced into the target plant structure by means of *Agrobacterium tumefaciens* as the further vector, or indeed by particle bombardment or microinjection.

In one aspect of the present invention, special methods for introducing vectors and/or recombinant constructs in accordance with the present invention into meristematic plant cells and tissues are disclosed. For the transformation or transfection of meristematic cells and tissue, accessibility to them is a deciding factor, wherein the accessibility of the various plant meristem types in the various stages of development in a plant differ widely.

In one embodiment in accordance with the present invention, then, a method for providing a target plant structure is proposed, comprising at least one meristematic cell, wherein at least one recombinant construct in accordance with the present disclosure may be introduced into the target plant structure. The method of this embodiment comprises, as a vital step, ensuring that a meristematic structure of interest which does not yet comprise differentiated meristematic cells is rendered accessible. If the target plant structure is a meristem in embryo, then it is essential to select a plant embryo of the right size and to direct the at least one recombinant construct in accordance with the present invention towards the deeper, i.e. inwardmost-lying meristematic cells as a target for transformation or transfection therewith, since the meristematic cells in the outer layers may already have reached a certain degree of differentiation and thus are no longer in accordance with the present invention. Preferably, the plant embryos are selected for their size such that they are provided with an exposed meristem. For maize embryos, this means that embryos of less than a 1.5 mm maximum diameter, preferably less than 1 mm as a maximum diameter, particularly preferably less than 0.7 mm as a maximum diameter and more particularly preferably less than 0.5 as a maximum diameter may advantageously be used in accordance with the invention. A meristematic cell in the context of the present invention is thus a meristematic cell the degree of differentiation of which still allows it to produce from the cells, after specific modification of a nucleic acid region of interest, all desired types of plant cells, in particular those types from which a fertile plant can be regenerated either directly or indirectly.

In a further embodiment, a method for preparing a target plant structure comprising at least one meristematic cell is disclosed, into which at least one recombinant construct in accordance with the present disclosure may be introduced, wherein the meristematic cell is a cell of a seedling or an older plant.

In accordance with this embodiment, the meristem must be completely or almost completely dissected out. In addition, care must be taken that the deeper lying, i.e. innermost-lying meristematic cells are targeted for a transformation or transfection with at least one recombinant construct in accordance with the present invention, since the meristematic cells in the outer layers may already have reached a certain degree of differentiation and thus are no longer suitable for use in the present invention. In accordance with this embodiment, the exposed meristem undergoes an oxidation. In order to avoid damage to the meristematic cells, then, preferably, suitable antioxidizing protective measures are employed such as, for example, the use of an anti-oxidation agent or further protective measures to ensure further development of the target plant structure comprising at least one meristematic cell.

Sequence Listing—Free Text

The following details show the translation into German of the details provided in the sequence listing as the free text (numerical identification <223>), respectively supplied for the corresponding sequence identification number. All sequences contain under the numerical identification <213> the information about an 'artificial sequence'.

SEQ ID NO:1

<223> VP16 Activator-comprising sequence

SEQ ID NO:2

<223> VP16 Activator

SEQ ID NO:3 <223> VP64 Activator with glycine serine spacers

SEQ ID NO:23

<223> Vector1_TaU6

SEQ ID NO:24

<223> Vector1_ZmU3

SEQ ID NOS: 41 to 48

Protospacer region guide RNA 14, protospacer region guide RNA 16, protospacer region guide RNA 37, protospacer region guide RNA 38, protospacer region guide RNA 39, protospacer region guide RNA 43, protospacer region guide RNA 18 or protospacer region guide RNA 52.

EXAMPLES

The present invention will now be explained in more detail with the aid of the following examples, which are not limiting in any way.

Example 1: Production of CRISPR SPR/Cas Constructs

The constructs were produced on the basis of the publication by Mali et al, 2013. The promoters were specifically used against specific plant promoters and adapted to the gRNA of the respective target genes.

Constructs for Monocotyledonous Plants:

The promoters used were, inter alia, the maize-Ubi-Intron promoter (SEQ ID NO:7), the maize U3 promoter (SEQ ID NO:10), the wheat U6 promoter (SEQ ID NO:8), the rice U3 promoter (SEQ ID NO: 9) and the Brachipodium EF1 promoter (SEQ ID NO: 40). An exemplary construct had SEQ ID NO: 23 (vector1_TaU6 standard).

Constructs for Dicotyledonous Plants:

Here, a parsley-Ubi4 (SEQ ID NO:5) and an *Arabidopsis* U6 promoter (SEQ ID NO:6) were used. An exemplary construct had SEQ ID NO:24 (Vector 1_ZmU3 standard).

The various gRNAs were determined specifically for the respective target genes and cloned into the corresponding position in the vectors mentioned above. The position of the gRNA sequence corresponded to the nucleotides denoted "n" in SEQ ID NOs: 23 and 24.

In order to reduce the number of gRNAs that must be inserted into the plant to obtain a genome editing, an in vitro assay was established for testing the candidate gRNAs, so that only the most suitable candidates are inserted in the plants.

For this, potentially suitable gRNAs are first defined by in silico analysis. This definition depends on the nucleic acid target region of interest, due to the dual function of the gRNA, as explained in the introductory part of the desCRISPR ption, particularly a PAM motif, as well as the desired CRISPR nuclease or the catalytically active fragment thereof, which are to be used.

In order to test the different gRNAs for different genes, in a first step, the nucleic acid target region of interest, or sub-regions thereof, are amplified by means of PCR and cloned in standard vectors. "Standard vectors" in this sense indicates commercially available vectors or vector systems, which can be readily adapted to the requirements of the desired assay through means known to the person skilled in the art, in particular in that they function as a backbone for the cloning of nucleic acids of interest. Exemplary vectors can be selected from: pJet (Thermo Fisher Scientific, Inc., USA), pGEM-T (Promega BioSciences, LLC, USA) or pBluesCRISPR pt (Addgene, USA). These vectors serve as a substrate in the newly developed in vitro assay. In a second step, the various gRNAs are produced by means of in vitro transCRISPR ption (Invitrogen MAXIsCRISPR pt T7 Kit; Cat. No. AM1312M).

Figure 14:
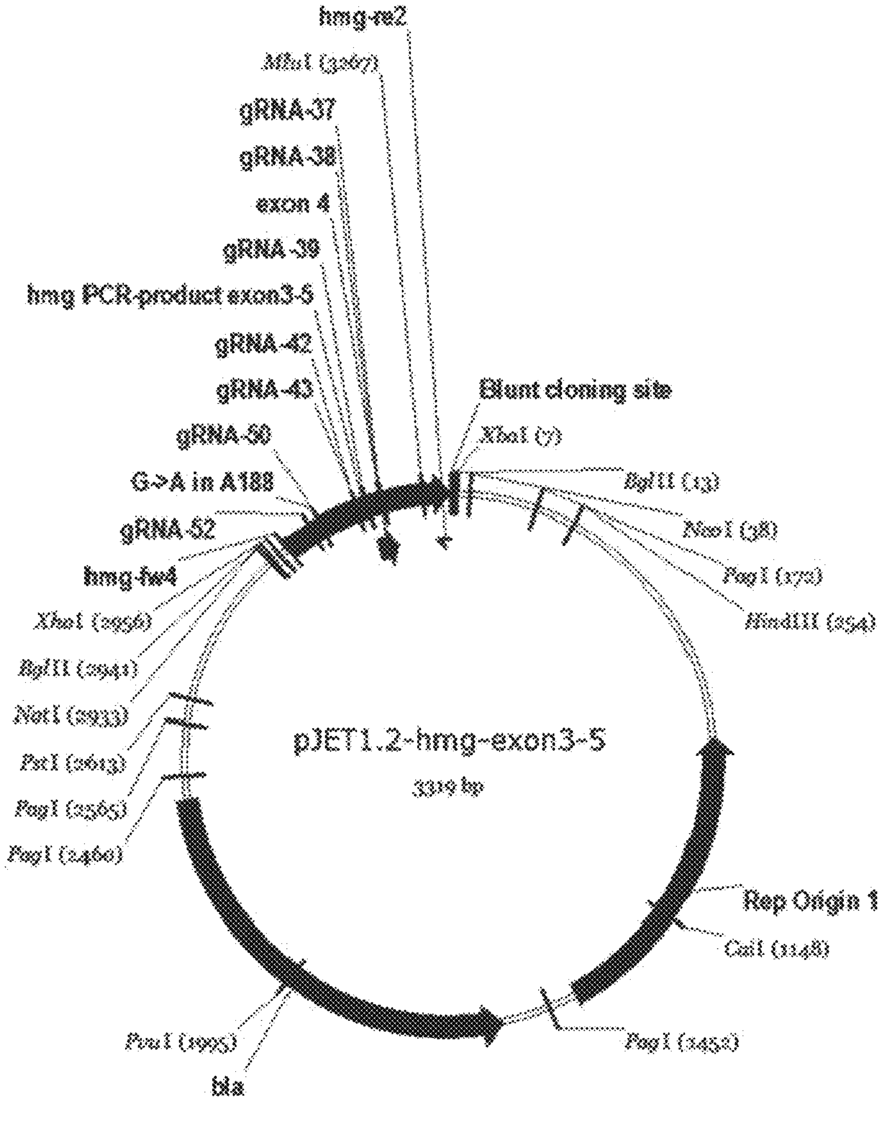
FIG. 14 shows an exemplary vector map of the plasmid pJET1.2-hmg-exon3-5 in accordance with example 1.
Figure 15:
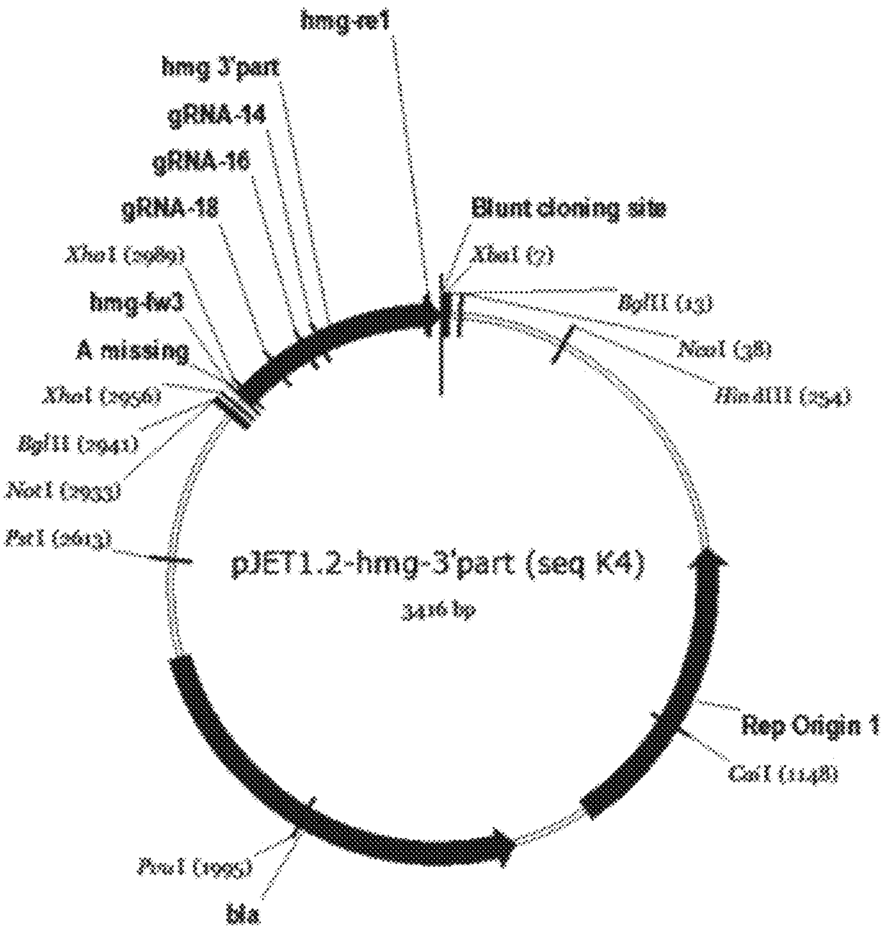
FIG. 15 shows an exemplary vector map of the plasmid pJET1.2-hmg-3' part/part in accordance with example 1.
Figure 16:
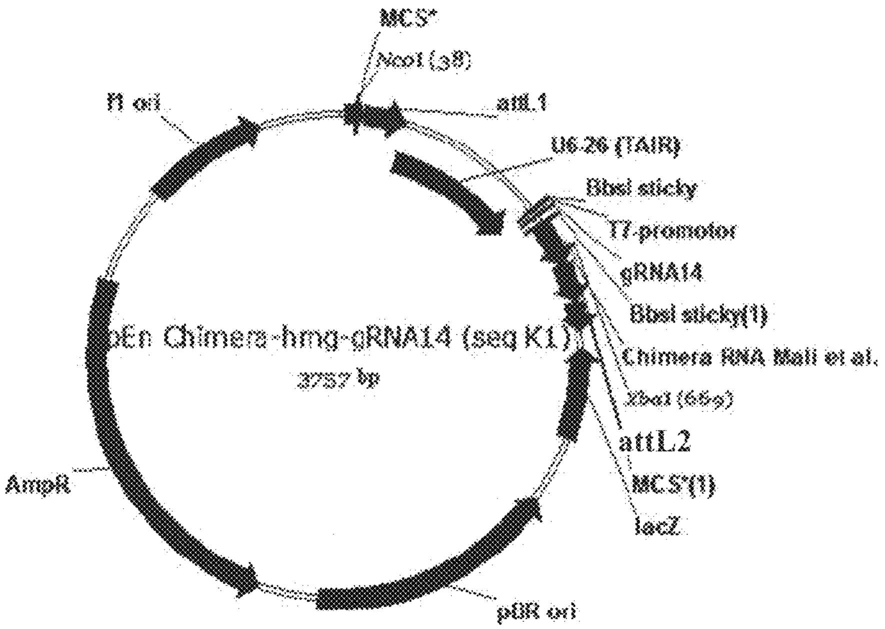
FIG. 16 shows an exemplary vector map of the plasmid pEn Chimera-hmg-gRNA14, in accordance with example 1.

The gRNAs were subsequently tested in an in vitro assay, and the potentially best candidates were selected and used for the further in planta tests. For this, among others, a maize plant A188 hmg13 gene was used as an exemplary nucleic acid region of interest (HMG transCRISPR ption factor 13; see gene GRMZM2G066528 from EnsemblePlants or the maize genome data base). These were amplified by means of PCR, and cloned in the multiple cloning site from pJET1.2 accordingly, firstly the part comprising Exon 3-5 (hmg-fw4 and hmg-432, see FIG. 14), and secondly the hmg-3' part (hmg-fw3 and hmg-re1, see FIG. 15). After this, the plasmids were linearized through digestion with Pvul, and in order to prevent the recirculation, the vector backbone was dephosphorylated. The resulting product was applied to a preparative gel. Subsequently, the concentration of the resulting, linearized vectors was measured. For a typical assay, ca. 3 µl of a 30 nM vector were used as a substrate for the Cas digestion, carried out in each case at least three times. The gRNAs variations that were to be tested were cloned in the vector pEn-chimera (see, by way of example, FIG. 16 regarding the gRNA14). The cloning in this vector was carried out in accordance with standard methods in molecular biology, as shall be explained below by way of example. The sequence from pEn-chimera was located in SEQ ID NO: 59. An RNA chimera was located thereon, which could be specified relatively easily via Bbsl+Oligo. Subsequently, it can be transferred into the pDe-CAS9 via a gateway LR reaction. The RNA chimera is controlled by the promoter AtU6-26. The resulting vector was then digested with Ncol and Xbal, wherein the resulting fragment comprises the gRNA of interest. The desired fragment comprising the gRNA was gel-separated, extracted and cleaned by typical methods. For the assays, ca. 1 µg of the resulting fragment was used as a template for the in vitro transCRISPR ption (Invitrogen MAXIsCRISPR pt T7 Kit; Cat. No. AM1312M). An exemplary preparation comprises: 10 µl template (1 µg); 2 µl 10× transCRISPR ption factor (Invitrogen); 1 µl 10 mM ATP; 1 µl 10 mM CTP; 1 µl 10 mM GTP; 1 µl 10 mM UTP; 2 µl T7-RNA polymerase (Invitrogen); 4 µl $H_2O$. The preparation is normally incubated for 2 hours at 37° C. $H_2O$ is added to obtain a volume of 100 µl, and the RNA is purified according to the manufacturer's instructions (Qiagen RNeasy Kit). Following elution (two times with 50 µl $H_2O$), the exact volume and the concentration of the resulting RNA is determined. For the further assays, ca. 15 ng/µl of the in vitro transCRISPR ption was used, so that with an RNA that is 140 nucleotides long, 300 nM were needed. Subsequently, an in vitro digestion was carried out as follows: the reaction preparation was typically in a volume of 30 μl. In order to ensure an optimal cleavage efficiency, it was important to maintain a molar ratio of Cas9 and gRNA to the respective nucleic acid target region of 10:10:1 or higher. First, 300 nM of the respected gRNA that is to be tested was provided. In addition, 30 nM of substrate DNA, comprising in each case a single nucleic acid target region, was provided for each case. The reaction preparation was combined in the following order:

Components 30 μl preparation
Nuclease-free water 20 μl
(NEB)
10× Cas9 Nuclease reaction buffer 3 μl
300 nM gRNA (~15 ng/μl) 3 μl (30 nM final)
1 μM Cas9 nuclease 1 μl (~30 nM final)
reaction volume 27 μl
pre-incubation for 10 min, at 37° C.
30 nM Substrate DNA 3 μl (3 nM final)
Total-reaction volume 30 μl This was then carefully mixed and briefly spun before the preparation was incubated for another hour at 37° C. Optionally, a treatment with proteinase K may then take place by adding 1 μl enzyme and incubating for 15-30 minutes at 37° C. At this point, the fragment analysis can then take place.

Figure 8:
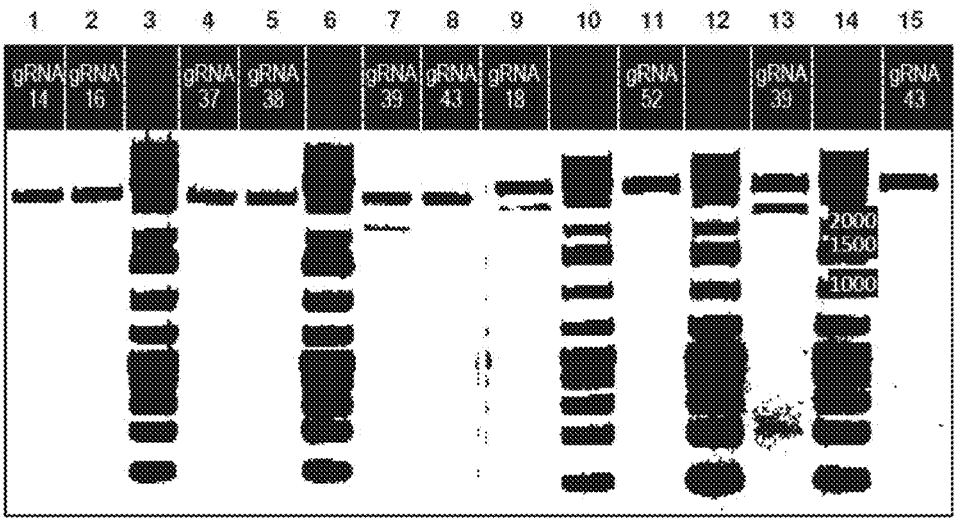
FIG. 8 shows the results of an in vitro assay for assessing the efficiency of a gRNA of interest. The starting plant here is a maize plant, the target gene is the hmg13 gene (HMG transCRISPR ption factor 13; GRMZM2G066528). The figure shows the results of a separation in a 1% gel with the default parameter of 100 V and visualization via fluorescence provided by ethidium bromide. The molecular size markers (given in base pairs; GeneRuler 1 kb plus DNA ladder (Thermo Fisher Scientific Inc., USA; SM1331) 20000, 10000, 7000, 5000, 4000, 3000, 2000, 1500, 1000, 700, 500, 400, 300, 200, 75 bp) are located in columns 3, 6, 10, 12, and 14. The results for the gRNA 14 (SEQ ID NO: 41), gRNA 16 (SEQ ID NO: 42), molecular marker, gRNA 37 (SEQ ID NO: 43), gRNA 38 (SEQ ID NO: 44), molecular marker, gRNA 39 (SEQ ID NO: 45), gRNA 43 (SEQ ID NO: 46), gRNA 18 (SEQ ID NO: 47), molecular marker, gRNA 52 (SEQ ID NO: 48), molecular marker, gRNA 39 (SEQ ID NO: 45) and gRNA 43 (SEQ ID NO: 46) are shown from left to right in the other columns. The given SEQ ID NOS indicate the respective individual, different protospacer regions in the gRNAs, and the remaining regions of the gRNA are identical in all of the gRNAs used herein.

The results for 10 selected gRNAs, here, by way of example, in interaction with a Cas9 nuclease, are listed in FIG. 8. It is clear from these results that there are qualitative as well as quantitative differences in the efficiencies of the respective gRNAs and partner CRISPR nucleases regarding the cleavage efficiency of a nucleic acid target region of interest.

Further experiments (data not shown) were carried out with CRISPR nucleases from sources other than *S. pyogenes*, and with Cas nucleases that carry at least one point mutation, e.g.: a Cas nicking enzyme, in order to test in vitro the efficiency of these other Cas nucleases on a plant nucleic acid target region of interest in interaction with the respective gRNA. Moreover, first successful in vitro experiments were carried out, which showed that Cas nuclease gRNA pairs of interest that have been identified in a pre-screening are also suitable for the targeted modification of an RNA as well as plant mitochondrial or plastid DNA, as is proven by the broad application spectrum of the present assay.

In order to test the broad applicability of the method for further important crop plants, the novel in vitro screening process was likewise carried out using nucleic acid target regions derived from other crop plants, such as *Beta vulgaris, Brassica napus* and *Sorghum bicolour.*

For this, due to the specificity of the plant genome, it was necessary to carry out new in silico analyses, in order to be able to define suitable target regions, and thus suitable gRNAs. In addition, in the framework of the development of the process, other Cas nucleases, nicking enzymes, Cpf endonucleases and enzymatically active fragments derived therefrom were employed, which additionally carry an effector domain. Furthermore, alternative Cas proteins, or Cas proteins with point mutations, for example, could also be used in the assay in order to test the efficiencies of the different Cas proteins. In particular, also in direct interaction with the tested gRNAs.

This was intended to resolve numerous questions: (1) which gRNAs display particularly high activity?; (2) what are the effects of the modifications in the gRNA, such as different lengths of protospacers or mismatches?; (3) which Cas proteins integrate best with which gRNAs?; (4) which CRISPR nucleases have an effect on the enzymatic effects of the enzyme?; and (5) does the coupling of an effector domain, and thus the creation of a sterically more demanding Cas construct, affect the interaction with the gRNA in question and thus the efficiency of the targeted modification of a nucleic acid region of interest? In the course of this further series of experiments, it has so far been determined that particularly the reduction of a CRISPR nuclease on a catalytically active minimum fragment thereof is advantageous regarding the targeted cleavage efficiency. Moreover, it has been discovered that it is possible for effector domains to bond to the CRISPR nuclease, or the gRNA. Particularly here, the in vitro screening was indispensible, because the efficiency of these modified CRISPR nucleases or gRNAs was lower due to the larger steric demands by the effector domain, resulting in the interaction of the Cas and gRNA being more difficult for the pairs that were tested. Nevertheless, effective Cas-gRNA effector domain pairs were still identified.

Surprisingly, it was discovered that the results of the in vitro pre-testing, i.e. the screenings, also correlate with their efficacy in subsequent tests.

In a further test, all of the gRNAs shown in FIG. 8 were tested with regard to their efficiency in the actual, site oriented modification in a plant meristem. As a result, the in vitro assay proved to be ideal for assessing the efficiency of the gRNA that was used, because not all of the gRNAs that were used resulted in an in vivo or in vitro cleavage in the template. Specifically with the Cas-gRNA pairs, which have proven to be particularly efficient in in vitro screening assays, this efficiency was also confirmed in the subsequent testes in which plant material was employed, either in vitro or in vivo. A maize plant functioned as the starting plant for these subsequent studies, and the target gene hmg13 functioned specifically as the target.

Example 2: Introduction of CRISPR SPR/Cas Constructs

The constructs desCRISPR bed above in Example 1 were introduced into the meristems using various methods. The basis for this was accessibility to the meristems; the material used determined the various methods used (see Example 4).

Figure 5A:
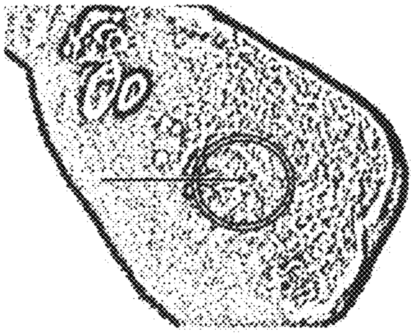
FIGS. 5A and B (FIGS. 5A and B) shows the biolistic test bombardment for the maize embryo meristems.
Figure 5B:
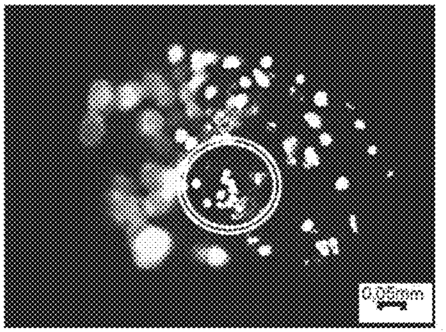
In FIG. 5 (A) a diagrammatic image of an embryo with the discoid meristem structure (highlighted by a double ring and an arrow) is shown.
Figure 7A:
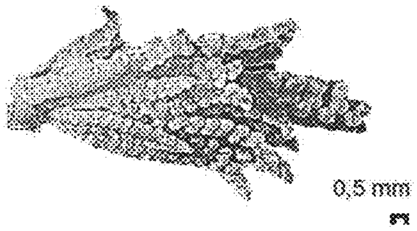
FIGS. 7A and B (FIGS. 7A and B) shows the biolistic test bombardment of an exposed tassel meristem from maize.
Figure 7B:
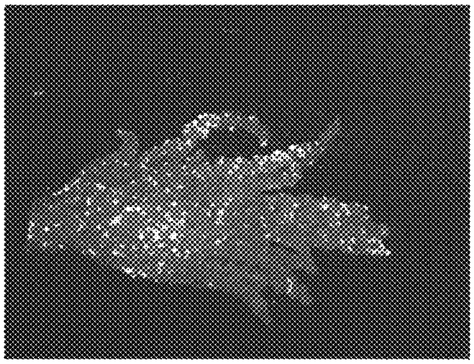
FIG. 7 (A) is a diagrammatic image of the meristem tissue of the maize tassel.
Figure 9B:
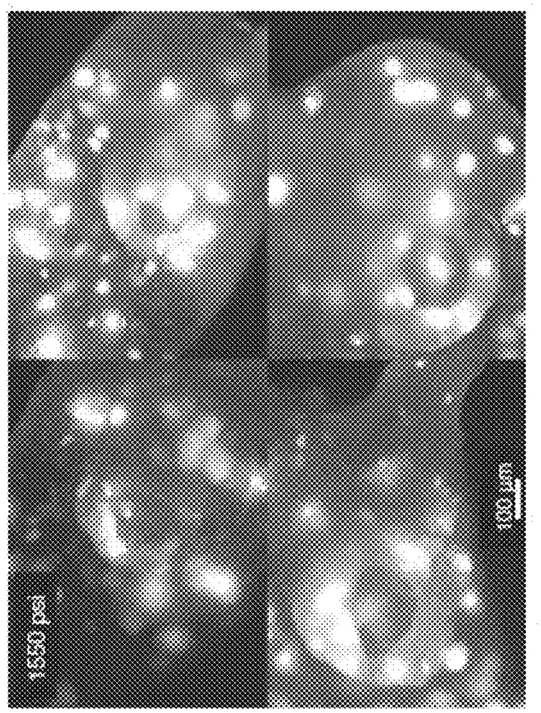
FIG. 9(B) shows the bombardment with 1550 psi in the four individual illustrations. In comparison, significantly more fluorescence can be seen in the lower illustrations, indicated by the brighter regions in the black-and-white illustration. An increased fluorescence/brightness, i.e. an increased efficiency in the insertion, may however be accompanied by a reduced germination of the embryos.
Figure 9A:
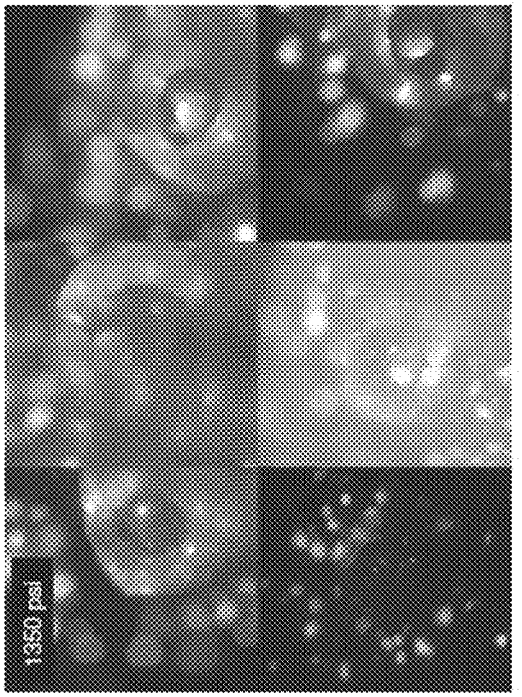
FIGS. 9A and B (FIGS. 9A and B) show the results of a test bombardment of maize embryos at different pressures (given in psi: pounds per square inch). The maize embryos were fired at 7-10 days after pollination, and 2 days later, the microscopic analysis was carried out. An expression vector was used as the plasmid, which encodes, among other things, a fluorescent marker.

The following methods were employed:

Particle Bombardment:

Particle bombardment can be used in all of the meristems employed. Bombardment was carried out with dsplasmid DNA, linear dsDNA, RNA and protein as well as virus particles. For instances, Gold and tungsten could be used as the carrier material. Test bombardments of embryo meristems (FIG. 5) and tassel meristems (FIG. 7) were carried out with the aid of the red fluorescing protein; it was shown that it was possible to introduce DNA into these cells by particle bombardment. The important thing to observe thereby is that the suitable bombardment settings were used, depending on the respective materials. Thus, a higher bombardment may lead to an increased transient transfection (see FIG. 9 for images in this regard), but, e.g., also strongly damage the embryos, making germination and development impossible. Therefore, certain preliminary work was necessary, depending on the plant material of interest, which served as the target structure, in order to adjust suitable conditions of the particle bombardment to the respective requirements of the experiment.

Establishing suitable bombardment methods for the plant material that is used, as well as the desired effect (transient versus stable insertion) without damaging the plant tissue, or destroying the construct that is to be inserted, was therefore indispensible.

Microinjection:

Microinjection can be carried out for all meristems, preferably using a microscope with a micromanipulator. Because of the size of certain meristem structures such as prepared tassel and ear meristems, the microinjection could also be carried out with microscopic monitoring. The injection could be carried out using various methods and, as discussed above for particle bombardment (Example 1), with different molecules. On the one hand, dsplasmid DNA, linear dsDNA, RNA and proteins in liquid solution were injected into the meristematic cells through a micro- or nano-canula, and on the other hand dsplasmid DNA, linear dsDNA, RNA and protein, also virus particles, was applied to micro or nano needles and transferred to the meristematic cells by stabbing with the needles.

A further development of this technology comprises the use of a combination of silicon carbide (SiC) whiskers (e.g. Silar® silicon carbide whisker) and microinjections. A dsplasmid DNA, linear DNA, RNA, protein or virus particle is precipitated on the silicon carbide thereby, and injected into the meristems by means of microinjection cannulas.

This offers the advantage that not only one meristematic cell can transfect, but instead, through the distribution of the whiskers, there is the possibility of penetrating numerous cells in parallel. Because it is not necessary to penetrate the cell with the cannula, and the whiskers are significantly smaller, there is less damage to the cells.

Vascular Puncture Infection/Inoculation (VPI):

"Vascular puncture infection" or inoculation, is a method desCRISPR bed in Benavente, 2012 (Virus-Induced Gene Silencing in the Diverse Maize Lines Using the Brome Mosaic Virus-based silencing vector) and Louie, 1995 (Louie R, 1995. Vascular puncture of maize kernels for the mechanical transmission of maize white line mosaic virus and other viruses of maize. Phytopathology 85:139-143), which is used to introduce viruses, virus particles, agrobacteria, and naked DNA into intact maize kernels. This technique enables targeted insertion in the proximity of the embryo and the meristematic tissue. It offers the advantage that no preparatory steps are necessary, and the germinated seeds can be used immediately. This results in minimal damage to the tissue and only minor disruption of the plant development. This method has been modified and implemented as follows: seeds containing a nucleic acid target region of interest are soaked in water for 4 hours at 30° C. The seeds are then incubated overnight in moist towels at room temperature. Subsequently, a plasmid or plasmid mixture, or a virus of interest, is pipetted onto the side of the seed kernel carrying the embryo. Normally, a 100 μl plasmid mixture is prepared in a concentration of 37.5 μg/100 μl, or 1.5 μg/4 μl for each plasmid. Using a notching tool, the inoculum is moved 1-2 mm in the scutellum along the embryo, toward the vascular bundle. Retaining pins are inserted at an angle of 45° to the surface of the kernel that is to be treated. Two inoculations are carried out at a distance of 1 mm to the embryo, in order to avoid injuring the embryo. The drops are then left on the kernel.

Figure 2A:
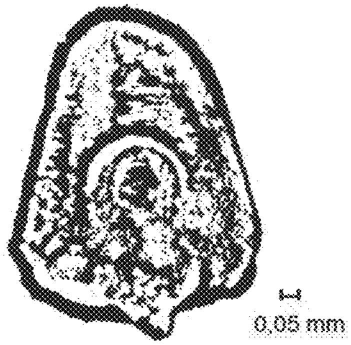
FIGS. 2A and B (FIGS. 2A and B) show a direct comparison of the meristems of a 0.5 mm (A) and a 1 mm maize embryo (B). In both cases, the meristem can be seen as the discoid structure in the centre of the embryo, but in the 1 mm embryo, the meristem is already surrounded by a great deal of leaf tissue. This makes access to the meristem more difficult, so that smaller embryos with an exposed meristem are preferred.
Figure 2B:
Figure 10B:
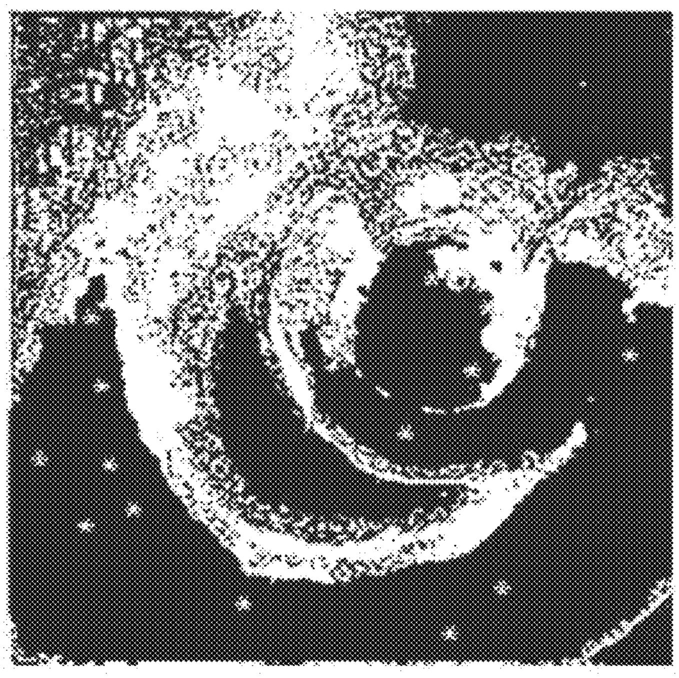
FIGS. 10A and B (FIGS. 10A and B) show two views of a maize embryo, as well as localized meristematic tissue. Initially, these data were indicated by a fluorescent marker. The accumulation of fluorescence in the original assay is indicated with stars in FIGS. 10 (A) and (B).
FIG. 10 (A) shows the embryo, FIG. 10 (B) shows a deeper layer in which the fluorescence can also be seen in the meristematic region (marked with stars). The images were recorded with a laser scanning microscope, the vector used for the bombardment was an expression vector, which encodes a fluorescent protein. The embryo layers have been dyed with a suitable pigment.
Figure 10A:
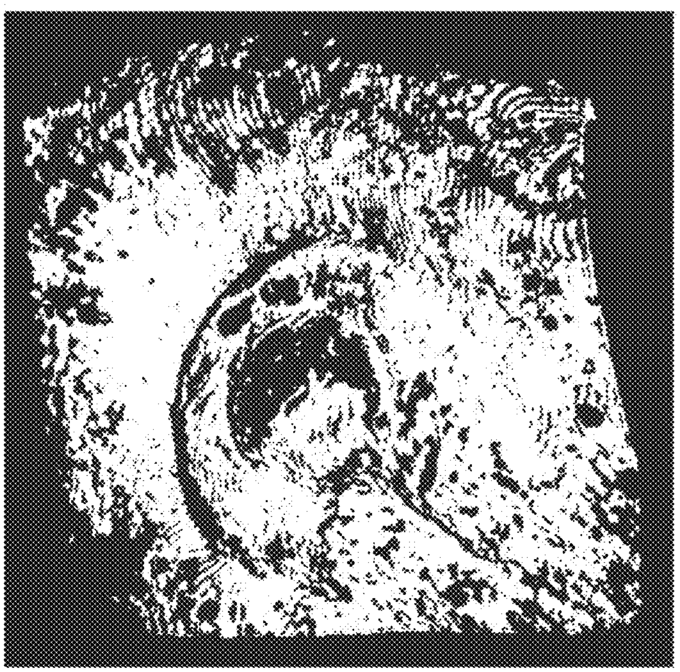
Figure 11B:
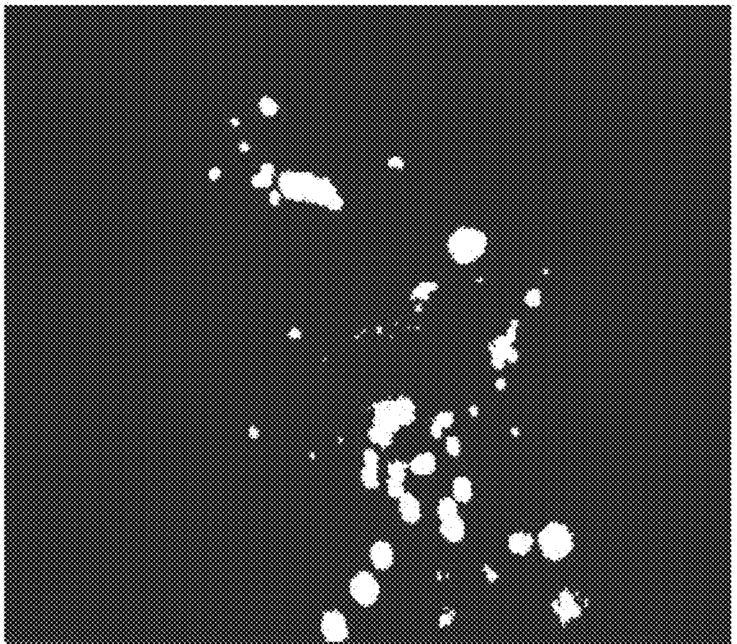
FIG. 11(B) shows the detected fluorescence in this side view (white dots). The embryo layers have been dyed with a suitable pigment.
Figure 11A:
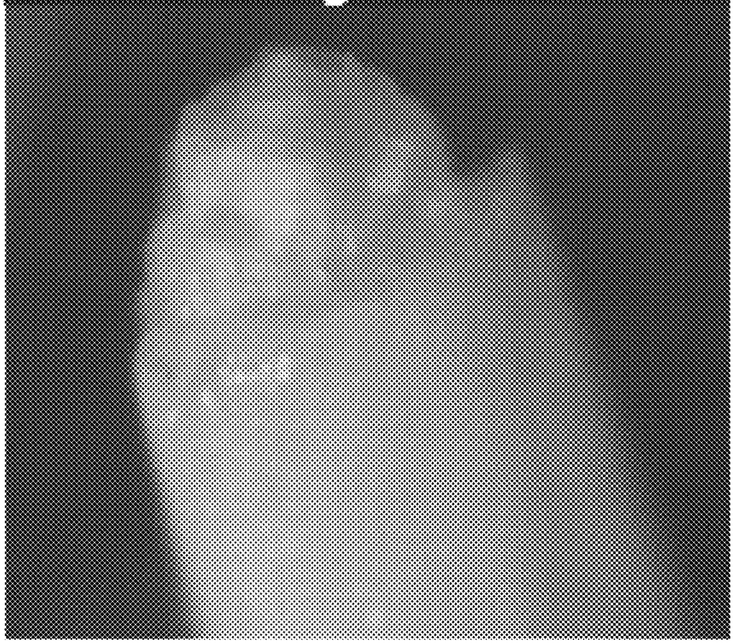
FIGS. 11A and B (FIGS. 11A and B) show the horizontal bombardment of the exposed meristems in older maize plants (5-10 day old seedlings) in accordance with example 3. Because the meristem in older plants, as in seedlings, is completely surrounded by leaves, it must be prepared in advance, in order to be accessible for bombardment, etc. For this, all of the outer leaves are removed. The images were recorded one day after the bombardment, with a laser scanning microscope, the vector used for the bombardment was a fluorescent protein-encoding expression vector.

Example 3: Transient Meristematic Transformation of Maize Seedlings and/or Embryos/Inventive Treatment of Meristem Tissue Accessibility to the meristem in the individual stages varies widely. Thus, in the embryo (FIGS. 1 and 2), the meristem is relatively easily accessible, provided that embryos of the right size are used. What is important is that the deeper-located cells of the meristem are transformed, since the upper cells have already undergone a certain amount of differentiation and are no longer suitable. FIGS. 10 and 11 show two views of a maize embryo, as well as the locations of meristematic tissue, indicated by stars. Initially, these data were made visible through a fluorescent marker. It is clear from this that the targeting of plant meristematic cells and tissue is made possible through the provision of the novel method. As a result, a novel method is obtained for inserting nucleic acid structures, e.g. vectors, as well as, in particular, RNAs and amino acids, into a plant target cell. The application of spectrum comprises numerous possible constructs thereby for the targeted genetic engineering modification of a plant cell, such as a CRISPR SPR/Cas construct, viral vectors, RNAi constructs, etc., in order to obtain targeted knock-ins, knock-outs, or targeted point mutations in the nucleic acid target region of the plant cell.

Figure 4A:
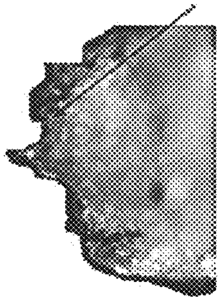
FIGS. 4A-C (FIG. 4A-C) show prepared meristems in older maize plants. Since the meristem in older plants as well as in seedlings is completely surrounded by leaves, it has to be prepared in order to be accessible for bombardment, microinjection etc. To this end, the outer tissue structures are completely removed so that the meristem (arrows) is exposed.
Figure 4B:
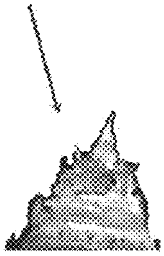
Figure 4C:
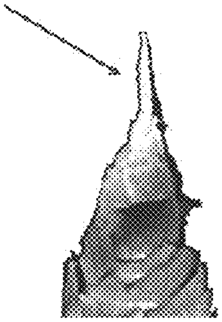
Figure 12A:
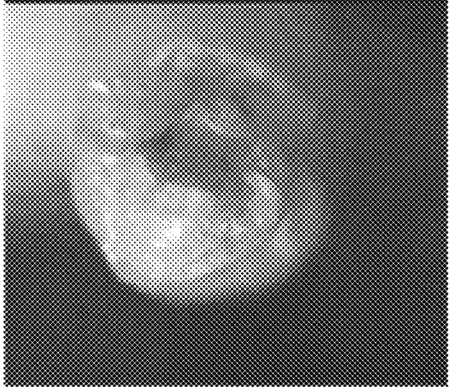
FIGS. 12A-C (FIGS. 12A-C) show the vertical bombardment of the exposed meristems in older maize plants (5-10 day old seedlings) in accordance with example 3. Because the meristem in older plants, as in seedlings, is entirely surrounded by leaves, it must be prepared in order to be accessible for a bombardment. For this, the outer leaves are removed entirely. The images were recorded one day after the bombardment, with a laser scanning microscope, the vector used for the bombardment was a fluorescence protein encoding expression vector.
Figure 12B:
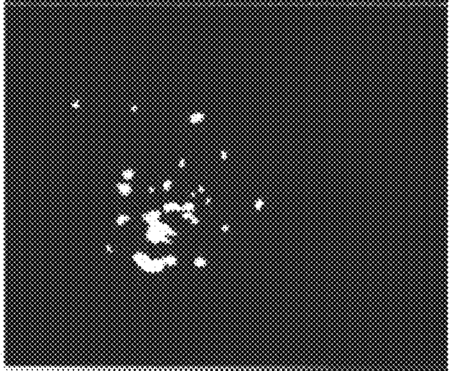
Figure 12C:
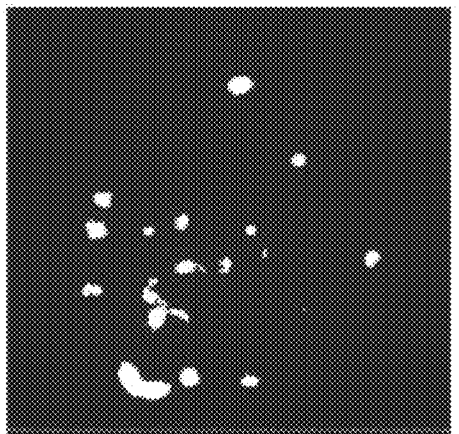
Figure 13A:
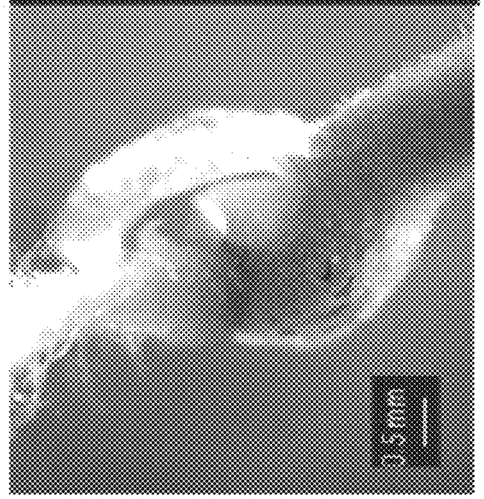
FIGS. 13A and B (FIGS. 13A and B) show a germinating embryo which also has transient fluorescence in the meristematic regions. The embryonic target structure can be seen in FIG. 13(A), and the same target structure is shown in FIG. 14(B) with the fluorescence of the inserted marking made visible by means of a fluorescence microscope. The fluorescence is obtained here by insertion of a suitable fluorescent marker. In the black-and-white image, the white regions in FIG. 13 (B) correspond to the regions in which fluorescence has been detected.
Figure 13B:
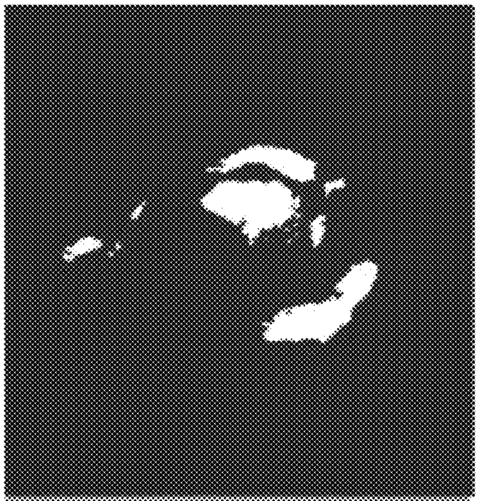

Meristems in seedlings and older plants must be completely dissected out since they are already surrounded by so many layers of tissue that they are not accessible to bombardment or a microinjection. FIGS. 3 and 4 show the prepared meristems which may be used for the transformation. Here again, as for the embryo meristems, the upper cells have already undergone a certain amount of differentiation and are no longer suitable. Thus, the cells further inside in the meristems have to be transformed. The exposed meristems can be bombarded horizontally as well as vertically. In detailed studies it has been discovered that through the vertical bombardment, the hit-rate in the suitable meristematic regions is increased significantly (see FIGS. 11 and 12). This shows once again that although particle bombardment is a known and established method, its effective application nevertheless requires optimization of various parameters (construct to be inserted, shape and stage of the material to be transformed, pressure, orientation, etc.) for a specific problem in the transformation of specific plant tissues.

Since the isolated meristems are free and thus are exposed to a great deal of oxidation and resulting dying off, they were treated with antioxidant in order to allow the seedling to develop into a plant.

Figure 6:
FIG. 6 shows the preparation of tassel meristems in adult maize plants. The meristems (arrow) are partially exposed through a window-like aperture. The recombinant constructs can then be introduced, for example by bombardment or microinjection and the like. The advantage is that the plant is not badly damaged and the meristems are not completely exposed (about 1-2 days later, the tassel meristem can no longer be seen in the opening, since it is moved further up), and thus oxidation and further damage is reduced.

In order to make the tassel meristem accessible, a method was developed which damaged the plant and meristem as little as possible. To this end, at the level of the tassel meristem, a kind of window was cut through the leaves (FIG. 6). This ensured that the leaves would not die off and that the plant could develop further completely normally and that the meristem would still be protected from the remaining leaves. In addition, the meristem very quickly (within a few hours/days) moved upwards so that it was then once more completely protected. This reduced the probability of the meristem oxidizing and therefore dying. It is possible with this method to ensure a nearly normal flower development, and to obtain pollen for selfing or pollination. This offers the advantage, in turn, that reproductive cells modified in a targeted manner can already be obtained from the plant, making tedious in vitro cultivation steps unnecessary.

The transfection then took place using the methods desCRISPR bed above (see Example 2).

The embryos germinated and plants were cultivated to self-fertilization and harvest. Similar results have been achieved with the seedlings and the adult plants, there was no germination.

Example 4: Detection of Successful Specific Genetic Modification

Detection is possible using various methods and at various times:

The presence of the desired specific modification of a target nucleic acid region can be analysed in the early phases of the seedling, the developing plant and the pollen so that indications of successful mutations can be obtained. A clear result is only obtained, however, when the descendants of the self-fertilization are analysed, as these provide the proof of an inherited mutation.

Enrichment PCR:

This method is of application when a restriction enzyme site is destroyed by the specific mutation. In this case, the isolated genomic or extrachromosomal DNA is digested with the enzyme which cuts at this site so that wild type DNA is cleaved. Next, a PCR is carried out with primers which lie upstream or downstream of the restriction enzyme site on the genome.

In the ideal case, only one product is then obtained when a mutation has taken place and the DNA was not cut at this site. Since as a rule, digestion of the genomic or extrachromosomal DNA is not 100%, the PCR amplification material obtained is then digested anew with the enzyme in order to establish that a mutation has occurred and the restriction enzyme site has been mutated. The undigested fragments are then cloned and sequenced in order to carry out a precise analysis of the mutation. If the nucleic acid target region is an RNA, then it can first be transCRISPR bed into DNA using a method which is known to the skilled person before an enrichment PCR is carried out.

Sequencing:

If enrichment PCR is not possible, a Next Generation Sequencing (NGS) strategy is used to sequence the specific region and the sequences obtained are examined for their mutations Whole genome sequencing (WGS) to identify off-target effects:

In order to exclude the possibility of unwanted mutations, a WGS is carried out on the candidates with the desired mutations.

Additional analyses are constituted by absence detection of the constructs and viruses used using specific PCR and qPCR systems.

Example 5: Viral Vectors

Viruses offer the advantage that they can be introduced into a target plant structure as whole viral particles and also as DNA or RNA. The insertion of the viruses is achieved via the delivery methods listed in Example 2. By these means, a targeted insertion into the respective meristematic target regions of interest is obtained.

In addition, viruses offer the possibility of propagation in the cells. Prerequisite for that is, that this function has not been destroyed by modification to their RNA/DNA sequence. This has the advantage that firstly, the meristem does not have to be directly infected, or it is sufficient to infect only a few cells and notwithstanding this, propagation into several cell or tissue types occurs.

With this application, there are other possibilities, in addition to the delivery methods desCRISPR bed in Example 2, for inserting viruses or virus particles.

Virus particles, in vitro transCRISPR pts of the viruses, or *Agrobacterium* that carry an encoding T-DNA for the viruses, are inserted by rubbing them into the leaves, or via infiltration (with and without a vacuum), in order to generate primary infections. The respective target cells and target tissues are then infected through a systematic spreading.

In addition, plant sap that has a high titre of plant viruses is used for the infection. For this, either tobacco or spinach is infected with the viruses, and subsequently, the plant sap containing the viruses is isolated and used for infecting the maize plants.

Aside from the broad spectrum of infection possibilities, and the spreading capabilities, DNA viruses offer the advantage of providing DNA templates for homologous recombination (HR). In this case, a large quantity of templates is provided by the replication of the virus inside one or more cells for homologous recombination after the double-strand break has been introduced. As a result, homologous recombination and incorporation of the template fragment occur with greater frequency.

In one series of tests, different BMVs (see SEQ ID NOS: 25-31 or DSMZ filing number: BMV Virus-Inoculum: PV-0945; reference for BMV plasmids (C13/F1+F2 & C13/F3-13m): Benavente et al., Maydica, Vol. 57, No. 3 (2012): "Virus-Induced Gene Silencing in Diverse Maize Lines Using the Brome Mosaic Virus-based silencing vector.") and BSMVs (comprising at least one sequence selected from the SEQ ID NOS: 32-37 or DSMZ filing number: BSMV Virus-Inoculum: PV-0330; Reference for BSMV plasmids (pCaBS-& pCaBS-β & pCa-γbLIC): Yuan, C., et al., (2011). PLOS One 6 (10): e26468: "A high throughput barley stripe mosaic virus vector for virus induced gene silencing in monocots and dicots."), virus particles, plasmids, or plasmid mixtures, were therefore inserted into a plant or plant cell of interest. Among others, *Nicotiana benthamiana*, maize A188, maize Va35, and *Spinacia oleracea* are infected with corresponding viruses, plasmids or a plasmid mixture. A rubbing inoculation, vascular puncture infection/inoculation, or transformations conveyed by agrobacteria were used.

For the rubbing inoculation, a DNA plasmid coating containing similar concentrations of different plasmids is prepared for the primary inoculation. By way of example, each plasmid is used in a concentration of 6 μg/μl. The different plasmids of the same concentration are then mixed in the same volume ratios. For each leaf, 6 μl plasmid mix was applied in drops to the surface of the leaves, on which the carborundum has already been distributed. The plasmid mixture was then rubbed into the surface of the leaves with one's fingers. Alternatively, a plant sap infected with a virus can be used as the starting material. For the second inoculation, fresh or frozen plant leaves infected with a virus were ground in a homogeniser, and the resulting powder/product was dissolved in a 3-4 ml inoculation buffer (0.2406 g $KH_2PO_4$+0.543 g $Na_2HPO_4$ in 500 ml deionized water). At this point, a small quantity of carborundum was added to the plasmid mixture or plant sap. The plasmid mixture or plant sap was introduced into the upper and lower surfaces of the leaf through rubbing, wherein this is achieved by submerging one or more fingers into the inoculum and then carefully applying the inoculum to at least one leaf by hand, wherein the leaf is preferably supported by the other hand. The rubbing inoculation can also be combined with a prior injury (incision) to a plant leaf, wherein an incision is first made in the leaf with a scalpel, and the rubbing inoculation then takes place directly in the injured leaf.

For the transformation conveyed by the Agrobacteria (Ab), Ab cultures were first cultivated overnight at 28° C. in 30 ml liquid Luria broth, comprising a suitable antibiotic, 10 mM MES, and 200 μm ACE. The next day, the overnight cultures were centrifuged at 4,400 rpm for 15 minutes. The precipitation was discarded, and the pellet was then centrifuged again at 4,400 rpm for 2 minutes. The remaining precipitation was discarded, and the pellet was re-suspended in a re-suspension medium (5 ml $H_2O$, 10 mM MES, 10 mM $MgCl_2$+20 UM ACE). The optical density $OD_{600}$ of the suspension was adjusted to 1.5 using the re-suspension medium. The diluted Ab suspension was then incubated for 4 hours at room temperature. The infiltration of the Ab suspension then preferably takes place on the undersurface of a leaf of interest, e.g. a leave from *Nicotiana benthamiana*, wherein, normally, 2 leaves from each plant are inoculated.

The following Table 2 shows exemplary results for selected viruses and plant species, using different transformation methods:

longer exists there, and the selected restriction enzyme cannot cleave this DNA. Subsequently, a PCR amplification takes place with primers that bond upstream and downstream of the two gRNA target regions, i.e. they can accumulate under suitable reaction conditions through hybridization. If necessary, a renewed re-PCR can be carried out with a nested primer set. After the successful editing, the resulting PCR product is smaller than the product from a non-edited DNA (see FIG. 17 B). The illustration in FIG. 17 B shows the results of the analysis of an editing after use of the 2-gRNA strategy with genomic DNA of a maize plant.

TABLE 2

Overview of virus infection experiments (Wpl: weeks post infection)

| Virus Material | Infected Plant Species | Methods | Results |
|---|---|---|---|
| BMV - Virus particle DSMZ | *N. benthamiana* | Rub + Carborundum | 2 Wpl: 2/2 Plants with systemic BMV infection |
| BMV - Virus particle DSMZ | Maize A188 | Rub + Carborundum | 2 Wpl: 2/2 Plants with local BMV infection |
| BMV - Tobacco sap infected with virus particles DSMZ | *N. benthamiana* | Rub + Carborundum | 2 Wpl: 4/6 Plants with systemic BMV infection |
| BMV - Tobacco sap infected with virus particles DSMZ | Maize A188 | Rub + Carborundum | 2 Wpl: 3/4 Plants with local BMV infection |
| BMV - Tobacco sap infected with virus particles DSMZ | Maize Va35 | Rub + Carborundum | 2 Wpl: 1/6 Plants with local BMV infection |
| BMV - Tobacco sap infected with virus particles DSMZ | Maize Va35 | Sheet-Incision + Rub + Carborundum | 2 Wpl: 1/2 Plants with systemic BMV infection |
| BMV - Plasmids C13/F1 + F2 und C13/F3-13m | *N. benthamiana* | After Infiltration | 1 Wpl: 12/12 Plants with systemic BMV infection |
| BMV - Plasmids C13/F1 + F2 und C13/F3-13m-GFP | *N. benthamiana* | After Infiltration | 5 Wpl: 12/12 Plants with systemic BMV infection |
| BMV - Tobacco sap infected with plasmids C13/F1 + F2 & C13/F3-13m | Maize Va35 | Rub + Carborundum | 4 Wpl: 1/2 Plants with systemic BMV infection |
| BMV - Tobacco sap infected with plasmids C13/F1 + F2 & C13/F3-13m-GFP | Maize Va35 | Rub + Carborundum | 4 Wpl: 3/4 Plants with systemic BMV infection |
| BMV - Virus particle DSMZ | *Spinacia oleracea* | Rub + Carborundum | 2 Wpl: 5/5 Plants with local BSMV infection; 3 thereof also systemic |
| BMV - Virus particle DSMZ | Maize A188 | Rub + Carborundum | 2 Wpl: 4/6 Plants with local BSMV infection |
| BMV - Spinach sap infected with virus particles DSMZ | *Spinacia oleracea* | Rub + Carborundum | 2 Wpl: 5/ Plants with systemic BSMV infection |
| BSMV - Plasmids pCaBS-α & pCaBS-β & pCa-γLIC | *Spinacia oleracea* | Rub Plasmid mix + Carborundum | 2 Wpl: 11/11 Plants with local BSMV infection |
| BSMV - Plasmids pCaBS-α & pCaBS-β & pCa-γLIC | *N. benthamiana* | After Infiltration | 2 Wpl: 14/14 Plants with systemic BSMV infection |
| BSMV - Plasmids pCaBS-α & pCaBS-β & pCa-γLIC | Maize A188 | Vascular Puncture inoculation | 2 Wpl: 1/15 Plants with systemic BSMV infection |
| BMV - Virus particles DSMZ | Maize A188 | Vascular Puncture inoculation | 2 Wpl: 1/12 plants with systemic BSMV infection |

The white background in table 2 indicates that for this experiment, a systemic infection could be obtained. A light grey background indicates a local infection, while a dark grey background indicates a low infection rate.

Proof of a successful infection is obtained from either an ELISA or by means of an RT-PCR.

Example 6:2-gRNA Strategy

Figure 17A:
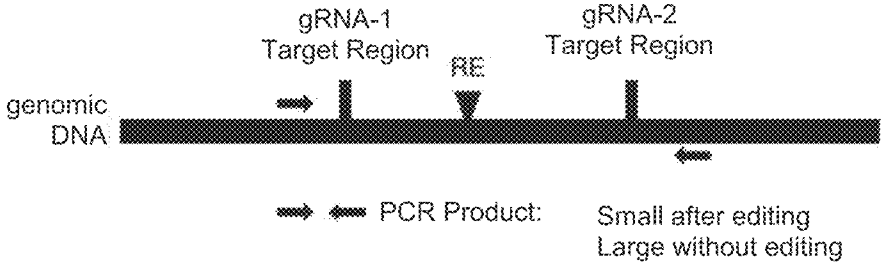
FIGS. 17A and B (FIGS. 17A and B) show the 2-gRNA strategy used for the method disclosed herein.

For the targeted spreading of genomic DNA and to specifically excise a nucleic acid target region of interest from the genome through the use of a CRISPR nuclease, a so-called 2-gRNA strategy was established (cf. FIGS. 17A and B). As is shown in FIG. 17A, genomic DNA is first isolated for this, and digested by a restriction enzyme (RE) of interest, the cleavage site of which lies within the PCR product of interest. Any RE can be used that can cleave between the two gRNA target regions. In this manner, an accumulation of potentially edited DNA takes place, because the region between the gRNA target regions no The genomic DNA was isolated from maize plants and the target gene hmg13-gene (HMG-transCRISPR ption factor 13; GRMZM2G066528) was amplified with PCR. The sequence for the HMG-transCRISPR ption factor 13 gene without an editing is shown in SEQ ID NO: 60.

The nucleotide positions 1-98 of the SEQ ID NO: 60 and the nucleotide positions 912-1023 of the SEQ ID NO: 60 correspond to the region of the hmg gene that remains after a successful editing. Nucleotide positions 82-101 of the SEQ ID NO: 60 and nucleotide positions 909-928 of the SEQ ID NO: 60 are each gRNA target regions.

Figure 17B:
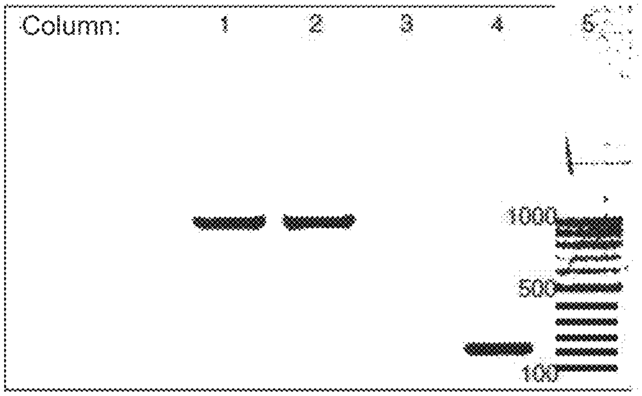
FIG. 17B shows the results of the analysis of an editing event after using the 2-gRNA strategy on the genome of a maize plant. For this, the genomic DNA is isolated from maize plants, and the target gene, the hmg13 gene (HMG-transCRISPR ption factor 13; GRMZM2G066528), is amplified with PCR.

FIG. 17 B shows the results of a separation in a 1% gel with the standard parameter of 100 V and visualization via fluorescence obtained with ethidium bromide, with different contrast levels. Columns 1 and 2 show the results for non-edited maize plants, and column 4 shows the results after successful editing. The PCR product is smaller because the region between the two gRNA target regions has been excised. This approach thus represents a quick and efficient strategy for experimentally confirming a successful genome editing.

SEQ ID NO: 61 shows the results of the sequencing of the small PCR product after hmg13 editing with the 2-gRNA strategy. The deletion has taken place through a targeted editing between the two bases, C and T, at positions 98 and 99 of the SEQ ID NO: 61.

Example 7: Genome Editing in Tobacco

NbTTG1 was selected as the target gene in *Nicotiana benthamiana* for the genome editing work, the orthologous gene of which results in a trichome phenotype in *Arabidopsis thaliana* when dysfunctional. Mutants are desCRISPR bed for the corresponding *Arabidopsis* gene AtTTG1 (AT5G24520):

ttg1 (EMS-mutants): no trichomes on the leaf surfaces and stem.
- yellow seeds resulting from the absence of brown pigments.

ttg1-13 (fast neutron mutants):
- no trichomes, transparent seed casings, increased number of root hairs.

Figure 18:
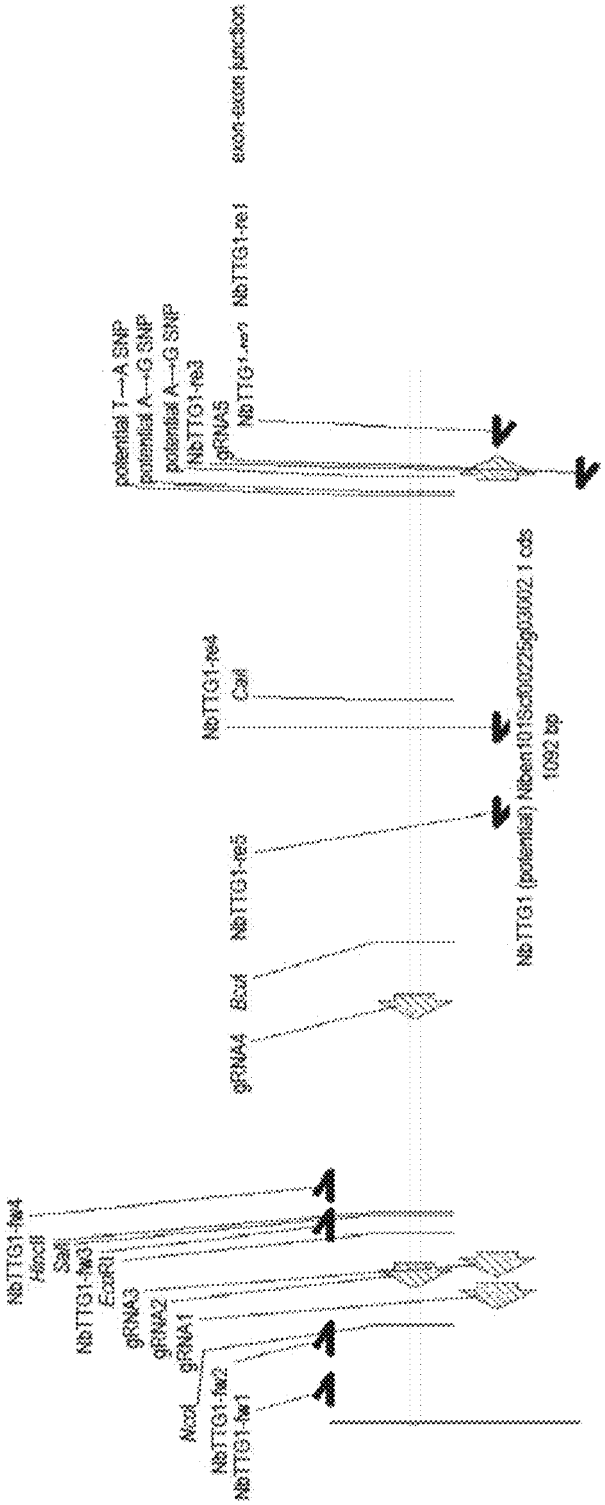
FIG. 18 shows a portion of *Nicotiana benthamiana* NbTTG1 Gene. The gRNA target regions are indicated by shaded arrows, and primer bonding sites (fw: forward, re: reverse) are indicated by black arrows. Moreover, cleavage points for restriction enzymes are indicated, which are used in the framework of the analysis of an editing result.

The orthologous gene in *Nicotiana benthamiana* was identified via sequence comparisons and the genomic locus was amplified via PCR. The section in question is shown in FIG. 18. Appropriate gRNAs were selected on the basis of this sequence, as desCRISPR bed above. The components for the genome editing were introduced into the plant via TRV (tobacco rattle virus) (see example 8, below). The 2-gRNA strategy outlined above in example 6 was also used here for analysing a successful editing.

As can be seen in table 3 below, different sized deletions could be generated in the NbTTG1 gene through various combinations of two gRNAs. A Cas9 nuclease was used for this test, although the approach can be used for any of the CRISPR nucleases.

TABLE 3

| gRNAs | Deletion |
|---|---|
| gRNA1 + gRNA4 | 232 bp |
| gRNA2 + gRNA4 | 216 bp |
| gRNA3 + gRNA4 | 206 bp |
| gRNA4 + gRNA5 | 446 bp |
| gRNA1 + gRNA3 | 25 bp |

Example 8: Expressions of CRISPR SPR-Cas in *Nicotiana benthamiana* Conveyed by Tobacco Rattle Virus (TRV)

Figure 19:
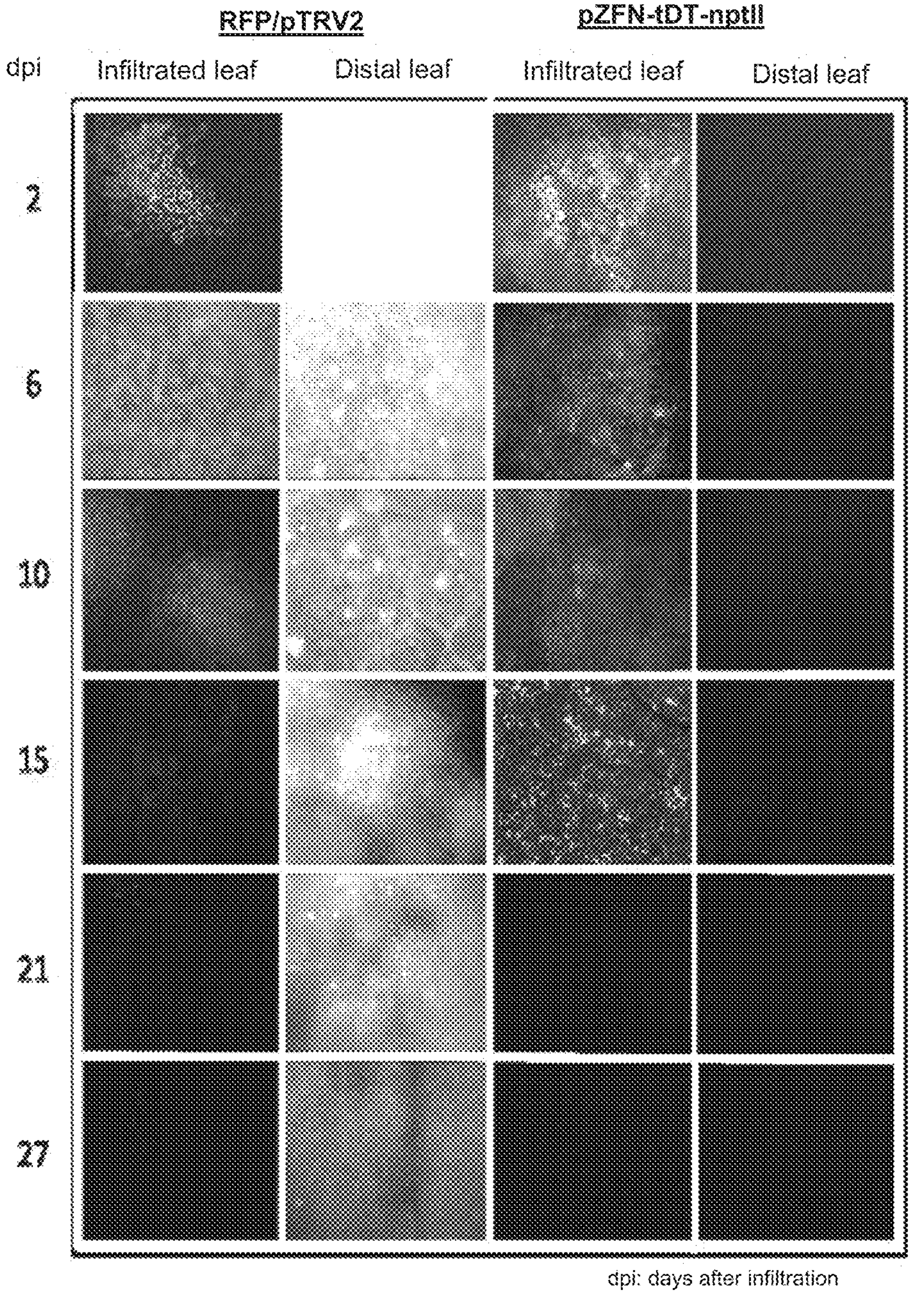
FIG. 19: TRV obtained in un-inoculated distal *Nicotiana benthamiana*, leaf tissue.
Figure 20A:
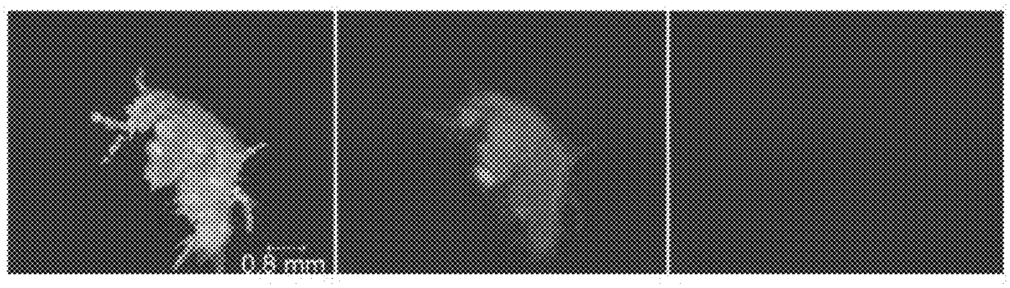
FIGS. 20A-H (FIGS. 20A-H) show fluorescence microscope recordings of various blossom structures that have been infected with TRV, which can express a red fluorescent protein. All of the figures A to H show a light-field recording on the left, a recording with a red filter in the middle, and a recording with a green (GPF) filter on the right. The latter serves as a control for autofluorescence. A blossom meristem is shown in FIGS. 20A (original recording in black-and-white) and B (counterpart to A with contrast/exposure adjustment).
Figure 20B:
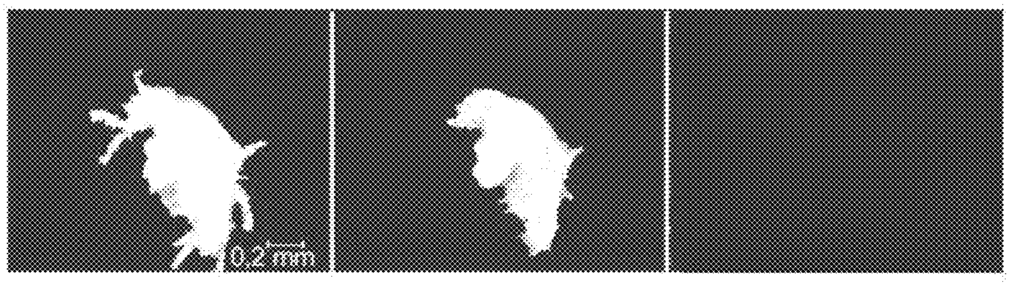
Figure 20C:
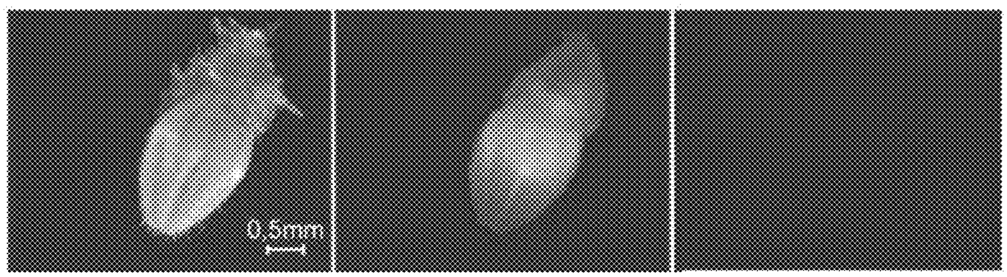
Figure 20D:
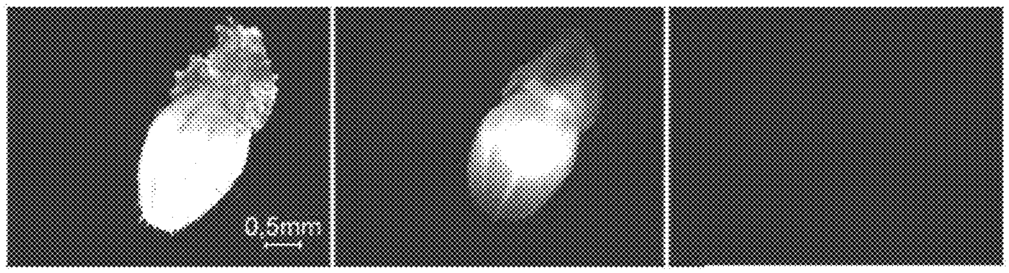
Figure 20E:
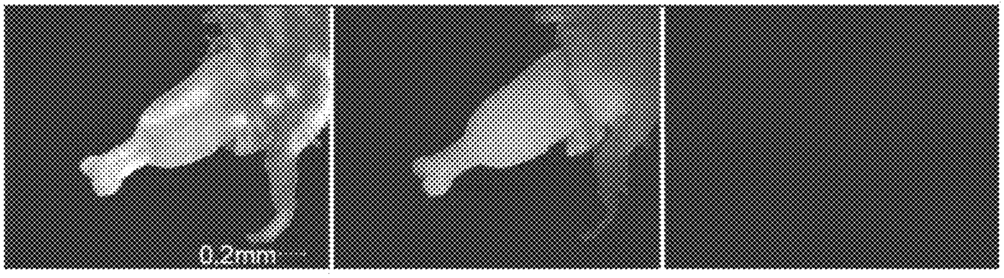
Figure 20F:
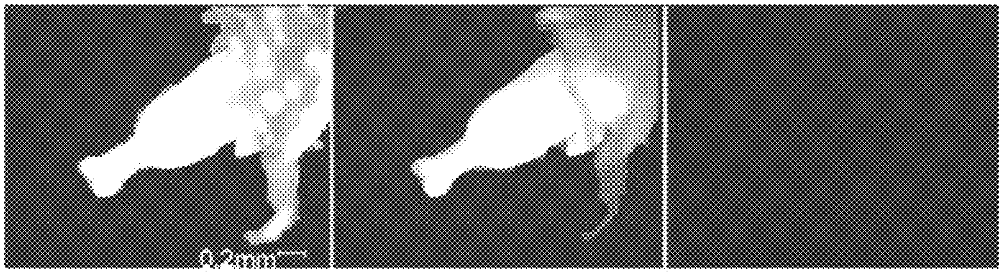
Figure 20G:
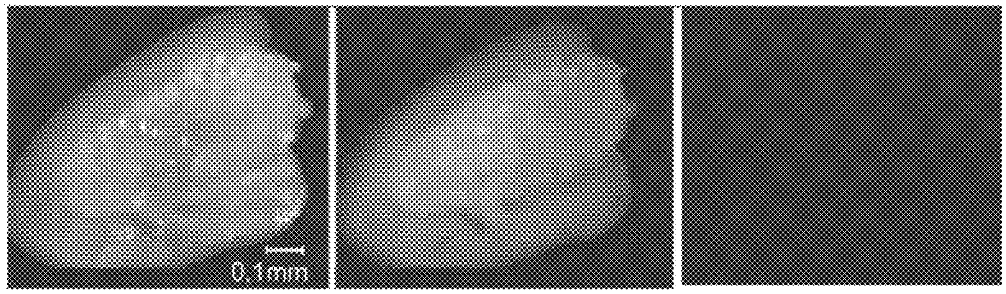
Figure 20H:
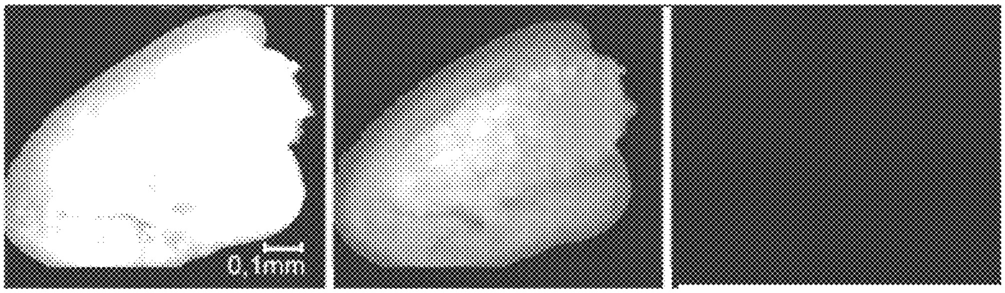

For the leaf inoculation of tobacco, first *Agrobacterium* (Ab) cultures were cultivated overnight at 28° C. in 30 ml liquid Luria broth (LB) medium, which contains a selective antibiotic. The next day, the overnight cultures were centrifuged at 4,400 rpm for 15 minutes. The precipitation was discarded and the pellet was again centrifuged at 4,400 rpm for 2 minutes. The remaining precipitation was discarded, and the pellet was re-suspended in 5 ml re-suspension medium (10 mM MES, 10 mM $MgCl_2$, 20 μM ACE). The optical density at 600 nm ($OD_{600}$) of the suspension was adjusted to 0.8 using the re-suspension medium. The diluted Ab suspension was then incubated for 4 hours at room temperature. The Ab suspension was subsequently infiltrated with a syringe or cannula on the undersurface of a leaf of interest, e.g. a leaf from *Nicotiana benthamiana*, wherein 3 leafs of each plant were normally inoculated. In order to make the systemic spreading efficiency of TRV visible, the leaves were inoculated with an RFP/pTRV2 (red fluorescent marker+TRV as a viral vector) and with pZFN-tDT-nptII as a control. As can be seen in FIG. 19, a clear RFP fluorescence can be detected in the directly inoculated leaves, as well as in the non-inoculated distal leaves (originally red fluorescence is indicated by the light and/or white regions in FIG. 19). The construct pZFN-tDT-nptII functions as a control, which only allows the expression of the RFP in the inoculated leaves, but not in the distal leaves.

Moreover, it has been confirmed that even meristematic tissue can be activated through these TRV methods, allowing for a targeted modification of this type of tissue through the specific CRISPR methods. For this, *Nicotiana benthamiana* plants were infected with TRV, wherein the construct comprises a gene that encodes a red fluorescent protein, e.g. tdT or the like. Through detection of the red fluorescence with appropriate means (fluorescence microscope, binocular), it was possible to determine where the TRV is in the plant. It may be advantageous here to use fluorescent markers with a high intensity, because these can also be readily detected in deeper tissue layers. FIGS. 20A to H show images of recordings of a flower meristem, a flower bud, a pistil, or a prepared pistil with exposed ovaries. All of the images demonstrate the successful expression of the fluorescent marker in the respective plant meristematic cells, or tissues as a target structure, and thus the efficiency of the selected insertion method.

Figure 21:
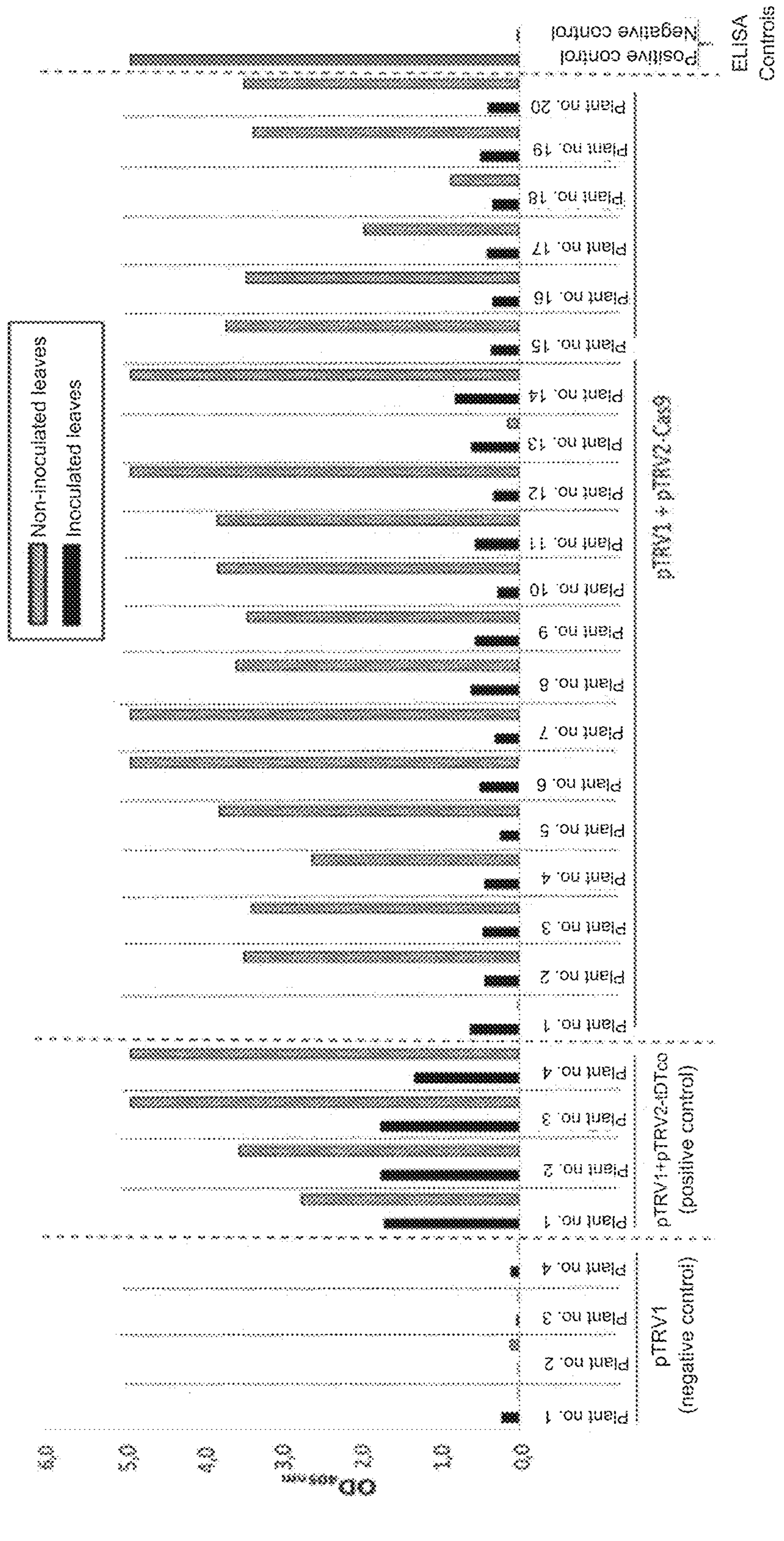
FIG. 21 shows the quantifying of TRV titres in *N. benthamiana* inoculated with pTRV1 (=Negative control), pTRV1+pTRV2-tDTco (=Positive control) and pTRV1+pTRV2-Cas9 10 dpl.

Lastly, TRV titres were quantified in the inoculated and non-inoculated tobacco leaves by means of a standard double antibody sandwich (DAS) ELISA. For this, 10-12 dpl leaf material was harvested from each plant that was to be analysed as the starting material for the ELISA, wherein for each plant, the following mixture samples were created: (i) mixture samples, each from two TRV inoculated leaves; (ii) mixture samples, each from two non-inoculated leaves. The harvested leaf material was pressed and the collected plant sap was used at a dilution of 1:50 in the DAS-ELISA. The DAS-ELISA was carried out using a polyclonal antiserum from rabbits. The antiserum was obtained from the company Loewe®, and labelled "Tobacco Rattle Tobravirus BroadRange TRV" (catalogue no. 07152S). The evaluation of the ELISAs takes place 60 minutes after application to the substrate 4-nitrophenylphosphate, through photometric measurement of the $OD_{405}$. In this manner, the TRV titres were quantified in N. *Benthamiana* inoculated with (i) pTRV1 (=negative control); (ii) pTRV1+pTRV2-tDTco (=positive control) and (iii) pTRV1+pTRV2-Cas9. The results are shown in FIG. 21.

Example 9: Quantification of CRISPR Tools

By way of example, Cas9 transCRISPR pts were detected by means of RT-PCR. For this, 10-12 dpl leaf material was harvested from each plant that was to be analysed as the starting material for the ELISA, wherein the following mixture samples were created for each plant: (i) mixture samples, each from two TRV inoculated leaves; (ii) mixture samples, each from two non-inoculated leaves (see example 8). First, RNA was extracted from the harvested leaf material, using an RNeasy Mini Kit (Qiagen). In each case, 500 ng RNA was subsequently transCRISPR bed into cDNA using the REvertAid H Minus First Strand cDNA Synthesis Kit (Thermo Fisher Scientific). The cDNA served as a template in a subsequent PCR for detecting Cas9. Cas9-specific primers were used.

Figure 22:
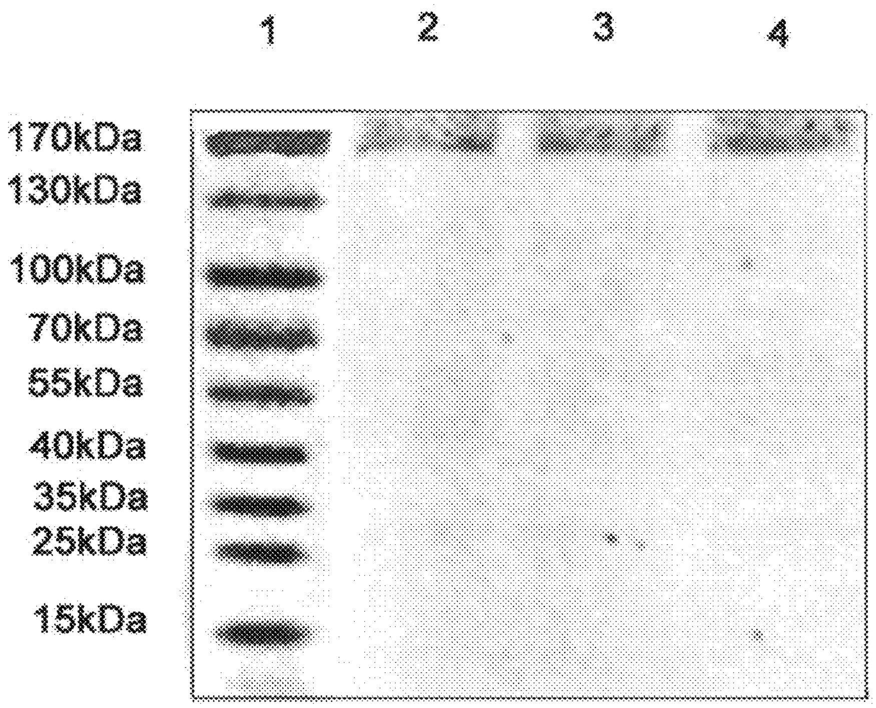
FIG. 22 shows the protein indication in Cas9 (160 kDa) expressed in and subsequently isolated from leaf material of transgenic maize plants. The PageRuler Prestained Protein Ladder (10-170 kDa; from top to bottom 170, 130, 100, 70, 55, 40, 35, 25, 15, 10 kDa) was used for the size standard. Exposure time was 30 minutes. Column 1: pre-dyed protein marker; column 2: 10 μg protein from maize expressing Cas9; column 3: 15 μg protein from maize expressing Cas9; column 4: 20 μg Protein from maize expressing Cas9.

Protein extracts were produced from leaf material of transgenic maize plants, and separated on a 4%-20% SDS- PAGE gradient gel. The detection of the 160 kDa Cas9 took place with a monoclonal antibody from ActiveMotif (catalogue no. 61577). The documentation of this detection system is shown in FIG. 22.

Figure 23:
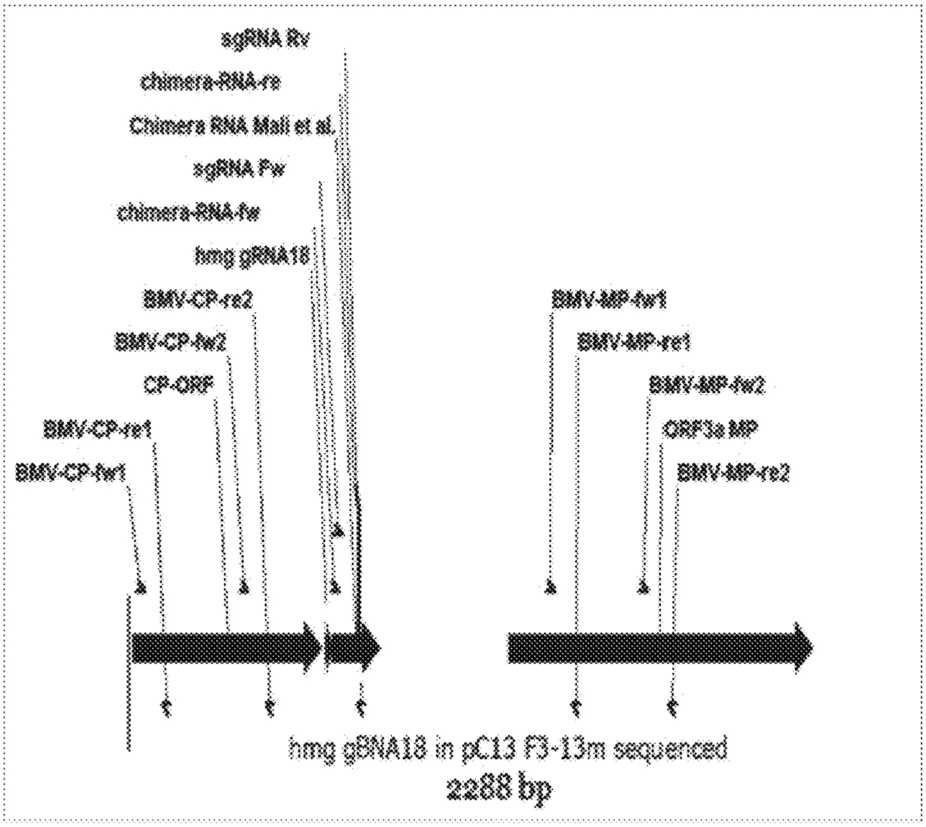
FIG. 23 shows an exemplary virus sequence (BMV). The various primer combinations used for the quantifying system of the gRNA are indicated by arrows. "Fw" indicates forward primers, and "re" indicates reverse primers, flanking a sequence of interest. A specific gRNA for the HMG transCRISPR ption factor gene integrated in the construct of interest that is to be analysed is indicated by "hmg gRNA." The illustrated chimera RNA ("Chimera RNA Mali et al.") desCRISPR bes a chimeric, artificial RNA construct, supported by the disclosure of Mali et al., 2013 above, wherein the gRNAs desCRISPR bed therein have been specifically adapted for use in plant cells, as explained in the example.

In order to quantify RNAs and to determine whether or not an expression by the gRNAs, conveyed through a sub-genomic promoter, takes place, quantitative RT-PCR systems on the basis of SYBR green were established. When amplified with the same PCR efficiency, a quantification could be conducted through a comparison of the gRNA quantity with the transCRISPR ption level a viral proteins. This system is shown in FIG. 23, using the brome mosaic virus (BMV) by way of example.

Example 10: Viral Expression Systems

In addition to the viral vectors desCRISPR bed above, the CRISPR tools and methods of this invention can likewise be virally introduced in other plant systems. Different methods may be used, depending on the target plant of interest, and the type of transformation, and the target tissue that is to be infected.

The system from Ugaki et al. (1991, Nucleic Acids Res., Replication of a geminivirus derived shuttle vector in maize endosperm cells) is suitable for maize endosperm cells serving as the primary target structure. Using the wheat dwarf virus (WDV) as a vector, an infected culture can thus be obtained through protoplast transformation of maize endosperm cultures. For this, a modified virus is used, which carries a neomycin phosphotransferase gene II (nptII) in place of the coat protein (CP). A transient replication system with the wheat dwarf virus as cargo, in accordance with Matzeit et al. (1991, Nucleic Acid Res., 19(2), 371-377) can be used for *Triticum* target plants. Protoplasts derived from *Triticum* suspension cultures are transfected thereby. The CP gene of the virus is again replaced by a marker gene of interest.

Moreover, systems on the basis of the Maize Streak Virus can be used, which are known to the skilled person in the field, and desCRISPR bed in Palmer & Rybicki (2000, Archives of Virology, 146(6), 1089-1104). Three day old seedlings are infected at coleoptile nodes, and a transient expression of a recombinant construct of interest can be obtained. By exchanging the viral CP and MP genes, a systematic spreading of the virus can be prevented, such that only the first two or three leaves are infected.

As explained above, the barley stripe mosaic virus (BSMV) is also suitable as a viral vector. The BSMV genome is intensively transformed in order to establish a known plant protoplast vector (cf. Joshi et al., 1991, EMBO J., 9(9), 2663-2669). This vector, which carries a luciferase (luc) reporter gene according to Joshi et al., 1990, is suitable for protoplast transfection of maize and tobacco protoplasts.

BSMV (see Manning et al., 2010, New Phytologist, 187 (4), 1034-1047), WDV, Wheat Strike Mosaic Virus (WSMV) (Choi et al., 2000, Plant J., 23 (4), 547-55), Tomato Yellow Leaf Curl Virus (TYLCV) (Peretz et al., 2007, Plant Physiol., 145 (4), 12514-1263) and Brome Mosaic Virus (BMV) (French et al., 1986, Science 231 (4743), 1294-7) are also suitable as systems for transfection of protoplasts, seedlings, petioles and other plant cells or tissues in wheat, as well as barley and tobacco, as is comprehensively desCRISPR bed in the references. In particular, BSMV vectors (see Manning et al., 2000, above) are suitable in a modified form as vectors for virus-induced gene silencing. For this, the BSMV genome is modified through site oriented mutagenesis by supressing the expression of the viral coat protein. TYLCV (see Peretz et al., above, or EP 2 436 769 A1)) is attenuated in this regard, and made available for use as a viral shuttle vector for plants, as well as *E. coli*, which have been deleted in the viral coat protein of a sequence comprising 60 base pairs in the proximity of the N-terminus of the gene.

Specific approaches for sugar beet transformation on the basis of viral vectors are likewise known. For this, in particular, the beat curly top virus (BCTV) (Kim et al., Plant Mol. Biol., 2007, 64 (1-2): 103-12), the beet yellows virus (BYV) (Prokhnevsky et al., Molecular Biotechnology, 57 (2), 101-110, 2015), the beet soil-borne mosaic virus (BSBMV) (Dach et al., 2015 ASSBT proceedings conference transCRISPR pt, 47$^{th}$ annual meeting of the work group, Virus Diseases of Plants ", Section C), or the beet necrotic yellow vein virus (BNYVV) (Hamza et al., 2015, ASSBT proceedings) are suitable. These vectors are not only suitable as vectors for sugar beets, but also for other dicotyledons, e.g. spinach.

Numerous methods are likewise available for tobacco as the model plant, for transformation thereof by means of viral vectors. Many of these methods are based on *Agrobacterium* infiltration. Suitable viruses comprise the tobacco mosaic virus (TMV), potato virus X (PVX), cowpea mosaic virus (CPMV), bean yellow dwarf virus (BeYDV), plum pox virus (PPV) (see Gleba et al., 2014, or Slazar-Gonzalez et al., 2015, Plant Mol. Biol., 87:203-217). Moreover, diverse other systems have been desCRISPR bed, that use, e.g., cabbage leaf curl virus (CaLCuV) (Yin et al., 2015, Nature Scientific Reports, 5:14926, 2015), tobacco rattle virus (TRV) (Ali et al., 2015, Genome Biology, 16:238), or tobacco yellow dwarf Gemini virus (TYDV) (Dugdale et al., 2014, Nat. Protoc., 9 (5), 1010-27) as a virus.

All of the vectors above contain cloning sites for introducing target genes of interest. Specific cleavage sites can also be introduced easily into a viral genome of interest through available mutagenesis methods.

Example 11: Optimized Methods for Windowing Plants

To further optimize the targeted introduction of CRISPR constructs, and thus the effect of the genome editing, the method outlined in example 3, above, was further improved. The original method comprises the closing of the artificially inserted window with a closure, such as a special tissue paper. This may, however, be associated with the disadvantage, depending on the exposition, that the injured and exposed plant tissue can be more easily infected with fungi, or that a portion of the exposed tassel, the bombarded portion, comes in too much contact with air, which may result in a drying out of the exposed tassel structures, or immature flowers, and thus the individual tassel branching. For this reason, the exposed tassel tissue, transformed as desCRISPR bed above, was covered with a moistened cotton pad or tissue in a first step. As a result, the drying could be significantly reduced, although this method is still prone to fungi infections. In order to address this problem, waxes or Vaseline-like substances were applied to the injured site (after transformation). Diverse substances were tested, comprising Vaseline, mixtures of natural waxes with Vaseline and other commercially available products, which are offered for healing wounds, specifically for trees. This approach is well known to the person skilled in the art, specifically in the field of grafting. In addition, the injured site was wrapped with a special grafting tape, which significantly improves the closing of the wound, and thus the protection against fungi infection, such that the transformed meristematic tissue can fully ripen to maturity. With this strategy, a majority of the tassels in their transformed form could ripen to maturity. Success rates of 75% and more, i.e. events in which the exposed and transformed tassel tissue could ripen to full maturity in planta, were obtained therewith.

Example 12: *Agrobacterium* Injection

Figure 24:
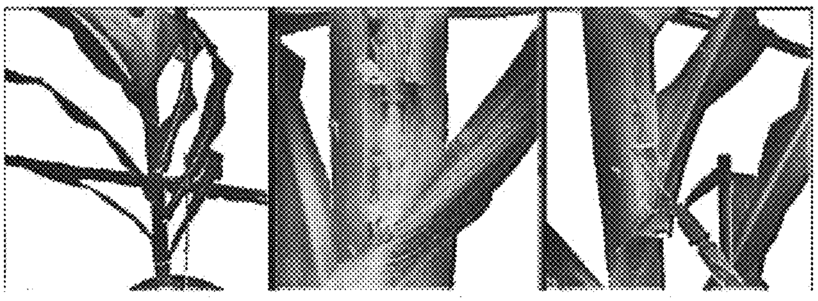
FIG. 24 shows a maize plant of the genotype A188 in the V7 stage (left-hand image), the same plant after insertion of an artificial window in the region protecting the tassel tissue (middle image), and the subsequent injection of an *Agrobacterium* solution in the region of the exposed tassel (right-hand image).

In order to further expand the breadth of the possible field of application, the method outlined in example 3 was carried out, modified such that instead of the particle bombardment, transformations caused by *Agrobacterium* (Ab) were used. In a preliminary test, the susceptibility to immature tassel tissue was first tested for Ab. For this, a red fluorescent protein was transformed in vitro in immature tassel tissue, which was previously isolated from the plant. At the time of the isolation, the plants were in the V6-V7 stage, and the tassels were ca. 2-3 cm long. Ab was set to an OD600 of 1.0, and the tassels were incubated for 10 minutes with the Ab suspension. The red fluorescence was observed two days after the infection. Numerous red fluorescent points dots were observed in the tassels, confirming the suitability of Ab infiltration for the transformation of tassel tissue. In a next step, plants in the V6-V7 stage were used, and the plants were windowed, as desCRISPR bed above, in the region of the immature tassel tissue. Ab, which contain a red fluorescent expression construct, was injected directly into the tassel tissue in an OD of 0.7. Approximately 100-200 μl of the Ab suspension was injected into each tassel. The windowing sequence as well as the Ab injection sequence are shown in FIG. 24.

At this point, the tassels were covered with Vaseline/paraffin, as desCRISPR bed above, and the development of red fluorescence was monitored two days after the injection. In order to suppress an excessive growth of Ab, an antibiotic solution was applied to the infected tissue 2 to 7 days after the initial injection. The treated tassels were able to ripen to maturity, and self-pollination was carried out. Molecular analyses in the T1 generation confirm the successful transformation. It is thus confirmed that an in planta method is suitable for transforming meristematic cells in planta, without impairing the further development of the tassels, such that the resulting pollen can be obtained directly from the plant, without lengthy (in vitro) cultivation processes, and can be used directly for pollination.

Example 13: Applicability to Different Maize Genotypes

The tassel transformation experiments outlined above were tested for different maize genotypes, specifically A188, Va35 and A632. For each genotype, the vegetation stage in which the tassel tissue can be transformed is naturally different. This can, however, be easily determined. In A188, the stage is V6-V7, by way of example, while A632 was targeted in stages V7 to V9. It was possible in all of these genotypes to expose the tassels in a suitable manner, i.e. it was possible to window the plants without damaging them or the tassel tissue, and to obtain mature, pollen-producing anthers.

Example 14: Embryo Meristem Bombardment

In order to further optimize the methods desCRISPR bed herein, a so-called embryo meristem bombardment was established, which allows for plants to be efficiently obtained directly from immature embryos, without a time consuming and contamination-prone cell culture as an intermediate step. For this, the particle bombardment of meristem regions of embryos was carried out in the pipeline mode for the genotypes A188 and A632. Approximately 100 embryos (FIG. 25A) were bombarded with CRISPR SPR/Cas9 constructs, together with a plasmid expressing a red fluorescent protein. Fluorescent development was observed one day after the bombardment (FIG. 25 B). Numerous embryos demonstrated fluorescence, and thus the successful and functional introduction of the CRISPR construct. Work was continued with the successfully transformed embryos. After germination, 25% of the plants were analysed on the molecular level. All of the other fluorescent-positive plants were allowed to ripen to maturity in a greenhouse. As soon as the plants reached the reproductive stage, a sample was removed from the tassels, as well as the ears, and examined for CRISPR SPR/Cas9 activity. When a successful result was identified, by means of PCR, for example, the plants were used for self-pollination, and the resulting descendants were likewise analysed.

The plants produced in this manner produced seeds for both genotypes, and were fertile. The plants displayed a slower growth rate and a slightly curved growth (FIG. 25 C), although fertile plants could be produced through this method without difficulty, the pollen of which could be used directly in further experiments. This type of transformation is thus also a highly efficient method for quickly and effectively introducing CRISPR constructs, or the genome editing obtained therefrom, in a meristematic tissue or a cell of interest, and to then be able to directly obtain and further use reproductive tissue from this tissue.

Example 15: Meristem Access in Different Types of Plants

As specified above, it is desirable to create an in planta transformation for numerous different plants, and to combine this with the methods disclosed herein, such that a targeted modification of numerous meristematic target structures can be obtained through the CRISPR systems. Specifically, the transient insertion of CRISPR constructs of interest into a plant meristematic target structure is of great interest, because this would allow for a targeted modification of a nucleic acid target region of interest, and this modification, but not the CRISPR construct itself, would then be passed on to further generations.

The tissues that can develop in planta to reproductive organs are limited. The most important thereof is the shoot meristem. This meristem is defined by the group of cells that can differentiate into all vegetative organs and cells, as well as reproductive organs and cells that are above ground. It is composed of a limited number of cells that can be (re) programmed, in order differentiate themselves into all of the organs of a plant. This meristem normally has the shape of a dome. The outer lines of the cells, called the L1 layer, form the basis for all epidermal tissue. The inner layers (L2 and L3) of the meristem form the rest of the organs, and are thus interesting targets for the purposes of the present invention. The meristem is formed very early in the development of the embryo. After the vegetative growth, the meristem develops in the flower meristem in order to generate the reproductive organs of the plant. The tissues that can produce the modified reproductive organs are: (1) the shoot meristem of the embryo, (2) the shoot meristem of plantlets or plants in the vegetative stage, and (3) the flower meristems or the inflorescences.

When the genetic information of this tissue is modified by non-viral approaches (gene guns, microinjections, *Agrobacterium*, etc.) it may be the case that not all of the cells of these meristems are modified in a targeted manner. Consequently, some of the differentiating plant organs are modified, and some retain the wild genotype. Chimeras are obtained in this manner.

One alternative for the targeted manipulation of numerous different grain plants is to transform microspores (immature pollen) or pollen grains. These tissues can then be used to pollinate further plants and obtain modified descendants. There are only a few examples in the reference sources, most of which are in the context of bombardment and transient expression analysis of the inserted genes (Twell et al., 1989, Obert et al., 2008). Nevertheless, the technology has been further developed for allowing microspores or pollen to ripen in a targeted manner, and to obtain modified descendants through subsequent pollination. The methods for these technologies are very similar for various crop plants. Microspores can be targeted directly into immature anthers, or by releasing microspores into a culture medium. This targeting can take place, for example, through bombardment or microinjections. This technique has been used successfully for producing transgenic tobacco plants (Touraev et al., 1997) and cotton (Gounaris et al., 2005). As with the targeting of mature pollen, recently obtained pollen can be treated through bombardment, or sonically (Eapen (2011)), and used immediately for the pollination of, e.g., maize ears (Horikawa et al., 1997). The descendants can then be analysed for the presence of transgenes or genomic events introduced in a targeted manner.

*Beta vulgaris:*

Immature embryos may be obtained, as desCRISPR bed in Zhang et al. (2008), for the transformation of meristematic tissues in sugar beets. Flower spikes were obtained from plants grown in a greenhouse, 14 days after anthesis. They were sterilized in a 30% bleaching agent for 30 minutes. Immature embryos (IEs) were isolated, and subsequently cultivated for 4 weeks on a solid MS medium that has various plant growth regulators. An image of such an immature embryo is shown in FIG. 26. The apical shoot meristems can be treated in a targeted manner, directly in these immature embryos, wherein a targeted activation of the meristem regions can be obtained with the aid of a microscope. Alternatively, random targeting technologies, such as bombardment, can be implemented. The plants continue to mature after the targeting. This embryo maturation takes place in an incubator, in the dark, at a temperature of ca. 20°-30° C. The maturation period lasts approximately 1 to 4 weeks. As soon as the embryo has reached maturity and begins to germinate, it is transferred to a solid MS medium and exposed to light, so that the plantlet can develop. When these plantlets are robust enough, they are transferred into soil, after an acclimation phase of ca. 1 to 4 weeks. These plants are then cultivated and the descendants are analysed.

The targeting of mature embryos from sugar beets requires the removal of the hard seed involucre (Hermann et al., 2007). The embryo is located in the middle and the apical shoot meristem is accessible. Prior to removal of the pericarp, the seed must be sterilized by bleaching in ethanol. The pericarp can then be removed with scalpels or other sharp tools, and the embryo is exposed. This embryo is then placed in a suitable medium for the specific methods for the transformation of interest. The meristem of the mature embryo, or the entire embryo, can then be subjected directly, with the use of a microscope, to a transformation that randomly activates meristem regions. After a resting phase of ca. 1 to 10 days in an incubator, in the dark, at 20°-30° C., the embryo germinates, and the plantlets can be planted. The sugar beet plants are then grown to maturity, and the descendants are analysed.

The shoot meristems in sugar beet shoots can be targeted through targeted incisions in meristem regions (Artschwager, 1926). For this, these types of shoot meristems were already targeted, e.g., through particle bombardment. Particle penetration tests were carried out prior to checking the gene expression. Transient GUS expressions were detected in the first and second cell layers of the meristem. Dividing cells with GUS activity showed that the cells survived the bombardment (Mahn et al., 1995). It was also proposed that meristems with attenuated *Agrobacterium* strains could be used for *Beta vulgaris* transformation (Kerns et al., 1988). Different methods (microinjection, *Agrobacterium*) and different plant tissues in different development stages could be used thereby. For the purposes of the present invention, a bombardment of meristematic tissues from seedlings that reproduced in vitro was carried out. The leaf material was removed, until the meristematic tissue was exposed. Vertical incisions were then made in the meristematic regions, or the regions were provided vertically, without an incision. After the bombardment with a gene cannon, the explants were left in vitro. One day after the bombardment of the cells, it was shown that the cells displayed beta-glucuronidase activity, which was introduced as a marker into the cells, confirming that meristematic regions of sugar beets are suitable for particle bombardment and thus for the insertion of genome editing tools, e.g. CRISPR tools.

In addition, the inflorescence of sugar beets can also be modified in a targeted manner, during maturation, either prior to flowering, or directly in the immature flowers. The flowers can then continue to mature, and after pollination, the seeds are harvested, and the descendants are analysed. In *Beta vulgaris*, the inflorescence is composed of an open main axis that has numerous closed, dichasial and sympodial branched inflorescences. The end flower of each inflorescence unit, and lateral flowers, merge at a later developmental stage. The five stamen primordial come from one another, and they occur in the course of flower development through the formation of an (intra) staminal ring from an annular intercalating meristem (Olvera et al., 2008).

*Triticum aestivum:*

Another approach has been developed for wheat used as the target plant. For this, immature kernels from immature spikes were collected 5 to 20 days after flowering. These kernels were sterilized through surface treatments with bleaching agents and ethanol. The immature embryos were then extracted with a scalpel under a microscope. These embryos displayed meristems exposed to different extents. These meristems were then subjected to various transformation methods, such as desCRISPR bed in Sautter et al. (1995). FIGS. 27 A and B show images thereof. After the embryos were treated thus, they were further cultivated, specifically in an embryo cultivation medium, as desCRISPR bed in Matthys-Rochon et al. (1998). The germinating plantlets (FIG. 27 C) were then transferred to the greenhouse, after acclimation. The plants were cultivated in the normal manner, and the descendants were subsequently analysed.

The shoot meristem in wheat can likewise be targeted for modification, as desCRISPR bed in Sautter et al., 1995. For this, seeds were sterilized and washed for the production of vegetative shoot apical meristems through soaking in 70% ethanol for 2 minutes, followed by a sodium hypochlorite treatment and four rinsings in water. The sterile seeds were then sown in test tubes on an MS medium, supplemented with 100 mg/l cefotaxime, 2% sucrose, and 0.8% Difco agar. Shoot apical meristems from 6-10 day old plants were subsequently exposed through the removal of the coleoptiles and the first three to five leaves. Roots were then trimmed to approximately 5 mm. The explants were then supplemented with different sucrose concentrations (optimum: 10%) and placed on an MS base medium (0.8% agarose). Following particle bombardment, the explants were then transferred to a further culture on MS agarose.

Moreover, the flower organs can also be targeted in wheat. The shoot meristem differentiates itself very early in the development to immature spikes, or shoots, a few weeks after seeding. These immature spikes can be found on the bottom of the shaft (see FIG. 28, left-hand image). A window is formed in these immature spikes through an incision in the shoot. The meristematic tissues can be reached through this window with various transformation techniques. After the transformation, the wound is closed, and the transformed system is further cultivated until the seeds reach maturity (see FIG. 28, middle, left- and right-hand image), and the descendants are subsequently analysed. Alternatively, the immature spikelets are removed from the inflorescence, sterilized in vitro, and detached in a targeted manner. The maturation and seed production can then be carried out in vitro, on the basis of Barnabas et al., 1992.

It has furthermore been shown for wheat that it is possible to target immature inflorescence using a gene gun (Leduc et al., 1994, Sautter et al., 1995). It has been shown that after the bombardment, the cells in the tissue treated in this manner express inserted reporter genes, and can continue to divide.

*Brassica napus:*

It has also been shown for rapeseed that the shoot apical meristem has already developed in the so-called "heart stage." A transformation process for rapeseed in this stage that can also be used with the method disclosed herein is desCRISPR bed in Huang et al., 2009.

Moreover, when rapeseed is used as the target plant, the shoot meristem can be transformed in a targeted manner after germination, or when the plants have reached the 2-8 leaf stage. For this, the leaf primordials covering the meristem are carefully removed with a scalpel. The exposed meristems are then preferably treated with an antioxidant for their protection. Subsequently, the meristematic regions can be transformed by means of various transformation techniques. Here as well, the plants can subsequently be cultivated until the reproductive organs have reached maturity, and the descendants thereof can be analysed for the presence of the modification that has been introduced in a targeted manner.

Rapeseed flowers can also be targeted. The flowers in a rapeseed inflorescence are produced continuously. New flowers are produced on the tips of the flower clusters. Two approaches can be taken for the transformation of rapeseed flower organs. In the first approach, immature flowers can be opened in situ, and the reproductive tissues can be activated in a targeted manner. After the treatment, untreated inflorescence and husks are removed, and the inflorescence is then covered, in order to promote self-pollination. The seeds are harvested, and the descendants are analysed. In the second approach, all of the differentiated flowers are carefully removed from the flower clusters/panicles, and the flower meristem is left exposed. These meristems are then treated with various types of transformations. The meristems are then covered, in order to allow the normal development to continue. All of the husks/pods are harvested, and the descendants are tested in terms of their molecular biology and their phenotypes.

*Glycine max:*

For soya bean transformation, meristematic regions can likewise be activated in a targeted manner.

The shoot meristem from an embryo is exposed to light and transformed, as desCRISPR bed in McCabe (McCabe et al., 1988). For this, mature soya seeds (BR-16, Doko RC, BR-91 and Conquista) are subjected to a surface sterilization in 70% ethanol for 1 minute, followed by immersion in 1% sodium hypochlorite for 20 minutes, and then three rinsings in sterilized distilled water. The seeds are soaked in distilled water for 18-20 hours. The embryonic axes are cut out of the seeds, and the apical meristems are exposed by removing the primary leaves. The embryonic axes are placed in a bombardment medium (BM: MS (Murashige and Skoog, 1962) simple salt, 3% sucrose, and 0.8% Phytagel™ sigma, pH 5.7), the apical is oriented upward in 5 cm culture dishes with 12 ml culture medium. As soon as the shoots derived from the embryonic axes have reached a length of 2-3 cm, a 1 mm long section from the base of each leaf is removed for the GUS analysis (beta-blucuronidase) (McCabe et al., 1988). The shoots, or sprouts, that express the exogenous DNA are transferred individually into a plastic pot containing 0.2 l autoclaved, fertilized soil (vermiculite (1:1)), and then kept covered in a sealed manner with a plastic bag and rubber band in the greenhouse. The rubber band is removed after 1 week. After another week, the plastic bag is likewise removed. As soon as the acclimated plantlets have reached a length of about 10 cm, they are transferred into pots with 5 l of fertilized soil, until seeds start to develop (McCabe et al., 1988). As soon at the plantlets have grown, leaf samples are removed for analysis. The plants are then grown to maturity, in order to analyse the descendants thereof for targeted modification.

Alternatively, the meristems of the immature embryos are activated for a targeted transformation. For this, the pods are harvested 5 to 20 days after flowering, and the embryos are extracted with a scalpel and gripping tool between the heart and cotyledon stages. These embryos are placed on an embryo growth medium, and the shoot apical meristem is transformed in a targeted manner with various delivery/transformation methods. The embryos are then grown in the dark for 1 to 10 weeks, until reaching full maturity, as desCRISPR bed in Buchheim et al. (1989), and exposed to light for embryo germination. The plantlets grown in this manner are cultivated to maturity in a greenhouse. The seeds are harvested, and the descendants are analysed. The targeted introduction of recombinant constructs in the shoot meristems of the germinating soya bean plantlets is carried out as desCRISPR bed in Chee et al., 1989. Seeds from *Glycine max* L. Merr (Cv A0949) are sterilized by immersion for 15 minutes in a 15% Clorox solution, followed by numerous rinsings with sterilized distilled water. Seeds are place for 18 to 24 hours on sterilized, moistened paper towels in Petri dishes for germination, at 26° C. in darkness. The seed coverings are removed, and one of the two cotyledons of each germinated seed is removed, and the half-seeds, together with the shoot bud of the seedling (Plumula), the cotyledon nodes, and the neighbouring cotyledon tissue, are inoculated overnight with liquid cultures of an avirulent *Agrobacterium* line, C58Z707, which contains the binary plasmid pGA482G. *Agrobacterium* transformation can also be replaced by other introduction or transformation methods. Another approach is desCRISPR bed in Chowrira et al., 1995. The terminal buds of plantlets (7-10 days old) are exposed through removal of the surrounding leaf tissue. Foreign DNA is injected with a syringe, also containing lipofectin as a transfection agent, and the meristem is subsequently electroporated. The plants are grown to maturity without selection, and chimeric plants can subsequently be obtained in this manner. The descendants thereof are then analysed.

Access to the scars of the pollinated soya bean flowers is obtained as desCRISPR bed in Shou et al. (2002). In brief, all of the experiments were carried out in the late afternoon, with flowers that were naturally pollinated that same morning. Two petals and one keel petal were removed, in order to expose the stigmas/scars of soya bean flowers to light. Stigmas were severed at the border between the ovary and the stigma, and plasmid DNA (concentrations of 25, 80, 100 or 150 μg/ml) was applied to the exposed scar. The treated flowers were tagged, and untreated flowers and buds on the same node were removed. The shoots that form on the treated flowers were harvested individually. Alternatively, the soya bean inflorescence flower meristem could be transformed in a targeted manner, before it reached the end stage, in that the primordial were removed when the flowers start to develop further. This exposition is obtained through excision of the primordial with a scalpel. The flower meristem is covered as soon as it is transformed. After inflorescence can develop, and self-pollination has begun, the shoots of the treated plants can be harvested, the seeds processed, and the descendants can be tested for the targeted genomic modification.

*Gossypium* sp.:

Experiments according to the present invention for inserting a targeted modification of interest could be carried out for cotton, in that the meristems from embryos were treated as desCRISPR bed in Aragão et al. (2005). For this, seeds (variation 7mH, CD-401, Antares and ITA94) were harvested by hand, and fibrous material is removed with an acid treatment. Concentrated sulphuric acid was added, and the seeds (3 ml/g seeds) were stirred thoroughly for 1 minute with a glass rod. The seeds were then transferred immediately into 5 l water, rinsed three times with distilled water, and dried on a paper towel. Mature seeds were surface-sterilized with 70% ethanol for 10 minutes, followed by 1 minute treatment in 2.5% calcium hypochlorite, and rinsed three times in sterilized distilled water. The seeds were then soaked in distilled water for 24 hours, upon which the seeds were able to germinate for 16 hours at room temperature in darkness. Embryonic axes were cut out of seeds, and apical meristems were exposed by removal of the cotyledons. Explants were transferred to an MS medium, containing 3% glucose (5 mg/l benzylaminopurine (BAP), 0.8% Phytagel (Sigma)). The pH value was set to 5.7 for the autoclaving. Embryonic axes were produced as desCRISPR bed above, and positioned in a bombardment medium (MS simple salt medium, 3% glucose, 5 mg/l BAP, and 0.8% Phytagel Sigma, pH 5.7), apical at the top, in 5 cm culture dishes with 12 ml culture medium. At this point, the meristems could be transformed or transfected. The treated apical meristems were cultivated in darkness. The meristems exhibiting growth were transferred to a growth chamber. The plantlets were then transferred to a greenhouse and cultivated to maturity. The descendants were then analysed.

Alternatively, embryo meristems are transformed, as desCRISPR bed in Rajasekaran (2013).

In another approach, immature embryo meristems were targeted in vitro, according to the protocol desCRISPR bed by Mauney (1961). The culture medium that was used was composed of White's nutrient mixture, with all of its ingredients, plus five times the normal concentration of supplements (40 mg/l adenine sulphate, 250 mg/l casein hydrolysate, 150 ml/l coconut milk, and 7 g/l NaCl). The medium was stiffened with 8 g/l bacto-agar, and 20 g/l sucrose as a carbohydrate source. The most important feature of this medium for the success of the cultivation method was the adjustment of the osmotic pressure to a high level, which can be achieved through the addition of 7 g/l NaCl. After the embryos grew on this medium for 3-4 weeks, they were transferred to a medium with a medium osmotic pressure (3 g/l NaCl, instead of the 7 g/l), and then into a medium without NaCl after a further growth period of 2 weeks. The successfully cultivated embryos in the last medium germinated, and were planted in soil.

In order to transform shoot meristems in cotton plantlets, meristems were transformed in a first approach desCRISPR bed in Zapata et al. (1999). Seeds were surface-sterilized with concentrated sulphuric acid (1 hour) at 50 rpm in a rotational shaker (50% Clorox (1 hour)), and rinsed at least three times with sterilized, doubly-distilled water. The seeds were then placed on a medium solidified with 0.15% (mass/volume) Gelrite, pH 5.7, which contains the inorganic salt from Murashige and Skoog (MS) (Murashige and Skoog, 1962), and 2% sucrose, for germination. The seeds were incubated for about 3-4 days at 28° C., in the dark. The shoot tips were isolated, and then transferred into MS inorganic salts (Murashige and Skoog, 1962), with 100 mg/l myo-inositol, 0.5 mg/l thiamine/HCl, 0.5 mg/l nicotinic acid, 0.5 mg/l pyridoxine/HCl, 3% sucrose, and 0.15% (mass/volume) Gelrite, at pH 5.7. After isolation, the delivery of a recombinant construct of interest could be carried out, and the plant material could subsequently be transferred to a new medium. The vital transformed apices were transferred to a fresh medium. The surviving apices were then transferred to the same medium, but without kanamycin. As soon as roots started to develop, the plants with roots (T0) were transferred to soil, and allowed to grow to maturity in a greenhouse. The descendants could then be analysed.

Alternatively, the cotton meristems were transformed as desCRISPR bed in Keshamma et al. (2008). For this, seeds from a strain, viz. NC-71, were soaked overnight in distilled water, and the surface was sterilized, first with 1% Bavistin for 10 minutes, and then with 0.1% $HgCl_2$ for a few seconds, and subsequently washed thoroughly with distilled water. The seeds were able to germinate later at 30° C. in darkness on Petri dishes. Two day old seedlings were used as explants. The seedlings with straight plumula/shoot buds were infected, in that they were separated from the cotyledons, without damaging them, such that the meristem was visible. A transfection or transformation method of interest could then be used. The seedlings were subsequently transferred to autoclaved Soilrite (Vermiculite equivalent), watered, and covered for germination under aseptic conditions in a growth chamber, 5 seedlings per pot. After 5 to 6 days, the seedlings were transferred into pots with Soilrite, and allowed to grow for at least 10 days before they were transferred to the greenhouse. The mature plants could then be analysed.

In another approach, cotton meristems were transformed according to the protocol desCRISPR bed in McCabe et al. (1993).

In yet another approach, cotton flowers could be transformed in a targeted manner according to the method from Gounaris et al. (2005). For this, cotton plants of the Christina type were used for the transformation. Flowers that were to be used as pollen receptors had to be separated from male plants two days prior to the expected dehiscence. On the morning of the pollination day, donor flowers with intact stamina were collected 1-2 hours after blooming. Each donor flower could then be treated with a transformation or transfection method of interest. These inflorescences were used for further pollination of receptor flowers (after prior removal of the male germ cell). The pollinated flowers could continue to develop and produce seeds. The descendants could then be analysed in terms of molecular biology. In another approach, flower meristems or immature flowers could be genetically modified in a targeted manner. For this, the meristem forming the flowering branch, the flower bud, and the immature flower were exposed by removing the primordials and floral bracts. A delivery method (transformation/transfection, biological, chemical or mechanical) of interest could then be used according to the present disclosure. Subsequently the treated zones were covered, and allowed to continue to grow. The flowers were then harvested. The descendants could be analysed with regard to their molecular biology, as well as their phenotypes.

*Oryza sativa:*

If the target plant of interest is rice, the following methods could be used for introducing a targeted genomic modification in a meristematic target structure.

According to the methods from Naseri et al., 2014, rice seeds (*O. sativa*, Hashimi) were sterilized through soaking in 90% ethanol (1 minute), and washed three times with water. Sterile seeds were placed on wet cotton for two days at 22° C. The inoculation with *A. tumefaciens* took place in embryonic apical meristems of the saturated seeds, on the surface of the seed where a shoot would later develop. The surface was penetrated to a depth of approximately 1 to 1.5 mm with a needle (Ø 0.7 mm, previously immersed in *A. tumefaciens* inoculum) The inoculated seeds were then covered with aluminium foil in bottles, placed on filter paper on wet perlite, and incubated for nine days at 23° C. in darkness. 70% to 75% of the inoculated seeds germinated. In order to kill off *A. tumefaciens*, the seedlings were immersed at room temperature in an aqueous solution (1000 ppm) of cefotaxime for 1 hour. For root formation, the seedlings were placed in a Yoshida solution. Lastly, the seedlings were planted in pots, and grown to maturity (T0) under unsterilized conditions. This enabled self-pollination, and thus the production of a T1 generation.

In another approach, the meristems of immature embryos were activated for a targeted modification with the CRISPR tools disclosed herein. Immature seeds were harvested 3-12 days after pollination. The immature embryos were placed in a maturation medium (Ko et al., 1983), and the transformation/transfection methods of interest could then be used. The embryos were raised to maturity, as desCRISPR bed in Ko et al. (1983). The seeds were harvested, and the descendants analysed in terms of their molecular biology.

Meristems from rice plants were treated as desCRISPR bed in Muniz de Pèadua et al. (2001). For this, rice seeds were surface sterilized and brought to germination in vitro. After ca. 4 days, the shoot apices were excised from the distal part of the first internode of the epicotyl, and the coleoptile. After exposition, a delivery system of interest could be used. This enabled root formation. The plants were then transferred to the greenhouse, and further cultivated, and the descendants were subsequently analysed.

Immature rice spikes were treated for the targeting of flower organs as desCRISPR bed in Rodin et al. (2014). The inflorescence were used in stage 51 (start of panicle development: tips of the inflorescence protrude out of the pod) in accordance with the BBCH scale (Lancashire et al., 1991), and could then be treated, and the descendants could be subsequently analysed. Moreover, the flower meristems could be activated. For this, the meristems had to be exposed by removing the surrounding tissue, and subsequently transformed and further cultivated, and the descendants were subsequently analysed. Furthermore, the immature spikes could be treated, either before differentiation, or after the surrounding primordials were removed, through transformation or transfection. The treated spikes could then continue to develop. The resulting seeds of these flowers were harvested, and the descendants were examined for targeted editing events (Itoh et al., 2005).

Example 16: Transient Transformation Methods

In particular for in planta transformation of meristematic tissue, there is a large interest in creating transient transformation methods, in particular for the introduction of CRISPR tools of interest, because as a result, only the targeted modification that is to be introduced, and not the tool itself, can be passed on to the descendants of a cell. Methods that are controlled and can be controlled in this manner have become increasingly important in the field of plant breeding, due to the regulatory provisions and contingent on safety concerns.

Transformation methods, both transient and stable, must, as a matter of course, be adapted to the tissue that is to be transformed. For this reason, the following experiments were carried out, which can be used, in part broadly and in general, and in part for specific tissues (pollen, meristems, flowers, etc.).

Cas9:

Cas9 was obtained from New England Biolabs (NEB), PNA BIO, ToolGen, LDBIOPHARMA or ABM, or Cas9 was purified, as desCRISPR bed in Liu et al. (2015).

In vitro transCRISPR ption of sgRNAs:

The in vitro transCRISPR ption was carried out as desCRISPR bed by Zuris et al. (2015). Linear DNA fragments containing a T7 promoter bonding site followed by the 20 bp sgRNA target sequence were transCRISPR bed in vitro using the T7 RNA High Yield Synthesis kit (NEB) in accordance with the directions by the manufacture. RNA, transCRISPR bed in vitro, was precipitated with ethanol, and purified by gel electrophoresis on a 10% polyacrylamide CRISPR terion TBE urea gel (Bio-Rad). Excised gel fragments were extracted in 420 μl 300 mM NaCl overnight, on a shaker surface at 4° C. Gel-purified sgRNA was precipitated with ethanol, and dissolved in water, and the sgRNA concentration was then quantified through UV absorption. The sgRNA could then be snap-frozen and stored at −80° C. Alternatively, gRNAs were obtained as desCRISPR bed in Kim et al. (2014). For this, RNA was transCRISPR bed in vitro through a T7-RNA-polymerase run-off reaction, using the MEGAshortsCRISPR pt T7 kit (Ambion). Templates for sgRNA or crRNA were generated through accumulation and extension of two complementary oligonucleotides. The transCRISPR bed RNA was purified through phenol-chloroform extraction, chloroform extraction, and ethanol precipitation. The purified RNA was quantified through spectrometry.

Alternatively, another protocol (desCRISPR bed in Ramakrishna et al., 2014) could be carried out. For this, the RNA was transCRISPR bed in vitro, through run-off reactions through the T7-RNA polymerase. Templates for the sgRNA transCRISPR ption were generated through annealing/hybridisation and extension of two complementary oligonucleotides. The transCRISPR bed RNA was separated on a 8% denatured urea-PAGE gel. The RNA was received in nuclease-free water, and subsequently purified and obtained through phenol-chloroform extraction, chloroform extraction, and ethanol precipitation. The purified RNA was quantified through spectrometry.

Complexation Protein Cas9 and gRNA:

As desCRISPR bed in Zuris et al. (2015), 1 μl 200 μM Cas9 protein was mixed with 2 μl 50 μM sgRNA and incubated for 5 minutes at room temperature for the introduction of Cas9-sgRNA complexes, prior to mixing the complex with 3 μl of either RNAiMAX or Lipofectamine 2000, and incubated for a further 30 minutes, prior to the injection. Alternatively, the complexation is carried out as desCRISPR bed in Kim et al., 2014. For this, Cas9 protein (4.5-45 mg) was pre-mixed with in vitro-transCRISPR bed sgRNA (6-60 mg). Cas0 protein in a storage buffer (20 mM HEPES, pH 7.5, 150 mM KCl, 1 mM DTT, and 10% glycerine) were dissolved with sgRNA in nuclease-free water, mixed, and incubated for 10 minutes at room temperature.

*Agrobacterium* (Ab)

Pollen Transformation with Ab:

The pollen transformation was carried out as desCRISPR bed in Li et al. (2004). For this, flowers with freshly developed and exposed anthers were collected. An aliquot of an Ab solution was transferred into sterilized 1.5 ml test tubes, and centrifuged for 10 minutes at 3,000 rpm. The pellet was re-suspended (in pollen germination medium, with ca. 50 mg pollen/ml) and a vacuum (−80 Pa) was applied for 30 minutes, and then slowly released. The suspension was subsequently centrifuged at 3,000 rpm for 5 minutes, and the pellets, i.e. the pollen, were used directly for pollination.

Shoot Apical Meristem Transformation with Ab:

Meristems from seedlings were transformed on the basis of the protocol from Chee et al., 1989. Inoculations were carried out at three different sites, in that a 30'/2 gauge needle was inserted into the plumule, cotyledon nodes and adjacent regions, and 30 ml of the Ab cells were injected at each injection point. The germination process of the seeds infected with Ab was continued in that the seeds were transferred to sterilized moist paper and further incubated at 28° C. (in darkness for about 4 hours). For full development, the seedlings were then planted in the ground. Alternatively, the protocol desCRISPR bed in Keshamma et al. (2008) can be used. The seedlings were then infected, as soon as the plumule exists, by separating the cotyledons, without destroying them, such that the meristem is visible. The meristems were then pierced, and then dipped in an *Agrobacterium* culture for 60 minutes. After the infection, the seedlings were washed briefly with sterilized water, and later placed on autoclaved Soilrite.

Particle Bombardment:

Bombardment, or bombarding, of embryo meristems was carried out as follows: embryos in the coleoptile stage, or the heart stage, were placed in in embryo maturation medium supplemented with osmoticum 0-6 hours prior to the bombardment. The particle processing and preparation was carried out according to a routine DNA precipitation with spermidine. With protein/RNA mixtures, the protocol from Martin-Ortigosa et al. (2014) was carried out, wherein the mixture was dried or freeze-dried, together with the gold particles. 16-24 hours after the bombardment, the embryos were placed on a ripening medium without osmoticum.

Bombardment of Anthers:

Bombardment of anthers can be carried out in accordance with Twell et al., 1989. For this, 1d plant anthers were surface-sterilized prior to releasing pollen in 10% Clorox for 10 minutes, and rinsed in sterilized distilled water. The anthers were sliced transversely with a sterilized razor blade, and 20 anther sections were placed on solid MSO medium with a surface area of 4 $cm^2$, with exposed thecae. In another approach, anthers were bombarded, as desCRISPR bed in Obert (Obert et al., 2008). For this, spikes/anthers were harvested as soon as the microspores were in a middle mononuclear development stage. Two different pre-treatments were used in our studies, together with the use of untreated material. For a cold treatment, the plant material was placed on a moist filter paper in a cold room at 5° C. (Dedicova et al., 1999). After the pre-treatment of the material (14 days in cold storage), the specific portions of the spikes that contain microspores were selected in exactly the suitable stage, and used as further experimental material. The material is surface-sterilized (in 70% (vol./vol.) alcohol), and washed three times with sterilized distilled water. For the mannitol pre-treatment, suitable portions of the fresh spikes containing microspores in the correct stage were surface-sterilized (in 70% alcohol) and washed three times with sterilized distilled water. The anthers were isolated in sterile conditions, or placed on the surface of a cultivation medium (FHG media, Kasha et al., 2001) after pre-treatment. The bombardment conditions were: distance (macro-carrier-anthers in Petri dishes): 9 cm; pressure settings of 650, 900 and 1,100 psi. Anther cultures were then cultivated at 26° C. in darkness, in a tissue culture growth chamber.

In another approach, (Touraev et al. (1997)), single-cell microspores and pollen grains in a middle bi-cellular stage were bombarded in the respective culture media immediately after isolation. The suspension (0.7 ml), containing ca. $5 \times 10^5$ cells, was evenly spread on a sterile filter paper (Whatman No. 1), and transferred into a 10 cm Petri dish (Sterilin, Great Britain). The helium-driven PDS-1000/He particle discharge system (Bio-Rad, USA) was used for the biolistic transformation. The bombardment was substantially carried out as desCRISPR bed in Sanfor et al. (1993). Plasmid DNA was precipitated onto gold particles (Bio-Rad, USA), having a mean diameter of 1.1 μm. Each transformation comprised three bombardments. The bombarded microspores, or mid-bi-cellular pollen grains, were washed off of the filter paper, and incubated in a separate ripening medium.

Bombardment of Flowers:

On the basis of a protocol from Twell et al., 1989, groups of 10 flowers with intact curved petals were bombarded, wherein the truncated pedicels were suspended in distilled water.

Bombardment of Pollen:

On the basis of a protocol from Twell et al., 1989, pollen from mature flowers was collected in sterilized micro-centrifuge test tubes. Prior to bombardment, dried pollen samples were suspended in a liquid MSO medium with a density of approx. 106 grains/ml. The pollen suspension (1 ml) was immediately pipetted onto the surface of a 9 cm Petri dish, containing an MSO medium thickened with agar, on which a sterile Whatman no. 1 filter paper with a nylon membrane (Genescreen, NEN) was previously placed. The bombardment was carried out within 60 minutes after the plant material was transferred to the MSO medium. The precipitation of plasmid DNA onto tungsten micro-projectiles and the bombardment took place as desCRISPR bed in Klein et al. After bombardment, the Petri dishes or intact flowers were incubated in distilled water at 26° C., in light.

In another approach, pollen bombardment was carried out as desCRISPR bed in Horikawa et al. (1997). For this, mature pollen grains were collected from extruded tassels. The subsequent bombardment preparation steps were carried out very quickly, because the life expectancy of the pollen decreases quickly. The pollen was immersed in a liquid MS medium containing 30 g/l sucrose (pH 5.8). The $4.0\times10^5$ pollen grains (in 1 ml medium) were adsorbed on the surface of a piece of microfilter (pore size 0.45 μm, Fuji Film Co., Tokyo) through vacuum filtration. The microfilter was placed on 1% agar plates in a Petri dish in preparation for the bombardment with a particle cannon.

Pollination with the Treated Pollen:

For the pollination with the bombarded pollen, the protocol desCRISPR bed in Touraev et al., 1997, was carried out. For this, mature flowers were emasculated shortly before flowering, while they still had closed anthers, one day prior to pollination. The pollen that matured in vitro was washed repeatedly in a GK medium without quercetin, and then transferred to scar tissue in droplets of 3 μl. Those scars that display a good scar secretion production were selected for the pipette pollination. To prevent cross-pollination, all of the other flower buds in the climate chamber were removed one day before opening. Mature seed capsules or pods were collected 3-4 weeks later.

In another approach, the method desCRISPR bed in Horikawa et al. (1997) is used. For this, pollen was placed in 1 ml liquid MS medium. The pollen was used immediately for pollination by pipetting it onto the threads of a spike (previously covered with spike sacs), three days after thread development. The pollination treatments were carried out on 20 spikes. As control, pollen was pollinated by a sample without DNA.

Bombardment of Flowers with HELIOS:

The bombardment of flowers or inflorescence was carried out with the hand pistol "Helios" from Bio-Rad, according to the manufacture's instructions. As soon as the inflorescence or the flowers were exposed, they were bombarded with 1 to 5 shots at 50-300 psi. The exposed meristems were then covered and the inflorescence, or the flowers, were able to continue ripening.

In another approach, the protocol desCRISPR bed by Gounaris et al., 2005, was carried out. Flowers that are to serve as pollen receptors were emasculated two days prior to the expected pollination. On the morning of the pollination day, intact stamens were collected from the donor flowers 1-2 hours after opening. Each of the donor flowers was treated with 4-5 shots from the particle cannon while they lay on a flat surface in a Petri dish, covered with a nylon net. The particle cannon was operated with a helium pressure of 400 psi, and was equipped with a particle diffusion screen. The helium gas purity was class 4.5 (99.994%). Each bombarded inflorescence was used to pollinate ca. 15-20 emasculated receptor flowers. The pollinated flowers were able to continue developing, and thus produce seeds.

Microinjection: DNA/RNA/Protein and Combinations

Embryo Microinjection:

The method desCRISPR bed in Neuhaus et al., 1987, was used for the embryo microinjection. For this, embryos positioned on a cover glass were individually selected visually using a manual micro-capillary, connected to a silicone tube, and transferred into a medium on a object carrier in ca. 2 μl droplets for the microinjection (Spangenberg et al., 1986). The microinjection was carried out in that the embryoid bodies were secured in place with a retention capillary, and microinjected into the respective cells. Exogenous DNA was injected as a 1:1 mixture of lineated (through cleaving the plasmids outside the inserted genes) and super-coiled molecules, in a quantity of ca. 0.5 μg/μl in 50 mM NaCl, 50 mM tris-HCl, pH 7.8.

Microinjection of Shoot Meristems with *Agrobacterium* (Ab):

Shoot meristem microinjection with Ab was carried out as desCRISPR bed by Sivakumar et al. (2014). 100 μl of the culture was microinjected with an insulin syringe into the embryonic shoot apical meristems of germinated cotton seeds. The culture was microinjected 1-5 times (0.5-1.0 mm depth), in order to check the effect of the number of microinjections in and around the embryonic shoot apical meristem. Excess bacteria culture was removed after dabbing the infected seeds on sterilized filter paper (Whatman no. 1). The seeds were co-cultivated in darkness for two days on a ½ strength MS medium. After the co-cultivation, the seedlings were washed with cefotaxime (200 mg/l), and transferred into an antibiotic selection medium, containing cefotaxime and hygromycin B.

Microinjection of DNA in Shoot Meristems:

The microinjection was carried out as desCRISPR bed in Lusardi et al., (1994). Mature, dried seeds were washed for 30 seconds with absolute ethanol, followed by sterilization with commercial bleach (2.5% NaClO), supplemented with 0.01% Tween 80 (20 minutes while shaking). The seeds were then rinsed four to five times with sterilized distilled water. The germination was induced by incubating the seeds in a 9 cm Petri dish between filter papers with sterilized distilled water at 27° C. in the dark for 3-4 days. During this time, the shoot passed through nucleus integument and reached a length of ca. 0.8 to 1.0 cm. At this point, the shoot was removed from the seed at the scutellar node level. The coleoptile and the five or six embryonic cotyledons were removed under a stereomicroscope. After the embryonic leaves were prepared, the uncovered apices, surrounded by two leaf layers, were exposed in various stages of development. The isolated apices were cultivated in 9 cm Petri dishes in an MS medium (Murashige and Skoog, 1962), supplemented with 2% sucrose and thickened with 0.8% Difco Bacto-Agar (Difco Lab. Detroit), and grown further with a 27° C./22° C. temperature regimen and a 16/8 hour light/dark lighting schedule. Normal plants developed within 10 days. Over the next 15-20 days, they reached a sufficient size for transferring into pots, and were placed in the greenhouse. For the microinjection, the plasmids for the injection were dissolved in injection buffer (10 mM Tris-HCl and 0.1 M EDTA, pH 7.5). The injection buffer was filtered through a 0.2 μm disposable filter unit (Schleicher and Schuell, Germany), in order to sterilize the solution and prevent particle contamination. All of the injections were carried out under sterile conditions. The isolated shoot meristems from maize were transferred into 9 cm Petri dishes, the MS medium was supplemented with 2% sucrose, and thickened with 0.8% Difco Bacto Agar. The apices were oriented on the medium such that the apical domes were clearly visible. The cells of the L2 layers of the meristems were injected with a (high power) stereomicroscope (up to 200× enlargement; SV 8, Zeiss, Germany) equipped with an embryo splitter system from Research Instruments (UK). In some experiments, a co-injection of FITC dextran was used in order to better identify the injected cells (Neuhaus et al., 1993; Schnorf et al., 1991). An injection capillary (tip diameter of less than 1 μm) was mounted on the mechanical micromanipulator of the system, which was connected to a microinjector (Eppendorf 5242 microinjector), which delivered approximately 3 μl into the cells at a constant volume (Neuhaus et al., 1986, 1987; Schnorf et al., 1991). The second manipulator of the embryo splitter system was used to stabilize and move the apices during the injection. The manipulator was also equipped with a micro-needle for this, in order to be able to move and secure the apical meristems, such that they could be treated in the correct position.

Whiskers

Delivery by whiskers in the various meristems was carried out as desCRISPR bed in Frame et al. (1994). The exposed tissue was treated with 40 μl 5% whisker suspension in 25 μl of plasmid DNA. The contents of the reaction vessel were first lightly stirred, and then placed either upright in a multi-sample head on a Vortex Genie II vortex mixer (Scientific Industries Inc., Bohemia, NY), or horizontally in the retainer of a Mixomat amalgam mixer (Degussa Canada Ltd. Burlington, Ontario). The transformation was carried out for 60 seconds by mixing at full speed (Vortex Genie II), or at a fixed speed for 1 second (Mixomat).

Alternatively, whiskers were loaded, together with DNA/RNA or protein mix whiskers, into the pipette of a micromanipulator, and then macroinjected into meristematic tissue.

Cell Penetrating Peptides: DNA/RNA/Protein and Combinations Thereof

Mixing Cell Penetrating Peptides and Cas9 Protein and gRNA:

A protocol on the basis of Ramakrishna et al., 2014, was used for the use of cell penetrating peptides. One day after plating, the cells were washed with Opti-MEM and with Ca9-M9R and sgRNA: 9R, either successively or simultaneously. The sgRNA: 9R complex was formed during a 30 minute incubation of 10 mg sgRNA and 30-50 mg 9R peptide in 250 ml (for the sequential treatment) or 100 ml (for the simultaneous treatment) of Opti-MEM medium at room temperature.

Embryo:

TAT peptides (Tat, Tat2, M-Tat) were used for introducing GUS enzymes into wheat embryos. The TAT peptide and GUS enzyme are first prepared in separate micro-centrifuge test tubes. An unmarked TAT peptide (4 μg) was added to sterilized water (end volume: 100 μl). Likewise, 1 μg of the GUS enzyme (Sigma Aldrich) was added to sterilized water, to obtain an end volume of 100 μl. The contents of the two test tubes were mixed together, resulting in a 4:1 ratio of peptide to protein in the mixture. The mixture was incubated for 1 hour at room temperature, and then added to the isolated, immature embryos (in a 2 ml micro-centrifuge test tube) in the presence or absence of the permeating agent (tuluol/ethanol 1:40, vol./vol. with respect to the overall volume of the peptide/protein mixture). After 1 hour incubation at room temperature, the embryos were washed twice with the buffer, and subjected to a permeability and trypsin treatment (1:1 (vol./vol.) permeability buffer) for 5 minutes at room temperature. The embryos were washed twice with permeability buffer, followed by a histochemical GUS analysis of the embryos. 1 μg of the GUS enzyme is transfected for the delivery by the Chariot Protein Transduction kit (Active Motif, Carlsbad, CA, USA), according to the manufacturer's instructions. Permeable and non-permeable embryos were incubated for 1 hour with the chariot-GUS complex. All of the post-incubation steps were the same as those desCRISPR bed for the TAT peptides.

Transformation of Microspores:

The transformation of microspores using cell-penetrating peptides was carried out in accordance with Shim et al. (2012). The extraction of microspores was carried out in accordance with Eudes and Amundsen (2005), and all of the steps for isolating microspores were carried out using the NPB-99 liquid medium (Zheng et al., 2001; Eudes and Amundsen, 2005). After washing the microspores with NPB-99, 2-3 ml microspore solution were layered onto 2 to 3 ml 30% Percoll solution, containing 400 mM mannitol and 10 mM MES, pH 7.0. The microspores were centrifuged for 5 minutes at 100× g, at 4° C. The cells that formed a band at the Percoll/NPB-99 cleavage site were diluted to 15 ml in a fresh 15 ml centrifuge test tube with NPB-99, and then centrifuged again. The precipitation was decanted off, and the microspores were re-suspended in approximately 1 ml NPB-99 medium. The microspore concentration was determined using a hemocytometer, and adjusted to $2.5\times10^5$ cells/ml.

Five treatments, including the control, were applied to microspore suspensions of the same extraction as follows: T1, control treatment, comprising 200 μl sterilized water; T2, 1 μg dsDNA in 100 μl sterilized water was added to 4 μg TAT2, diluted in 100 μl sterilized water, and mixed lightly, resulting in a 1:4 ratio of dsDNA to TAT2 (dsDNA: TAT2); T3, 1 μg dsDNA, diluted in 100 μl sterilized water, and 6 μl Chariot (Active Motif, Carlsbad, CA), diluted in 100 μl sterilized water, were mixed together (dsDNA-Pep1); T4, 4 μg RecA (MJS Biolynx, Brockville, Canada; #UB70028) in 50 μl sterilized water and 1 μg dsDNA in 50 μl sterilized water were mixed together for 15 minutes, and 6 μl Chariot in 100 μl sterilized water was added to the dsDNA-RecA solution, to obtain an end volume of 200 μl in a 2 ml micro-centrifuge test tube (dsDNA-RecA-TAT2). After incubation for 15 minutes at room temperature (RT), 5 μl Lipofectamine (Invitrogen, Carlsbad, Ca; #11,668 to 019) was added to all of the preparations, and they were then incubated for a further five minutes at RT. The mixtures were then added immediately to 50,000 pelleted microspores in 2 ml micro-centrifuge test tubes, and incubated for 15 minutes. 100 μl NPB-99 was then added to each test tube, and they were incubated for 45 minutes at RT. The transfected microspores were then pelleted, the precipitation was removed, and the cells were washed twice with NPB-99. 1 ml NPB-99 was then added to the microspores in each of the test tubes, they were carefully mixed, and aliquots of 500 μl were pipetted into 35 mm Petri dishes, containing 3 ml NPB-99+10% Ficoll (Sigma, St. Louis, MO; F4375; NPB-99-10F) and 100 mg/l of the antibiotic cefotaxime (Sigma; #C7039).

Electroporation

Pollen Transformation:

Pollen transformation through electroporation was carried out according to the protocol established by Shi et al. (1996). For this, mature pollen, germinating pollen, or pollen without an exine layer was electroporated with a field strength of 750-1250 V/cm, having a constant impulse of 13 ms.

Ultrasonic Treatment

Pollen Ultrasonic Treatment:

Pollen transformation through ultrasonic treatment was carried out as desCRISPR bed by Wang et al. (2000). For this, 0.3 g fresh pollen was collected in the morning, and mixed in 20 ml of a solution containing 5% sucrose with approximately 10 μg of the plasmid DNA of interest. The solution was treated with ultrasound, both before and after the plasmid DNA was added. Using a JY92-II ultrasound device from the Ningbo Xinzi Scientific Instrument Institute, the parameters that were used for the ultrasonic treatment were: sonic intensity: 300 W, eight treatments for 5 and 10 second intervals. Subsequently clipped maize silk was pollinated with the treated pollen.

LIST OF REFERENCES CITED IN THE EXAMPLE PORTION

Aragão, F. J., et al. (2005). "Germ line genetic transformation in cotton (*Gossypium hirsutum* L.) by selection of transgenic meristematic cells with a herbicide molecule." *Plant Science* 168(5): 1227-1233/Record #: 2408

Artschwager, E. (1926). "Anatomy of the vegetative organs of the sugar beet." *J. agric. Res* 33:143-176/Record #: 2352

Barnabas, B., et al. (1992). "In vitro pollen maturation and successful seed production in detached spikelet cultures in wheat (*Triticum aestivum* L.)." *Sexual Plant Reproduction* 5(4): 286-291/Record #: 2374

Buchheim, J. A., et al. (1989). "Maturation of Soybean Somatic Embryos and the Transition to Plantlet Growth." *Plant Physiology* 89(3): 768-775/Record #: 2402

Chee, P. P., et al. (1989). "Transformation of soybean (*Glycine max*) by infecting germinating seeds with *Agrobacterium tumefaciens*." Plant Physiology 91(3): 1212-1218/Record #: 2392

Chowrira, G., et al. (1995). "Electroporation-mediated gene transfer into intact nodal meristemsin planta." *Molecular Biotechnology* 3(1): 17-23/Record #: 2393

Eapen, S. (2011). "Pollen grains as a target for introduction of foreign genes into plants: an assessment." *Physiology and Molecular Biology of Plants* 17(1): 1-8/Record #: 2384

Frame, B. R., et al. (1994). "Production of fertile transgenic maize plants by silicon carbide whisker-mediated transformation." *The Plant Journal* 6(6): 941-948/Record #: 1755

Gounaris, Y., et al. (2005). "Pollen-mediated genetic transformation of cotton with the *Arabidopsis thaliana* hmgr cDNA using the particle gun." *Journal of Food Agriculture and Environment* 3(2): 157-160/Record #: 2330

Grandjean, O., et al. (2004). "In Vivo Analysis of Cell Division, Cell Growth, and Differentiation at the Shoot Apical Meristem in *Arabidopsis." The Plant Cell* 16(1): 74-87/Record #: 2387

Hermann, K., et al. (2007). "1-Aminocyclopropane-1-carboxylic acid and abscisic acid during the germination of sugar beet (*Beta vulgaris* L.): a comparative study of fruits and seeds." *Journal of Experimental Botany* 58(11): 3047-3060/Record #: 2370

Horikawa, Y., et al. (1997). "Transformants through pollination of mature maize (*Zea mays* L.) pollen delivered bar gene by particle gun." *Journal of Japanese Society of Grassland Science* (*Japan*)/Record #: 2383

Huang, Y., et al. (2009). "Probing the endosperm gene expression landscape in *Brassica napus." BMC Genomics* 10(1): 256/Record #: 2377

Itoh, J.-I., et al. (2005). "Rice Plant Development: from Zygote to Spikelet." *Plant and Cell Physiology* 46(1): 23-47/Record #: 2416

Keshamma, E., et al. (2008). "Tissue culture-independent in planta transformation strategy: an *Agrobacterium tumefaciens*-mediated gene transfer method to overcome recalcitrance in cotton (*Gossypium hirsutum* L.)." *Journal of Cotton Science* 12(3): 264-272/Record #: 2405

Kim, S., et al. (2014). "Highly efficient RNA-guided genome editing in human cells via delivery of purified Cas9 ribonucleoproteins." *Genome Research* 24(6): 1012-1019/Record #: 2288

Ko, S.-W., et al. (1983). "A simplified method of embryo culture in rice of *Oryza sativa* L." *Bot. Bull. Acad. Sin* 24: 97-101/Record #: 2415

Krens, F. A., et al. (1988). "Transformation and regeneration in sugar beet (*Beta vulgaris* L.) induced by 'shooter' mutants of *Agrobacterium tumefaciens." Euphytica* 39(3): 185-194/Record #: 1426

Leduc, N., et al. (1994). "Gene transfer to inflorescence and flower meristems using ballistic micro-targeting." *Sexual Plant Reproduction* 7(2): 135-143/Record #: 2345

Li, X., et al. (2004). "Improvement of cotton fiber quality by transforming the acsA and acsB genes into *Gossypium hirsutum* L. by means of vacuum infiltration." *Plant Cell Reports* 22(9): 691-697/Record #: 2419

Liu, J., et al. (2015). "Efficient delivery of nuclease proteins for genome editing in human stem cells and primary cells." *Nat. Protocols* 10(11): 1842-1859/Record #: 2421

Lusardi, M. C., et al. (1994). "An approach towards genetically engineered cell fate mapping in maize using the Lc gene as a visible marker: transactivation capacity of Lc vectors in differentiated maize cells and microinjection of <i>Lc</i> vectors into somatic embryos and shoot apical meristems." *The Plant Journal* 5(4): 571-582/Record #: 82

Mahn, A., et al. (1995). "Transient gene expression in shoot apical meristems of sugarbeet seedlings after particle bombardment." *Journal of Experimental Botany* 46(10): 1625-1628/Record #: 2367

Martin-Ortigosa, S., et al. (2014). "Proteolistics: a biolistic method for intracellular delivery of proteins." *Transgenic Research:* 1-14/Record #: 2260

Matthys-Rochon, E., et al. (1998). "In vitro development of maize immature embryos: a tool for embryogenesis analysis." *Journal of Experimental Botany* 49(322): 839-845/Record #: 2285

Mauney, J. R. (1961). "The Culture In vitro of Immature Cotton Embryos." *Botanical Gazette* 122(3): 205-209/Record #: 2409

McCabe, D. E., et al. (1993). "Transformation of elite cotton cultivars via particle bombardment of meristems." *Nature Biotechnology* 11(5): 596-598/Record #: 2404

McCabe, D. E., et al. (1988). "Stable transformation of soybean (*Glycine max*) by particle acceleration." *Nature Biotechnology* 6(8): 923-926/Record #: 2391

Muniz de Péadua, V., et al. (2001). "Transformation of Brazilian elite Indica-type rice (*Oryza sativa* L.) by electroporation of shoot apex explants." *Plant Molecular Biology Reporter* 19(1): 55-64/Record #: 2412

Naseri, G., et al. (2014). "In planta transformation of rice (*Oryza sativa*) using thaumatin-like protein gene for enhancing resistance to sheath blight." *African Journal of Biotechnology* 11(31)/Record #: 2411

Neuhaus, G., et al. (1987). "Transgenic rapeseed plants obtained by the microinjection of DNA into microspore-derived embryoids." *Theoretical and Applied Genetics* 75(1): 30-36/Record #: 2123

Obert, B., et al. (2008). "Genetic transformation of barley microspores using anther bombardment." *Biotechnology Letters* 30(5): 945-949/Record #: 2068

Olvera, H. F., et al. (2008). "Floral and Inflorescence Morphology and Ontogeny in *Beta vulgaris*, with Special Emphasis on the Ovary Position." *Annals of Botany* 102(4): 643-651/Record #: 2372

Rajasekaran, K. (2013). Biolistic Transformation of Cotton Zygotic Embryo Meristem. *T Transgenic Cotton.* 958:47-57/Record #: 2403

Ramakrishna, S., et al. (2014). "Gene disruption by cell-penetrating peptide-mediated delivery of Cas9 protein and guide RNA." *Genome Research* 24(6): 1020-1027/Record #: 2287

Ritchie, G. L., et al. (2007). "Cotton growth and development." from cotton.tamu.edu/mwg-internal/de5fs23hu73ds/progress?id=–gCnQaUKI-guBsRa08L1m_QGIEFw5-bHQ3iPfT8R-CI,/Record #: 2410

Rod-in, W., et al. (2014). "The floral-dip method for rice (*Oryza sativa*) transformation." *Journal of Agricultural Technology* 10(2): 467-474/Record #: 2414

Sautter, C., et al. (1995). Ballistic microtargeting of visible marker genes to the shoot meristem of wheat. *Gene Transfer to Plants*, Springer: 152-156/Record #: 2339

Sautter, C., et al. (1995). "Shoot apical meristems as a target for gene transfer by microballistics." *Euphytica* 85(1-3): 45-51/Record #: 2373

Shi, H., et al. (1996). "Exine-detached pollen of *Nicotiana tabacum* as an electroporation target for gene transfer." *Acta Botanica Sinica* 38(8): 626-630/Record #: 2417

Shim, Y.-S., et al. (2012). "dsDNA and protein co-delivery in triticale microspores." *In Vitro Cellular & Developmental Biology—Plant:* 1-10/Record #: 1253

Shou, H., et al. (2002). "Irreproducibility of the soybean pollen-tube pathway transformation procedure." *Plant Molecular Biology Reporter* 20 (4): 325-334/Record #: 2399

Sivakumar, S., et al. (2014). "Optimization of factors influencing microinjection method for *Agrobacterium*-Mediated transformation of Embryonic Shoot Apical Meristem in Cotton (*Gossypium hirsutum* L. cv.SVPR-2)." *International Journal of Current Biotechnology*/Record #: 2420

Touraev, A., et al. (1997). "Plant male germ line transformation." *The Plant Journal* 12(4): 949-956/Record #: 2380

Twell, D., et al. (1989). "Transient expression of chimeric genes delivered into pollen by microprojectile bombardment." *Plant Physiology* 91(4): 1270-1274/Record #: 2316

Vain, P., et al. (1993). "Osmotic treatment enhances particle bombardment-mediated transient and stable transformation of maize." *Plant Cell Reports* 12(2): 84-88/Record #: 20

Wang, J., et al. (2000). "Transgenic maize plants obtained by pollen-mediated transformation." *Acta Botanica Sinica* 43(3): 275-279/Record #: 2418

Wiebold, W. J. (2012). "Arrested Development in the Soybean Field." from ipm.missouri.edu/IPCM/2012/10/Arrested-Development-in-the-Soybean-Field//Record #: 2400

Zapata, C., et al. (1999). "Transformation of a Texas cotton cultivar by using *Agrobacterium* and the shoot apex." *Theoretical and Applied Genetics* 98(2): 252-256/Record #: 2407

Zhang, C.-L., et al. (2008). "Efficient somatic embryogenesis in sugar beet (*Beta vulgaris* L.) breeding lines." *Plant Cell, Tissue and Organ Culture* 93(2): 209-221/Record #: 1461

Zuris, J. A., et al. (2015). "Cationic lipid-mediated delivery of proteins enables efficient protein-based genome editing in vitro and in vivo." *Nat Biotech* 33(1): 73-80/Record #: 2303

The invention claimed is:

1. A method for the production of a plant comprising:

(i) providing an immature inflorescence which comprises at least one meristematic cell, wherein the at least one meristematic cell comprises at least one target nucleic acid region, and wherein the immature inflorescence is placed scutellum side down;

(ii) providing (I) at least one gRNA; or providing a first recombinant construct, the first recombinant construct comprising (a) a nucleic acid sequence coding for a gRNA, (b) optionally at least one regulatory sequence and/or a localization sequence, and (c) optionally at least one DNA repair matrix, and providing at least one CRISPR nuclease or a catalytically active fragment thereof and/or an effector domain, or providing a second recombinant construct, the second recombinant construct comprising (a) a nucleic acid sequence coding for a CRISPR nuclease or a catalytically active fragment thereof, and/or at least one effector domain or a nucleic acid sequence coding for an effector domain, and (b) optionally at least one regulatory sequence and/or a localization sequence, or providing (II) one recombinant construct, the one recombinant construct comprising (a) at least one gRNA or a nucleic acid sequence coding for a gRNA, and (b) at least one CRISPR nuclease or a catalytically active fragment thereof, or a nucleic acid sequence coding for a CRISPR nuclease or catalytically active fragment thereof and/or at least one effector domain or a nucleic acid sequence coding for an effector domain, and (c) optionally at least one regulatory sequence and/or a localization sequence, wherein the gRNA is both able to hybridize with a section of the target nucleic acid region and to interact with the CRISPR nuclease or the catalytically active fragment thereof and/or the effector domain;

(iii) introducing by bombardment into the immature inflorescence (a) the gRNA or the first recombinant construct; and (b) the CRISPR nuclease or the catalytically active fragment thereof and/or the effector domain or the second recombinant construct; or (c) the one recombinant construct;

(iv) culturing the immature inflorescence under conditions which allow activation of the introduced gRNA or the first recombinant construct and the CRISPR nuclease or the catalytically active fragment thereof and/or the effector domain or the second recombinant construct or the one recombinant construct and thus a specific modification of the target nucleic acid region in the immature inflorescence, in order to obtain an immature inflorescence comprising at least one meristematic cell which comprises the specific modification of the target nucleic acid region;

wherein the immature inflorescence has the capacity to germinate without an intermediate step of cell culture in the form of callus production and regeneration and without manipulation of the immature inflorescence;

(v) obtaining a plant directly without an intermediate step of cell culture in the form of callus production and regeneration from the specifically modified at least one meristematic cell by cell division and differentiation and optionally by an additional step of cross-fertilization or self-fertilization, and wherein the obtained plant comprises the specific modification of the target nucleic acid region.

2. The method of claim 1, wherein the first recombinant construct and/or the second recombinant construct or the one recombinant construct are transiently transformed into the plant cell of step (v).

3. The method of claim 1, in which in step (ii), the gRNA or the nucleic acid sequence coding for the gRNA and/or the CRISPR nuclease or a catalytically active fragment thereof or a nucleic acid sequence coding for CRISPR nuclease or a catalytically active fragment thereof and/or the effector domain or a nucleic acid sequence coding for an effector domain is adapted to application in a plant cell.

4. The method of claim 1, further comprising providing at least one vector for introducing the first and/or second recombinant constructs or the one recombinant construct between steps (ii) and (iii).

5. The method of claim 1, wherein at least one third recombinant construct comprising a recombinant nucleic acid fragment is provided between steps (ii) and (iii) for specific homology-directed repair of the target nucleic acid region in the immature inflorescence or insertion into the target nucleic acid region in the immature inflorescence and optionally at least one further vector for introducing the at least one third recombinant construct.

6. The method of claim 1, wherein the meristematic cell is a cell of a monocotyledonous or dicotyledonous plant.

7. The method of claim 4, wherein the at least one vector is selected from the group consisting of *Agrobacterium* spp., a virus comprising a nucleic acid sequence selected from the group consisting of SEQ ID NOs: 12-15 and 25-38, or an agent which is suitable for transfection of a peptide or polypeptide sequence or of nucleic acid sequences or a combination thereof.

8. The method of claim 1, wherein (a) the gRNA is introduced into the immature inflorescence directly as a synthetic nucleic acid;

(b) the CRISPR nuclease, or the catalytically active fragment thereof, is introduced directly as a polypeptide; and/or (c) the effector domain is introduced directly as a nucleic acid or polypeptide.

9. The method of claim 1, wherein the gRNA or the nucleic acid sequence coding for the gRNA or the CRISPR nuclease or the catalytically active fragment thereof or the nucleic acid sequence coding for the CRISPR nuclease or the catalytically active fragment thereof or the effector domain or the nucleic acid sequence coding for the effector domain additionally comprises a localization sequence selected from a nuclear localization sequence, a plastid localization sequence, a mitochondrial localization sequence and a chloroplast localization sequence.

10. The method of claim 1, wherein an inhibitor of the endogenous non-homologous end joining (NHEJ) repair mechanism is introduced into the immature inflorescence.

11. The method of claim 1, wherein the recombinant construct comprises a nucleic acid sequence selected from SEQ ID NOs: 23 and 24.

* * * * *